United States Patent
Tabori et al.

(10) Patent No.: US 11,773,449 B2
(45) Date of Patent: Oct. 3, 2023

(54) PROFILING AND TREATMENT OF HYPERMUTANT CANCER

(71) Applicant: The Hospital for Sick Children, Toronto (CA)

(72) Inventors: Uri Tabori, Toronto (CA); Adam Shlien, Toronto (CA)

(73) Assignee: The Hospital for Sick Children, Toronto (CA)

( * ) Notice: Subject to any disclaimer, the term of this patent is extended or adjusted under 35 U.S.C. 154(b) by 584 days.

(21) Appl. No.: 16/643,636

(22) PCT Filed: Aug. 31, 2018

(86) PCT No.: PCT/CA2018/051054
§ 371 (c)(1),
(2) Date: Mar. 2, 2020

(87) PCT Pub. No.: WO2019/041045
PCT Pub. Date: Mar. 7, 2019

(65) Prior Publication Data
US 2020/0332365 A1 Oct. 22, 2020

Related U.S. Application Data

(60) Provisional application No. 62/553,375, filed on Sep. 1, 2017.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,736,330 A | 4/1998 | Fulton |
| 6,045,997 A | 4/2000 | Futreal et al. |
| 6,165,713 A | 12/2000 | Liskay et al. |
| 7,229,755 B1 | 6/2007 | Kolodner et al. |
| 7,319,023 B2 | 1/2008 | Sidransky |
| 7,749,706 B2 | 7/2010 | Bacher et al. |
| 7,939,263 B2 | 5/2011 | Clarke et al. |
| 8,889,361 B2 | 11/2014 | Chen |
| 9,340,830 B2 | 5/2016 | Lipson et al. |
| 2001/0039016 A1 | 11/2001 | Waldman et al. |
| 2003/0138787 A1 | 7/2003 | Bitter et al. |
| 2003/0198970 A1 | 10/2003 | Roberts |
| 2004/0096855 A1 | 5/2004 | Stratton et al. |
| 2006/0019277 A1 | 1/2006 | Traverso et al. |
| 2007/0275404 A1 | 11/2007 | Van De Rijn et al. |
| 2008/0038723 A1 | 2/2008 | Bitter et al. |
| 2012/0088687 A1 | 4/2012 | Goel et al. |
| 2012/0115735 A1 | 5/2012 | Vogelstein et al. |
| 2012/0295267 A1 | 11/2012 | Goel et al. |
| 2013/0040853 A1 | 2/2013 | Chin et al. |
| 2013/0184999 A1 | 7/2013 | Ding |
| 2013/0267426 A1 | 10/2013 | Lambrechts |
| 2014/0137274 A1 | 5/2014 | Ishikawa |
| 2014/0220559 A1 | 8/2014 | Nystrom et al. |
| 2014/0336996 A1 | 11/2014 | Sun et al. |
| 2014/0359422 A1 | 12/2014 | Bassett, Jr. et al. |
| 2015/0045369 A1 | 2/2015 | Lambrechts |
| 2015/0240317 A1 | 8/2015 | Grandis et al. |
| 2015/0284806 A1 | 10/2015 | Rahman |
| 2015/0353922 A1 | 12/2015 | Altschuler et al. |
| 2016/0040254 A1 | 2/2016 | Garner et al. |
| 2016/0076093 A1 | 3/2016 | Shendure et al. |
| 2017/0002422 A1 | 1/2017 | Santin |
| 2017/0017749 A1 | 1/2017 | Carmeli et al. |
| 2017/0032082 A1 | 2/2017 | Nguyen et al. |

FOREIGN PATENT DOCUMENTS

| | | |
|---|---|---|
| EP | 1254895 A1 | 11/2002 |
| EP | 3133165 A1 | 2/2017 |
| WO | 2006010938 A1 | 2/2006 |
| WO | 2008047128 A3 | 10/2008 |
| WO | 2008142521 A3 | 2/2009 |

(Continued)

OTHER PUBLICATIONS

Catalogue of Somatic Mutations in Cancer (COSMIC), v2—Mar. 2015, available via URL: <//cancer.sanger.ac.uk/signatures/signatures_v2/> (Year: 2015).*
Albertson et al., "DNA Polymerase Epsilon and Delta Proofreading Suppress Discrete Mutator and Cancer Phenotypes in Mice," Proceedings of the National Academy of Sciences of the United States of America, Oct. 2009, vol. 106(40), pp. 17101-17104.
Alexandrov et al., "Deciphering Signatures of Mutational Processes Operative in Human Cancer," Cell Reports, Jan. 2013, vol. 3 (1), pp. 246-259.
Alexandrov et al., "Signatures of Mutational Processes in Human Cancer," Nature, Aug. 2013, vol. 500, 10 pages.
Alexandrov et al., "Mutational Signatures: The Patterns of Somatic Mutations Hidden In Cancer Genomes," Current Opinion in Genetics and Development, Feb. 2014, vol. 24, pp. 52-60.

(Continued)

*Primary Examiner* — Carla J Myers
(74) *Attorney, Agent, or Firm* — Graeme Boocock; BORDEN LADNER GERVAIS LLP

(57) ABSTRACT

There is provided a method of profiling a tumour, the method comprising determining a relative proportion for each of 96 mutation types, wherein the 96 mutation types are defined as the six possible sequence changes C>A, C>G, C>T, T>A, T>C, or T>G in the context of each of four possible nucleotides (A, C, G, or T) at the position immediately 5' to the mutation and each of four possible nucleotides at the position immediately 3' to the mutation; assigning the tumour, using the determined relative proportion for each of the 96 mutation types, to at least one of eight clusters defined herein; and determining at least one tumour characteristic based on the assignment to a cluster.

11 Claims, 19 Drawing Sheets

(56) References Cited

FOREIGN PATENT DOCUMENTS

| WO | 2012038744 A3 | 6/2012 |
|---|---|---|
| WO | 2012110620 A1 | 8/2012 |
| WO | 2016090273 A1 | 6/2016 |
| WO | 2017008165 A1 | 1/2017 |

OTHER PUBLICATIONS

Amayiri et al., "High Frequency of Mismatch Repair Deficiency Among Pediatric High Grade Gliomas in Jordan," International Journal of Cancer, 2016, vol. 138(2), pp. 380-385.

Bouffet et al., "Immune Checkpoint Inhibition for Hypermutant Glioblastoma Multiforme Resulting From Germline Biallelic Mismatch Repair Deficiency," Journal of Clinical Oncology, Mar. 2016, vol. 34(19), 9 pages.

Brohl et al., "The Genomic Landscape of the Ewing Sarcoma Family of Tumors Reveals Recurrent STAG2 Mutation," Plos Genetics, Jul. 2014, vol. 10(7), pp. e1004475.

Campbell et al., "Comprehensive Analysis of Hypermutation in Human Cancer," Cell, Nov. 2017, vol. 171 (5), pp. 1042-1056.

Campbell et al., "Distinct Patterns of Somatic Genome Alterations in Lung Adenocarcinomas and Squamous Cell Carcinomas," Nature Genetics, Jun. 2016, vol. 48(6), pp. 607-616.

Cancer Genome Atlas Network., "Comprehensive Molecular Characterization of Human Colon and Rectal Cancer," Nature, Jul. 2012, vol. 487, pp. 330-337.

Cancer Genome Atlas Network., "Genomic Classification of Cutaneous Melanoma," Cell, Jun. 2015, vol. 161 (7), 1681-1696.

Cancer Genome Atlas Research Network., Comprehensive Molecular Characterization of Urothelial Bladder Carcinoma, Nature, 2014, vol. 507(7492), pp. 315-322.

Daee et al., "A Cancer-Associated DNA Polymerase Delta Variant Modeled in Yeast Causes a Catastrophic Increase in Genomic Instability," Proceedings of the National Academy of Sciences of the United States of America, Jan. 2010, vol. 107, pp. 157-162.

Diaz and Le., "PD-1 Blockade in Tumours with Mismatch-Repair Deficiency," The New England Journal of Medicine, 2015, vol. 373, 1979.

Dossett et al., "Cutaneous Angiosarcoma," Current Problems in Cancer, 2015, vol. 39(4), 16 pages.

Durno et al., "Phenotypic and Genotypic Characterisation of Biallelic Mismatch Repair Deficiency (BMMR-D) Syndrome," European Journal of Cancer, 2015, vol. 51(8), pp. 977-983.

Frampton et al., "Development and Validation of a Clinical Cancer Genomic Profiling Test Based on Massively Parallel DNA Sequencing," Nature Biotechnology, Nov. 2013, vol. 31(11), 11 pages.

Govindan et al., "Genomic Landscape of Non-small Cell Lung Cancer in Smokers and Never-smokers," Cell, 2012, vol. 150(6), 9 pages.

Herr et al., "Mutator Suppression and Escape from Replication Error-Induced Extinction in Yeast," PLoS Genetics, Oct. 2011, vol. 7, pp. e1002282.

International Patent Application No. PCT/CA2018/051054, International Preliminary Reporton Patentability and Written Opinion dated Mar. 3, 2020.

International Patent Application No. PCT/CA2018/051054, International Search Report and Written Opinion dated Nov. 30, 2018.

Johanns et al., "Immunogenomics of Hypermutated Glioblastoma A Patient with Germline POLE Deficiency Treated with Checkpoint Blockade Immunotherapy," Cancer Discovery, Sep. 2016, vol. 6(11), pp. 1230-1236.

kane and Shcherbakova., "A Common Cancer-associated DNA Polymerase Mutation Causes an Exceptionally Strong Mutator Phenotype, Indicating Fidelity Defects Distinct From Loss of Proofreading," Cancer Research, Feb. 2014, vol. 74(7), pp. 1895-1901.

Le et al., "PD-1 Blockade in Tumors with Mismatch-Repair Deficiency," The New England Journal of Medicine, Jun. 2015, vol. 372(26), pp. 2509-2520.

Lek et al., "Analysis of Protein-coding Genetic Variation in 60,706 Humans," Nature, Aug. 2016, vol. 536, pp. 285-291.

Meier et al., "Mutational Signatures of DNA Mismatch Repair Deficiency in C. Elegans and Human Cancers," Genome Research, May 2018, vol. 28 (5), pp. 666-675.

Miller et al., "SciClone Inferring Clonal Architecture and Tracking the Spatial and Temporal Patterns of Tumor Evolution," Plos Computational Biology, Aug. 2014, vol. 10(8), pp. e1003665.

Morganella et al., "The Topography of Mutational Processes in Breast Cancer Genomes," Nature Communications, May 2016, vol. 7, pp. 11383.

Muggeo., "Estimating Regression Models with Unknown Break-Points," Statistics in Medicine, 2003, vol. 22, pp. 3055-3071.

Nguyen et al., "Novel MSH6 Mutations in Treatment-naïve Glioblastoma and Anaplastic Oligodendroglioma Contribute to Temozolomide Resistance Independently of MGMT Promoter Methylation," Clinical Cancer Research, Sep. 2014, vol. 20(18), pp. 4894-4903.

Nik-Zainal et al., "Landscape of Somatic Mutations in 560 Breast Cancer Whole-genome Sequences," Nature, 2016, vol. 534(7605), pp. 47-54.

Pfeifer et al., "Mutations Induced by Ultraviolet Light," Mutation Research, 2005, vol. 571(1-2), pp. 19-31.

Pleasance et al., "A Small-cell Lung Cancer Genome With Complex Signatures of Tobacco Exposure," Nature, Jan. 2010, vol. 463, pp. 184-190.

Poon et al., "Genome-wide Mutational Signatures of Aristolochic Acid and Its Application as a Screening Tool," Science Translational Medicine, Aug. 2013, vol. 5(197), pp. 197ra101.

Rizvi et al., "Cancer Immunology Mutational Landscape Determines Sensitivity to PD-1 Blockade in Non-small Cell Lung Cancer," Science, Apr. 2015, vol. 348(6230), pp. 124-128.

Roberts et al., "An APOBEC Cytidine Deaminase Mutagenesis Pattern is Widespread in Human Cancers," Nature Genetics, Aug. 2013, vol. 45(9), pp. 970-976.

Rosenthal et al., Deconstructsigs: Delineating Mutational Processes in Single Tumors Distinguishes DNA Repair Deficiencies and Patterns of Carcinoma Evolution, Genome Biology, 2016, vol. 17(31).

Sage., "Distribution and Repair of Photolesions in DNA: Genetic Consequences and the Role of Sequence Context," Photochemistry and Photobiology, 1993, vol. 57(1), pp. 163-174.

Santin et al., "Regression of Chemotherapy-resistant Polymerase ε (POLE) Ultra-mutated and MSH6 Hyper-mutated Endometrial Tumors With Nivolumab," Clinical Cancer Research, Dec. 2016, vol. 22(23), pp. 5682-5687.

Scarpa et al., "Whole-genome Landscape of Pancreatic Neuroendocrine Tumours," Nature, Mar. 2017, vol. 543 (7643), pp. 65-71.

Schlesner et al., "Hypermutation Takes the Driver's Seat," Genome Medicine, Mar. 2015, vol. 7 (1), 3 pages.

Shinbrot et al., "Exonuclease Mutations in DNA Polymerase Epsilon Reveal Replication Strand Specific Mutation Patterns and Human Origins of Replication," Genome Research, Sep. 2014, vol. 24(11), pp. 1740-1750.

Shlien et al., "Combined Hereditary and Somatic Mutations of Replication Error Repair Genes Result in Rapid Onset of Ultra-hypermutated Cancers," Nature genetics, 2015, vol. 47(3), pp. 257-262.

Snyder et al., "Genetic Basis for Clinical Response to CTLA-4 Blockade in Melanoma," The New England Journal of Medicine, Dec. 2014, vol. 371(23), pp. 2189-2199.

Stratton et al., "The Cancer Genome," Nature, Apr. 2009, vol. 458, pp. 719-724.

Swann et al., "Role of Postreplicative DNA Mismatch Repair in the Cytotoxic Action of Thioguanine," Science, Aug. 1996, vol. 273, pp. 1109-1111.

The Cancer Genome Atlas Research Network, "Integrated Genomic Characterization of Endometrial Carcinoma," Nature, May 2013, vol. 497 (7447), pp. 67-73.

Topalian et al., "Mechanism-driven Biomarkers to Guide Immune Checkpoint Blockade in Cancer Therapy," Nature Reviews Cancer, May 2016, vol. 16(5), pp. 275-287.

(56) References Cited

OTHER PUBLICATIONS

Van Allen et al., "Genomic Correlates of Response to CTLA-4 Blockade in Metastatic Melanoma," Science, Oct. 2015, vol. 350(6257), pp. 207-211.

Van Thuijl et al., "Evolution of DNA Repair Defects During Malignant Progression of Low-grade Gliomas After Temozolomide Treatment," Acta Neuropathologica, Feb. 2015, vol. 129(4), pp. 597-607.

Zahurancik et al., "Significant Contribution of the 3'-5' Exonuclease Activity to the High Fidelity of Nucleotide Incorporation Catalyzed by Human DNA Polymerase," Nucleic Acids Research, 2014, 42(22), 13853-13860.

Zhang et al., "Germline Mutations in Predisposition Genes in Pediatric Cancer," The New England Journal of Medicine, Apr. 2016, vol. 374(14), pp. 1391.

\* cited by examiner

| Pol E | $k_{exo}(s^{-1})$ | $k_{exo\,(WT)}/k_{exo\,(Mut)}$ |
|---|---|---|
| WT | 0.86±0.08 | 1 |
| L424V | 0.0097±0.0003 | 89 |
| L424I | 0.00171±0.00005 | 500 |

Figure 10

PROFILING AND TREATMENT OF HYPERMUTANT CANCER

RELATED APPLICATION

This claims priority from U.S. Provisional Application No. 62/553,375 filed Sep. 1, 2017 and entitled "PROFILING AND TREATMENT OF HYPERMUTANT CANCER", which is herein incorporated by reference in its entirety.

FIELD

The present disclosure relates generally to tumour profiling and treatment. More specifically, the disclosure relates to the profiling and treatment of hypermutant cancer.

BACKGROUND

Neoplastic cells circumvent the usual DNA repair safeguards, allowing for the accumulation of mutations that drive cancer. Yet, even a cancer cell's mutation burden is typically kept within specific bounds.

Recently, a group of cancers with high mutation burden (hypermutation) has been reported (Shlien, et al *Nat Genet* 2015). Patients with these cancers often have very different outcomes than those with the same tumour type lacking a high mutation burden, and are the only group responsive to immune checkpoint inhibition (Bouffet et al *J Clin Onc* 2016).

However, due to limited sample sizes, the threshold and extent of hypermutation across cancer, as well as the exact tumour types involved, are currently unknown.

Furthermore, since different tumour types with hypermutation have never been considered together before, it is not currently known if their hypermutation arises via similar molecular mechanisms, or at the same time during tumour evolution.

It would be desirable to provide a means of profiling hypermutant cancers.

It would be desirable to provide profiles indicative of tumour biology.

It would be desirable to establish treatments for hypermutant cancers.

SUMMARY

It is an object of the present disclosure to obviate or mitigate at least one disadvantage of previous approaches.

In a first aspect, the present disclosure provides a method of profiling a tumour, the method comprising sequencing nucleic acid from a sample obtained from the tumour; identifying mutations relative to a reference sequence, wherein a mutation is defined with respect to the pyrimidine of a base pair; determining a relative proportion for each of 96 mutation types, wherein the 96 mutation types are defined as each of six possible pyrimidine base changes C>A, C>G, C>T, T>A, T>C, or T>G in the context of each of four possible nucleotides (A, C, G, or T) at the position immediately 5' to the mutation and each of four possible nucleotides (A, C, G, or T) at the position immediately 3' to the mutation; assigning the tumour, using the determined relative proportion for each of the 96 mutation types, to at least one of eight clusters, wherein the at least eight clusters are depicted as 1 to 8 in the heat map of FIG. 19, wherein each of the clusters is defined by a visual representation the relative proportions of each of the 96 mutation types for the cluster; and determining at least one tumour characteristic based on the assigning.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 1A) Tumour mutation burden for 2,885 pediatric cancers. Tumours with 10 mut/mb or more are considered hypermutant, tumours with 100 mut/mb are considered ultra-hypermutant. FIG. 1B) Breakdown of hypermutation pediatric cohort by tumour type. Corresponding pie graphs for each mutation range depicts the proportion of tumours harboring mutations in genes implicated in replication repair deficiency (RRD) (MSH2, MLH1, MSH6, PMS2 POLE, POLD1). FIG. 1C) Tumour mutation burden range for 78,452 adult tumours and tumour type breakdown in ultra-hypermutant and hypermutant groups. Tumour types are ranked in descending order by median mutation burden. FIG. 1D) Tumour types that show enrichment for MSI-MSI-H tumours cluster in the 10-100 mut/mb range while tumours with both mismatch repair and polymerase proofreading in the same types occupy the ultra-hypermutant range. FIG. 1E) Pie graphs represent the proportion of ultra-hypermutant, hypermutant and lowly mutated tumours and their correlation with MSI-H and MMR/POL mutations. Acronyms: GI=Gastrointestinal, AML=Acute Myeloid Leukemia, NBL=Neuroblastoma, RMS=Rhabdomyosarcoma, STS=Soft tissue sarcoma, OS=Osteosarcoma, EWS=Ewing's sarcoma, WLMS=Wilm's tumour, RCC=Renal cell carcinoma, NP&PNS=nasopharynx and paranasal sinuses undifferentiated carcinoma, MM&MDS=Bone marrow myelodysplastic syndrome FIG. 2 (2A to 2D) depicts characterization of known and novel POLE and POLD1 driver mutations FIG. 2A) Examples of tumours with three or more POLE/POLD1 mutations and the corresponding number of tumours found in the entire dataset harboring those mutations (grey bars). The height of bars corresponds to mutation burden of other tumours with that mutation. No bars indicates no other tumours were identified with this mutation. One clear driver emerges in each case.

FIG. 3A) Top panel: Unsupervised hierarchical clustering of 1521 tumours by trinucleotide context reveals 8 distinct clusters (colored dendrogram). Middle: Disease type, MSI status. Bottom panel: Heatmap colored by proportion of mutations from each class of mutational signatures. FIG. 3B) Top: Range of tumours types found in clusters C1, C2 and C3, size of circle indicates number of tumours. Middle: Box plots displaying mutation burden (mut/MB) in each of C1, C2, C3. Bottom: Pie charts displaying proportion of tumours in each cluster, which are MSI-High, POLE-mutant and children respectively. FIG. 3C) Average proportion of mutations attributed by 4 mutational signature classes, Tobacco Smoke (Signature 4), Alkylating agents (Signature 11), UV Light (Signature 7) and APOBEC (Signature 2 and 13). Color of circles indicates cluster tumours belong to, size indicates number of tumours in this cluster and tumour type and y axis indicates average proportion of mutations attributed to each signature.

FIG. 4A) Left: Average proportion of mutations by trinucleotide context from panel sequencing. Germline status and treatment history unknown. N indicates number of tumour samples used to calculate average proportions. Right: Average proportion of mutations by trinucleotide context in exomes with known germline status/treatment history. N indicates number of tumour samples used to calculate average proportions. FIG. 4B) Example mutational signatures in exomes from tumours with known germline status/treatment history. FIG. 4C-F) Examples of subclonal mutational signatures determined from allelic read depth calculations on panel sequencing data. N indicates number of mutations in cluster. Signatures 21, 6, 15, and 14 are those previously associated with MMR deficiency, Signature 10 was previously associated with POLE mutations, and Signature 11 was previously associated with treatment with alkylating agents. FIG. 4C) Subclonal mutational signatures in an adult colorectal carcinoma with somatic POLE mutation reveal early mutations due to POLE mutations and later mutations due to POLE mutation and mismatch repair defiance FIG. 4D) Subclonal mutational signatures in a pediatric glioblastoma reveal early mutations due to deficits in mismatch repair and later mutations due to mismatch repair and POLE proofreading mutation FIG. 4E) Mutational signatures present in subclonal clusters of mutations in a lung adenocarcinoma reveal early mutations due to smoking and later mutations due to replication repair deficiency. FIG. 4F) Mutational signatures present in 3 subclonal clusters of mutations in a skin melanoma reveal early mutations due to primarily UV light exposure and later mutations due mostly to exposure to alkylating agents.

FIG. 5A) Signature analysis for all ultra-hypermutant (>100 mut/mb) pediatric tumours. All signatures associated with replication repair deficiency were combined (black). Signatures associated with alkylating agents are shown (originally coloured turquoise). 19 patients with ultra-hypermutant tumours were confirmed for germline cancer predisposition involving replication repair genes. Numbers above each bar represent the mutation burden for that tumour. FIG. 5B) Signature analysis for hypermutant pediatric tumours (10-100 mut/mb)-hypermutant pediatric tumours of the three tumour types typically associated with CMMRD (brain, GI, leukemia/lymphoma) were enriched for RRD signatures. Two brain tumour patients were retrospectively confirmed as CMMRD (50 mut/mb) and Lynch (34 mut/mb) respectively.

FIG. 6A) Linear correlation between tumour mutation burden derived from whole exome sequencing (WES) and tumour mutation burden derived from 1.1-3.25 MB of targeted panel sequencing (R-squared=0.94). FIG. 6B) Tumour mutation burden on a test dataset of 14 tumours that underwent targeted panel sequencing, whole exome sequencing, and whole genome sequencing.

FIG. 10 shows that L424I and L424V Pol ε mutations vary in their degree of reduced exonuclease function. Excision rate constants of 3'-5' exonuclease activity catalyzed by Pol ε and the indicated mutants at 37° C.

FIG. 11A) Proportion of Signature 7 versus Signature 4 (Smoking) in 100 hypermutant lung cancer samples run on cancer panel. Circle sizes indicate tumour mutation burden in mut/mb, and colors represent lung cancer subtype (i.e. adenocarcinoma, squamous cell carcinoma, non-small cell (not otherwise specified) and other. FIG. 11B) Proportion of Signature 4 in lung cancers by subtype. FIG. 11C) Proportion of Signature 7 in lung cancers by subtype.

FIG. 13A) Histogram displaying number of SNVs by variant allele fraction (VAF) in each of the 8 major clusters identified by hierarchal clustering in FIG. 3. Colors indicate type of SNV (Stopgain, missense and synonymous mutations). FIG. 13B) VAF vs median cumulative mutation burden plotted for each of the 3 replication repair clusters. Cluster 1 tumours exhibit an early burst of mutations (around 0.4 VAF) with a second burst of mutations later in tumour evolution (around 0.2 VAF). Cluster 3 tumours display a single burst of mutations around 0.2 VAF, and Cluster 2 tumours exhibit a more gradual accumulation of mutations throughout their evolution. FIG. 13C) Kaplan-Meier plot of overall survival for tumours with mutational signatures consistent with clusters 1, 2, or 3. Cluster 3, n=27. Cluster 2, n=168. Cluster 1, n=22. P<0.0001.

DETAILED DESCRIPTION

Generally, the present disclosure provides a method of profiling a tumour, the method comprising determining a relative proportion for each of 96 mutation types for the tumour, wherein the 96 mutation types are defined as the six possible sequence changes C>A, C>G, C>T, T>A, T>C, or T>G in the context of each of four possible nucleotides (A, C, G, or T) at the position immediately 5' to the mutation and each of four possible nucleotides at the position immediately 3' to the mutation; assigning the tumour, using the determined relative proportion for each of the 96 mutation types, to one of at least eight clusters defined herein; and determining at least one tumour characteristic based on the assignment to a cluster.

Methods of Tumour Profiling

Figure 19:
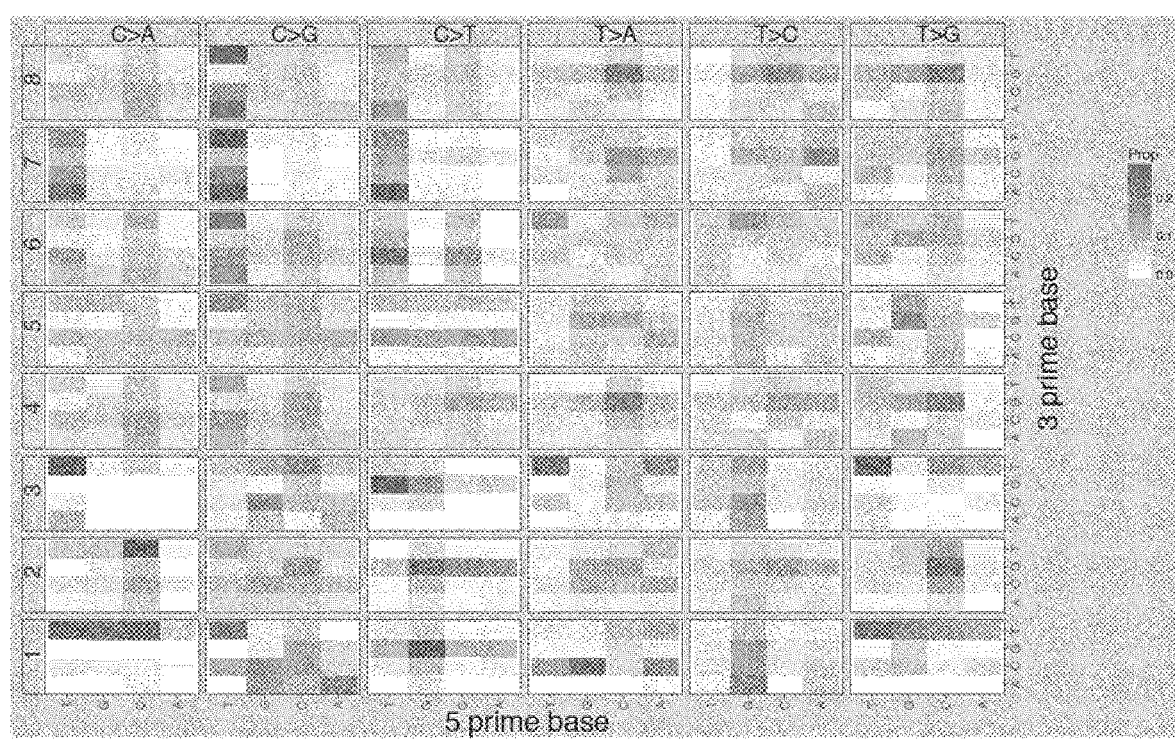
FIG. 19 depicts a heat map providing a visual representation of the relative proportions of each of the 96 mutation types for each of the clusters 1 to 8.

In one aspect, there is provided a method of profiling a tumour, the method comprising sequencing nucleic acid from a sample obtained from the tumour; identifying mutations relative to a reference sequence, wherein a mutation is defined with respect to the pyrimidine of a base pair; determining a relative proportion for each of 96 mutation types, wherein the 96 mutation types are defined as each of six possible pyrimidine base changes C>A, C>G, C>T, T>A, T>C, or T>G in the context of each of four possible nucleotides (A, C, G, or T) at the position immediately 5' to the mutation and each of four possible nucleotides (A, C, G, or T) at the position immediately 3' to the mutation, assigning the tumour, using the determined relative proportion for each of the 96 mutation types, to at least one of eight clusters, wherein the at least eight clusters are depicted as 1 to 8 in the heat map of FIG. 19, wherein each of the clusters is defined by a visual representation of the relative proportions of each of the 96 mutation types for the cluster; and determining at least one tumour characteristic based on the based on the assigning.

The shading of the heat map depicted in FIG. 19 corresponds to the numerical values for the mean proportion for each mutation type for each cluster, 1 to 8, as shown in Table 1, wherein "Mut" is indicative of the mutation, "5'" is indicative of the 5' base, and "3'" is indicative of the 3' base.

TABLE 1

Mean Proportion of Mutation Types for Clusters 1 to 8

| | | | Mean Proportion for Clusters | | | | | | | |
|---|---|---|---|---|---|---|---|---|---|---|
| Mut | 5' | 3' | 1 | 2 | 3 | 4 | 5 | 6 | 7 | 8 |
| C > A | A | A | 6.7E−05 | 0.001303 | 0.00119 | 0.017772 | 0.001499 | 0.002243 | 0.002892 | 0.019454 |
| C > A | A | C | 0.002389 | 0.003823 | 0.003755 | 0.026454 | 0.002257 | 0.001905 | 0.004423 | 0.026279 |
| C > A | A | G | 0 | 0.00119 | 0.000792 | 0.017313 | 0.000452 | 0.000727 | 0.001758 | 0.014491 |
| C > A | A | T | 0.009421 | 0.002499 | 0.006822 | 0.016983 | 0.000599 | 0.000833 | 0.001252 | 0.014017 |
| C > A | C | A | 0.003067 | 0.00708 | 0.003819 | 0.05069 | 0.001325 | 0.003465 | 0.003623 | 0.048299 |
| C > A | C | C | 0.004592 | 0.011953 | 0.002766 | 0.05509 | 0.001926 | 0.002554 | 0.0033 | 0.045063 |
| C > A | C | G | 0.00161 | 0.007254 | 0.002327 | 0.034315 | 0.001284 | 0.001854 | 0.002787 | 0.030886 |
| C > A | C | T | 0.037945 | 0.029925 | 0.014682 | 0.036224 | 0.000878 | 0.00349 | 0.003352 | 0.029591 |
| C > A | G | A | 0.001125 | 0.002937 | 0.002638 | 0.021099 | 0.001394 | 0.001877 | 0.00328 | 0.022232 |
| C > A | G | C | 0.005352 | 0.004551 | 0.002743 | 0.032029 | 0.001812 | 0.001296 | 0.003621 | 0.024923 |
| C > A | G | G | 0.001282 | 0.002862 | 0.00103 | 0.023932 | 0.000308 | 0.00086 | 0.001465 | 0.021978 |
| C > A | G | T | 0.032471 | 0.008021 | 0.008659 | 0.014444 | 0.002057 | 0.001507 | 0.002714 | 0.016893 |
| C > A | T | A | 0.002468 | 0.002416 | 0.030984 | 0.02373 | 0.000599 | 0.002695 | 0.023976 | 0.028258 |
| C > A | T | C | 0.006074 | 0.004215 | 0.008444 | 0.038228 | 0.001522 | 0.004612 | 0.015313 | 0.037669 |
| C > A | T | G | 0.000658 | 0.001553 | 0.003072 | 0.012278 | 0.000797 | 0.001133 | 0.009061 | 0.01494 |
| C > A | T | T | 0.041834 | 0.006319 | 0.190779 | 0.03142 | 0.001709 | 0.002654 | 0.015214 | 0.027702 |
| C > G | A | A | 0.000569 | 0.001268 | 0.000741 | 0.006863 | 0.000744 | 0.000844 | 0.003019 | 0.00775 |

TABLE 1-continued

Mean Proportion of Mutation Types for Clusters 1 to 8

| Mut | 5' | 3' | Mean Proportion for Clusters | | | | | | | |
|---|---|---|---|---|---|---|---|---|---|---|
| | | | 1 | 2 | 3 | 4 | 5 | 6 | 7 | 8 |
| C > G | A | C | 0.000114 | 0.002475 | 0.000842 | 0.004127 | 0.001494 | 0.001292 | 0.003434 | 0.004868 |
| C > G | A | G | 0.000251 | 0.001332 | 0.000468 | 0.003539 | 0.000665 | 0.00116 | 0.001847 | 0.003259 |
| C > G | A | T | 0 | 0.001943 | 0.000872 | 0.004021 | 0.000726 | 0.001104 | 0.002654 | 0.005493 |
| C > G | C | A | 0.00032 | 0.00168 | 0.00023 | 0.008079 | 0.000856 | 0.001644 | 0.00432 | 0.007216 |
| C > G | C | C | 0.000559 | 0.002767 | 0.001219 | 0.011364 | 0.001386 | 0.002353 | 0.004633 | 0.006497 |
| C > G | C | G | 0.000379 | 0.003067 | 0.000998 | 0.012243 | 0.0013 | 0.002673 | 0.004404 | 0.007152 |
| C > G | C | T | 0.000202 | 0.001803 | 0.001843 | 0.006568 | 0.001703 | 0.00159 | 0.004905 | 0.005911 |
| C > G | G | A | 0.000238 | 0.001606 | 0.000929 | 0.005728 | 0.000382 | 0.000724 | 0.001759 | 0.00454 |
| C > G | G | C | 0.000404 | 0.003352 | 0.001803 | 0.006832 | 0.001102 | 0.001522 | 0.002245 | 0.008064 |
| C > G | G | G | 5.71E−05 | 0.001414 | 0.00021 | 0.005349 | 0.000993 | 0.001158 | 0.002204 | 0.005642 |
| C > G | G | T | 7.05E−05 | 0.001991 | 0.001271 | 0.003366 | 0.001426 | 0.000885 | 0.004135 | 0.005597 |
| C > G | T | A | 0 | 0.001682 | 0.000244 | 0.01032 | 0.000721 | 0.002827 | 0.088732 | 0.026979 |
| C > G | T | C | 0.000343 | 0.002414 | 0.000753 | 0.01316 | 0.000957 | 0.003088 | 0.027984 | 0.016404 |
| C > G | T | G | 0 | 0.001217 | 0.000503 | 0.004416 | 0.000578 | 0.001376 | 0.014448 | 0.003659 |
| C > G | T | T | 0.001043 | 0.004031 | 0.000942 | 0.013253 | 0.00256 | 0.004521 | 0.105522 | 0.03456 |
| C > T | A | A | 0.009098 | 0.015807 | 0.002356 | 0.012255 | 0.018988 | 0.003111 | 0.007497 | 0.008034 |
| C > T | A | C | 0.021673 | 0.014512 | 0.007633 | 0.008304 | 0.107317 | 0.028438 | 0.006307 | 0.006785 |
| C > T | A | G | 0.080822 | 0.098997 | 0.029695 | 0.024394 | 0.018757 | 0.009504 | 0.01971 | 0.008963 |
| C > T | A | T | 0.01273 | 0.008974 | 0.006131 | 0.00745 | 0.061462 | 0.008133 | 0.004222 | 0.006623 |
| C > T | C | A | 0.005011 | 0.009953 | 0.002726 | 0.016459 | 0.026098 | 0.069057 | 0.015157 | 0.018233 |
| C > T | C | C | 0.013316 | 0.012312 | 0.003786 | 0.016002 | 0.119295 | 0.116254 | 0.010024 | 0.015242 |
| C > T | C | G | 0.075944 | 0.103416 | 0.024621 | 0.028195 | 0.024174 | 0.052378 | 0.031736 | 0.020032 |
| C > T | C | T | 0.013479 | 0.012866 | 0.006972 | 0.016392 | 0.07329 | 0.07903 | 0.012472 | 0.018323 |
| C > T | G | A | 0.024254 | 0.028917 | 0.005288 | 0.011127 | 0.024443 | 0.00376 | 0.01157 | 0.008069 |
| C > T | G | C | 0.059279 | 0.046541 | 0.024879 | 0.014863 | 0.093441 | 0.027676 | 0.009702 | 0.01053 |
| C > T | G | G | 0.222447 | 0.148718 | 0.070994 | 0.015991 | 0.02658 | 0.007628 | 0.022776 | 0.012521 |
| C > T | G | T | 0.038951 | 0.030229 | 0.021253 | 0.011066 | 0.064453 | 0.013225 | 0.009746 | 0.007571 |
| C > T | T | A | 0.007213 | 0.010064 | 0.004939 | 0.014983 | 0.023016 | 0.072722 | 0.171925 | 0.041898 |
| C > T | T | C | 0.028449 | 0.011086 | 0.016469 | 0.010613 | 0.122659 | 0.197681 | 0.05397 | 0.019335 |
| C > T | T | G | 0.078732 | 0.052801 | 0.219143 | 0.014147 | 0.01483 | 0.08704 | 0.065382 | 0.021316 |
| C > T | T | T | 0.027756 | 0.008177 | 0.02943 | 0.012661 | 0.078928 | 0.065168 | 0.077588 | 0.027306 |
| T > A | A | A | 0.000295 | 0.001176 | 0.000209 | 0.002711 | 0.00066 | 0.001701 | 0.001204 | 0.002119 |
| T > A | A | C | 0.001226 | 0.003815 | 0.000852 | 0.005563 | 0.001046 | 0.001309 | 0.001153 | 0.002691 |
| T > A | A | G | 0.0004 | 0.001401 | 0.000458 | 0.008168 | 0.000793 | 0.00164 | 0.002408 | 0.008367 |
| T > A | A | T | 0.001352 | 0.002917 | 0.001796 | 0.002225 | 0.000307 | 0.00301 | 0.000762 | 0.00305 |
| T > A | C | A | 0 | 0.000781 | 0.000352 | 0.005749 | 0.000273 | 0.000998 | 0.000917 | 0.003744 |
| T > A | C | C | 0.000369 | 0.002485 | 0.001001 | 0.008503 | 0.000572 | 0.001611 | 0.002477 | 0.006996 |
| T > A | C | G | 0.0005 | 0.004052 | 0.001149 | 0.019982 | 0.001139 | 0.001982 | 0.003061 | 0.019045 |
| T > A | C | T | 0.000809 | 0.001423 | 0.000821 | 0.006551 | 0.000594 | 0.002184 | 0.001376 | 0.006358 |
| T > A | G | A | 0 | 0.0012 | 0.000226 | 0.003155 | 0.000839 | 0.001257 | 0.000893 | 0.006023 |
| T > A | G | C | 0.002031 | 0.002942 | 0.000182 | 0.003327 | 0.000677 | 0.000932 | 0.000955 | 0.002762 |
| T > A | G | G | 0.00019 | 0.003729 | 0.000445 | 0.008214 | 0.001309 | 0.001757 | 0.001271 | 0.00739 |
| T > A | G | T | 0.000321 | 0.00107 | 0.000202 | 0.00161 | 0.00086 | 0.001172 | 0.001481 | 0.00341 |
| T > A | T | A | 0 | 0.000781 | 0.000138 | 0.003102 | 0.000457 | 0.001356 | 0.00024 | 0.003029 |
| T > A | T | C | 0.001246 | 0.00113 | 0.000725 | 0.003455 | 0.000207 | 0.002091 | 0.000854 | 0.004073 |
| T > A | T | G | 0.000229 | 0.000808 | 0.00015 | 0.005573 | 0.000305 | 0.001333 | 0.000518 | 0.005702 |
| T > A | T | T | 0.000267 | 0.000915 | 0.00279 | 0.002261 | 0.000528 | 0.004013 | 0.001072 | 0.003578 |
| T > C | A | A | 0.006228 | 0.010066 | 0.004417 | 0.006428 | 0.002687 | 0.002514 | 0.004557 | 0.004975 |
| T > C | A | C | 0.005627 | 0.00713 | 0.004952 | 0.003248 | 0.002543 | 0.001447 | 0.001645 | 0.0029 |
| T > C | A | G | 0.004509 | 0.021637 | 0.005165 | 0.008724 | 0.003567 | 0.003323 | 0.009699 | 0.007189 |
| T > C | A | T | 0.00324 | 0.007429 | 0.004211 | 0.003789 | 0.002231 | 0.002848 | 0.005327 | 0.003113 |
| T > C | C | A | 0.001378 | 0.007187 | 0.000923 | 0.002191 | 0.001319 | 0.001957 | 0.001896 | 0.003062 |
| T > C | C | C | 0.004677 | 0.009799 | 0.003691 | 0.00541 | 0.002954 | 0.002671 | 0.003789 | 0.00364 |
| T > C | C | G | 0.003798 | 0.025847 | 0.003957 | 0.011165 | 0.002454 | 0.003085 | 0.004987 | 0.010078 |
| T > C | C | T | 0.002998 | 0.009297 | 0.003321 | 0.005057 | 0.002592 | 0.004473 | 0.003038 | 0.004469 |
| T > C | G | A | 0.014476 | 0.017372 | 0.01155 | 0.004864 | 0.003773 | 0.001411 | 0.002532 | 0.003809 |
| T > C | G | C | 0.012038 | 0.011524 | 0.015514 | 0.00185 | 0.004029 | 0.001397 | 0.002503 | 0.0027 |
| T > C | G | G | 0.012999 | 0.020376 | 0.008717 | 0.005925 | 0.004941 | 0.003671 | 0.006668 | 0.00738 |
| T > C | G | T | 0.008026 | 0.011538 | 0.012768 | 0.005125 | 0.003119 | 0.007672 | 0.003825 | 0.003653 |
| T > C | T | A | 0.002157 | 0.00638 | 0.002805 | 0.004462 | 0.00213 | 0.003264 | 0.002 | 0.001159 |
| T > C | T | C | 0.003458 | 0.007139 | 0.00666 | 0.003498 | 0.002031 | 0.002641 | 0.002223 | 0.001386 |
| T > C | T | G | 0.002926 | 0.009561 | 0.005562 | 0.004882 | 0.001529 | 0.002926 | 0.001109 | 0.00204 |
| T > C | T | T | 0.002948 | 0.005824 | 0.005819 | 0.002753 | 0.001366 | 0.002989 | 0.001503 | 0.000691 |
| T > G | A | A | 6.7E−05 | 0.000486 | 0.001478 | 0.000183 | 0.000228 | 0.000604 | 0.000496 | 0.000545 |
| T > G | A | C | 0.001077 | 0.001094 | 0.003775 | 0.000771 | 8.55E−05 | 0.000615 | 0.000651 | 0.000557 |
| T > G | A | G | 0.000499 | 0.001114 | 0.001846 | 0.000516 | 0.000706 | 0.001337 | 0.001154 | 0.001011 |
| T > G | A | T | 0.003055 | 0.00097 | 0.011338 | 0.000525 | 0.000155 | 0.000611 | 0.000462 | 0.000783 |
| T > G | C | A | 0.000196 | 0.00167 | 0.002233 | 0.001327 | 0.000868 | 0.000933 | 0.001278 | 0.002199 |
| T > G | C | C | 0.000731 | 0.004141 | 0.001955 | 0.001327 | 0.000715 | 0.001481 | 0.001622 | 0.00119 |
| T > G | C | G | 0.000628 | 0.00923 | 0.003836 | 0.005045 | 0.000693 | 0.002199 | 0.002348 | 0.004793 |
| T > G | C | T | 0.003131 | 0.005064 | 0.015868 | 0.001173 | 0.000679 | 0.001849 | 0.001671 | 0.001068 |

TABLE 1-continued

Mean Proportion of Mutation Types for Clusters 1 to 8

| Mut | 5' | 3' | Mean Proportion for Clusters | | | | | | | |
|---|---|---|---|---|---|---|---|---|---|---|
| | | | 1 | 2 | 3 | 4 | 5 | 6 | 7 | 8 |
| T > G | G | A | 0.000365 | 0.000912 | 0.001333 | 0.002413 | 0.000422 | 0.000424 | 0.000223 | 0.000884 |
| T > G | G | C | 0.001875 | 0.001146 | 0.002466 | 0.000516 | 0.000595 | 0.000523 | 0.000749 | 0.00071 |
| T > G | G | G | 0.001543 | 0.002292 | 0.00168 | 0.003201 | 0.002064 | 0.002655 | 0.001429 | 0.002581 |
| T > G | G | T | 0.003994 | 0.003071 | 0.004097 | 0.001524 | 0.001203 | 0.001403 | 0.001174 | 0.000958 |
| T > G | T | A | 0 | 0.000364 | 0.004756 | 0.000764 | 0.000183 | 0.000486 | 0.000504 | 0.000471 |
| T > G | T | C | 0.001569 | 0.001778 | 0.006492 | 0.001079 | 0.001107 | 0.00163 | 0.001786 | 0.001199 |
| T > G | T | G | 0.000386 | 0.001434 | 0.001971 | 0.002192 | 0.000242 | 0.001367 | 0.001185 | 0.002327 |
| T > G | T | T | 0.006112 | 0.001191 | 0.048665 | 0.001796 | 0.000477 | 0.001973 | 0.001265 | 0.001102 |

Thus, in some embodiments, the relative proportion for each of the 96 mutation types for each cluster is the corresponding numerical value for the mean proportion depicted in Table 1.

It will be understood in the above that the definition of mutations and mutation types by reference to pyrimidines is merely a convention, and the method would inherently encompass methods in which the analogous definitions, types, and cluster heat maps were instead defined with respect to purines.

By "profiling," is meant determination of at least one tumour characteristic.

By "tumour characteristic" is meant any feature of the tumour, including e.g. aspects of its present biology and/or tumour origin or development. This could include, as non-limiting examples, gene mutations, oncogenic mutations, germline mutations, early mutations, late mutations, tissue origin, mutational history (or a step thereof), order of mutational events, mutagen exposure, order of mutagen exposure, prior treatment, etc. It could also include, e.g., a correlation with histology, biomarker status, tumour grade, tumour staging, tumour metastasis, resistance to a therapeutic, and/or prognosis.

By "assigning" is meant associating the tumour with at least one of the eight clusters. Any suitable means of achieving an assignment may be employed, including the following non-limiting examples. The tumour could be categorized based on the relative prevalence of each of the 96 mutation types. Categories could be established for each of the eight categories base, e.g. on numerical ranges or absolute values plus or minus 5%, 10%, 15%, 20%, 25%, etc. A tumour could be assigned to a cluster based, e.g., on the best categorization. Statistical methods could be employed to assess matching or best fist.

In some embodiments, not all relative proportions need be used for making the assignment of a tumour to a cluster. In some embodiments, the assigning is carried out using the relative proportion of one of the 96 mutation types determined for the tumour. In some embodiments, the assigning is carried out using the relative proportions of at least one of the 96 mutation types determined for the tumour. In some embodiments, the assigning is carried out using the relative proportions of at least two of the 96 mutation types determined for the tumour. In some embodiments, the assigning is carried out using the relative proportions of at least three of the 96 mutation types determined for the tumour. In some embodiments, the assigning is carried out using the relative proportions of at least four of the 96 mutation types determined for the tumour. In some embodiments, the assigning is carried out using the relative proportions of at least five of the 96 mutation types determined for the tumour. In some embodiments, the assigning is carried out using the relative proportions of at least six of the 96 mutation types determined for the tumour. In some embodiments, the assigning is carried out using the relative proportions of at least 12 of the 96 mutation types determined for the tumour. In some embodiments, the assigning is carried out using the relative proportions of at least 24 of the 96 mutation types determined for the tumour. In some embodiments, the assigning is carried out using the relative proportions of at least 36 of the 96 mutation types determined for the tumour. In some embodiments, the assigning is carried out using the relative proportions of at least 48 of the 96 mutation types determined for the tumour. In some embodiments, the assigning is carried out using the relative proportions of at least 60 of the 96 mutation types determined for the tumour. In some embodiments, the assigning is carried out using the relative proportions of at least 72 of the 96 mutation types determined for the tumour. In some embodiments, the assigning is carried out using the relative proportions of at least 84 of the 96 mutation types determined for the tumour. In some embodiments, the assigning is carried out using all 96 of the relative proportions determined for the tumour.

In the above embodiments involving subsets of the 96 mutation types, in some embodiments the relative proportions used in the assigning are the most informative of the relative proportions. By "most informative" of the relative proportions is meant those relative proportions that are most distinguishing. For examples, they may be significantly depleted or enriched in a cluster relative to others.

In some embodiments, the step of assigning comprises assigning to the cluster based on highest cosine similarity to the mean proportion values for the cluster recited in Table 1.

In some of these embodiments, a minimum of 0.75 cosine similarity may be employed as a threshold value for the assignment. In another embodiment, the threshold may be 0.7. In another embodiment, the threshold may be 0.8. In another embodiment, the threshold may be 0.9. In another embodiment, the threshold may be 0.95.

In another embodiment, the assigning could be carried out by clustering. In one embodiment, the assigning may be based on based on distance. For example Levenshtein's distance may be used for the assigning. For example, Euler's distance may be used for the assigning. Other distance metrics may also be used, according to requirements.

In some embodiments, the step of assigning comprises assigning to the cluster based on ranges for the frequencies of each mutation type calculated based on the mean proportions of Table 1 and the corresponding standard deviation values (Std Dev) for clusters 1 to 8 that are depicted in Table 2.

TABLE 2

Standard Deviations for the Mean Proportions for Clusters 1 to 8

| Mut | 5' | 3' | Std Dev for Clusters ||||||||
|---|---|---|---|---|---|---|---|---|---|---|
| | | | 1 | 2 | 3 | 4 | 5 | 6 | 7 | 8 |
| C > A | A | A | 0.0002595 | 0.0041439 | 0.0032608 | 0.0119057 | 0.0048422 | 0.005093 | 0.0072993 | 0.0144502 |
| C > A | A | C | 0.0030569 | 0.0072622 | 0.0046601 | 0.0189826 | 0.0058685 | 0.0042982 | 0.0079754 | 0.0178127 |
| C > A | A | G | 0 | 0.0042131 | 0.0024838 | 0.0114635 | 0.002336 | 0.0024988 | 0.0053597 | 0.0124883 |
| C > A | A | T | 0.0054846 | 0.0058485 | 0.0059137 | 0.0118644 | 0.002766 | 0.0025598 | 0.0041304 | 0.0109158 |
| C > A | C | A | 0.0024806 | 0.0103239 | 0.00497 | 0.0214626 | 0.00375 | 0.0079367 | 0.0077395 | 0.0236659 |
| C > A | C | C | 0.0033922 | 0.0130088 | 0.006124 | 0.0260265 | 0.0048793 | 0.0051591 | 0.0078407 | 0.0230598 |
| C > A | C | G | 0.0017717 | 0.009823 | 0.0038129 | 0.0185407 | 0.0032862 | 0.0038233 | 0.0070639 | 0.0162666 |
| C > A | C | T | 0.0205006 | 0.0239408 | 0.0141586 | 0.0201944 | 0.0023286 | 0.0056525 | 0.0069079 | 0.0194444 |
| C > A | G | A | 0.0013321 | 0.0061895 | 0.003773 | 0.0156266 | 0.004379 | 0.0039386 | 0.0067378 | 0.0141242 |
| C > A | G | C | 0.0040586 | 0.0079601 | 0.0037048 | 0.0163821 | 0.0045099 | 0.0036569 | 0.0081921 | 0.0187841 |
| C > A | G | G | 0.0019012 | 0.0063641 | 0.0033833 | 0.0221213 | 0.0014713 | 0.0029913 | 0.0045468 | 0.0144501 |
| C > A | G | T | 0.0137013 | 0.0119439 | 0.007969 | 0.0112118 | 0.0045037 | 0.0036695 | 0.0061766 | 0.013116 |
| C > A | T | A | 0.003762 | 0.0061854 | 0.019322 | 0.025547 | 0.0021934 | 0.0051413 | 0.0219588 | 0.0176898 |
| C > A | T | C | 0.0031478 | 0.0078095 | 0.0065275 | 0.0201077 | 0.0035549 | 0.0065461 | 0.0142899 | 0.0195741 |
| C > A | T | G | 0.001048 | 0.0043533 | 0.0037029 | 0.0101746 | 0.0028682 | 0.0030056 | 0.0131488 | 0.0118502 |
| C > A | T | T | 0.0181503 | 0.0113834 | 0.0726526 | 0.0374747 | 0.0037857 | 0.0049425 | 0.0141139 | 0.0158362 |
| C > G | A | A | 0.0010317 | 0.0041451 | 0.0014682 | 0.0087312 | 0.0023622 | 0.0026852 | 0.0065718 | 0.0094584 |
| C > G | A | C | 0.0004421 | 0.0055014 | 0.0020643 | 0.0062467 | 0.0038456 | 0.0030985 | 0.0073949 | 0.007776 |
| C > G | A | G | 0.0006614 | 0.0045739 | 0.0023585 | 0.0057338 | 0.0025753 | 0.0032575 | 0.0057987 | 0.0055832 |
| C > G | A | T | 0 | 0.00492 | 0.002179 | 0.0058164 | 0.0028106 | 0.0032393 | 0.0063967 | 0.006244 |
| C > G | C | A | 0.0007 | 0.0047322 | 0.0009632 | 0.0082992 | 0.0028212 | 0.0039723 | 0.0088852 | 0.0091725 |
| C > G | C | C | 0.0013797 | 0.0065612 | 0.0028974 | 0.0099251 | 0.0035483 | 0.004847 | 0.0085915 | 0.0068398 |
| C > G | C | G | 0.0007969 | 0.0062266 | 0.0028908 | 0.0111333 | 0.0032713 | 0.0047066 | 0.0078663 | 0.0085754 |
| C > G | C | T | 0.0005603 | 0.0048111 | 0.0030163 | 0.0084157 | 0.0049312 | 0.0037096 | 0.0081422 | 0.0075746 |
| C > G | G | A | 0.0006947 | 0.0045624 | 0.002038 | 0.0095707 | 0.0016727 | 0.0023972 | 0.0046031 | 0.0060832 |
| C > G | G | C | 0.0007638 | 0.0066215 | 0.0033749 | 0.0092563 | 0.0030308 | 0.0039541 | 0.0058586 | 0.0093659 |
| C > G | G | G | 0.0002211 | 0.0040916 | 0.0008422 | 0.0071569 | 0.0032841 | 0.0033122 | 0.0066091 | 0.0069762 |
| C > G | G | T | 0.0002729 | 0.0049018 | 0.0022559 | 0.0066613 | 0.0057428 | 0.0029432 | 0.0075003 | 0.0069928 |
| C > G | T | A | 0 | 0.0055823 | 0.0008283 | 0.0142574 | 0.0039999 | 0.0084125 | 0.0417002 | 0.0360654 |
| C > G | T | C | 0.000751 | 0.0056184 | 0.0024403 | 0.0119991 | 0.0028617 | 0.0057843 | 0.0211052 | 0.0113682 |
| C > G | T | G | 0 | 0.003799 | 0.0021326 | 0.0066024 | 0.0024752 | 0.0035604 | 0.0149763 | 0.0062463 |
| C > G | T | T | 0.0015205 | 0.0085396 | 0.0025392 | 0.0121808 | 0.0052453 | 0.0090779 | 0.0467566 | 0.0550912 |
| C > T | A | A | 0.0066265 | 0.0157468 | 0.0030307 | 0.0117878 | 0.0115829 | 0.0055374 | 0.0104628 | 0.0091602 |
| C > T | A | C | 0.0129305 | 0.0142151 | 0.0065761 | 0.0081682 | 0.0317933 | 0.015375 | 0.0106645 | 0.0087731 |
| C > T | A | G | 0.0247868 | 0.05085 | 0.0181394 | 0.01494 | 0.0168833 | 0.0100254 | 0.0180587 | 0.0083301 |
| C > T | A | T | 0.0057859 | 0.0106363 | 0.0068695 | 0.00802 | 0.0227499 | 0.0087477 | 0.0076722 | 0.0079624 |
| C > T | C | A | 0.0033377 | 0.0114202 | 0.003669 | 0.0144497 | 0.0150796 | 0.0228448 | 0.015854 | 0.0122498 |
| C > T | C | C | 0.0080867 | 0.0125512 | 0.0053586 | 0.0158169 | 0.041537 | 0.0367514 | 0.0131713 | 0.0128216 |
| C > T | C | G | 0.0202904 | 0.0507454 | 0.0171792 | 0.0211806 | 0.0192641 | 0.0244128 | 0.0214387 | 0.0150531 |
| C > T | C | T | 0.0065427 | 0.0140946 | 0.0064929 | 0.0145021 | 0.0259832 | 0.0276278 | 0.0152985 | 0.0109122 |
| C > T | G | A | 0.0124183 | 0.0210376 | 0.0056939 | 0.010441 | 0.0141201 | 0.006271 | 0.0124556 | 0.0090126 |
| C > T | G | C | 0.0163492 | 0.0283639 | 0.0125448 | 0.0130065 | 0.039711 | 0.0162894 | 0.0109415 | 0.009643 |
| C > T | G | G | 0.04068 | 0.0703008 | 0.0401502 | 0.0104244 | 0.0202383 | 0.0096827 | 0.0197295 | 0.0096317 |
| C > T | G | T | 0.0086611 | 0.0220909 | 0.0095118 | 0.0098223 | 0.0261977 | 0.0107361 | 0.0125057 | 0.0103458 |
| C > T | T | A | 0.003614 | 0.0148287 | 0.0059801 | 0.0121183 | 0.0138185 | 0.0323985 | 0.0621188 | 0.0285873 |
| C > T | T | C | 0.0102873 | 0.0124219 | 0.00927 | 0.0106852 | 0.0350252 | 0.0451308 | 0.029443 | 0.0139328 |
| C > T | T | G | 0.0278252 | 0.0308167 | 0.072775 | 0.0135731 | 0.0113412 | 0.036986 | 0.0314477 | 0.0195188 |
| C > T | T | T | 0.010273 | 0.0118584 | 0.0107872 | 0.0134295 | 0.0274868 | 0.0232987 | 0.0368886 | 0.017879 |
| T > A | A | A | 0.0007871 | 0.0041769 | 0.0008831 | 0.0054006 | 0.0024975 | 0.0038955 | 0.0049019 | 0.0047918 |
| T > A | A | C | 0.0034941 | 0.0069411 | 0.0017901 | 0.007299 | 0.0027845 | 0.0035111 | 0.0038967 | 0.0050771 |
| T > A | A | G | 0.0010935 | 0.0042195 | 0.0014062 | 0.0103353 | 0.0030325 | 0.0036055 | 0.0060319 | 0.008509 |
| T > A | A | T | 0.0017405 | 0.0060937 | 0.0027753 | 0.0049731 | 0.0013625 | 0.0051449 | 0.0032603 | 0.0050987 |
| T > A | C | A | 0 | 0.0033265 | 0.0014546 | 0.0078634 | 0.0012155 | 0.0029254 | 0.0037785 | 0.0058558 |
| T > A | C | C | 0.0011786 | 0.005607 | 0.0019025 | 0.0101123 | 0.0020752 | 0.0037969 | 0.0060544 | 0.0075074 |
| T > A | C | G | 0.0010009 | 0.0076966 | 0.0024896 | 0.0149125 | 0.003107 | 0.004439 | 0.0071564 | 0.0141123 |
| T > A | C | T | 0.0010563 | 0.0042866 | 0.0015635 | 0.0099675 | 0.0022963 | 0.0046869 | 0.0055776 | 0.0081023 |
| T > A | G | A | 0 | 0.0038308 | 0.000825 | 0.0049977 | 0.0031311 | 0.0032647 | 0.0036468 | 0.0069156 |
| T > A | G | C | 0.0040031 | 0.0057509 | 0.0006919 | 0.0053191 | 0.0024275 | 0.0028705 | 0.0038908 | 0.0058725 |
| T > A | G | G | 0.0007367 | 0.0071128 | 0.0016335 | 0.0068918 | 0.003584 | 0.0040722 | 0.0044361 | 0.0086161 |
| T > A | G | T | 0.0006885 | 0.0035647 | 0.0007714 | 0.00358 | 0.0033467 | 0.0031455 | 0.0047852 | 0.0054034 |
| T > A | T | A | 0 | 0.0029489 | 0.0006674 | 0.0062995 | 0.0020975 | 0.0035245 | 0.001789 | 0.0045921 |
| T > A | T | C | 0.0016816 | 0.0038294 | 0.0016767 | 0.005077 | 0.0015763 | 0.0044968 | 0.0033028 | 0.0053856 |
| T > A | T | G | 0.0006063 | 0.0032448 | 0.0008153 | 0.0083736 | 0.0014849 | 0.0034758 | 0.0027489 | 0.0080295 |
| T > A | T | T | 0.0005865 | 0.0036501 | 0.0035182 | 0.0056041 | 0.0023488 | 0.0059528 | 0.0039545 | 0.0068197 |
| T > C | A | A | 0.0043032 | 0.0123779 | 0.0053456 | 0.0074281 | 0.0059307 | 0.0049681 | 0.0084087 | 0.0058366 |
| T > C | A | C | 0.0039151 | 0.0097116 | 0.0050443 | 0.0057317 | 0.0045614 | 0.0037033 | 0.0046872 | 0.0056801 |
| T > C | A | G | 0.0034793 | 0.0197224 | 0.0048826 | 0.0087596 | 0.0055127 | 0.0054823 | 0.0129302 | 0.0103419 |
| T > C | A | T | 0.0022726 | 0.0098358 | 0.0050127 | 0.0057195 | 0.0041368 | 0.0051976 | 0.0104551 | 0.0044841 |
| T > C | C | A | 0.0019843 | 0.0092097 | 0.0019979 | 0.0040958 | 0.0039623 | 0.0040624 | 0.0066636 | 0.0053682 |
| T > C | C | C | 0.0046538 | 0.0114502 | 0.0052466 | 0.0068469 | 0.0056999 | 0.0049614 | 0.0072185 | 0.0051033 |
| T > C | C | G | 0.0024242 | 0.0220666 | 0.0042274 | 0.0130391 | 0.0055162 | 0.0057134 | 0.0088471 | 0.0105015 |
| T > C | C | T | 0.0019631 | 0.0129148 | 0.0039328 | 0.0068022 | 0.0055377 | 0.0062782 | 0.0064333 | 0.0063119 |
| T > C | G | A | 0.0084245 | 0.0187299 | 0.0106856 | 0.0066819 | 0.0105541 | 0.0040895 | 0.0063614 | 0.0068431 |
| T > C | G | C | 0.0072351 | 0.0149648 | 0.0116742 | 0.0041276 | 0.0075331 | 0.0035488 | 0.0057544 | 0.0051587 |

TABLE 2-continued

Standard Deviations for the Mean Proportions for Clusters 1 to 8

| Mut | 5' | 3' | Std Dev for Clusters | | | | | | | |
|---|---|---|---|---|---|---|---|---|---|---|
| | | | 1 | 2 | 3 | 4 | 5 | 6 | 7 | 8 |
| T > C | G | G | 0.0081675 | 0.019088 | 0.007555 | 0.0062124 | 0.0065655 | 0.0061082 | 0.0105821 | 0.0082351 |
| T > C | G | T | 0.0027813 | 0.0132836 | 0.0084494 | 0.007911 | 0.0055616 | 0.0089018 | 0.0074425 | 0.0059076 |
| T > C | T | A | 0.00232 | 0.0096929 | 0.0033157 | 0.006331 | 0.0049397 | 0.0054976 | 0.0051958 | 0.0034565 |
| T > C | T | C | 0.0033433 | 0.0097908 | 0.0054282 | 0.0063694 | 0.0046408 | 0.0046156 | 0.0061161 | 0.0032024 |
| T > C | T | G | 0.002704 | 0.0117797 | 0.0056605 | 0.0064651 | 0.0033823 | 0.0054129 | 0.004246 | 0.0043711 |
| T > C | T | T | 0.0029444 | 0.00896 | 0.0051954 | 0.0071857 | 0.0037035 | 0.0054088 | 0.0050798 | 0.0026365 |
| T > G | A | A | 0.0002595 | 0.002508 | 0.0022859 | 0.0010487 | 0.0014028 | 0.0022766 | 0.002766 | 0.0020063 |
| T > G | A | C | 0.0013774 | 0.0035956 | 0.0038721 | 0.0024862 | 0.0006668 | 0.0022185 | 0.0032677 | 0.002079 |
| T > G | A | G | 0.00087 | 0.0037953 | 0.0027905 | 0.0020745 | 0.0024564 | 0.0035213 | 0.004519 | 0.0035771 |
| T > G | A | T | 0.0029299 | 0.0034326 | 0.0090542 | 0.0021008 | 0.001523 | 0.0022227 | 0.0025711 | 0.0024628 |
| T > G | C | A | 0.000547 | 0.0045258 | 0.0033842 | 0.0032886 | 0.0024278 | 0.0027251 | 0.0044246 | 0.0043926 |
| T > G | C | C | 0.0010438 | 0.0074306 | 0.0026307 | 0.0037417 | 0.0021872 | 0.0038184 | 0.0046714 | 0.0033817 |
| T > G | C | G | 0.0010004 | 0.0102325 | 0.0039628 | 0.0094587 | 0.0022028 | 0.0045527 | 0.0064928 | 0.0063998 |
| T > G | C | T | 0.0031236 | 0.0086819 | 0.0123496 | 0.0033005 | 0.0026843 | 0.0040113 | 0.0048141 | 0.0030168 |
| T > G | G | A | 0.0011658 | 0.0033709 | 0.0025441 | 0.0059632 | 0.0018842 | 0.0018375 | 0.0017334 | 0.0025622 |
| T > G | G | C | 0.0020052 | 0.0037429 | 0.0039376 | 0.0020627 | 0.0026466 | 0.0021084 | 0.0032899 | 0.0026635 |
| T > G | G | G | 0.001898 | 0.005848 | 0.0038156 | 0.0050707 | 0.0049083 | 0.0050319 | 0.0044534 | 0.0044921 |
| T > G | G | T | 0.0035029 | 0.0068018 | 0.0044141 | 0.0043791 | 0.0038 | 0.003344 | 0.0040229 | 0.0030112 |
| T > G | T | A | 0 | 0.0019468 | 0.0049872 | 0.0043885 | 0.0010459 | 0.0018732 | 0.0027206 | 0.0021444 |
| T > G | T | C | 0.0017265 | 0.004624 | 0.0043574 | 0.002988 | 0.00285 | 0.0035284 | 0.0050522 | 0.0030884 |
| T > G | T | G | 0.0008683 | 0.0043617 | 0.0029477 | 0.0048767 | 0.0012387 | 0.0034131 | 0.0039386 | 0.0049239 |
| T > G | T | T | 0.0048424 | 0.004117 | 0.0234712 | 0.0047025 | 0.0023416 | 0.0044935 | 0.004293 | 0.0030385 |

For example, in some embodiments the step of assigning may be carried out by categorizing a tumour into a cluster defined by the mean proportion values depicted in Table 1 plus or minus the corresponding standard deviation value depicted in Table 2. In some embodiments the step of assigning may be carried out by categorizing a tumour into a cluster defined by the mean proportion values depicted in Table 1 plus or minus twice the corresponding standard deviation value depicted in Table 2.

In some embodiments, the step of assigning is carried out by categorizing the tumour into a cluster defined by the mean proportion values depicted in Table 1 plus or minus the corresponding 95% confidence (95% CI) interval depicted in Table 3.

TABLE 3

95% Confidence Intervals for the Mean Proportions for Clusters 1 to 8

| Mut | 5' | 3' | 95% CI for Clusters | | | | | | | |
|---|---|---|---|---|---|---|---|---|---|---|
| | | | 1 | 2 | 3 | 4 | 5 | 6 | 7 | 8 |
| C > A | A | A | 0.0001437 | 0.000356 | 0.0008498 | 0.0042216 | 0.0008866 | 0.0004231 | 0.0011698 | 0.004503 |
| C > A | A | C | 0.0016929 | 0.0006238 | 0.0012144 | 0.0067309 | 0.0010746 | 0.0003571 | 0.0012781 | 0.0055508 |
| C > A | A | G | 0 | 0.0003619 | 0.0006473 | 0.0040648 | 0.0004277 | 0.0002076 | 0.0008589 | 0.0038916 |
| C > A | A | T | 0.0030373 | 0.0005024 | 0.0015411 | 0.0042069 | 0.0005065 | 0.0002127 | 0.0006619 | 0.0034016 |
| C > A | C | A | 0.0013737 | 0.0008868 | 0.0012952 | 0.0076103 | 0.0006867 | 0.0006594 | 0.0012403 | 0.0073748 |
| C > A | C | C | 0.0018786 | 0.0011175 | 0.0015959 | 0.0092286 | 0.0008934 | 0.0004286 | 0.0012565 | 0.0071859 |
| C > A | C | G | 0.0009812 | 0.0008438 | 0.0009936 | 0.0065742 | 0.0006017 | 0.0003176 | 0.0011321 | 0.005069 |
| C > A | C | T | 0.0113528 | 0.0020566 | 0.0036898 | 0.0071619 | 0.0004264 | 0.0004696 | 0.0011071 | 0.0060593 |
| C > A | G | A | 0.0007377 | 0.0005317 | 0.0009832 | 0.0055409 | 0.0008018 | 0.0003272 | 0.0010798 | 0.0044014 |
| C > A | G | C | 0.0022476 | 0.0006838 | 0.0009655 | 0.0058088 | 0.0008258 | 0.0003038 | 0.0013128 | 0.0058535 |
| C > A | G | G | 0.0010528 | 0.0005467 | 0.0008817 | 0.0078439 | 0.0002694 | 0.0002485 | 0.0007287 | 0.004503 |
| C > A | G | T | 0.0075875 | 0.001026 | 0.0020757 | 0.0039755 | 0.0008247 | 0.0003049 | 0.0009898 | 0.0040872 |
| C > A | T | A | 0.0020833 | 0.0005313 | 0.0050353 | 0.0090586 | 0.0004016 | 0.0004271 | 0.0035191 | 0.0055125 |
| C > A | T | C | 0.0017432 | 0.0006709 | 0.0017011 | 0.0071299 | 0.0006509 | 0.0005438 | 0.0022901 | 0.0060997 |
| C > A | T | G | 0.0005804 | 0.000374 | 0.000972 | 0.0036078 | 0.0005252 | 0.0002497 | 0.0021072 | 0.0036928 |
| C > A | T | T | 0.0100513 | 0.0009779 | 0.0189334 | 0.013288 | 0.0006932 | 0.0004106 | 0.0022619 | 0.0049349 |
| C > G | A | A | 0.0005714 | 0.0003561 | 0.0030959 | 0.0004325 | 0.0002231 | 0.0010532 | 0.0029474 | |
| C > G | A | C | 0.0002448 | 0.0004726 | 0.000538 | 0.002215 | 0.0007042 | 0.0002574 | 0.0011851 | 0.0024232 |
| C > G | A | G | 0.0003663 | 0.0003929 | 0.0006146 | 0.0020331 | 0.0004716 | 0.0002706 | 0.0009293 | 0.0017399 |
| C > G | A | T | 0 | 0.0004226 | 0.0005678 | 0.0020624 | 0.0005146 | 0.0002691 | 0.0010251 | 0.0019458 |
| C > G | C | A | 0.0003876 | 0.0004065 | 0.000251 | 0.0029428 | 0.0005166 | 0.00033 | 0.0014239 | 0.0028583 |
| C > G | C | C | 0.0007641 | 0.0005636 | 0.0007551 | 0.0035193 | 0.0006497 | 0.0004027 | 0.0013769 | 0.0021314 |
| C > G | C | G | 0.0004413 | 0.0005349 | 0.0007533 | 0.0039477 | 0.000599 | 0.000391 | 0.0012606 | 0.0026723 |
| C > G | C | T | 0.0003103 | 0.0004133 | 0.0007861 | 0.0029841 | 0.0009029 | 0.0003082 | 0.0013049 | 0.0023604 |
| C > G | G | A | 0.0003847 | 0.0003919 | 0.0005311 | 0.0033936 | 0.0003063 | 0.0001992 | 0.0007377 | 0.0018957 |
| C > G | G | C | 0.000423 | 0.0005688 | 0.0008795 | 0.0032822 | 0.000555 | 0.0003285 | 0.0009389 | 0.0029186 |
| C > G | G | G | 0.0001224 | 0.0003515 | 0.0002195 | 0.0025377 | 0.0006014 | 0.0002752 | 0.0010592 | 0.0021739 |
| C > G | G | T | 0.0001511 | 0.0004211 | 0.0005879 | 0.002362 | 0.0010516 | 0.0002445 | 0.001202 | 0.0021791 |
| C > G | T | A | 0 | 0.0004795 | 0.0002159 | 0.0050555 | 0.0007324 | 0.0006989 | 0.0066828 | 0.0112388 |
| C > G | T | C | 0.0004159 | 0.0004826 | 0.000636 | 0.0042547 | 0.000524 | 0.0004805 | 0.0033823 | 0.0035426 |
| C > G | T | G | 0 | 0.0003263 | 0.0005558 | 0.0023405 | 0.0004532 | 0.0002958 | 0.0024001 | 0.0019465 |

TABLE 3-continued

95% Confidence Intervals for the Mean Proportions for Clusters 1 to 8

| | | | 95% CI for Clusters | | | | | | | |
|---|---|---|---|---|---|---|---|---|---|---|
| Mut | 5' | 3' | 1 | 2 | 3 | 4 | 5 | 6 | 7 | 8 |
| C > G | T | T | 0.000842 | 0.0007336 | 0.0006617 | 0.0043191 | 0.0009605 | 0.0007542 | 0.0074931 | 0.0171676 |
| C > T | A | A | 0.0036696 | 0.0013527 | 0.0007898 | 0.0041798 | 0.0021209 | 0.00046 | 0.0016767 | 0.0028545 |
| C > T | A | C | 0.0071607 | 0.0012211 | 0.0017137 | 0.0028963 | 0.0058216 | 0.0012773 | 0.0017091 | 0.0027339 |
| C > T | A | G | 0.0137265 | 0.0043681 | 0.0047272 | 0.0052975 | 0.0030915 | 0.0008329 | 0.0028941 | 0.0025958 |
| C > T | A | T | 0.0032041 | 0.0009137 | 0.0017902 | 0.0028438 | 0.0041657 | 0.0007267 | 0.0012295 | 0.0024813 |
| C > T | C | A | 0.0018484 | 0.000981 | 0.0009561 | 0.0051236 | 0.0027612 | 0.0018979 | 0.0025407 | 0.0038173 |
| C > T | C | C | 0.0044783 | 0.0010782 | 0.0013965 | 0.0056084 | 0.0076058 | 0.0030532 | 0.0021108 | 0.0039955 |
| C > T | C | G | 0.0112365 | 0.0043592 | 0.0044769 | 0.0075103 | 0.0035274 | 0.0020282 | 0.0034357 | 0.0046909 |
| C > T | C | T | 0.0036232 | 0.0012108 | 0.0016921 | 0.0051422 | 0.0047578 | 0.0022953 | 0.0024517 | 0.0034005 |
| C > T | G | A | 0.006877 | 0.0018072 | 0.0014838 | 0.0037022 | 0.0025855 | 0.000521 | 0.0019961 | 0.0028085 |
| C > T | G | C | 0.0090539 | 0.0024365 | 0.0032692 | 0.0046119 | 0.0072714 | 0.0013533 | 0.0017535 | 0.003005 |
| C > T | G | G | 0.0225278 | 0.006039 | 0.0104632 | 0.0036963 | 0.0037058 | 0.0008044 | 0.0031618 | 0.0030014 |
| C > T | G | T | 0.0047964 | 0.0018977 | 0.0024788 | 0.0034828 | 0.004797 | 0.0008919 | 0.0020041 | 0.003224 |
| C > T | T | A | 0.0020013 | 0.0012738 | 0.0015584 | 0.004297 | 0.0025303 | 0.0026916 | 0.0099551 | 0.0089084 |
| C > T | T | C | 0.0056969 | 0.0010671 | 0.0024158 | 0.0037888 | 0.0064134 | 0.0037494 | 0.0047185 | 0.0043418 |
| C > T | T | G | 0.0154091 | 0.0026472 | 0.0189653 | 0.0048128 | 0.0020767 | 0.0030727 | 0.0050398 | 0.0060825 |
| C > T | T | T | 0.005689 | 0.0010187 | 0.0028113 | 0.0047619 | 0.0050331 | 0.0019356 | 0.0059117 | 0.0055715 |
| T > A | A | A | 0.0004359 | 0.0003588 | 0.0002301 | 0.001915 | 0.0004573 | 0.0003236 | 0.0007856 | 0.0014932 |
| T > A | A | C | 0.001935 | 0.0005963 | 0.0004665 | 0.0025881 | 0.0005099 | 0.0002917 | 0.0006245 | 0.0015821 |
| T > A | A | G | 0.0006056 | 0.0003625 | 0.0003664 | 0.0036617 | 0.0005553 | 0.0002995 | 0.0009667 | 0.0026516 |
| T > A | A | T | 0.0009639 | 0.0005235 | 0.0007232 | 0.0017634 | 0.0002495 | 0.0004274 | 0.0005225 | 0.0015889 |
| T > A | C | A | 0 | 0.0002858 | 0.0003791 | 0.0027883 | 0.0002226 | 0.000243 | 0.0006055 | 0.0018248 |
| T > A | C | C | 0.0006527 | 0.0004817 | 0.0004958 | 0.0035857 | 0.00038 | 0.0003154 | 0.0009703 | 0.0023395 |
| T > A | C | G | 0.0005543 | 0.0006612 | 0.0006488 | 0.0052877 | 0.0005689 | 0.0003688 | 0.0011469 | 0.0043977 |
| T > A | C | T | 0.000585 | 0.0003682 | 0.0004074 | 0.0035343 | 0.0004205 | 0.0003894 | 0.0008939 | 0.0025249 |
| T > A | G | A | 0 | 0.0003291 | 0.000215 | 0.0017721 | 0.0005733 | 0.0002712 | 0.0005844 | 0.0021551 |
| T > A | G | C | 0.0022168 | 0.000494 | 0.0001803 | 0.0018893 | 0.0004445 | 0.0002385 | 0.0006235 | 0.00183 |
| T > A | G | G | 0.0004079 | 0.000611 | 0.0004257 | 0.0024437 | 0.0006563 | 0.0003383 | 0.0007109 | 0.002685 |
| T > A | G | T | 0.0003813 | 0.0003062 | 0.000201 | 0.0012694 | 0.0006128 | 0.0002613 | 0.0007669 | 0.0016838 |
| T > A | T | A | 0 | 0.0002533 | 0.0001739 | 0.0022337 | 0.0003841 | 0.0002928 | 0.0002867 | 0.001431 |
| T > A | T | C | 0.0009312 | 0.000329 | 0.000437 | 0.0018002 | 0.0002886 | 0.0003736 | 0.0005293 | 0.0016783 |
| T > A | T | G | 0.0003358 | 0.0002787 | 0.0002125 | 0.0029692 | 0.0002719 | 0.0002888 | 0.0004405 | 0.0025022 |
| T > A | T | T | 0.0003248 | 0.0003135 | 0.0009168 | 0.0019871 | 0.0004301 | 0.0004945 | 0.0006337 | 0.0021252 |
| T > C | A | A | 0.002383 | 0.0010633 | 0.0013931 | 0.0026339 | 0.001086 | 0.0004127 | 0.0013476 | 0.0018188 |
| T > C | A | C | 0.0021681 | 0.0008342 | 0.0013146 | 0.0020324 | 0.0008352 | 0.0003077 | 0.0007512 | 0.00177 |
| T > C | A | G | 0.0019268 | 0.0016942 | 0.0012724 | 0.003106 | 0.0010094 | 0.0004555 | 0.0020722 | 0.0032228 |
| T > C | A | T | 0.0012585 | 0.0008449 | 0.0013063 | 0.0020281 | 0.0007575 | 0.0004318 | 0.0016755 | 0.0013973 |
| T > C | C | A | 0.0010989 | 0.0007911 | 0.0005207 | 0.0014523 | 0.0007255 | 0.0003375 | 0.0010679 | 0.0016728 |
| T > C | C | C | 0.0025772 | 0.0009836 | 0.0013673 | 0.0024278 | 0.0010437 | 0.0004122 | 0.0011568 | 0.0015903 |
| T > C | C | G | 0.0013425 | 0.0018956 | 0.0011017 | 0.0046235 | 0.0010101 | 0.0004747 | 0.0014178 | 0.0032725 |
| T > C | C | T | 0.0010871 | 0.0011094 | 0.0010249 | 0.002412 | 0.001014 | 0.0005216 | 0.001031 | 0.0019669 |
| T > C | G | A | 0.0046653 | 0.0016089 | 0.0027847 | 0.0023693 | 0.0019326 | 0.0003398 | 0.0010195 | 0.0021325 |
| T > C | G | C | 0.0040066 | 0.0012855 | 0.0030423 | 0.0014636 | 0.0013794 | 0.0002948 | 0.0009222 | 0.0016076 |
| T > C | G | G | 0.004523 | 0.0016397 | 0.0019688 | 0.0022028 | 0.0012022 | 0.0005075 | 0.0016959 | 0.0025662 |
| T > C | G | T | 0.0015402 | 0.0011411 | 0.0022019 | 0.0028051 | 0.0010184 | 0.0007395 | 0.0011927 | 0.0018409 |
| T > C | T | A | 0.0012848 | 0.0008326 | 0.0008641 | 0.0022449 | 0.0009045 | 0.0004567 | 0.0008327 | 0.0010771 |
| T > C | T | C | 0.0018515 | 0.0008411 | 0.0014146 | 0.0022585 | 0.0008498 | 0.0003835 | 0.0009802 | 0.0009979 |
| T > C | T | G | 0.0014974 | 0.0010119 | 0.0014751 | 0.0022924 | 0.0006193 | 0.0004497 | 0.0006805 | 0.0013621 |
| T > C | T | T | 0.0016305 | 0.0007697 | 0.0013539 | 0.002548 | 0.0006781 | 0.0004494 | 0.0008141 | 0.0008216 |
| T > G | A | A | 0.0001437 | 0.0002154 | 0.0005957 | 0.0003718 | 0.0002569 | 0.0001891 | 0.0004433 | 0.0006252 |
| T > G | A | C | 0.0007628 | 0.0003089 | 0.0010091 | 0.0008816 | 0.0001221 | 0.0001843 | 0.0005237 | 0.0006478 |
| T > G | A | G | 0.0004818 | 0.000326 | 0.0007272 | 0.0007356 | 0.0004498 | 0.0002925 | 0.0007242 | 0.0011147 |
| T > G | A | T | 0.0016225 | 0.0002949 | 0.0023595 | 0.0007449 | 0.0002789 | 0.0001847 | 0.000412 | 0.0007675 |
| T > G | C | A | 0.0003029 | 0.0003888 | 0.0008819 | 0.0011661 | 0.0004446 | 0.0002264 | 0.0007091 | 0.0013688 |
| T > G | C | C | 0.000578 | 0.0006383 | 0.0006856 | 0.0013268 | 0.0004005 | 0.0003172 | 0.0007486 | 0.0010538 |
| T > G | C | G | 0.000554 | 0.000879 | 0.0010327 | 0.0033539 | 0.0004034 | 0.0003782 | 0.0010405 | 0.0019943 |
| T > G | C | T | 0.0017298 | 0.0007458 | 0.0032183 | 0.0011703 | 0.0004915 | 0.0003332 | 0.0007715 | 0.0009401 |
| T > G | G | A | 0.0006456 | 0.0002896 | 0.000663 | 0.0021145 | 0.000345 | 0.0001527 | 0.0002778 | 0.0007984 |
| T > G | G | C | 0.0011105 | 0.0003215 | 0.0010261 | 0.0007314 | 0.0004846 | 0.0001752 | 0.0005272 | 0.00083 |
| T > G | G | G | 0.0010511 | 0.0005024 | 0.0009944 | 0.001798 | 0.0008988 | 0.000418 | 0.0007137 | 0.0013998 |
| T > G | G | T | 0.0019398 | 0.0005843 | 0.0011503 | 0.0015527 | 0.0006958 | 0.0002778 | 0.0006447 | 0.0009384 |
| T > G | T | A | 0 | 0.0001672 | 0.0012997 | 0.0015569 | 0.0001915 | 0.0001556 | 0.000436 | 0.0006682 |
| T > G | T | C | 0.0009561 | 0.0003972 | 0.0011356 | 0.0010595 | 0.0005219 | 0.0002931 | 0.0008097 | 0.0009624 |
| T > G | T | G | 0.0004809 | 0.0003747 | 0.0007682 | 0.0017292 | 0.0002268 | 0.0002836 | 0.0006312 | 0.0015344 |
| T > G | T | T | 0.0026816 | 0.0003537 | 0.0061166 | 0.0016674 | 0.0004288 | 0.0003733 | 0.000688 | 0.0009469 |

In some embodiments involving ranges, the categorizing is based on highest cosine similarity to the mean proportion values for the ranges established, as described above, using mean proportion values depicted in Table 1 and the standard deviation value depicted in Table 2; or the mean proportion values depicted in Table 1 and the 95% CI values depicted in Table 3.

In some of these embodiments, a minimum of 0.75 cosine similarity may be employed as a threshold value for the assignment. In another embodiment, the threshold may be 0.7. In another embodiment, the threshold may be 0.8. In another embodiment, the threshold may be 0.9. In another embodiment, the threshold may be 0.95.

In another embodiment, the categorizing is by clustering. For example, in one embodiment, the categorizing may be based on based on distance. For example Levenshtein's distance may be used for the categorizing. For example, Euler's distance may be used for the categorizing. Other distance metrics may also be used, according to requirements.

By "Mutation", as used herein, will be understood as any sequence difference relative to reference sequence. Reference sequences may be selected according to a patient demographic. Reference sequences may be selected according to a sample type. By "early mutation", as used herein, is meant a mutation that occurs relatively early in tumourigenesis. Early mutations are, in some cases, known to influence tumour biology and/or the course of subsequent tumourigenesis. By "germline mutation", as used herein, is meant a subset of early mutations that are inherited, therefore constitutional in the subject. The subject may also be "mosaic" for some early mutations, meaning that only some somatic cells possess the mutation. A mosaic mutation may be present the entirety of cells of one or more lineage. By "driver mutation", as used herein, is meant a mutation that has contributed to tumourigenesis, and/or a mutation responsible for an aspect of current tumour biology. Such mutations could encompass mutations in an oncogene or a tumour suppressor.

The term "hypermutant", as used herein will be understood as any tumour bearing the requisite number of mutations per megabase (mut/Mb). A hypermutant tumour may comprise at least 3 mut/Mb, at least 4 mut/Mb, at least 5 mut/Mb, at least 6 mut/Mb, at least 7 mut/Mb, at least 8 mut/Mb, at least 9 mut/Mb, or at least 10 mut/Mb. It will be understood that the term "hypermutant" also encompasses "ultra-hypermutant", which tumours have a higher mutational burden. An ultra-hypermutant tumour may comprise at least 50 mut/Mb, at least 60 mut/Mb, at least 70 mut/Mb, at least 80 mut/Mb, at least 90 mut/Mb, or at least 100 mut/Mb. It will be further understood that the thresholds disclosed herein may be specific to the platform selected for determining mutations, and/o to the regions of DNA sequenced. These thresholds could be readily adapted and/or cognate thresholds could be established for other platforms.

By "deficient", as used herein with respect to a cellular state or pathway, will be understood as in comparison to normal tissue (e.g. healthy tissue), for example a healthy tissues-matched sample.

In one embodiment, the at least one tumour characteristic comprises timing of a mutagenic event in the development of the tumour. In one embodiment, the at least on tumour characteristic comprises an early mutation. In one embodiment, the at least one tumour characteristic comprises a germline mutation. In one embodiment, the at least one tumour characteristic comprises exposure to a mutagen. In one embodiment, the at least one tumour characteristic is a relative order of at least two tumourigenic events. In one embodiment, the at least one tumour characteristic comprises tissue origin. Information about tumour origin may help to identify metastatic tumours.

In one embodiment, the at least one tumour characteristic is further determined based on the presence of one or more driver mutation as defined in Table 6. In one embodiment, the one or more driver mutation comprise one or more of the mutations labelled 'New' in Table 6.

In one embodiment, the hypermutant tumour has mutation frequency of at least 5 mutation per megabase, and the tumour is a pediatric tumour. In one embodiment, the hypermutant tumour has a mutation frequency of at least 9 mutation per megabase. In one embodiment, the hypermutant tumour has a mutation frequency of at least 9.9 mutations per megabase, and the tumour is from an adult. In one embodiment, the hypermutant tumour is an ultra-hypermutant tumour having a mutation frequency of at least 100 mutations per megabase.

In one embodiment, wherein the nucleic acid comprises DNA.

In one embodiment, the nucleic acid comprises RNA.

In one embodiment, the sequencing is targeted sequencing. In one embodiment, the targeted sequencing is as defined herein the Examples.

In one embodiment, the sequencing is whole exome sequencing.

In one embodiment, the sequencing is whole genome sequencing.

Cluster 1

In one embodiment, cluster 1 is indicative of a hypermutant tumour with microsatellite stability. This hypermutant tumour indicated by cluster 1 may be ultra-hypermutant. In one embodiment, cluster 1 is indicative of an MMR gene mutation. In one embodiment, the MMR gene mutation is a germline mutation. In one embodiment, cluster 1 is indicative of a POLE gene mutation. In one embodiment, the POLE gene mutation indicated by cluster 1 is secondary to an MMR gene mutation.

Cluster 2

In one embodiment, cluster 2 is indicative of a hypermutant tumour with microsatellite instability. In one embodiment, cluster 2 is indicative of an MMR gene mutation. In one embodiment, the MMR gene mutation indicated by cluster 2 is an early MMR gene mutation.

Cluster 3

In one embodiment, cluster 3 is indicative of a hypermutant tumour with microsatellite stability. This hypermutant tumour indicated by cluster 3 may be ultra-hypermutant. The method of any one of claims 1 to 17, wherein cluster 3 is indicative of a POLE gene mutation. In one embodiment, the POLE mutation indicated by cluster 3 is an early POLE gene mutation. In one embodiment, cluster 3 is indicative of MMR gene mutation. In one embodiment, the MMR gene mutation indicated by cluster 3 is secondary to a POLE gene mutation.

Cluster 4

In one embodiment, cluster 4 is indicative of exposure to a mutagen in tobacco smoke. In one embodiment, cluster 4 is indicative of lung cancer. In one embodiment, the lung cancer is metastatic lung cancer. In one embodiment, this metastatic lung cancer may have been previously misdiagnosed.

Cluster 5

In one embodiment, cluster 5 is indicative of exposure to an alkylating agent. In one embodiment, cluster 5 is indicative of prior treatment with an alkylating agent. In one embodiment, cluster 5 is indicative of tumour resistance to alkylating agents.

Cluster 6

In one embodiment, cluster 6 is indicative of exposure to UV light. In one embodiment, cluster 6 is indicative of skin cancer. In one embodiment, the skin cancer is metastatic skin cancer. This metastatic skin cancer may have been previously misdiagnosed. In one embodiment, cluster 6 is indicative of a sarcoma induced by UV light exposure. In one embodiment, the sarcoma is metastatic. This metastatic sarcoma may have been previously misdiagnosed.

Cluster 7

In one embodiment, cluster 7 is indicative of deficient APOBEC cytidine deamination.

Cluster 8

In one embodiment, cluster 8 is indicative of exposure to a mutagen in tobacco smoke. In one embodiment, cluster 8 is indicative of lung cancer. In one embodiment, the lung cancer is metastatic lung cancer. In one embodiment, this metastatic lung cancer may have been previously misdiagnosed.

Medical Treatments and Uses

In one aspect, the above-described methods permit treatment and/or clinical intervention to be selected or applied based on the determined at least one tumour characteristic. Any suitable treatment and/or clinical intervention may be used based on the tumour characteristic(s) associated with the cluster(s) to which the tumour is assigned. For example, a suitable therapeutic agent could be selected based on the tumour characteristic.

In one embodiment, the method further comprises selecting a treatment for the patient from whom the tumour was obtained based on the at least one tumour characteristic determined with one of the above-described methods.

In one embodiment, the method further comprises treatment of a patient from whom the tumour was obtained based on the at least one tumour characteristic determined with one of the above-described methods.

In one embodiment, the tumour is matched to any one of clusters 1 to 3, and the treatment comprises immunotherapy. In one embodiment, the tumour is matched to any one of clusters 1 to 3, and the treatment comprises an immune checkpoint inhibitor.

In one embodiment, the tumour is matched to cluster 4 or 8 and the treatment comprises a lung cancer treatment.

In one embodiment, the tumour is matched to cluster 5 and the treatment does not comprise an alkylating agent. A treatment may be selected, in this case, for tumours known to be resistant to alkylating agents.

In one embodiment, the tumour is matched to cluster 5 and the treatment is skin cancer treatment. In one embodiment, the tumour is matched to cluster 5 and the treatment is treatment for sarcoma induced by UV light.

In one embodiment, the treatment is based on reclassification of the tumour based on the determined at least one tumour characteristic. Applying the above-described method may reveal misclassification or previously unknown details regarding e.g. tumour origin or tissue type, leading to reclassification or re-diagnosis. Treatment may be selected or applied on this basis.

In one embodiment, there is provided a use of a therapeutic agent, selected based on the at least one tumour characteristic identified by one of the above-described method, for treatment a subject from whom the sample was obtained.

In one embodiment, there is provided a use of a therapeutic agent, selected based on the at least one tumour characteristic identified by one of the above-described method, for preparation of a medicament for treatment of a subject from whom the sample was obtained.

In one embodiment, there is provided a therapeutic agent, selected based on the at least one tumour characteristic identified by one of the above-described method, for use in treatment of a subject from whom the sample was obtained.

By "therapeutic agent" is mean any small molecule or biologic suitable for treatment of the tumour.

In one embodiment, the method further comprises selecting a clinical intervention for the patient from whom the tumour was obtained based on the at least one tumour characteristic.

In one embodiment, the clinical intervention is based on reclassification of the tumour based on the at least one tumour characteristic.

In one embodiment, the tumour is matched to any one of clusters 1 to 3, and the clinical intervention comprises clinical surveillance for additional tumours caused by a germline mutation.

In one embodiment, the tumour is matched to any one of clusters 1 to 3, and the clinical intervention comprises genetic counseling or screening for a germline mutation. This may be extended to encompass methods comprising screening or counseling for family members who may also carry the germline mutation.

In one embodiment, there is provided a use of a tumour treatment for treatment of a patient comprising a tumour, wherein the tumour has been profiled according to the method of any one of the above-described methods, and wherein the tumour treatment has been determined based on the assigning of the tumour to a cluster.

In one embodiment, there is provided a tumour treatment for use in treatment of a patient comprising a tumour, wherein the tumour has been profiled according to the method of any one of the above-described methods, and wherein the tumour treatment has been determined based on the assigning of the tumour to a cluster.

In one embodiment, the tumour has been assigned to any one of clusters 1 to 3, and the tumour treatment comprises immunotherapy.

In one embodiment, the tumour has been assigned to any one of clusters 1 to 3, and the tumour treatment comprises an immune checkpoint inhibitor.

In one embodiment, the tumour has been assigned to cluster 5 and the tumour treatment is free of alkylating agents.

Devices and Automation

The above described method could be computer-implemented in some embodiments. A computational device could be configured to perform the above-describe methods. The device could output the assignment for a given tumour to print-out or display. The device could record or transmit the assignment. The device could also output, display, record, and/or transmit a pertinent confidence rating for the result, based on the step of assigning. The device may be configured to process the sample, e.g. to carry out nucleic acid extraction on the tumour sample. The device could be configured to carry out the sequencing. The device could comprise a processed programmed to identify mutations, classify mutations, and carry out the assigning.

The methods or devices described herein may be particularly useful in clinical settings in which extensive histological, pathological, cytological, and/or genetic testing capabilities are limited or otherwise unavailable.

EXAMPLES

Introduction

Mutations in cancer genes can be inherited, arise spontaneously in pre-malignant cells or be acquired over time during tumour evolution (Stratton et al., 2009). It is often difficult to determine, from the sequencing of the diagnostic specimen alone, which mutations arose first or whether their order is important. The ultimate aggregate mutation count in a tumour, termed mutation burden, is highly tissue type dependent. For example, the mutation burden of Ewing sarcoma is two orders of magnitude less than that of adult melanoma (Brohl et al., 2014). Although most tumours are driven by a select few major genetic and epigenetic events and have similar mutation burdens, there is emerging evidence that outliers with much higher mutation burdens (hypermutation) exist for many cancer types. Systematic retrospective sequencing efforts such as those of The Cancer Genome Atlas (TOGA) and the International Cancer Genome Consortium (ICGC) have confirmed frequent hypermutation in melanoma (Cancer Genome Atlas, 2015), lung (Govindan et al., 2012), bladder cancer (Cancer Genome Atlas Research, 2014) and uncovered rare cases of hypermutation in other cancers. However, these studies have used different thresholds as there is no agreed-upon definition of "hypermutation". Larger unbiased cohorts are needed to define the cut-offs for, identify the extent of, as well as the causes of hypermutation across human cancer.

Determining the frequency and causes of hypermutation, as well the temporal order in which it arises, is of immediate clinical importance. First, there is an urgent need to define driver mutations in cancer genomes. This is especially difficult in hypermutant cancers due to the sheer abundance of passenger variants that can obscure true drivers. Second, understanding early drivers of hypermutation may be useful for predicting the cancer's evolutionary trajectory and accumulation of additional mutations. Finally, hypermutation is strongly correlated with response to immune checkpoint inhibitors, which can lead to durable remissions in some patients (Bouffet et al., 2016; Johanns et al., 2016; Le et al., 2015; Rizvi et al., 2015; Santin et al., 2016; Van Allen et al., 2015).

Hypermutation can be caused by environmental factors (extrinsic exposures). UV light is the primary cause of the accumulation of high numbers of mutations in malignant melanoma (Pfeifer et al., 2005; Sage, 1993). Similarly, the >60 carcinogens in tobacco smoke are the primary cause of hypermutation in lung, larynx and many other tumours, due to direct mutagen exposure (Pleasance et al., 2010). Recently, several intrinsic sources of hypermutation have been described. Dysregulation of apolipoprotein B mRNA editing enzyme, catalytic polypeptide-like (APOBEC) family members, a group of cytidine deaminases, has been shown to result in increased levels of C to T transitions in a wide range of tumour types including breast, bladder and cervical cancer (Roberts et al., 2013). Defective DNA replication repair by mutations that compromise either proofreading, performed by the major replicative enzymes POLE and POLD1, or DNA mismatch repair, are associated with hypermutation in colorectal, endometrial and other cancers (Kandoth et al., 2013; Network, 2012). DNA replication repair mutations are also found in cancer predisposition syndromes, such as constitutional or biallelic mismatch repair deficiency (CMMRD), Lynch, and polymerase proofreading-associated polyposis (PPAP). While data gathered by the international bMMRD (biallelic mismatch repair deficiency) consortium revealed that all malignant CMMRD cancers are hypermutant (Bouffet et al., 2016), it is not known if the same is true in Lynch or PPAP. Furthermore, replication repair defects can lead to acquired resistance to common genotoxic therapies such as alkylating agents (van Thuijl et al., 2015). From the tumour sequence alone, it is currently impossible to define the sequence of events or the order of mutagen exposure leading to hypermutation.

Mutagenic processes leave imprints on the genome in the form of mutations arising in a specific nucleotide context that, when considered together, form a unique signature. This is especially true for hypermutant cancers whose vast numbers of non-random mutations form a signature that is deeply engraved on the cancer genome. The first taxonomic classification of signatures unveiled >20 signatures in 30 cancer types (Alexandrov et al., 2013). From this publication and subsequent work showing at least 30 signatures (Morganella et al., 2016; Nik-Zainal et al., 2016) with the common hypermutation-associated signatures have now become well characterized. However, the driving forces of rarer hypermutation-associated signatures, seen in fewer tumours, are mostly unknown.

Here, we examined 78,452 adult and 2,885 childhood cancers for hypermutation. Targeted regions of the genome were deeply sequenced using a validated cancer gene panel platform (Frampton et al., 2013). We analyzed the range and frequency of hypermutation between and within cancer types, measured the contribution of intrinsic and extrinsic mutators and used mutation signatures (also termed "clusters") to accurately predict past mutagen exposure. We also used exome sequencing of patients with CMMRD—whose mutations were acquired in an established order (Shlien et al., 2015)—as well as cancers whose hypermutation was treatment-induced to model mutation dynamics in the tumours. The data here have important implications for our understanding of how mutagenic forces govern tumour development and progression.

Methods

Patient and Sample Collection for Exome Sequencing

A cohort of germline replication-repair deficient patients with known clinical history was collected as described previously (Shlien et al., 2015). In brief, patients were registered as a part of the International Biallelic Mismatch Repair Consortium, which includes multiple centers worldwide. Following Institutional Research Ethics Board approval, all data were centralized in the Division of Haematology/Oncology at The Hospital for Sick Children (SickKids). Consent forms were obtained from the parents or guardians, or from the patients, where applicable. Family history, demographic and clinical data were obtained from the responsible physician and/or genetic counselor at the corresponding centers. Tumour and blood samples were collected from the SickKids tumour bank. The diagnosis of a replication repair deficiency-related cancer predisposition syndrome was made when a germline biallelic mutation in any of the four MMR genes (MLH1, MSH2, MSH6, PMS2) or a driver mutation in POLE, was confirmed by sequencing in a clinically approved laboratory. The sequencing of temozolomide-treated tumours was previously described (van Thuijl et al., 2015).

FoundationOne Panel Sequencing

FoundationOne Panel sequencing was performed for 81,337 tumours as previously described (Frampton et al., 2013). In brief, exonic hybridization capture of 315 cancer-related genes was applied to a minimum of 50 ng of DNA extracted from formalin-fixed paraffin-embedded clinical cancer specimens. Pathologic diagnosis of each case was confirmed by review of hematoxylin and eosin (H&E)

stained slides and samples were excluded if found to contain <20% tumour cells. Libraries were sequenced to high uniform median coverage (>500×) and assessed for base substitutions, copy number alterations, and gene fusions/rearrangements. For the purposes of the findings described in this study pediatric was defined as <25 years of age.

Exome Sequencing

High-throughput sequencing, read mapping and identification of mutations was performed at the Center for Applied Genomics at the Hospital for Sick Children, as previously described (Shlien et al., 2015). Briefly, tumour and matched blood derived DNA were run using Agilent's exome enrichment kit (Sure Select V4/V5; with >50% of baits above 25× coverage), on an Illumina HiSeq2500. Base calls and intensities from the Illumina HiSeq 2500 were processed into FASTQ files using CASAVA and/or HAS. The paired-end FASTQ files were aligned to UCSC's hg19 GRCh37 with BWA. Aligned reads were realigned for known insertion/deletion events using SRMA and/or GATK. Base quality scores were recalibrated using the Genome Analysis Toolkit26 (v1.1-28). Somatic substitutions were identified using MuTect (v1.1.4). Mutations were then filtered against common single-nucleotide polymorphisms (SNPs) found in dbSNP (v132), the 1000 Genomes Project (February 2012), a 69-sample Complete Genomics data set, and the Exome Sequencing Project (v6500) and the ExAc database.

Whole Genome Sequencing

Whole genome sequencing was performed at The Centre for Applied Genomics on an Illumina HiSeq 2500 or Illumina HiseqX at mean coverage >=30. Read alignment and variant calling/filtering were performed as described above for exome sequencing.

KiCS Panel Sequencing

The SickKids Cancer Sequencing (KiCS) gene panel utilizes the Agilent Sure Select capture kit technology, targeting 15,000 exons across 880 genes. Enriched libraries were prepared from both tumour DNA and matched normal (blood or skin) and sequenced on Illumina HiSeq2500 sequencers running in rapid mode producing paired end 100 base reads. Reads were aligned with BWA-MEM according to GATK best practices with coverage metrics meeting greater than 700× mean coverage, with >=98.5% of bases above 50×, >=95% of bases above 200× coverage, and >=75% of bases above 500× coverage. Substitution mutations were called using MuTect, with variants called above 50× coverage in tumour and normal. We achieved >95% sensitivity and specificity for variants above 5% allele frequency.

Determination of Hypermutation Threshold

In order to determine a threshold of hypermutation in human cancer, a segmented linear regression analysis or "broken-stick analysis" was performed on the mutation burdens from the pediatric (n=2,885) and adult (n=78,452) FoundationOne panel cohorts. Briefly, using the R package Segmented (Muggeo et al., 2003), an iterative process was used to determine segment breakpoints at which a statistically significant change in the slope of adjacent regression lines occurred. For the pediatric cohort, the first such breakpoint at which a statistically significant change occurred, accompanied by a visually observed uptick in the slope of the regression line, was at 9.91 mut/Mb. For the adult cohort a corresponding change occurred at 9 mut/Mb. This threshold was rounded up to 10 mut/Mb to account for statistical uncertainty and the purposes of simplicity.

Microsatellite Instability Analysis

To determine MSI status, 114 intronic homopolymer repeat loci with adequate coverage on the FoundationOne panel are analyzed for length variability and compiled into an overall MSI score via principal components analysis (PCA). Amongst the 1,897 microsatellites, the 114 that maximized variability between samples were chosen. Each chosen locus was intronic and had hg19 reference repeat length of 10-20 bp. This range of repeat lengths was selected such that the microsatellites are long enough to produce a high rate of DNA polymerase slippage, while short enough such that they are well within the 49 bp read length of NGS to facilitate alignment to the human reference genome. A detailed description can be found at Chalmer, Donelly et al., 2017, Genome Research in press.

Detection of POLE and POLD1 Driver Mutations

To identify polymerase mutations associated with hypermutation we built a model based on the following criteria: 1) Tumours harboring the variant must be hypermutant at a conservative cut-off of 50 mutations/mb. This number was selected since most POLE mutant tumours typically exceed 100 mut/mb (Shinbrot et al. 2014). 2) Variants found in hypermutant tumours must not co-occur with an existing known driver mutations in the same tumour. 3) Variants that were found both in hypermutant and lowly mutated tumours (<10 mut/mb) were excluded. 4) Variants must occur in a minimum of 2 hypermutant tumours. Variant allele fraction and tumour purity were also considered, as previously described (Frampton et al., 2013).

POLE Exonuclease Excision Rate Assay

Excision rate constants were measured as described (Zahurancik et al., NAR 2014). Briefly, a pre-incubated solution of Pol e (100 nM) and 5'-32P-labeled DNA substrate (20 nM) was rapidly mixed with Mg2+(8 mM) in reaction buffer at 37° C. After various incubation times, the reaction was quenched with the addition of EDTA. The excision rate constants for Polε wild type and L424V were measured using a rapid chemical quench-flow apparatus. Product concentration was plotted versus time and fit to a single-exponential equation, $[product]=A\exp(-k_{exo}t)$, to yield the excision rate constant, $k_{exo}$.

Unsupervised Clustering and Signature Analysis

A cohort of hypermutant samples was selected for hierarchal clustering and signature analysis by the following criteria:

Exclusion for all:
1. <50 exonic mutations detected in the FoundationOne panel.

Inclusion for Adults (>25 Years):
1. Any colon or uterine with MSI-H
2. Top 100 most-mutated lung cancers
3. Top 100 most-mutated skin cancers
4. For all other tumours, >50 Mut/Mb and/or >2 standard deviations above mean for that tumour type (provided there were >50 tumours of that type)

Inclusion for Children:
1. Any tumour with >50 exonic mutations.

This yielded a total of 1,521 tumours (1,491 adult and 30 pediatric) for clustering analysis.

The proportion of mutations corresponding to each of 96 trinucleotide contexts was determined for each of the 1,521 samples selected above using the pyrimidine-converted single base substitution and the corresponding tri-nucleotide sequence context (i.e., reference base at mutation position and its 5' and 3' neighbors). Unsupervised hierarchical clustering of the hypermutant cohort by trinucleotide context was performed using the diana clustering method.

The R package DeConstructSigs (Rosenthal et al., 2016) was used to determine the proportion of COSMIC signatures as defined by Alexandrov et al (http://cancer.sangerac.uk/cancergenome/assets/signatures_probabilities.txt) (Alexandrov et al., 2013).

Validation of Signature 7 in Sarcomas Using the TCGA Database

Somatic substitution calls (MuTect2) were obtained from 103 TCGA adult sarcoma exome samples, with a minimum of 50 substitutions. These samples were analysed using deconstructSigs as described above. Five tumours were found to be hypermutant (>10 Mut/Mb) and have significant contributions from Signature 7 (>0.5). Examination of the pathology reports of these tumours revealed all 5 to be located superficially (subcutaneous and/or extending into the dermis).

Subclonal Analysis

Tumour subclones (early and late) were determined using the R package SciClone.8 Variant allele fraction and percentage of alternate reads were used to determine the order of mutational events. Mutations with variant allele fraction greater than 0.45 were excluded from analysis to filter out germline mutations and somatic mutations in regions of copy number gain. For the determination of early and late mutations, clusters were limited to 6 (Miller et al., 2014). Subclonal mutational signatures were then determined using deconstructSigs as described above.

Clinical Genetic Information Collection for Ultra-Hypermutant Pediatric Cancers

Patients with FoundationOne panel results and who were concurrently enrolled in the International Biallelic Mismatch Repair Deficiency Consortium underwent germline sequencing services in accordance with the Clinical Laboratory Improvement Amendments (CLIA) program standards, following a rigorous consent process and genetic counseling consultation. Clinical diagnoses of a replication repair deficiency associated syndrome were made based on the presence of inherited predicted pathogenic mutations in MMR and polymerase genes. Physicians involved in patient care were notified of the diagnosis.

Results

Figure 6:
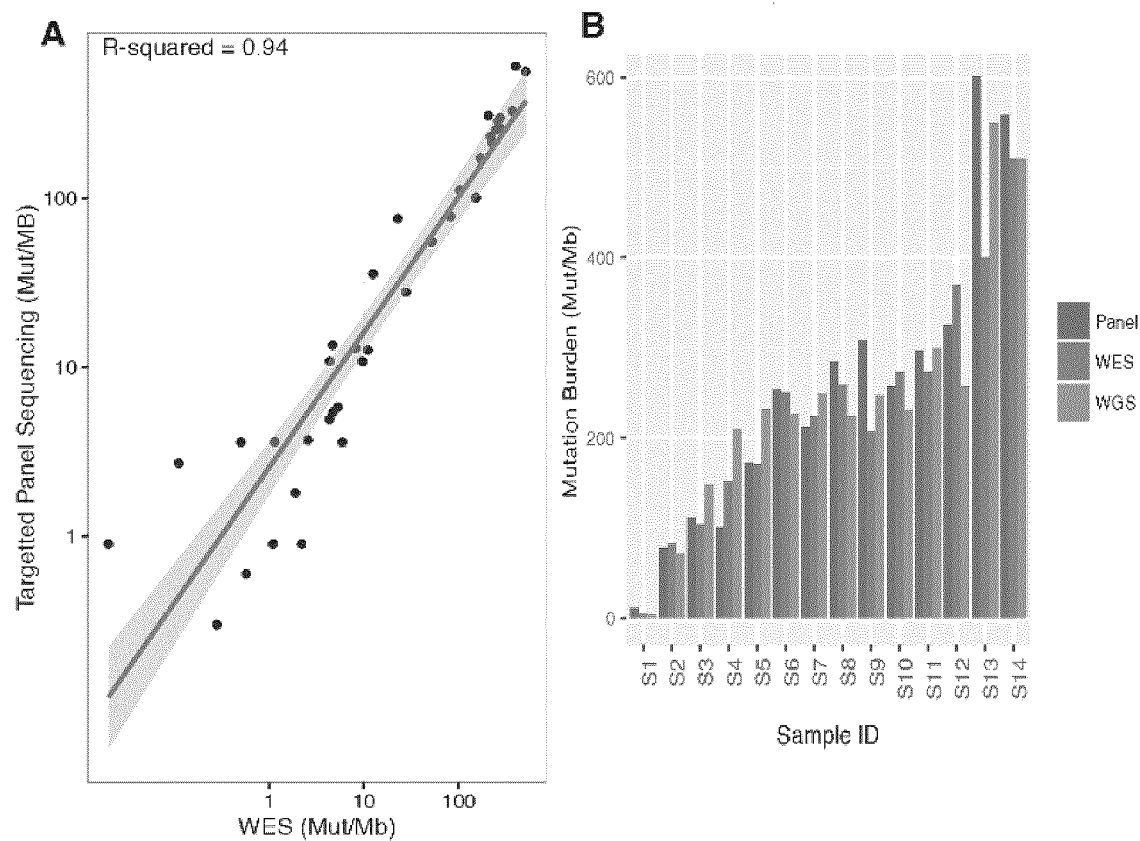
FIGS. 6 (6A and 6B) shows that targeted panel sequencing accurately predicts mutation burden determined by exome or whole genome sequencing.

Hypermutation is More Common than Previously Appreciated in Both Childhood and Adult Cancer We first wanted to define a minimal threshold for hypermutation—to create a common definition that could ultimately be used in a clinical setting. We sequenced a cohort of 35 tumour samples with low, medium and high number of substitutions by exome, genome and two separate targeted panel sequencing consisting of 315 and 884 genes covering 1.1 and 3.25 Mb, respectively (Table 4). We achieved excellent concordance in mutation burden between sequencing modalities when comparing either panel to the genome, exome or both ($R2=0.94$, FIG. 6). After carefully considering sequencing depth, the mutations' allele fractions, and the total footprint of each method, we found that every hypermutated cancer (>10 Mut/Mb) was successfully called by all sequencing methods.

Figure 7:
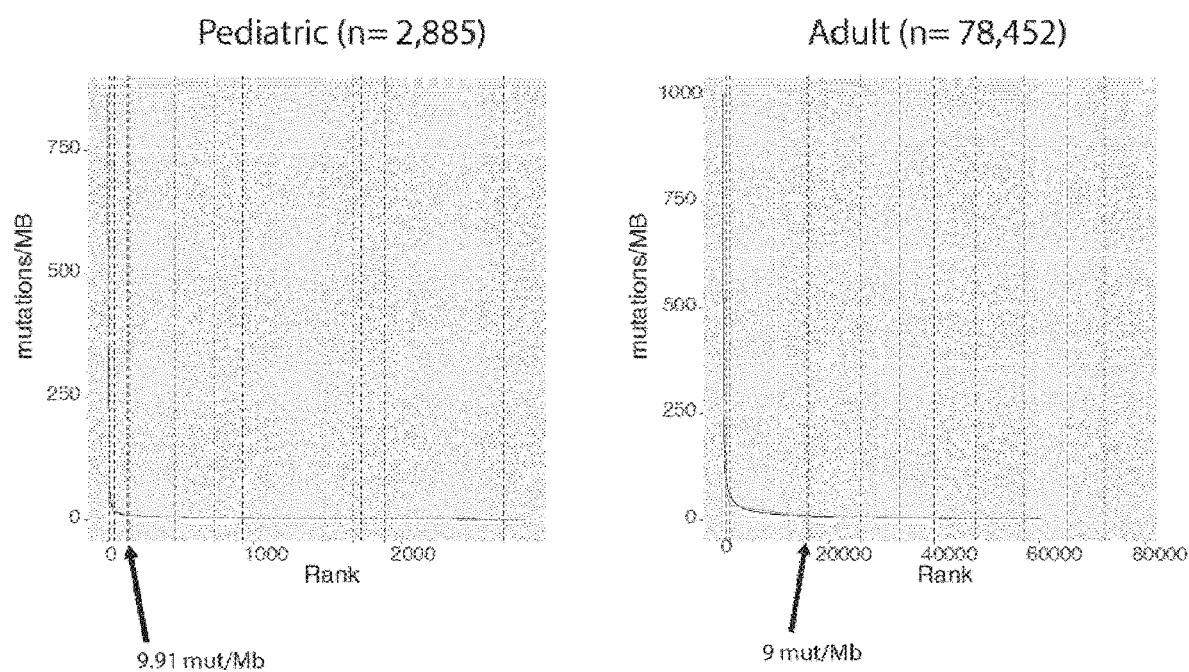
FIG. 7 shows determination of a hypermutation threshold in human cancer through segmented linear regression analysis. Left panel: Pediatric cohort of 2,885 tumours ranked by mutation burden (mutations/Mb). Right panel: Adult cohort of 78,452 tumours ranked by mutations burden (mutations/Mb). Dotted lines indicate segment boundaries determined by segmented linear regression analysis using an iterative method, selecting points at which there was a significant change in the slope of the linear regression. Grey solid lines (originally coloured red) indicate linear regression lines of individual segments. The boundary points at which there was observed to be a significantly large gain in the slope of the regression line, were selected as the thresholds of hypermutation (9.91 and 9 for pediatric and adult cohort respectively), which were rounded to 10 for the remainder of the analyses described in this study.

Having validated panel-based hypermutation testing, we examined the mutation burden in 2,885 pediatric tumours. Mutation frequency ranged from 0-864 Mut/Mb (FIG. 1A), with a mean and median of 6.78 Mut/Mb and 2.50 Mut/Mb, respectively. Using segmented linear regression analysis, we calculated 9.91 and 9.0 Mut/Mb as appropriate thresholds for hypermutation in childhood and adult cancers (FIG. 7 and Methods). For consistency, we use 10 Mut/Mb to define hypermutation in both cohorts. We also note that this coincides with the median mutation burden of patients previously reported to respond to checkpoint inhibition (Bouffet et al., 2016; Diaz and Le, 2015; Johanns et al., 2016; Le et al., 2015; Rizvi et al., 2015; Santin et al., 2016; Snyder et al., 2014; Van Allen et al., 2015).

While childhood cancer genomes are typically thought of as 'quiet', we found 160 tumours with >10 Mut/Mb (5.5%). Hypermutation was observed in childhood cancer types not typically associated with elevated numbers of mutations, including sarcomas, germ cell tumours, nephroblastomas and neuroblastomas. Importantly, across the whole cohort, hypermutant cancers were enriched for defects in mismatch repair pathway genes POLE and POLD1, responsible for synthesis of the leading and lagging strand ($P=<2.2\times10-16$, FIG. 1B). Pediatric tumours with >100 Mut/Mb—defined as ultra-hypermutated—were universally replication repair deficient. These were limited to malignant gliomas, colorectal cancers and leukemias/lymphomas—that is, the three tumour types observed in CMMRD syndrome.

Replication Repair Deficiency Drives a Mutator Phenotype in Many Tumour Types

Functioning DNA replication repair is required for every actively dividing cell in all tissue types. Yet, thus far, replication repair deficient hypermutation has been mainly observed in gliomas, gastrointestinal tract cancers and endometrial cancers.

Figure 1:
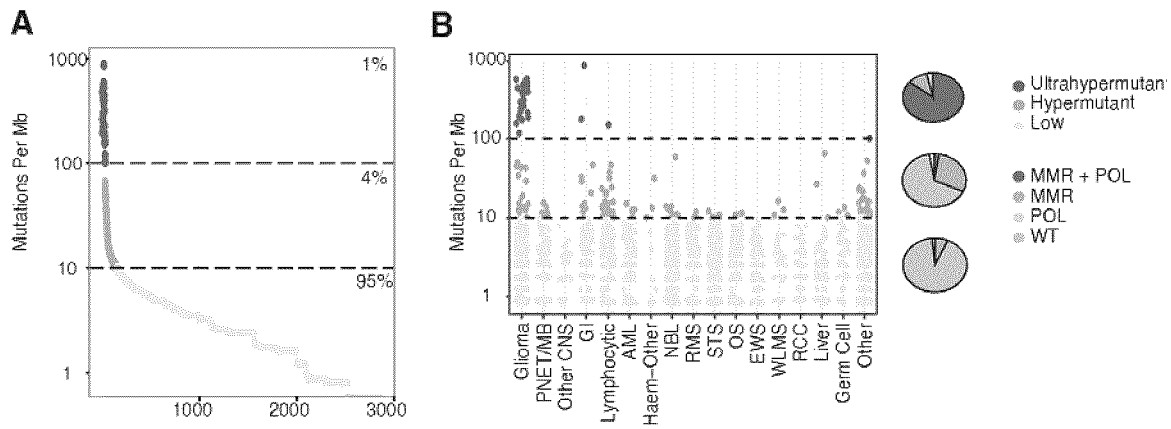
FIG. 1 (1A to 1E) depicts the landscape of hypermutation across 81,337 pediatric and adult cancers.
Figure 1:
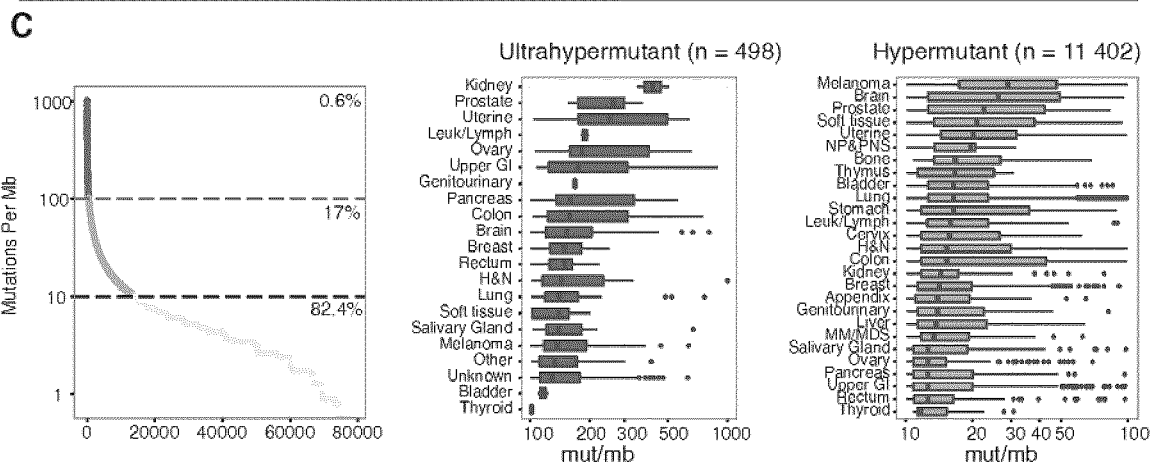
Figure 1:
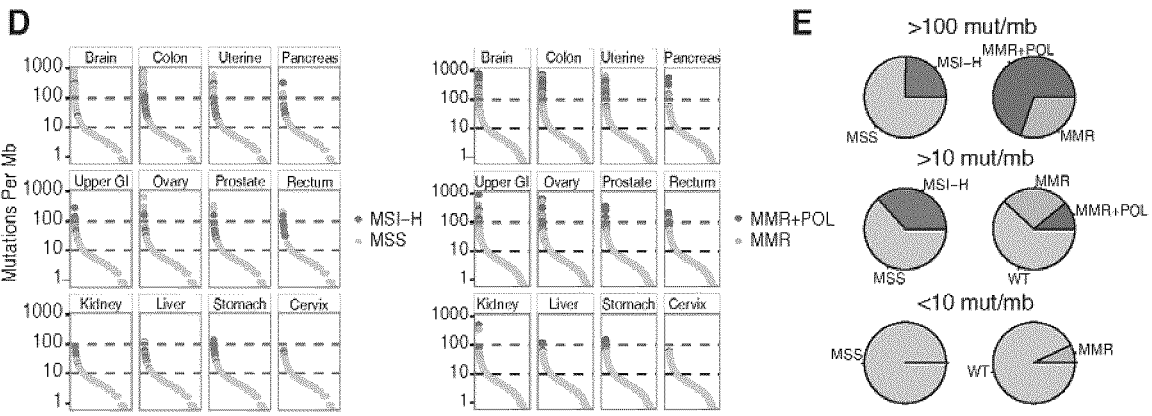
Figure 8:
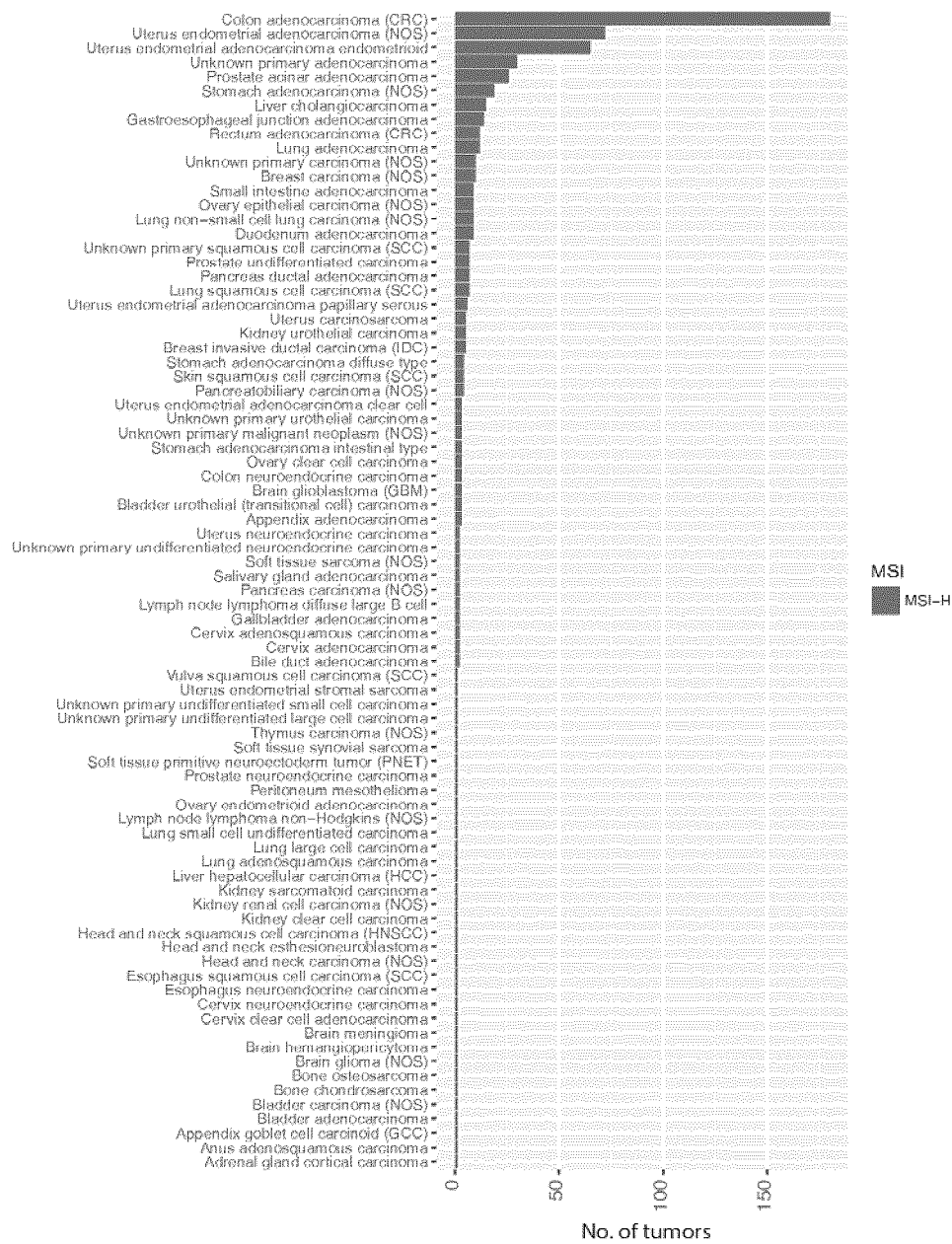
FIG. 8 shows that a large range of tumour types exhibit microsatellite instability. 81 unique tumour histologies with at least 1 MSI-H tumour.

We expanded our analysis of hypermutation to 78,452 adult cancers sequenced on the same targeted gene panel. Hypermutation and ultra-hypermutation were observed in 17% and 0.6%, respectively, of cases across a wide variety of tissues (FIGS. 1C and D). A close examination of these cancers revealed enrichment of replication repair mutations and microsatellite instability in 81 tumour types (FIG. 8). These include previously underreported hypermutant prostate, cervical and neuroendocrine tumours (87, 84 and 278 cancers).

A striking inverse association was observed between microsatellite instability (MSI), a marker of mismatch repair deficiency, and mutation burden. High levels of microsatellite instability (MSI-H) was mostly restricted to tumours in the 10-100 Mut/Mb range, whereas tumours with >100 Mut/Mb were microsatellite stable and enriched for replicative polymerase mutations. Thus, the loss of mismatch repair ability alone is mutagenic up to a point, while the additional loss of polymerase proofreading, causing total replication repair deficiency, leads to an ultra-hypermutated state with microsatellite stability. These data suggest that tumours with complete replication repair deficiency have elevated mutation burdens, acquired with different temporal dynamics (FIG. 1E).

Detection and Validation of Cancer Drivers Using an "In Vivo Human Mutagenesis Screen"

Figure 9:
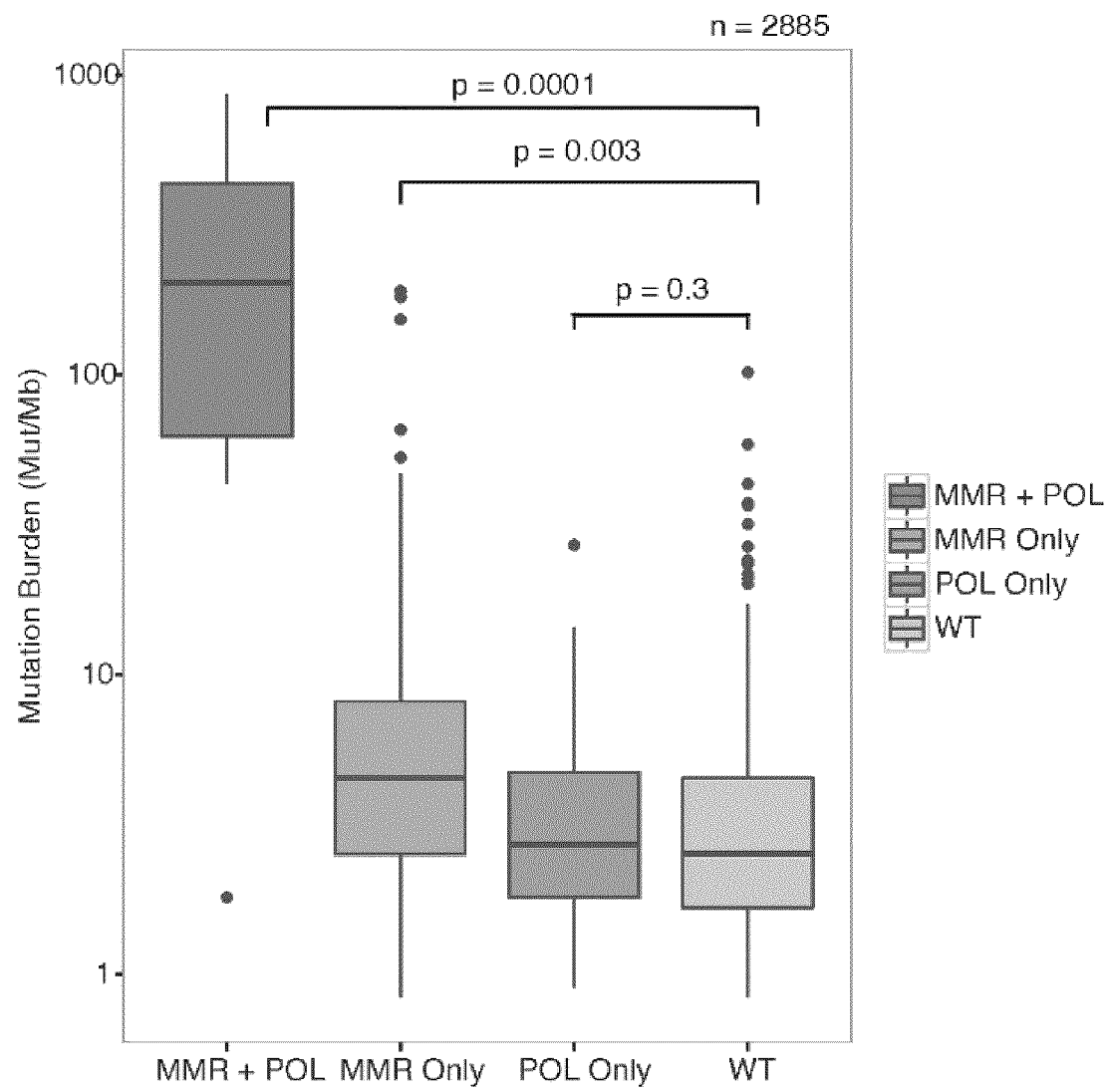
FIG. 9 shows that pediatric cancers with a combined mismatch repair deficiency and polymerase driver mutation display an ultra-hypermutant phenotype. Cohort of 2885 pediatric tumours harboring either MMR and polymerase mutations concurrently, only mismatch repair mutations, only polymerase mutations, or neither. The presence of a mismatch repair mutation is significantly associated with hypermutation, while a polymerase mutation alone is not.

Rare variants, whether found in the germline or acquired by a tumour, can be difficult to interpret on their own. In many cases, there is no functional assay available for these variants, and most are therefore typically classified as "variants of unknown significance" or "likely passengers" (depending if found in non-neoplastic or cancer material). A handful of missense mutations in the exonuclease domain of POLE have been established as driver variants—that is, they are known to cause hypermutation in human tumours and are functionally validated as drivers in cell line and animal models (Albertson et al., 2009; Daee et al., 2010; Kane and Shcherbakova, 2014). However, determining the pathogenicity of novel mutations in POLE and POLD1 is a challenge due to the large size of these genes and the frequency at which they can be mutated without functional impact. Indeed, in our cohort we observed 2,150 POLE and 1,123 POLD1 distinct variants, many of which encode changes at novel positions in the protein (Methods). As expected, among childhood cancers, most POLE and POLD1 mutations were not associated with hypermutation (FIG. 9).

Figure 2:
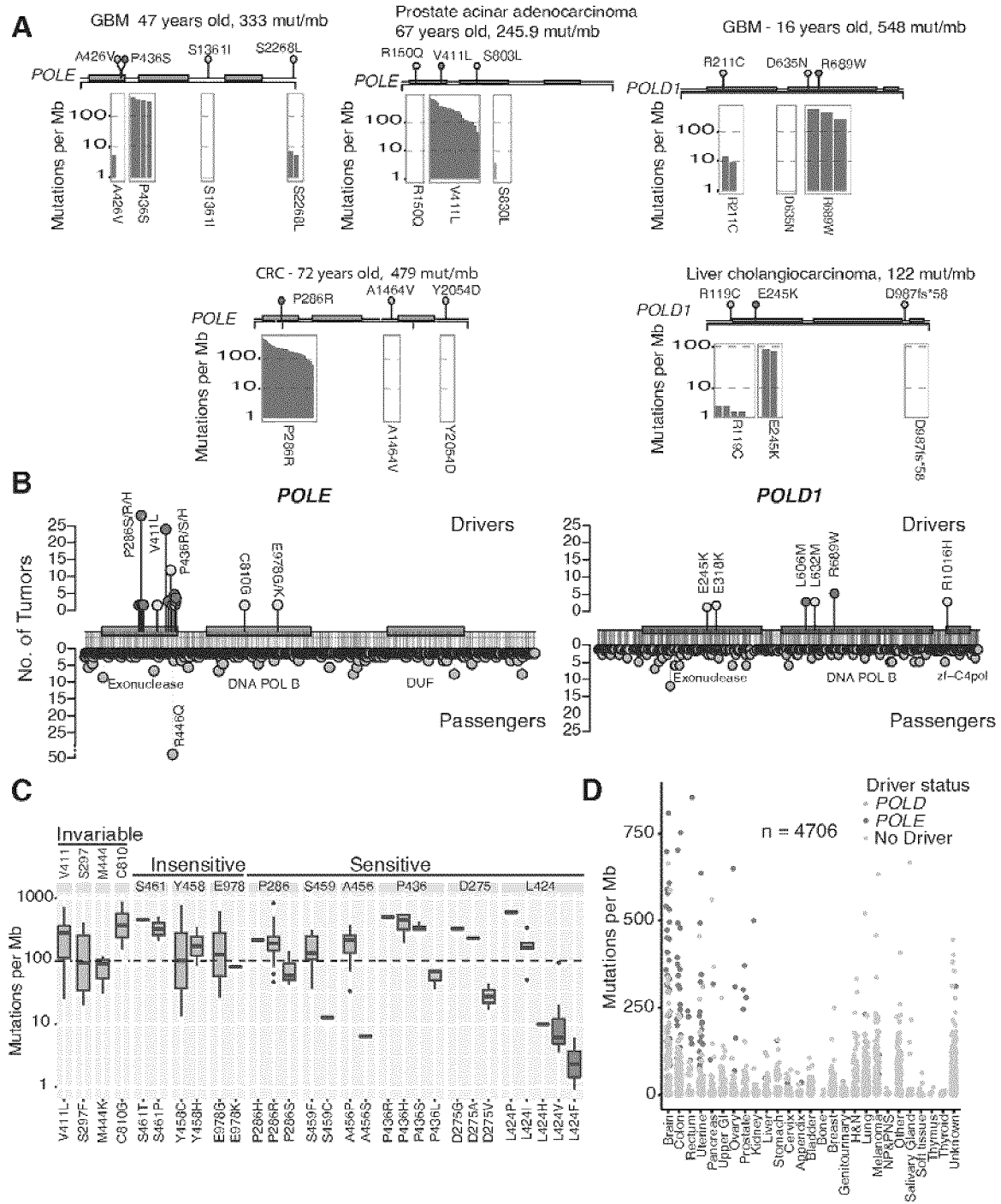
FIG. 2B) Graphical representation of all drivers (top) and passengers (bottom) identified in POLE (left panel) and POLD1 (right panel) following in-vivo mutagenesis screening criteria. Circles (originally coloured green) represent previously known drivers while other circles (originally coloured yellow) represent novel drivers, first described here.
FIG. 2C) Codons in POLE at which driver mutations are found and whether they are sensitive to amino acid changes. Invariable codons represent codons at which only one amino acid change was detected. Insensitive codons represent codons at which mutation burden was high, regardless of amino acid change. Sensitive codons represent codons at which certain amino acid changes would abrogate the mutator effect. Bars (originally shaded green, yellow, and red) represent strong, moderate and weak mutation burden phenotypes, respectively.
FIG. 2D) All tumours harboring POLE and POLD1 tumours, by type, colored by whether the mutation was a driver or passenger.

We reasoned that we could determine which variants are in fact true drivers by leveraging the large size of this cohort. A mutation was classified as a clear driver if it was found in a hypermutated tumour and was not observed in tumours with a low mutation burden (Methods). Using this approach—which can be thought of as an "in vivo human mutagenesis screen"—we re-discovered every known POLE and POLD1 driver (that is, every previously published and established driver mutation was correctly picked up by our screen). We then found 11 new driver mutations that are all consistently associated with hypermutation (7 new drivers in POLE and 4 in POLD1; Table 5). For POLD1, the lagging strand polymerase, driver mutations are less well characterized. POLD1 R689W was the most frequent driver in this gene. This variant has been shown to be a very strong mutator in yeast (Daee et al., 2010). To our knowledge this is the first series of primary tumours that validates this variant as a mutator in humans. The absence of hypermutation was also interesting—tumours with exonuclease mutations at highly conserved motifs of POLD1 (ExoI,II,III) were not consistently hypermutant. These variants may be so detrimental to the cell that it requires additional suppressor mutations to reduce the mutation burden (Herr et al., 2011). Just as importantly, through this analysis of POLE and POLD1 mutations, we determined that many mutations are mere passengers, even in tumours with multiple polymerase mutations (FIG. 2A). POLE R446Q is one such false positive—observed in a large group of non-hypermutated cancers. Confirming our classification as non-pathogenic, we also found this variant in non-affected individuals (>1/2000 individuals in ExAC (Lek et al., 2016)). In both POLE and POLD1, driver mutations were uncovered outside the exonuclease domain (FIG. 2B) suggesting that other domains are responsible for hypermutation.

These data allowed us to compare the impact of differing missense substitutions at the same residue. For example, we found that POLE V411 is associated with an extremely high mutation burden but only when valine is mutated to leucine (we labeled these residues as "invariable" as only a single possible amino acid change was found; FIG. 2C). Residues S461, Y458 and E978 in POLE seem to be insensitive to change, with all amino acid substitutions associated with hypermutation. In contrast, at other residues, the magnitude of mutation burden varies depending on the specific amino acid change. Leucine 424 is one such "sensitive" residue—it is associated with a strong mutator phenotype when replaced with a proline or isoleucine, but is associated with lower mutation burden when mutated to a valine or phenylalanine ($p=0.03$). To validate this finding, we measured the excision rate constants for wild type POLE, and the L424V and L424I mutations using a rapid chemical quench-flow apparatus ((Zahurancik et al., 2014); Methods). L424I had a 5.7-fold stronger excision effect than L424V, confirming the dramatic difference in mutation burden seen in the primary tumours (FIG. 10). In contrast, every D275 mutation mutates an essential active site residue, which coordinates a metal ion required for catalysis, and yet we see a 10-fold difference in mutation burden (between D275G, D275A and D275V). The difference between sensitive and insensitive amino acids can be related to the structure of the exonuclease and physical/biochemical interactions with the mismatches in the DNA.

Using this screen to triage functional variants, we mapped the landscape of driver somatic mutation in POLE and POLD1. These observations are key in the precise definition of real drivers in POLE and POLD1 cancers and can solve some issues raised by recent sequencing efforts, which uncovered POLE and POLD1 germline variants of unknown significance in children with cancer (Zhang et al., 2016).

Finally, although most POLE and POLD1 driver mutations were restricted to specific tumour types with no previously apparent signature (FIG. 2D), driver mutations were also observed in melanoma and lung cancer, both of which are malignancies with well-described extrinsic causes of hypermutation and a distinct signature. These data suggest that hypermutation can arise from a variety of sources in a single tumour histotype.

Previous Mutagen Exposure can be Inferred from the Cancer Genome.

To study the context and footprints of hypermutation across all cancers, we studied 217,086 mutations in 1,521 hypermutant tumours representing to our knowledge the largest collection of hypermutated cancers to be considered together (Table 6 and Methods). We classified every mutation, whether coding or not, by its nucleotide context (i.e., the bases immediately preceding and following it, forming a trinucleotide). Then, using the proportion of the 96 possible trinucleotides, we performed unsupervised clustering of all 1,521 tumours. Taking the whole map into view, several known clusters emerged, including replication repair dominated tumours (shown on the left in FIG. 3A), skin cancers known to have a distinctive UV-associated signature, and two tobacco smoking clusters (shown on the right in FIG. 3A).

Strikingly, within the replication repair associated tumours, one sees at least three sharply delineated subclusters (labeled C1, C2 and C3 in FIG. 3B). The largest group, C2, (n=523), is characterized by high microsatellite instability in a wide range of cancers (43 tumour types with >2 examples each). The middle-sized cluster, C3, which includes colorectal, uterine and seven other tumour types, is made up of cancers that are almost completely microsatellite stable and POLE mutated. The last DNA replication repair cluster, C1, includes many microsatellite stable brain cancers with mutated POLE. C1 is unique since it harbors a higher mutation burden (380.8 vs 277.5 Mut/Mb for C3 ($p=0.017$) and 80.4 Mut/Mb for C2 ($p=8.9E-5$) and also includes many children. Taken together, these results expand the spectrum of cancers associated with DNA replication repair and define three new subgroups—based on trinucleotide mutation context alone—with dramatic differences in microsatellite stability, polymerase deficiency, and age.

The non-replication repair deficient cancers comprised the remaining clusters (labeled C4 to C8 in FIG. 3A). Viewing the overall landscape, these could be seen as roughly divided by already known mutagenic signatures (Alexandrov et al., 2013): tobacco smoke (cluster C4 and C8), alkylating agents (C5), ultraviolet light (C6) and the APOBEC cytidine deamination signature (C7). These four mutagens "anchor" their clusters, which contain the expected cancer types (e.g. cluster C6 has a strong core of UV-associated skin cancers). There were additional smaller clusters of cancers that grouped together (unlabeled in FIG. 3A). Six tumours, including three urothelial and one hepatocellular carcinoma shared a spectrum suggestive of exposure to aristocholic acid (Poon et al., 2013). However, it is clear from our results that the major mutagens act more broadly than previously appreciated and that the canonical mutagen-tumour type relationships do not always hold, or are not exclusive.

Figure 11:
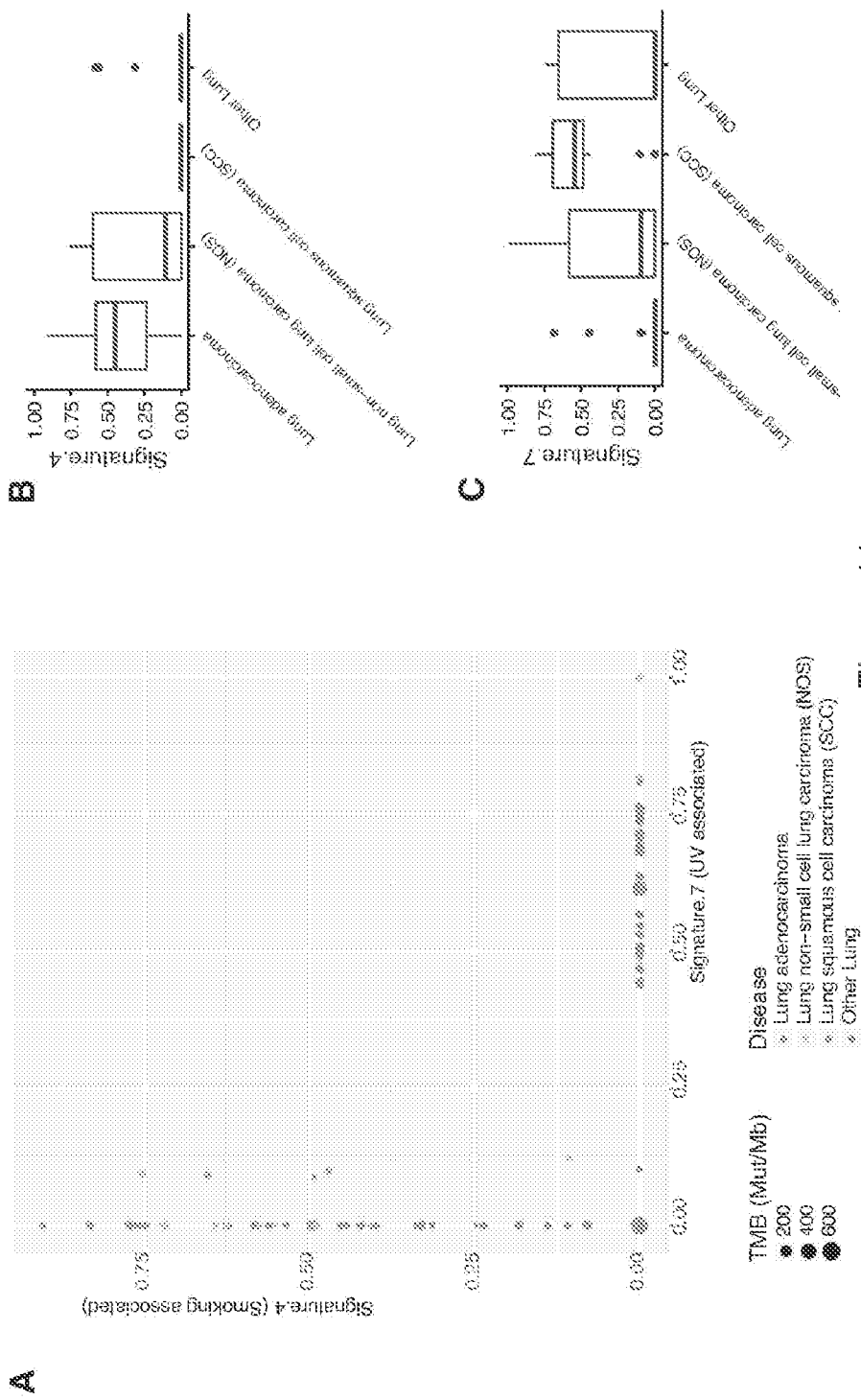
FIGS. 11 (11A to 11C) depicts signature analysis of hypermutant lung cancer reveals predominance of Signature 7 (UV Light) in hypermutant lung squamous cell carcinoma.

Lung cancer is one such example (FIG. 3C). Of the most abundantly mutated lung cancers examined here, only 40% harbor the signature for tobacco smoke. We find that 35% of hypermutated lung have a high proportion of the UV light signature (>40% contribution) and 5% have evidence for alkylating agent-associated mutations (n=100). Furthermore, the UV light-associated signature was almost exclusively observed in the squamous cell carcinoma subtype (FIG. 11). This observation was previously reported for three hypermutant lung squamous cell carcinomas (Campbell et al., 2016). Either these are all misdiagnosed skin cancers with metastasis to the lung, as has previously been suggested, or perhaps, when hypermutated they form a distinct group based on a nucleotide context that reflects their cell of origin.

Figure 12:
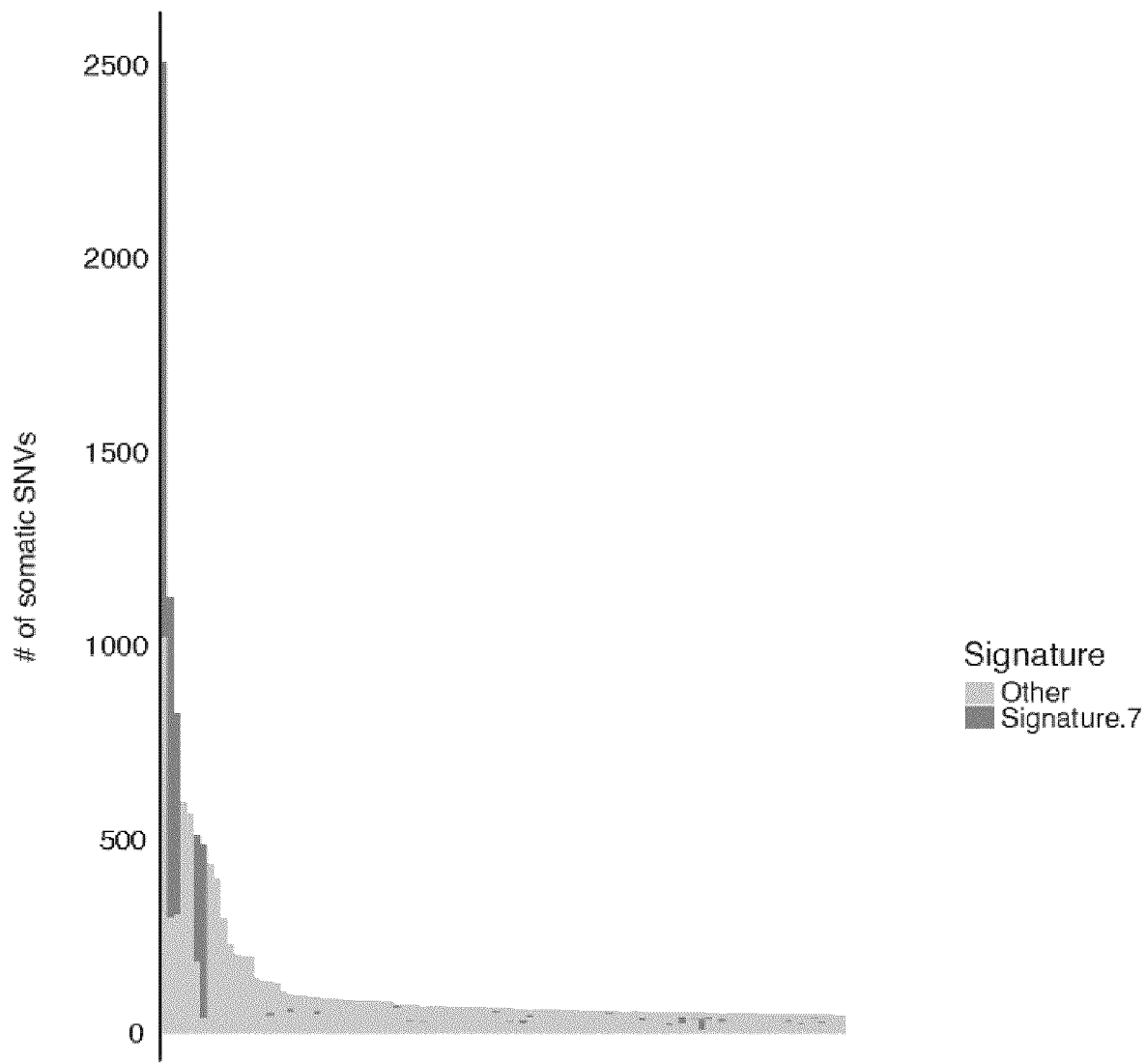
FIG. 12 shows that hypermutant soft tissue sarcomas from TCGA exhibit signature of SNVs consistent with UV light exposure. Number of somatic SNVs in 103 TCGA sarcoma exomes (minimum 50 somatic SNVs). Magenta indicates proportion of mutations explained by Signature 7 (UV light). Lighter grey indicates proportion of mutations explained by all other signatures.

Sarcomas—tumours not previously associated with hypermutation—also clustered in an unexpected way. Hypermutated sarcomas were primarily in cluster C6—a large proportion of cases (70%) had high levels of UV-associated mutations (FIG. 3C). We validated this finding using available TOGA sarcoma data (exome sequence; FIG. 12), confirming that most hypermutated sarcomas bear the imprint of sun exposure. Indeed, in cluster C6 we see an enrichment for soft tissue angiosarcomas, a rare and aggressive vascular tumour that often presents cutaneously, usually on the face and scalp (Dossett et al., 2015). Soft tissue malignant peripheral nerve sheath tumour (MPNST), which can also arise cutaneously, were similarly enriched in C6. We then examined the pathology records from TOGA and, likewise, found that sarcomas with high UV-associated mutations were mostly superficial cancers. Thus, through this unbiased analysis, we have shown that UV light is associated with mutagenesis of mesenchymal cells, not just skin epithelia.

Alkylating agents, such as temozolomide, are known mutagens that leave a specific imprint on the genome. One of our clusters, C5, is dominated by brain cancers with overwhelming contribution of alkylating-associated mutations (on average 72%). We observed similar signatures in skin cancers (14% of the top most mutated skin cancers in this cohort), lung cancers, pancreatic cancers and leiomyosarcomas (FIG. 3C). Hypermutation should be therefore be considered in any relapsed cancers treated with alkylators, regardless of its cell of origin. This data reinforces the notion that a small set of processes drives hypermutation in a wide variety of tumour types.

Mutational Signatures Mark the History of Cancer Development

Figure 4:
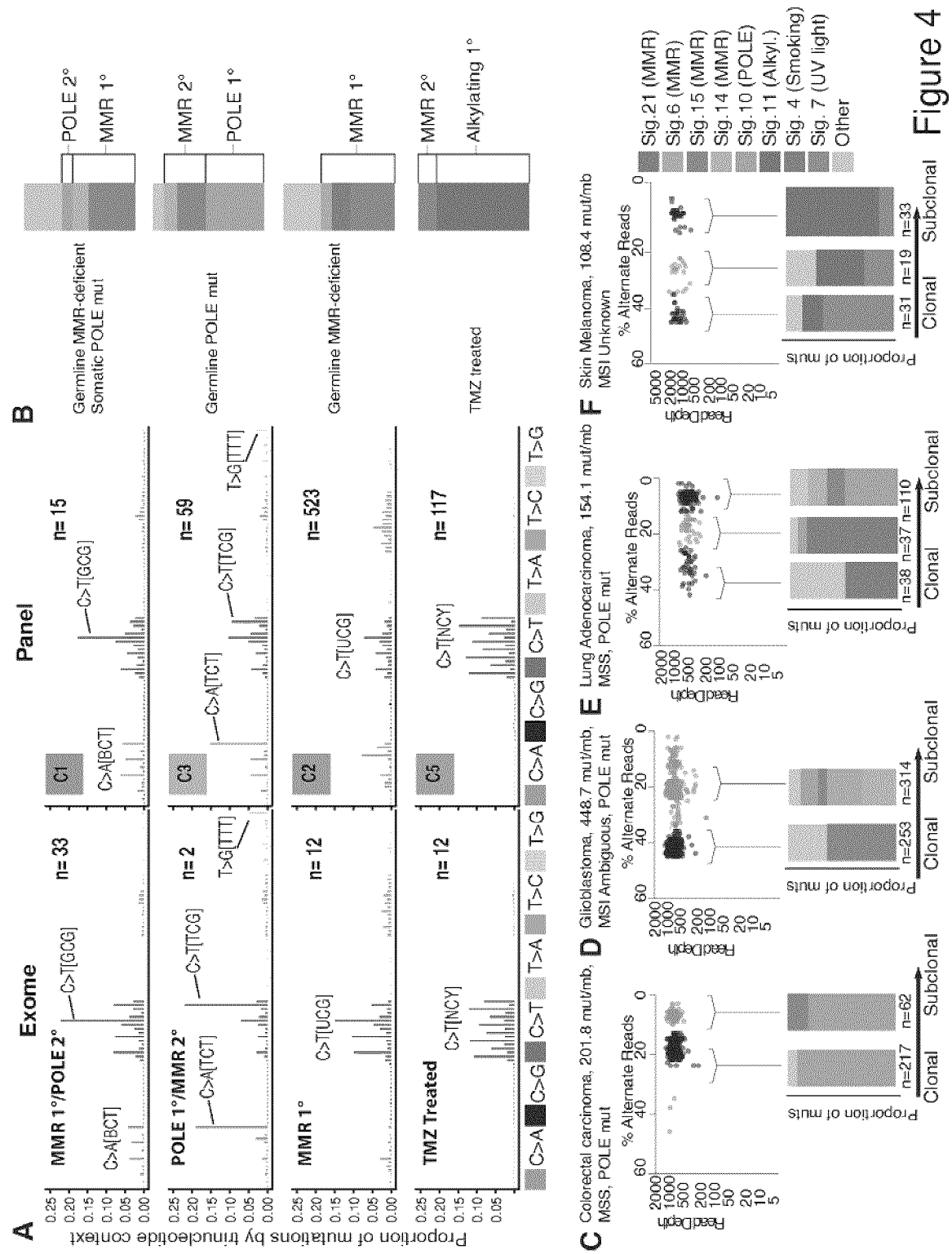
FIG. 4 (4A to 4F) depicts mutational context in hypermutant tumours determined by timing and etiology of mutation.

These data suggested that the signatures of hypermutation vary depending on the order of mutagen exposure. For example, the trinucleotide pattern of 01 resembles those of inherited gliomas in the CMMRD syndrome (Shlien et al., 2015) and would therefore suggest that these patients do in fact also harbor germline MMR mutations. If true, the overall trinucleotide composition of 01 represents an early constitutional MMR defect, followed by acquired secondary POLE, whereas tumours in cluster C3 have acquired POLE followed by MMR. To test this hypothesis directly, we sequenced a cohort of 1521 samples for which the temporal order of mutation was known (FIG. 4) from the international bMMRD consortium. This included: (1) cancers with germline MMR mutations plus either POLE, POLD1 mutations, or neither, as secondary event; (2) cancers arising in carriers of germline POLE mutations; and (3) gliomas whose hypermutation was due to temozolomide treatment.

We matched the nucleotide context of variants found in these childhood cancers, whose mutation order are known, to the clusters (FIG. 3), which were derived from an unannotated cohort of mostly adult cancers. Indeed, germline MMRD with secondary polymerase mutations matched cluster C1 whereas the cancers from patients with germline MMRD, such as Lynch or CMMRD without secondary polymerase deficiency matched cluster C2 (FIGS. 4A and B). C3 matched tumours from patients with germline POLE mutations. The difference between C2 and C3 suggests that MMR deficiency emerges early in the former and late in the latter. Therefore, in microsatellite stable tumours, ultra-hypermutation is driven by an early polymerase proofreading defect, while mismatch repair appears later. The timing of these events throughout the history of these cancers provides an explanation for the unexpected microsatellite stable phenotype observed in the POLE ultra-hypermutant, mismatch-repair deficient tumours seen here (FIG. 1D, FIG. 3B) and in other reports (Cancer Genome Atlas, 2012; Kandoth et al., 2013).

We next wanted to determine how the context of mutations changes over the course of each tumour's evolution. We summarized our observed mutation spectra using the established signature labels, as previously defined (Alexandrov et al., 2013). In this way, we ascribed specific causes to individual established signatures. We confirmed that "Signature 10" is associated with POLE exonuclease mutation. As expected, Signature 10 was high in those tumours where POLE was mutated early, from cluster C3 (e.g. germline POLE), and low in the late POLE tumours, seen in cluster C1. The mutation signature of POLD1 had not been previously described. We saw an enrichment of Signature 20 in cases with MMR and secondary POLD1. This is especially true for POLD1 L606M, a hotspot mutation in motif A of the polymerase domain. Significantly, Signatures 14 and 15 were enriched in all germline CMMRD hypermutant cancers, with much higher contribution than all other signatures. Gliomas with temozolomide-induced hypermutation were well matched to Signature 11. It was clear that many replication repair tumours present, at diagnosis, with a mix of signatures due to differing mutational histories. To separate out early and late signatures, we performed subclonal analysis (Methods). In childhood cases with MMR and secondary POLE (i.e. cluster C1), we do in fact see late-arising Signature 10, found exclusively in the subclone (FIG. 4C). Furthermore, high depth sequencing enabled us to detect subclones in multiple other cancers. For example, we see late-arising polymerase deficiency in a lung cancer, on the background of an abundance of smoking-associated mutations, and the late emergence of the treatment-associated alkylating agent signature in a skin cancer that is otherwise dominated by the UV light signature (FIGS. 4D, E and F).

Mutational Signatures Predict Germline Replication Repair Mutations

Finally, we tested whether somatic mutation burden combined with signatures—as determined by clinical panel sequencing—could reveal a germline cancer predisposition syndrome. We performed signature analysis on all ultra-hypermutant pediatric cancers and subsequently gathered clinical genetic information on most. As expected, all ultra-hypermutant cancers harbored mutations in either the MMR and/or DNA polymerases. Strikingly, a strong replication repair signature was observed in all tumours from patients with confirmed genetic diagnosis of germline MMR or POLE mutations (FIG. 5A). The only pediatric glioma that did not harbor the replication repair signature was found to have the alkylator signature (thus suggesting that the hypermutation was treatment induced, as seen in adults). Three tumours exhibited a small but significant alkylator signature. These were subsequently determined to be recurrent gliomas from CMMRD children whose treatment included temozolomide. In all cases, the initial biopsy did not reveal the alkylator signature, which further confirms the ability of mutational signatures to determine the natural history of cancer. These observations were also observed in hypermutant tumours with lower mutational burden (FIG. 5B).

Discussion

The mutations that accumulate during carcinogenesis leave imprints on the genome, and this is especially true in hypermutant cancers. Following these footprints can provide insight into tumour classification, help to pinpoint the true drivers that arose during the cancer's evolution—of which, some can even be traced back to the germline.

We found hypermutation in approximately 1 in 20 childhood cancers and 1 in 6 adult cancers. One sees an enrichment amongst tumours that have been subjected to continuous long term exposure to genotoxic agents, such as UV light in melanomas. For recurrent tumours, the treatment itself may be the primary cause of hypermutation. Exposure to chemotherapies such as alkylators or thiopurines can lead to replication repair deficiency (not unlike what occurs with germline predisposition or early somatic MMR mutations during initial tumour development) (Nguyen et al., 2014; Swann et al., 1996). These recurrent hypermutant cancers will be resistant to chemotherapy and other agents as they are driven by very different factors than the initial tumours. Knowledge of their mutational load and signatures could be used for targeted or immune based treatment strategies (Topalian et al., 2016) which are gaining success as cancer therapeutics, particularly in patients with high mutational load.

Driver mutations in POLE and POLD1 have only recently been described (Shinbrot et al., 2014). Our method for separating the drivers from the many passengers—the in vivo human mutagenesis screen—is likely the most direct way of measuring functional consequence of putative mutators (more so than conservation analysis or impact predictors such as PolyPhen and SIFT). Further research is required to fully understand why mutations in the polymerase domain are associated with hypermutation and putative loss of proofreading ability. A similar approach could be applied to other mutator phenotypes, driven by different genes, especially if associated with a unique signature (Scarpa et al., 2017).

Figure 3:
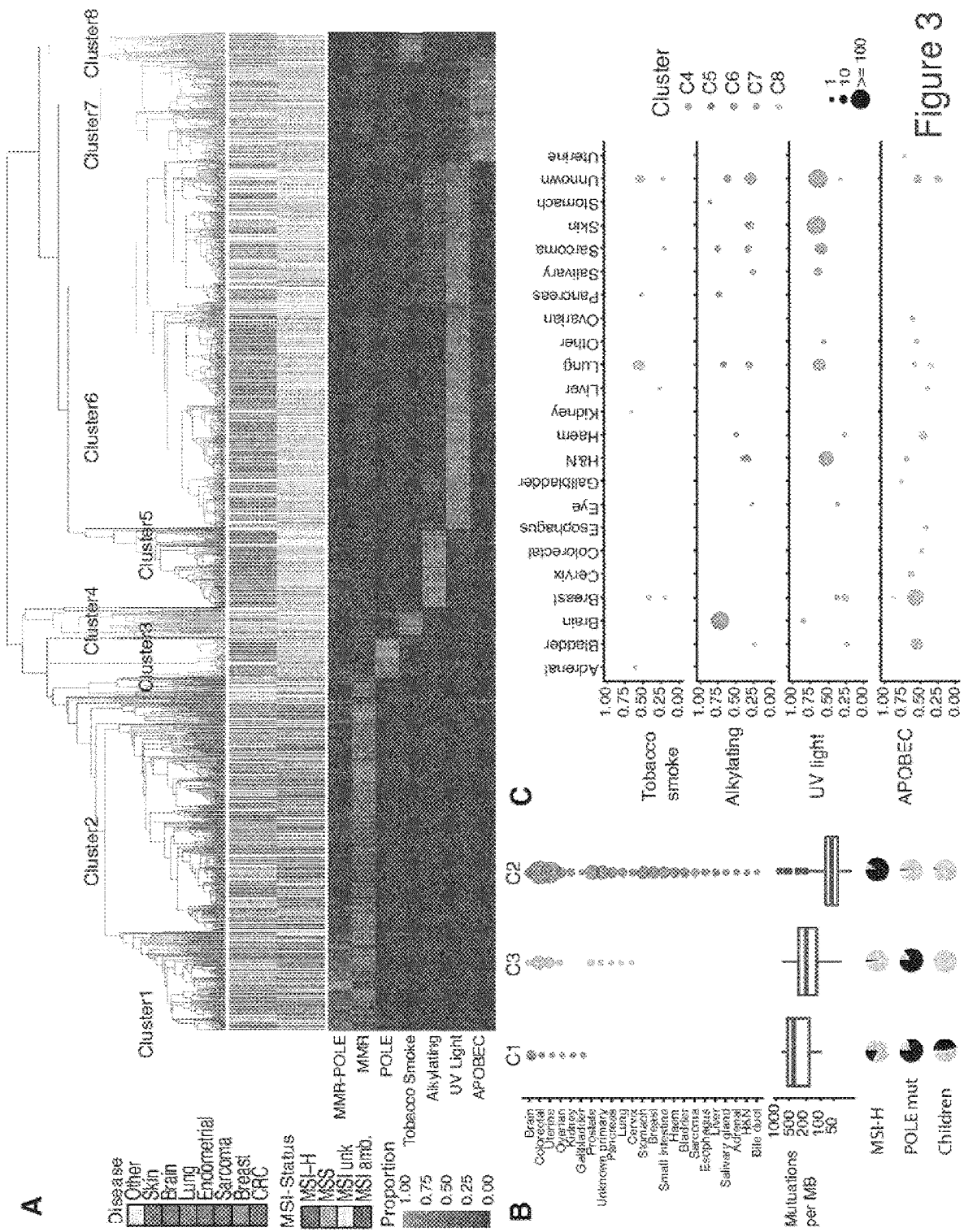
FIG. 3 (3A to 3C) depicts unsupervised clustering by trinucleotide context reveals mutational etiology of hypermutant tumours.

Hypermutated tumours acquire their many mutations over an extended time period, many of which likely have no, or very little, functional consequence. In contrast, non hypermutated tumours are driven by a select few drivers, each contributing some significant pro-neoplastic property. Despite the high amount of noise, the "information content" and ability to infer tumour evolution from the multitude of passengers in a hypermutant tumour may, in many cases, be superior to that of a non hypermutated cancer. As seen here, these passengers (i.e. the "noise"), when considered together, bear the imprint of specific signatures that can differentiate clinically relevant subgroups (FIG. 3). For example, microsatellite stable but ultra-hypermutant cancers could be differentiated on the basis of mutational signature alone. As could squamous cell carcinomas of the lung that likely originated from metastatic skin cancers, and peripheral sarcomas with evidence for UV-induced damage.

Furthermore, in hypermutant cancers mutational signatures helped demarcate early from late emerging landmarks. This was seen in temozolomide-induced hypermutant gliomas amongst other cancers. Late-arising signatures of hypermutation can increase at recurrence, altering treatment options, even in the background of an already hypermutated cancer (e.g. driven by UV light or smoking, FIG. 4). Finally, in replication repair deficiency, one can use these signatures to trace the drivers to the germline. The cancer genome becomes a powerful new diagnostic aid for an underlying germline susceptibility. As one specific example, if a young patient is found to have a hypermutant tumour with a signature similar to cluster C1, their family should be offered genetic counseling and testing for CMMRD—a syndrome that is underdiagnosed due to the lack of clear clinical warning signs (Amayiri et al., 2016; Durno et al., 2015).

In summary, through the analysis of tumour samples from 81,337 children and adults we defined thresholds for hypermutation, revealing many tumour types whose signatures helped to reveal subgroups—a new taxonomy of hypermutation cancers defined by the type and order of mutagen exposure. This can be exploited for better patient management, including the identification of patients who may be most likely to benefit from the use of checkpoint inhibitors.

Development of a Tumour Classification System Based on New Signatures

Although Alexandrov and Stratton have performed foundational work on mutational signatures, using non-negative matrix factorization, their exploration of hypermutant cancers has been limited. These were mostly considered as exceptional outliers rather than studied in their own right. Our method uses the cancer genome's overall trinucleotide makeup to look for similarity within and between every istological type of hypermutant cancer. Using this unbiased approach, in which cancers aren't "fitted" to previously defined common signature types, we discovered several new signatures that delineate important clinical and biological cancer subgroups, regardless of tissue of origin. For example, we found three novel subtypes of replication repair deficient cancer. These only imperfectly correspond to the common signature vocabulary (i.e. Sanger signatures 6, 10, 14, 15 and/or 20). Instead, we find that the timing in which the patient was exposed to specific mutagens creates a unique combination of mutations in their tumour, and these allow for accurate biological and clinical stratification.

Figure 13:
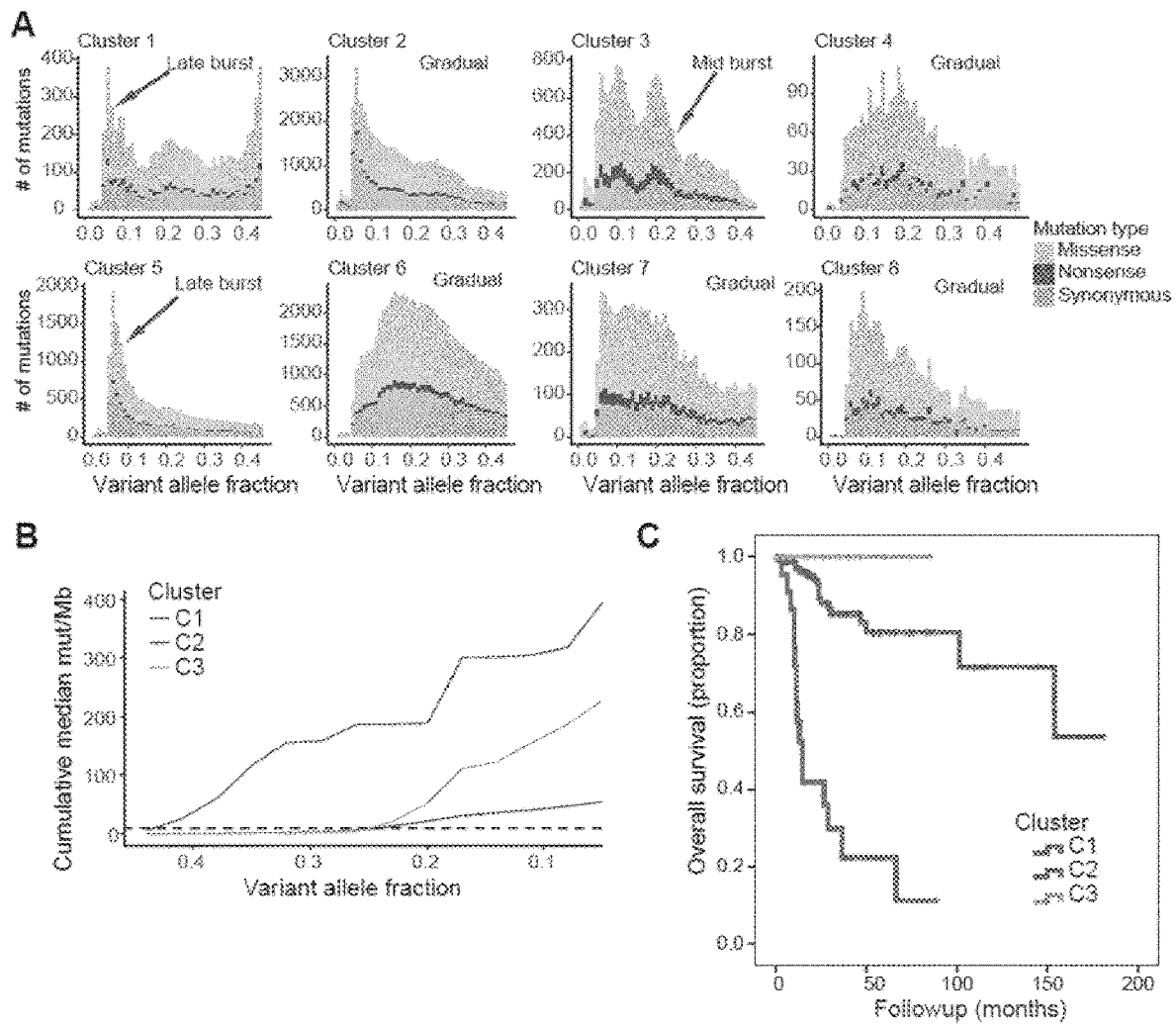
FIGS. 13 (13A to 13C) shows that clustering identifies tumours with differences in evolutionary dynamics and survival.

Uncovering the Clinical and Biological Impact of Mutation Bursts in Hypermutant Cancer We have additionally show that the subgroups, defined by internal and external mutagenic events, display dramatic differences in temporal dynamics (i.e. tumour evolution). As seen in FIG. 13, some tumour clusters accumulated mutations gradually, reaching hypermutation over an extended period, while others do so in dramatic bursts. Cancers with gradual mutation accumulation appeared to reach a mutation burden plateau, while explosive cancers (with bursts) did not.

Strikingly, these results are independent of the cancer's type and are instead determined by its mutagen exposure. UV light, smoking and MMR Cluster 2 resulted in only gradual mutation accumulation. Early-to-mid mutational bursts (caused by POLE mutations, Cluster 3) had a more benign outcome, however patients with tumours harboring late arising bursts of mutation—associated with complete replication repair deficiency or TMZ treatment (Clusters C1 and C5)—had significantly reduced survival.

Therefore, while the cancers studied here have all achieved the same minimal mutation threshold, we can now study the differing routes they took to reach hypermutation, and these have clear survival implications.

The Mutation Signature is a Robust Readout of the Life History of the Tumour

We retraced the evolutionary history of tumour development using the mutational signatures and burden found in the genome alone, and found that hypermutant tumours harbor clear landmarks, indicating when and how their mutations were acquired. To our knowledge, these have been missed in all previous reports.

Figure 5:
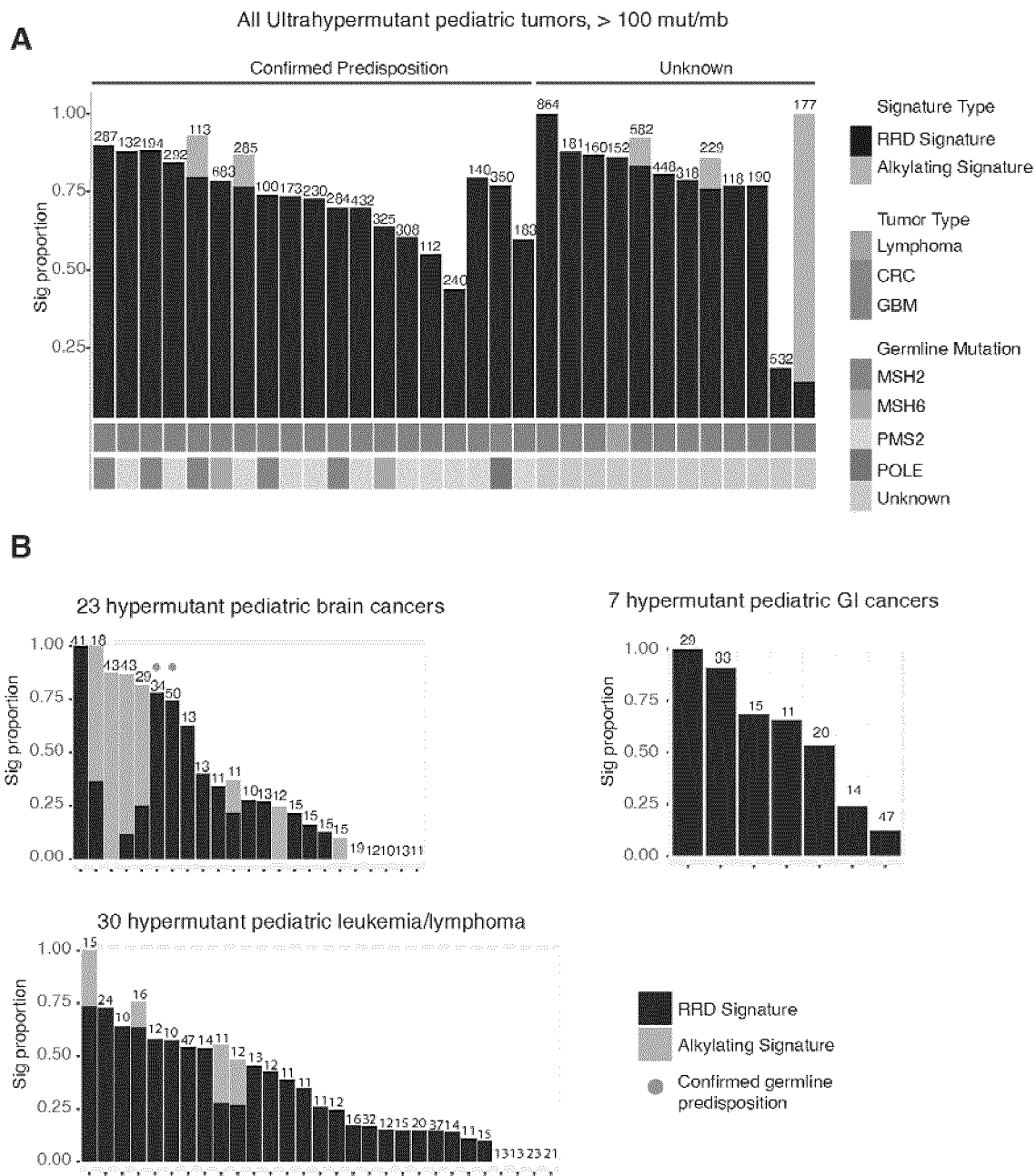
FIGS. 5 (5A and 5B) depicts that high mutation burden and specific signatures reveal predisposition and treatment history in pediatric cancers.
Figure 14:
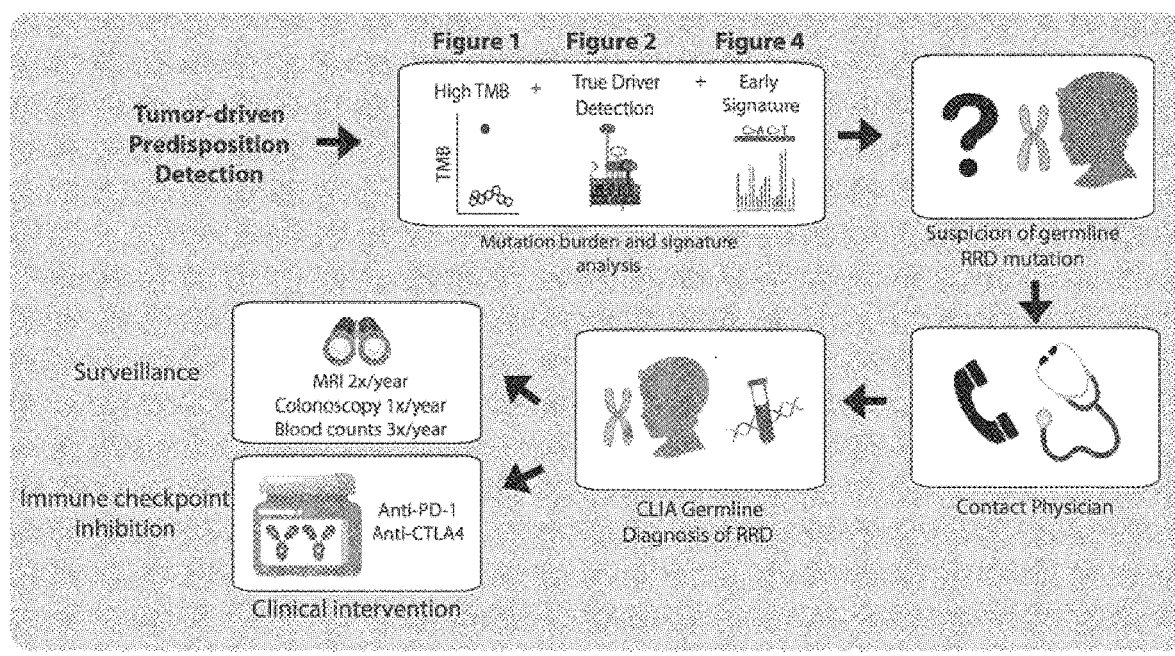
FIG. 14 shows procedure for diagnosing cancer predisposition syndrome via tumour-specific panel sequencing. Panel sequencing results displaying high tumour mutation burden (TMB), a driver mutation in POLE or POLD1 and signatures reflective of replication repair deficiency are highly specific for a Biallelic Mismatch Repair Deficiency diagnosis. Clinical intervention includes surveillance protocols and immune checkpoint inhibition therapy for active tumours.
Figure 15:
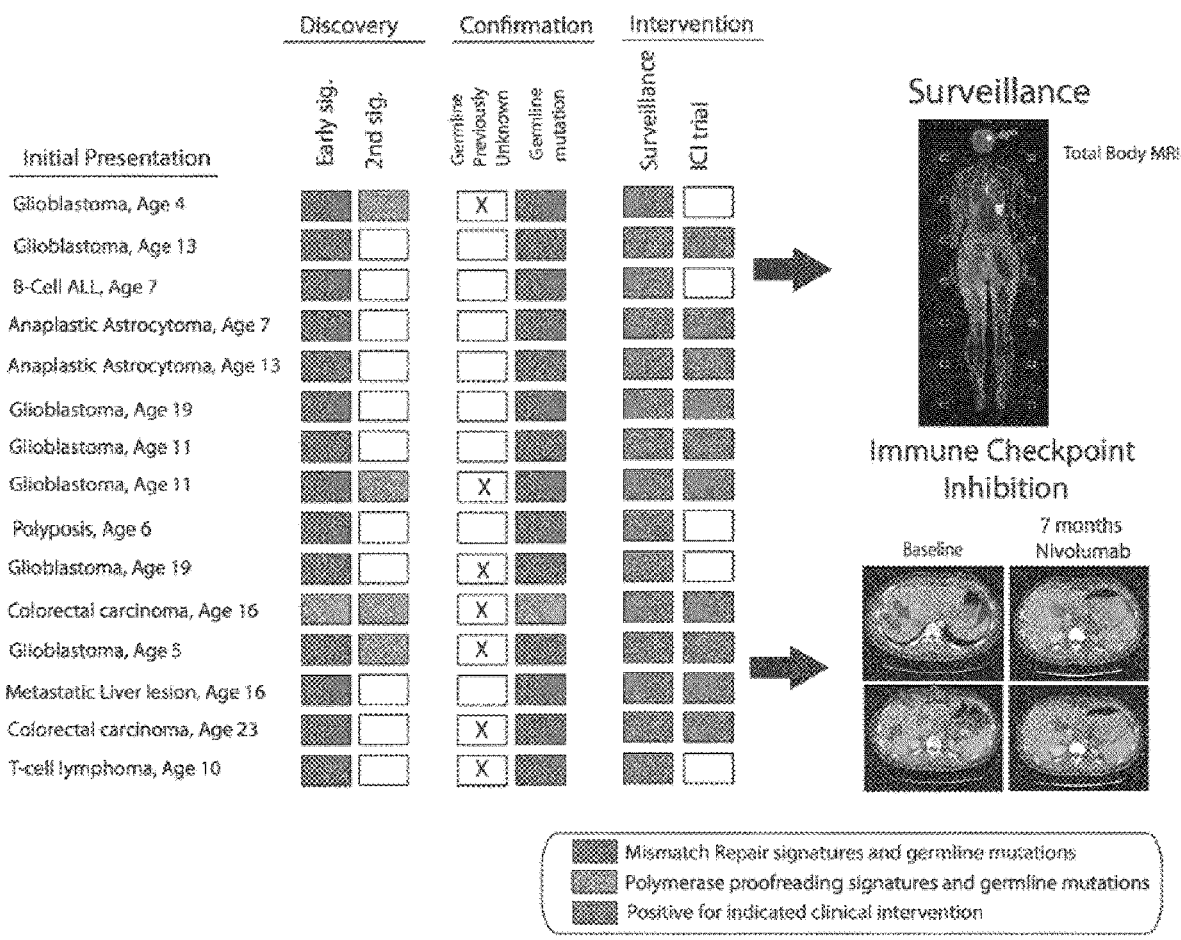
FIG. 15 depicts, in the left panel, 15 patients for which only panel sequencing was performed prior to confirmation of predisposition syndrome diagnosis. Darkest squares indicate signatures corresponding to MMR and the subsequent identification of a germline mutation in an MMR gene. Lightest grey squares indicate the same for POLE. In the right panel is shown an example of a glioma found via surveillance. In the bottom right panel is shown a colorectal cancer responding to Anti-PD1 therapy following confirmation of germline MMR mutation.
Figure 16:
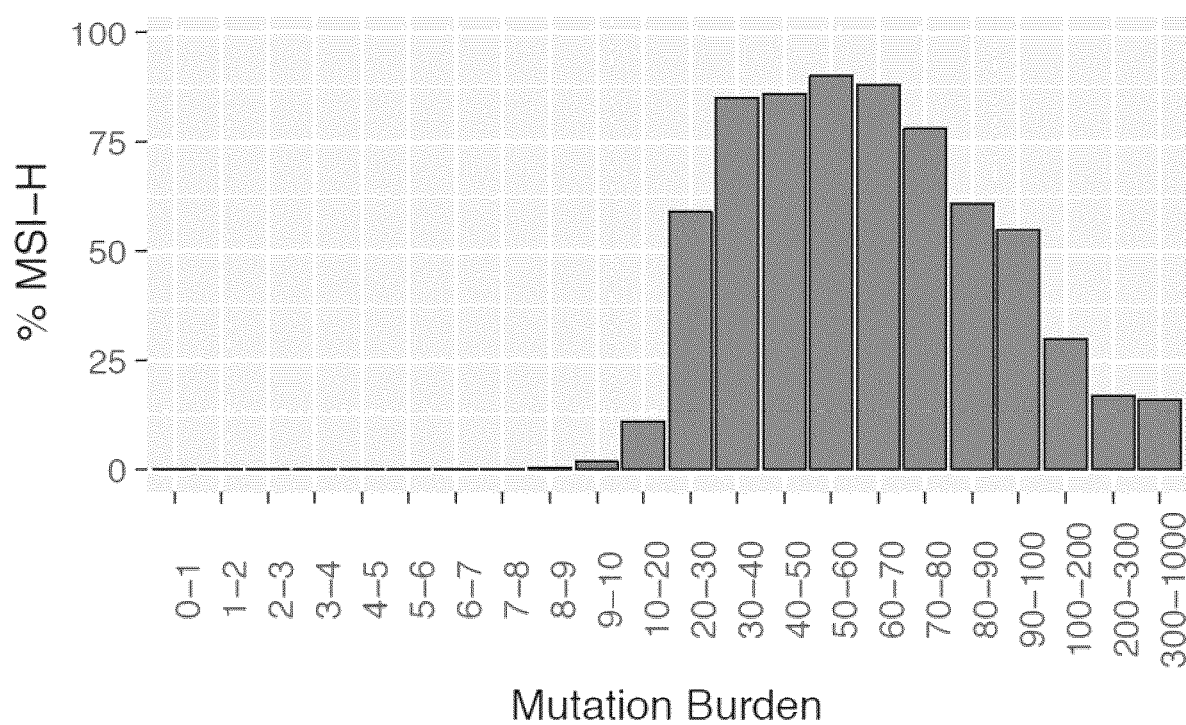
FIG. 16 depicts a barplot showing the percentage of MSI-H tumours out of all tumours at the respective mutation burden bin. MSI-H tumours concentrated in the 10-100 mutation burden range.
Figure 17:
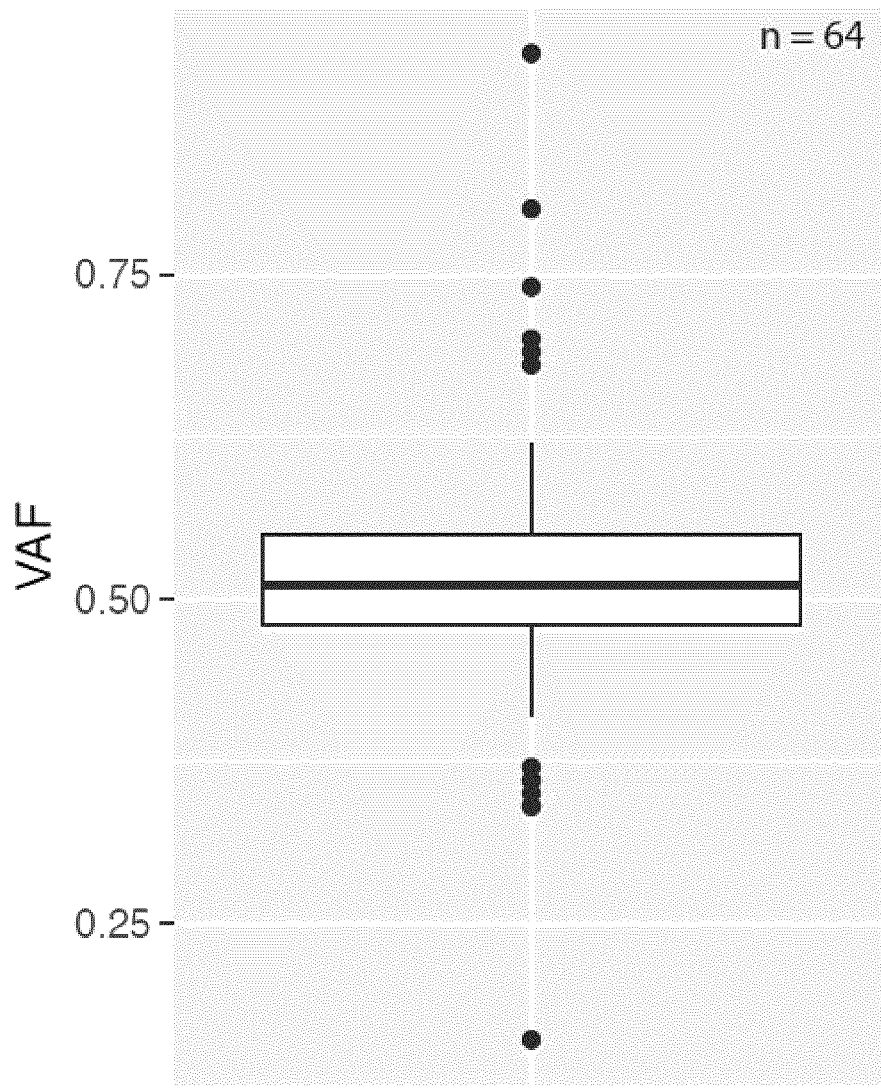
FIG. 17 depicts a boxplot showing the variant allele fraction of POLE R446Q mutation in 64 tumours. The majority of mutations clustered at 0.5, signifying that it is a germline SNP and not a hypermutation driver.
Figure 18:
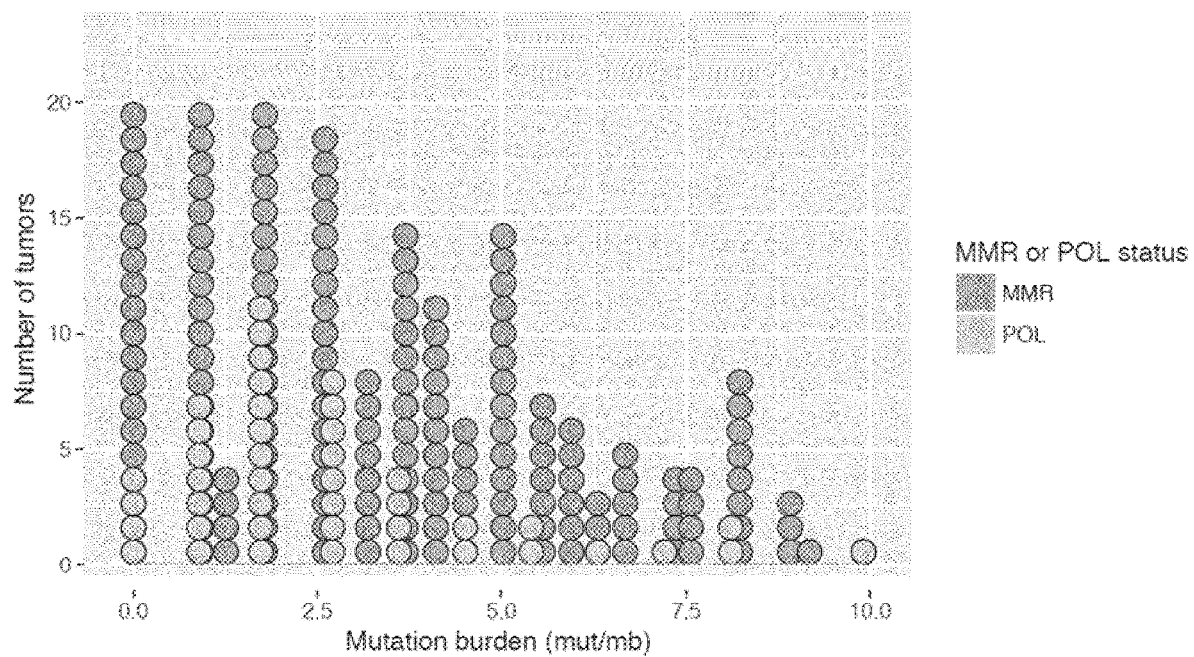
FIG. 18 shows that mutations in replication repair genes are randomly distributed and do not cluster around the hypermutation threshold further supporting that these specific alterations are passengers and not driving hypermutation.

These Results have Already Impacted the Management of Patients with Hypermutant Cancers We show that the evolutionary history of a cancer can be traced to the germline. This is a striking clinical implication, highlighted in FIGS. 14 and 15, showing a procedure for diagnosing cancer predisposition syndrome for a cohort of patients whose tumour sequence suggested an underlying germline mutation. This led us to contact the referring physicians and confirm the germline mutation. For these patients and their families, our results ultimately led to genetic testing and the following striking outcomes:

Immediate initiation of tumour surveillance and early tumour detection;

Suggestion of therapies to avoid. Children with hypermutant cancers should not be treated with common chemotherapies, such as alkylators and thioguanines, as their tumours are inherently resistant to those treatments (FIG. 5). This explains the poor survival of hypermutated childhood glioblastomas treated with temozolomide and leukemias treated with thioguanines. Thus, a better understanding of the evolutionary history of tumour development, as uniquely provided by our signature analysis, can impact patient management by ruling out specific therapies. As we have shown these signatures may arise late in tumour development, reflecting a recently acquired resistance mechanism;

Initiation of immune checkpoint inhibition therapy (FIG. 15). We now also describe the striking treatment response data for these same patients.

Taken together, these biological insights, which (1) reveal the causes of hypermutation in childhood cancer, (2) precisely define the key residues in the replicative polymerases that trigger hypermutation, (3) uncover a new classification scheme for replication repair deficient cancers, and (4) time the order of driver mutations, have extremely important clinical consequences. These data have already impacted the lives of multiple patients, who are now aware of their familial risk and are being seen by a genetic counselor, undergoing routine tumour surveillance, and are being offered rational therapy. Far from being a hypothetical clinical benefit, management for patients and families described in this manuscript has improved.

CONCLUSIONS

The landscape of hypermutation was analyzed using the DNA sequence of >81,000 adult and childhood cancers. This included individuals with hypermutation induced by chemotherapy, carcinogens, or established germline mutations. We uncovered common drivers of hypermutation across a wide range of tumour types, and identified clear driver mutations in recently described cancer genes—ultimately showing that these initiating events could be traced to the germline.

From these analyses of hypermutation across human cancer, several exciting observations emerged. These include:

The frequency of hypermutation is greater than previously appreciated, and extends to many new cancer types. We defined the first rational threshold for hyper and ultra-hypermutation in childhood and adult cancer. We found that nearly 1 in 20 childhood and 1 in 6 adults cancers are hypermutated across unexpected histotypes. This novel classification has immediate impact on patient stratification for clinical trials with immune checkpoint inhibition.

A precise definition of drivers in the DNA replicative polymerases, unveils key residues that trigger genome-wide hypermutation. Using hypermutation and signatures as a readout of replication-repair dysfunction, we built a model to validate driver mutations in the DNA polymerases. Specifically, we validated every known driver mutation in Polymerase and δ, from >3000 total reported variants, and found 11 new mutator residues.

1. The landscape of hypermutation across cancer reveals novel subgroups, showing that previous mutagen exposure can be inferred from the genome alone. Using unsupervised analyses, we grouped cancers into one of nine major categories. We discovered unexpected subgroupings—both within and between cancer types—such as ultra-hypermutated colorectal cancers that, strikingly, are microsatellite stable. We show that major mutagens, such as UV light and alkylators, act more broadly than previously thought.

2. The mutation signature is a robust readout of the life history of the tumour. Using nucleotide composition and subclonal analysis, we find that the order in which critical genes are mutated determines the mutational signature of the eventual tumour.

3. Identification of germline mutations can be determined from the cancer genome alone. Using this approach we identified patients with probable cancer susceptibility, then confirmed the presence of germline mutations after having contacted their physicians or families. This has already had clinically actionable relevance in terms of genetic counseling and cancer risk assessment to both patients and families.

Overall, our findings shed light on the extent and timing of common mechanisms for hyper-mutagenesis in human cancer. This data will immediately impact tumour classification for clinical trials and inform genetic testing and counselling.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

General References

Albertson, T. M., Ogawa, M., Bugni, J. M., Hays, L. E., Chen, Y., Wang, Y., Treuting, P. M., Heddle, J. A., Goldsby, R. E., and Preston, B. D. (2009). DNA polymerase epsilon and delta proofreading suppress discrete mutator and cancer phenotypes in mice. Proc Natl Acad Sci USA 106, 17101-17104.

Alexandrov, L. B., Nik-Zainal, S., Wedge, D. C., Aparicio, S. A., Behjati, S., Biankin, A. V., Bignell, G. R., Bolli, N., Borg, A., Borresen-Dale, A. L., et al. (2013). Signatures of mutational processes in human cancer. Nature 500, 415-421.

Amayiri, N., Tabori, U., Campbell, B., Bakry, D., Aronson, M., Durno, C., Rakopoulos, P., Malkin, D., Qaddoumi, I., Musharbash, A., et al. (2016). High frequency of mismatch repair deficiency among pediatric high grade gliomas in Jordan. Int J Cancer 138, 380-385.

Bouffet, E., Larouche, V., Campbell, B. B., Merico, D., de Borja, R., Aronson, M., Durno, C., Krueger, J., Cabric, V., Ramaswamy, V., et al. (2016). Immune Checkpoint Inhibition for Hypermutant Glioblastoma Multiforme Resulting From Germline Biallelic Mismatch Repair Deficiency. J Clin Oncol 34, 2206-2211.

Brohl, A. S., Solomon, D. A., Chang, W., Wang, J., Song, Y., Sindiri, S., Patidar, R., Hurd, L., Chen, L., Shern, J. F., et al. (2014). The genomic landscape of the Ewing Sarcoma family of tumours reveals recurrent STAG2 mutation. PLoS Genet 10, e1004475.

Campbell, J. D., Alexandrov, A., Kim, J., Wala, J., Berger, A. H., Pedamallu, C. S., Shukla, S. A., Guo, G., Brooks, A. N., Murray, B. A., et al. (2016). Distinct patterns of somatic genome alterations in lung adenocarcinomas and squamous cell carcinomas. Nat Genet 48, 607-616.

Cancer Genome Atlas, N. (2012). Comprehensive molecular characterization of human colon and rectal cancer. Nature 487, 330-337.

Cancer Genome Atlas, N. (2015). Genomic Classification of Cutaneous Melanoma. Cell 161, 1681-1696.

Cancer Genome Atlas Research, N. (2014). Comprehensive molecular characterization of urothelial bladder carcinoma. Nature 507, 315-322.

Daee, D. L., Mertz, T. M., and Shcherbakova, P. V. (2010). A cancer-associated DNA polymerase delta variant modeled in yeast causes a catastrophic increase in genomic instability. Proc Natl Acad Sci USA 107, 157-162.

Diaz, L. A., Jr., and Le, D. T. (2015). PD-1 Blockade in Tumours with Mismatch-Repair Deficiency. N Engl J Med 373, 1979.

Dossett, L. A., Harrington, M., Cruse, C. W., and Gonzalez, R. J. (2015). Cutaneous angiosarcoma. Curr Probl Cancer 39, 258-263.

Durno, C. A., Sherman, P. M., Aronson, M., Malkin, D., Hawkins, C., Bakry, D., Bouffet, E., Gallinger, S., Pollett, A., Campbell, B., et al. (2015). Phenotypic and genotypic characterisation of biallelic mismatch repair deficiency (BMMR-D) syndrome. Eur J Cancer.

Frampton, G. M., Fichtenholtz, A., Otto, G. A., Wang, K., Downing, S. R., He, J., Schnall-Levin, M., White, J., Sanford, E. M., An, P., et al. (2013). Development and validation of a clinical cancer genomic profiling test based on massively parallel DNA sequencing. Nat Biotechnol 31, 1023-1031.

Govindan, R., Ding, L., Griffith, M., Subramanian, J., Dees, N. D., Kanchi, K. L., Maher, C. A., Fulton, R., Fulton, L., Wallis, J., et al. (2012). Genomic landscape of non-small cell lung cancer in smokers and never-smokers. Cell 150, 1121-1134.

Herr, A. J., Ogawa, M., Lawrence, N. A., Williams, L. N., Eggington, J. M., Singh, M., Smith, R. A., and Preston, B. D. (2011). Mutator suppression and escape from replication error-induced extinction in yeast. PLoS Genet 7, e1002282.

Johanns, T. M., Miller, C. A., Dorward, I. G., Tsien, C., Chang, E., Perry, A., Uppaluri, R., Ferguson, C., Schmidt, R. E., Dahiya, S., et al. (2016). Immunogenomics of Hypermutated Glioblastoma: A Patient with Germline POLE Deficiency Treated with Checkpoint Blockade Immunotherapy. Cancer Discov 6, 1230-1236.

Kandoth, C., Schultz, N., Cherniack, A. D., Akbani, R., Liu, Y., Shen, H., Robertson, A. G., Pashtan, I., Shen, R., Benz, C. C., et al. (2013). Integrated genomic characterization of endometrial carcinoma. Nature 497, 67-73.

Kane, D. P., and Shcherbakova, P. V. (2014). A common cancer-associated DNA polymerase epsilon mutation causes an exceptionally strong mutator phenotype, indicating fidelity defects distinct from loss of proofreading. Cancer Res 74, 1895-1901.

Le, D. T., Uram, J. N., Wang, H., Bartlett, B. R., Kemberling, H., Eyring, A. D., Skora, A. D., Luber, B. S., Azad, N. S., Laheru, D., et al. (2015). PD-1 Blockade in Tumours with Mismatch-Repair Deficiency. N Engl J Med 372, 2509-2520.

Lek, M., Karczewski, K. J., Minikel, E. V., Samocha, K. E., Banks, E., Fennell, T., O'Donnell-Luria, A. H., Ware, J. S., Hill, A. J., Cummings, B. B., et al. (2016). Analysis of protein-coding genetic variation in 60,706 humans. Nature 536, 285-291.

Morganella, S., Alexandrov, L. B., Glodzik, D., Zou, X., Davies, H., Staaf, J., Sieuwerts, A. M., Brinkman, A. B., Martin, S., Ramakrishna, M., et al. (2016). The topography of mutational processes in breast cancer genomes. Nat Commun 7, 11383.

Network, C. G. A. (2012). Comprehensive molecular characterization of human colon and rectal cancer. Nature 487, 330-337.

Nguyen, S. A., Stechishin, O. D., Luchman, H. A., Lun, X. Q., Senger, D. L., Robbins, S. M., Cairncross, J. G., and Weiss, S. (2014). Novel MSH6 mutations in treatment-naive glioblastoma and anaplastic oligodendroglioma contribute to temozolomide resistance independently of MGMT promoter methylation. Clin Cancer Res 20, 4894-4903.

Nik-Zainal, S., Davies, H., Staaf, J., Ramakrishna, M., Glodzik, D., Zou, X., Martincorena, I., Alexandrov, L. B., Martin, S., Wedge, D. C., et al. (2016). Landscape of somatic mutations in 560 breast cancer whole-genome sequences. Nature 534, 47-54.

Pfeifer, G. P., You, Y. H., and Besaratinia, A. (2005). Mutations induced by ultraviolet light. Mutat Res 571, 19-31.

Pleasance, E. D., Stephens, P. J., O'Meara, S., McBride, D. J., Meynert, A., Jones, D., Lin, M. L., Beare, D., Lau, K.

W., Greenman, C., et al. (2010). A small-cell lung cancer genome with complex signatures of tobacco exposure. Nature 463, 184-190.

Poon, S. L., Pang, S. T., McPherson, J. R., Yu, W., Huang, K. K., Guan, P., Weng, W. H., Siew, E. Y., Liu, Y., Heng, H. L., et al. (2013). Genome-wide mutational signatures of aristolochic acid and its application as a screening tool. Sci Transl Med 5, 197ra101. Rizvi, N. A., Hellmann, M. D., Snyder, A., Kvistborg, P., Makarov, V., Havel, J. J., Lee, W., Yuan, J., Wong, P., Ho, T. S., et al. (2015). Cancer immunology. Mutational landscape determines sensitivity to PD-1 blockade in non-small cell lung cancer. Science 348, 124-128.

Roberts, S. A., Lawrence, M. S., Klimczak, L. J., Grimm, S. A., Fargo, D., Stojanov, P., Kiezun, A., Kryukov, G. V., Carter, S. L., Saksena, G., et al. (2013). An APOBEC cytidine deaminase mutagenesis pattern is widespread in human cancers. Nat Genet 45, 970-976.

Sage, E. (1993). Distribution and repair of photolesions in DNA: genetic consequences and the role of sequence context. Photochem Photobiol 57, 163-174.

Santin, A. D., Bellone, S., Buza, N., Choi, J., Schwartz, P. E., Schlessinger, J., and Lifton, R. P. (2016). Regression of Chemotherapy-Resistant Polymerase epsilon (POLE) Ultra-Mutated and MSH6 Hyper-Mutated Endometrial Tumours with Nivolumab. Clin Cancer Res 22, 5682-5687.

Scarpa, A., Chang, D. K., Nones, K., Corbo, V., Patch, A. M., Bailey, P., Lawlor, R. T., Johns, A. L., Miller, D. K., Mafficini, A., et al. (2017). Whole-genome landscape of pancreatic neuroendocrine tumours. Nature 543, 65-71.

Shinbrot, E., Henninger, E. E., Weinhold, N., Covington, K. R., Goksenin, A. Y., Schultz, N., Chao, H., Doddapaneni, H., Muzny, D. M., Gibbs, R. A., et al. (2014). Exonuclease mutations in DNA polymerase epsilon reveal replication strand specific mutation patterns and human origins of replication. Genome Res 24, 1740-1750.

Shlien, A., Campbell, B. B., de Borja, R., Alexandrov, L. B., Merico, D., Wedge, D., Van Loo, P., Tarpey, P. S., Coupland, P., Behjati, S., et al. (2015). Combined hereditary and somatic mutations of replication error repair genes result in rapid onset of ultra-hypermutated cancers. Nat Genet 47, 257-262.

Snyder, A., Makarov, V., Merghoub, T., Yuan, J., Zaretsky, J. M., Desrichard, A., Walsh, L. A., Postow, M. A., Wong, P., Ho, T. S., et al. (2014). Genetic basis for clinical response to CTLA-4 blockade in melanoma. N Engl J Med 371, 2189-2199.

Stratton, M. R., Campbell, P. J., and Futreal, P. A. (2009). The cancer genome. Nature 458, 719-724.

Swann, P. F., Waters, T. R., Moulton, D. C., Xu, Y. Z., Zheng, Q., Edwards, M., and Mace, R. (1996). Role of postreplicative DNA mismatch repair in the cytotoxic action of thioguanine. Science 273, 1109-1111.

Topalian, S. L., Taube, J. M., Anders, R. A., and Pardoll, D. M. (2016). Mechanism-driven biomarkers to guide immune checkpoint blockade in cancer therapy. Nat Rev Cancer 16, 275-287.

Van Allen, E. M., Miao, D., Schilling, B., Shukla, S. A., Blank, C., Zimmer, L., Sucker, A., Hillen, U., Geukes Foppen, M. H., Goldinger, S. M., et al. (2015). Genomic correlates of response to CTLA-4 blockade in metastatic melanoma. Science 350, 207-211.

van Thuijl, H. F., Mazor, T., Johnson, B. E., Fouse, S. D., Aihara, K., Hong, C., Malmström, A., Hallbeck, M., Heimans, J. J., Kloezeman, J. J., et al. (2015). Evolution of DNA repair defects during malignant progression of low-grade gliomas after temozolomide treatment. Acta Neuropathol.

Zahurancik, W. J., Klein, S. J., and Suo, Z. (2014). Significant contribution of the 3'-->5' exonuclease activity to the high fidelity of nucleotide incorporation catalyzed by human DNA polymerase. Nucleic Acids Res 42, 13853-13860.

Zhang, J., Nichols, K. E., and Downing, J. R. (2016). Germline Mutations in Predisposition Genes in Pediatric Cancer. N Engl J Med 374, 1391.

REFERENCES FOR METHODS

A. Shlien et al., Combined hereditary and somatic mutations of replication error repair genes result in rapid onset of ultra-hypermutated cancers. Nat Genet 47, 257-262 (2015).

H. F. van Thuijl et al., Evolution of DNA repair defects during malignant progression of low-grade gliomas after temozolomide treatment. Acta Neuropathol 129, 597-607 (2015).

G. M. Frampton et al., Development and validation of a clinical cancer genomic profiling test based on massively parallel DNA sequencing. Nat Biotechnol 31, 1023-1031 (2013).

V. M. R. Muggeo. Estimating regression models with unknown break-points. Statistics in Medicine 22, 3055-3071 (2003).

W. J. Zahurancik et al., Significant contribution of the 3'-*5' exonuclease activity to the high fidelity of nucleotide incorporation catalyzed by human DNA polymerase E. Nucleic Acids Research 42(22): 13853-13860 (2014).

R. Rosenthal, N. McGranahan, J. Herrero, B. S. Taylor, C. Swanton,

DeconstructSigs: delineating mutational processes in single tumours distinguishes DNA repair deficiencies and patterns of carcinoma evolution. Genome Biol 17, 31 (2016).

L. B. Alexandrov et al., Signatures of mutational processes in human cancer. Nature 500, 415-421 (2013).

C. A. Miller et al., SciClone: inferring clonal architecture and tracking the spatial and temporal patterns of tumour evolution. PLoS Comput Biol 10, e1003665 (2014).

All references referred to herein are expressly incorporated by reference in their entireties.

TABLE 4

Tumour samples analyzed using multiple platforms to demonstrate concordance in mutation burden.

| ID | Panel | WES | WGS | Mutation burden |
|---|---|---|---|---|
| S1 | X | X | X | Low |
| S2 | X | X | X | Medium |
| S3 | X | X | X | High |
| S4 | X | X | X | High |
| S5 | X | X | X | High |
| S6 | X | X | X | High |
| S7 | X | X | X | High |
| S8 | X | X | X | High |
| S9 | X | X | X | High |
| S10 | X | X | X | High |
| S11 | X | X | X | High |
| S12 | X | X | X | High |
| S13 | X | X | X | High |
| S14 | X | X | X | High |
| S15 | X | X | | Medium |
| S16 | X | X | | Medium |
| S17 | X | X | | Medium |

TABLE 4-continued

Tumour samples analyzed using multiple platforms to demonstrate concordance in mutation burden.

| ID | Panel | WES | WGS | Mutation burden |
|---|---|---|---|---|
| S18 | X | X | | Medium |
| S19 | X | X | | Medium |
| S20 | X | X | | Medium |
| S21 | X | X | | Low |
| S22 | X | X | | Low |
| S23 | X | X | | Low |
| S24 | X | X | | Low |
| S25 | X | X | | Low |
| S26 | X | X | | Low |
| S27 | X | X | | Low |
| S28 | X | X | | Low |
| S29 | X | X | | Low |
| S30 | X | X | | Low |
| S31 | X | X | | Low |
| S32 | X | X | | Low |
| S33 | X | X | | Low |
| S34 | X | X | | Low |
| S35 | X | X | | Low |

TABLE 5

All unique variants identified in POLE and POLD1 tested for driver ability Associated mutation burdens are representative for each variant

| | | |
|---|---|---|
| POLE | M1L | 2.7 |
| POLE | M1V | 0.9 |
| POLE | M1V | 17.1 |
| POLE | M1T | 0.9 |
| POLE | M1V | 3.6 |
| POLE | S2F | 4.5 |
| POLE | S2F | 15.3 |
| POLE | S2F | 7.2 |
| POLE | R4K | 52.3 |
| POLE | R4G | 0.9 |
| POLE | G6S | 1.8 |
| POLE | G6C | 20.7 |
| POLE | G6S | 1.8 |
| POLE | G6D | 2.7 |
| POLE | G6S | 0.9 |
| POLE | G7R | 1.8 |
| POLE | G7L | 6.3 |
| POLE | A11S | 1.8 |
| POLE | D12N | 12.6 |
| POLE | D12N | 4.5 |
| POLE | D12E | 0.9 |
| POLE | D12N | 5.4 |
| POLE | D12N | 27 |
| POLE | D12N | 18.9 |
| POLE | A15T | 17.1 |
| POLE | D16N | 14.4 |
| POLE | D16N | 27.9 |
| POLE | D16N | 7.2 |
| POLE | G17A | 2.7 |
| POLE | G17S | 53.2 |
| POLE | G17D | 68.5 |
| POLE | E18K | 29.7 |
| POLE | E18Q | 8.1 |
| POLE | E18* | 9 |
| POLE | E18K | 15.3 |
| POLE | E18K | 16.2 |
| POLE | E18K | 5.4 |
| POLE | E18* | 49.5 |
| POLE | E18* | 24.3 |
| POLE | E18Q | 36 |
| POLE | E18* | 29.7 |
| POLE | E18K | 12.6 |
| POLE | E18K | 42.3 |
| POLE | E18K | 21.6 |
| POLE | E18* | 44.1 |
| POLE | E18Q | 19.8 |
| POLE | E18K | 22.5 |
| POLE | E18Q | 12.6 |
| POLE | E18K | 5.4 |
| POLE | E18K | 5.4 |
| POLE | E18K | 27.9 |
| POLE | E18K | 17.1 |
| POLE | E18K | 14.4 |
| POLE | E18K | 6.3 |
| POLE | E18K | 6.3 |
| POLE | E18K | 5.4 |
| POLE | E18K | 11.7 |

TABLE 5-continued

All unique variants identified in POLE and POLD1 tested for driver ability
Associated mutation burdens are representative for each variant

| | | |
|---|---|---|
| POLE | A19D | 5.4 |
| POLE | S20I | 109 |
| POLE | R21G | 29.7 |
| POLE | D23G | 4.5 |
| POLE | D23N | 2.7 |
| POLE | D23G | 6.3 |
| POLE | D23G | 4.5 |
| POLE | D23N | 33.3 |
| POLE | A25S | 1.8 |
| POLE | A25V | 132.4 |
| POLE | A25T | 0 |
| POLE | A25S | 0.9 |
| POLE | S27F | 18 |
| POLE | S27F | 11.7 |
| POLE | S28* | 25.2 |
| POLE | S28L | 9 |
| POLE | S28* | 20.7 |
| POLE | S28L | 6.3 |
| POLE | V29D | 0.9 |
| POLE | S30L | 45.9 |
| POLE | S30* | 5.4 |
| POLE | S30L | 7.2 |
| POLE | S30L | 521.6 |
| POLE | S30L | 703.6 |
| POLE | S30L | 0 |
| POLE | L32R | 2.7 |
| POLE | L32R | 5.4 |
| POLE | R34C | 7.2 |
| POLE | R34L | 0.9 |
| POLE | R34H | 13.5 |
| POLE | R34C | 64.9 |
| POLE | R34L | 1.8 |
| POLE | L35Q | 18.9 |
| POLE | L35Q | 1.8 |
| POLE | R37P | 5.4 |
| POLE | R37Q | 106.3 |
| POLE | R37W | 3.6 |
| POLE | R37Q | 12.6 |
| POLE | R37Q | 17.1 |
| POLE | R37W | 44.1 |
| POLE | R37Q | 44.1 |
| POLE | S38N | 5.4 |
| POLE | S38N | 2.7 |
| POLE | S38N | 8.1 |
| POLE | S38C | 2.7 |
| POLE | S38C | 3.6 |
| POLE | S38R | 0.9 |
| POLE | Q39K | 753.2 |
| POLE | W40C | 12.6 |
| POLE | D42V | 3.6 |
| POLE | D42V | 0 |
| POLE | D42N | 320.7 |
| POLE | D42V | 1.8 |
| POLE | D42V | 2.7 |
| POLE | K43N | 16.2 |
| POLE | M44I | 43.2 |
| POLE | M44V | 5.4 |
| POLE | D45N | 99.1 |
| POLE | R47L | 9 |
| POLE | R47Q | 4.5 |
| POLE | R47L | 17.1 |
| POLE | R47Q | 12.6 |
| POLE | R47Q | 4.5 |
| POLE | G49D | 9.9 |
| POLE | E51Q | 21.6 |
| POLE | R52L | 33.3 |
| POLE | R52L | 38.7 |
| POLE | P56L | 47.7 |
| POLE | P56S | 753.2 |
| POLE | G57V | 13.5 |
| POLE | K59N | 9 |
| POLE | K59N | 11.7 |
| POLE | G61D | 5.4 |
| POLE | W62C | 5.4 |
| POLE | W62* | 8.1 |
| POLE | W62C | 53.2 |
| POLE | I64V | 58.6 |

TABLE 5-continued

All unique variants identified in POLE and POLD1 tested for driver ability
Associated mutation burdens are representative for each variant

| | | |
|---|---|---:|
| POLE | M66I | 10.8 |
| POLE | P68A | 16.2 |
| POLE | P68T | 19.8 |
| POLE | P68L | 209.9 |
| POLE | P68S | 10.8 |
| POLE | T69S | 6.3 |
| POLE | E70K | 12.6 |
| POLE | E70K | 6.3 |
| POLE | I71M | 227.9 |
| POLE | I71V | 49.5 |
| POLE | D73G | 2.7 |
| POLE | E74K | 18 |
| POLE | E74K | 36.9 |
| POLE | D75E | 3.6 |
| POLE | K76M | 34.2 |
| POLE | R77C | 69.4 |
| POLE | R77C | 9 |
| POLE | R77L | 9.9 |
| POLE | R77C | 1.8 |
| POLE | G79V | 2.7 |
| POLE | S80N | 5.4 |
| POLE | A81T | 1.8 |
| POLE | A81S | 60.4 |
| POLE | A81T | 34.2 |
| POLE | V82L | 3.6 |
| POLE | D83N | 85.6 |
| POLE | D83Y | 39.6 |
| POLE | Y84C | 0.9 |
| POLE | Y84H | 22.5 |
| POLE | I87V | 3.6 |
| POLE | I87V | 9 |
| POLE | D89A | 7.2 |
| POLE | D89A | 3.6 |
| POLE | D90Y | 36 |
| POLE | D90N | 5.4 |
| POLE | G91R | 0.9 |
| POLE | G91R | 2.7 |
| POLE | G91E | 3.6 |
| POLE | G91E | 5.4 |
| POLE | G91E | 0 |
| POLE | G91E | 4.5 |
| POLE | G91R | 2.7 |
| POLE | G91E | 6.3 |
| POLE | G91E | 3.6 |
| POLE | G91E | 2.7 |
| POLE | S92G | 2.7 |
| POLE | F94Y | 89.2 |
| POLE | F94C | 10.8 |
| POLE | K95N | 78.4 |
| POLE | K95N | 9.9 |
| POLE | A97T | 4.5 |
| POLE | A97G | 3.6 |
| POLE | K101I | 1.8 |
| POLE | K101R | 3.6 |
| POLE | K101E | 7.2 |
| POLE | P102L | 38.7 |
| POLE | P102S | 147.7 |
| POLE | F104L | 608.02 |
| POLE | F104L | 37.8 |
| POLE | F104L | 8.1 |
| POLE | F104I | 9.9 |
| POLE | Y105F | 6.3 |
| POLE | Y105F | 7.2 |
| POLE | Y105F | 14.4 |
| POLE | A107V | 541.36 |
| POLE | A107V | 608.02 |
| POLE | A107V | 409.18 |
| POLE | A107V | 41.4 |
| POLE | A107V | 3.6 |
| POLE | A107V | 26.1 |
| POLE | A107V | 238.7 |
| POLE | A107S | 43.2 |
| POLE | A107V | 27.9 |
| POLE | R109T | 24.3 |
| POLE | R109K | 18 |
| POLE | R109T | 41.4 |
| POLE | E113* | 19.8 |

TABLE 5-continued

All unique variants identified in POLE and POLD1 tested for driver ability
Associated mutation burdens are representative for each variant

| | | |
|---|---|---:|
| POLE | E113D | 29.7 |
| POLE | E113* | 6.3 |
| POLE | R114Q | 1.8 |
| POLE | R114* | 0 |
| POLE | R114Q | 0.9 |
| POLE | R114* | 3.6 |
| POLE | E115K | 155 |
| POLE | E115K | 409 |
| POLE | E115K | 0 |
| POLE | V116I | 6.3 |
| POLE | V116A | 65.8 |
| POLE | S118Y | 117.1 |
| POLE | F119S | 4.5 |
| POLE | F119L | 2.7 |
| POLE | F119L | 4.5 |
| POLE | F119L | 6.3 |
| POLE | L120V | 19.8 |
| POLE | L120V | 0 |
| POLE | K122E | 21.6 |
| POLE | K122N | 23.4 |
| POLE | K122N | 224.3 |
| POLE | K122N | 19.8 |
| POLE | K123N | 45.9 |
| POLE | Q125P | 8.1 |
| POLE | Q125* | 47.7 |
| POLE | Q125* | 26.1 |
| POLE | Q125H | 22.5 |
| POLE | Q125* | 73 |
| POLE | K127I | 82 |
| POLE | A129T | 3.6 |
| POLE | K130E | 13.5 |
| POLE | V131L | 8.1 |
| POLE | V131L | 0 |
| POLE | V131L | 10.8 |
| POLE | V131L | 14.4 |
| POLE | V131L | 0.9 |
| POLE | E132Q | 32.4 |
| POLE | V134I | 4.5 |
| POLE | P135S | 296 |
| POLE | P135S | 3.6 |
| POLE | P135S | 0 |
| POLE | P135S | 8.1 |
| POLE | K136R | 4.5 |
| POLE | E137K | 4.5 |
| POLE | E137Q | 38.7 |
| POLE | D138G | 3.6 |
| POLE | D138E | 4.5 |
| POLE | D138E | 72.1 |
| POLE | L139V | 35.1 |
| POLE | P142Q | 112.6 |
| POLE | P142L | 57.7 |
| POLE | N143S | 3.6 |
| POLE | N143D | 20.7 |
| POLE | N143H | 0 |
| POLE | H144L | 7.2 |
| POLE | L145F | 9 |
| POLE | G147V | 13.5 |
| POLE | G147C | 7.2 |
| POLE | G147V | 0 |
| POLE | L148F | 0.9 |
| POLE | L148F | 20.7 |
| POLE | K149R | 35.1 |
| POLE | K149R | 3.6 |
| POLE | R150* | 20.7 |
| POLE | R150Q | 245.9 |
| POLE | R150* | 0.9 |
| POLE | R150* | 117.1 |
| POLE | I153M | 10.8 |
| POLE | I153M | 2.7 |
| POLE | T159A | 14.4 |
| POLE | E161* | 37.8 |
| POLE | V164F | 1.8 |
| POLE | K165R | 16.2 |
| POLE | R167K | 11.7 |
| POLE | R167W | 26.1 |
| POLE | R167T | 8.1 |
| POLE | E169D | 21.6 |

TABLE 5-continued

All unique variants identified in POLE and POLD1 tested for driver ability
Associated mutation burdens are representative for each variant

| | | |
|---|---|---|
| POLE | E169G | 69.4 |
| POLE | I170M | 11.7 |
| POLE | S171F | 16.2 |
| POLE | P172L | 62.2 |
| POLE | P172S | 39.6 |
| POLE | V174M | 11.7 |
| POLE | V174L | 29.7 |
| POLE | V174L | 1.8 |
| POLE | V174L | 31.5 |
| POLE | N177S | 1.8 |
| POLE | N177S | 3.6 |
| POLE | R178M | 3.6 |
| POLE | E179G | 2.7 |
| POLE | H182R | 36 |
| POLE | H182Y | 130.6 |
| POLE | S184I | 29.7 |
| POLE | D185N | 4.5 |
| POLE | D185N | 22.5 |
| POLE | D185N | 5.4 |
| POLE | D185N | 13.5 |
| POLE | D185N | 3.6 |
| POLE | D185N | 6.3 |
| POLE | D185G | 41.4 |
| POLE | D185N | 30.6 |
| POLE | A186T | 5.4 |
| POLE | A186V | 1.8 |
| POLE | A186T | 2.7 |
| POLE | Y187* | 4.5 |
| POLE | Y187C | 10.8 |
| POLE | S192F | 38.7 |
| POLE | S192F | 7.2 |
| POLE | S193G | 2.7 |
| POLE | S193G | 4.5 |
| POLE | S193G | 3.6 |
| POLE | Q196H | 46.8 |
| POLE | Q196H | 3.6 |
| POLE | Q196H | 0 |
| POLE | R197S | 26.1 |
| POLE | G198S | 3.6 |
| POLE | G198S | 7.2 |
| POLE | G198C | 0.9 |
| POLE | G199C | 13.5 |
| POLE | G199C | 10.8 |
| POLE | V200I | 2.7 |
| POLE | I201T | 2.7 |
| POLE | I201T | 9.9 |
| POLE | T202I | 2.7 |
| POLE | E204K | 18.9 |
| POLE | E205Q | 36 |
| POLE | E206K | 115.3 |
| POLE | T207I | 386.5 |
| POLE | S208C | 9 |
| POLE | K209N | 3.6 |
| POLE | I211T | 2.7 |
| POLE | I211T | 4.5 |
| POLE | I211M | 8.1 |
| POLE | A212P | 12.6 |
| POLE | D216N | 6.3 |
| POLE | D216G | 2.7 |
| POLE | N217H | 8.1 |
| POLE | V219M | 1.8 |
| POLE | M221T | 18 |
| POLE | M221T | 2.7 |
| POLE | M221T | 4.5 |
| POLE | R222H | 19.8 |
| POLE | R222S | 0 |
| POLE | R222C | 71.2 |
| POLE | R222H | 3.6 |
| POLE | E223K | 62.2 |
| POLE | E223K | 6.3 |
| POLE | Y224* | 479.3 |
| POLE | Y224F | 93.7 |
| POLE | D225H | 18.9 |
| POLE | D225N | 40.5 |
| POLE | V226I | 27.9 |
| POLE | P227S | 82 |
| POLE | P227S | 140.5 |

TABLE 5-continued

All unique variants identified in POLE and POLD1 tested for driver ability
Associated mutation burdens are representative for each variant

| | | |
|---|---|---:|
| POLE | P227L | 91 |
| POLE | P227L | 2.7 |
| POLE | P227S | 38.7 |
| POLE | P227S | 634.2 |
| POLE | Y228C | 17.1 |
| POLE | H229Y | 5.4 |
| POLE | H229P | 3.6 |
| POLE | R231L | 5.4 |
| POLE | S233F | 636.9 |
| POLE | I234V | 1.8 |
| POLE | K237R | 0.9 |
| POLE | K237R | 13.5 |
| POLE | K237R | 9 |
| POLE | K237R | 9.9 |
| POLE | K237R | 6.3 |
| POLE | I238N | 180.2 |
| POLE | H239Y | 119.8 |
| POLE | V240M | 7.2 |
| POLE | V240M | 67.6 |
| POLE | V240M | 6.3 |
| POLE | R249* | 130.6 |
| POLE | R249L | 33.3 |
| POLE | R249Q | 12.6 |
| POLE | R249P | 18 |
| POLE | G250E | 4.5 |
| POLE | G250E | 9 |
| POLE | G250* | 7.2 |
| POLE | G250E | 52.3 |
| POLE | G250E | 8.1 |
| POLE | N251Y | 7.2 |
| POLE | N251Y | 3.6 |
| POLE | F253L | 7.2 |
| POLE | F253S | 1.8 |
| POLE | P254L | 3.6 |
| POLE | P254L | 0.9 |
| POLE | P254L | 14.4 |
| POLE | P254L | 76.6 |
| POLE | V255I | 17.1 |
| POLE | E256K | 101.8 |
| POLE | I257T | 5.4 |
| POLE | T258N | 9.9 |
| POLE | R259C | 9 |
| POLE | R259C | 9.9 |
| POLE | R259C | 0.9 |
| POLE | R259C | 10.8 |
| POLE | R259C | 0.9 |
| POLE | R260P | 38.7 |
| POLE | R260* | 15.3 |
| POLE | R260L | 20.7 |
| POLE | D261N | 9.9 |
| POLE | D262H | 2.7 |
| POLE | D262H | 0.9 |
| POLE | L263I | 4.5 |
| POLE | R266* | 3.6 |
| POLE | R266Q | 104.5 |
| POLE | R266Q | 3.6 |
| POLE | R266P | 5.4 |
| POLE | D268N | 63.1 |
| POLE | D268N | 3.6 |
| POLE | V271I | 5.4 |
| POLE | V271I | 10.8 |
| POLE | V271I | 227.9 |
| POLE | V271I | 2.7 |
| POLE | F274S | 1.8 |
| POLE | D275V | 43.2 |
| POLE | D275V | 17.1 |
| POLE | D275A | 226.1 |
| POLE | D275G | 318.9 |
| POLE | T278M | 12.6 |
| POLE | T278M | 68.5 |
| POLE | T278M | 2.7 |
| POLE | T278M | 37.8 |
| POLE | T278N | 39.6 |
| POLE | K280N | 4.5 |
| POLE | P286R | 259.5 |
| POLE | P286R | 493.7 |
| POLE | P286R | 479.3 |

TABLE 5-continued

All unique variants identified in POLE and POLD1 tested for driver ability
Associated mutation burdens are representative for each variant

| | | |
|---|---|---|
| POLE | P286R | 394.6 |
| POLE | P286R | 227.9 |
| POLE | P286R | 162.2 |
| POLE | P286R | 305.4 |
| POLE | P286R | 123.4 |
| POLE | P286R | 145.9 |
| POLE | P286S | 42.3 |
| POLE | P286R | 133.3 |
| POLE | P286R | 342.3 |
| POLE | P286R | 450.5 |
| POLE | P286R | 216.2 |
| POLE | P286S | 58.6 |
| POLE | P286R | 245 |
| POLE | P286R | 223.4 |
| POLE | P286R | 155 |
| POLE | P286R | 153.2 |
| POLE | P286R | 84.7 |
| POLE | P286R | 168.5 |
| POLE | P286R | 163.1 |
| POLE | P286R | 80.2 |
| POLE | P286R | 100.9 |
| POLE | P286R | 203.6 |
| POLE | P286R | 226.1 |
| POLE | P286R | 172.1 |
| POLE | P286R | 208.1 |
| POLE | P286R | 62.2 |
| POLE | P286H | 212 |
| POLE | D287N | 2.7 |
| POLE | D287N | 30.6 |
| POLE | A288V | 155.9 |
| POLE | A288V | 578.4 |
| POLE | A288V | 386.5 |
| POLE | E289* | 24.3 |
| POLE | D291Y | 71.2 |
| POLE | Q292K | 1.8 |
| POLE | M294I | 32.4 |
| POLE | M294I | 17.1 |
| POLE | M294I | 0 |
| POLE | M295I | 180.2 |
| POLE | I296V | 7.2 |
| POLE | S297F | 218 |
| POLE | S297F | 386.5 |
| POLE | S297F | 39.6 |
| POLE | S297F | 115.3 |
| POLE | Y298C | 7.2 |
| POLE | Y298C | 99.1 |
| POLE | M299V | 0 |
| POLE | M299V | 9 |
| POLE | I300N | 9.9 |
| POLE | I300F | 14.4 |
| POLE | D301G | 3.6 |
| POLE | D301G | 4.5 |
| POLE | G302D | 48.6 |
| POLE | Q303H | 311.7 |
| POLE | G304S | 179.3 |
| POLE | Y305F | 77.5 |
| POLE | Y305F | 98.2 |
| POLE | L306F | 226.1 |
| POLE | I307L | 14.4 |
| POLE | N309S | 2.7 |
| POLE | N309S | 18 |
| POLE | R310S | 8.1 |
| POLE | E311D | 10.8 |
| POLE | I312T | 12.6 |
| POLE | V313I | 6.3 |
| POLE | S314* | 5.4 |
| POLE | S314* | 5.4 |
| POLE | S314* | 18.9 |
| POLE | D316V | 6.3 |
| POLE | D316N | 4.5 |
| POLE | I317V | 10.8 |
| POLE | E318K | 9.9 |
| POLE | D319H | 4.5 |
| POLE | F320C | 1.8 |
| POLE | F320L | 7.2 |
| POLE | F322L | 20.7 |
| POLE | T323P | 134.2 |

TABLE 5-continued

All unique variants identified in POLE and POLD1 tested for driver ability
Associated mutation burdens are representative for each variant

| | | |
|---|---|---|
| POLE | T323A | 168.5 |
| POLE | P324L | 17.1 |
| POLE | P324F | 92.8 |
| POLE | K325* | 9 |
| POLE | E327V | 433 |
| POLE | Y328C | 0 |
| POLE | Y328C | 0.9 |
| POLE | G330A | 0 |
| POLE | C333F | 9.9 |
| POLE | F335S | 636.9 |
| POLE | E337K | 5.4 |
| POLE | D339V | 0 |
| POLE | D339V | 15.3 |
| POLE | D339V | 6.3 |
| POLE | D339V | 3.6 |
| POLE | E340D | 42.3 |
| POLE | E340K | 139.6 |
| POLE | A341P | 0.9 |
| POLE | A341T | 236 |
| POLE | A341P | 15.3 |
| POLE | H342Y | 11.7 |
| POLE | L343V | 7.2 |
| POLE | L343V | 4.5 |
| POLE | Q345* | 206.3 |
| POLE | Q345* | 95.5 |
| POLE | Q345* | 226.1 |
| POLE | W347C | 2.7 |
| POLE | W347C | 4.5 |
| POLE | W347S | 45.9 |
| POLE | W347C | 4.5 |
| POLE | E349Q | 12.6 |
| POLE | E349K | 7.2 |
| POLE | E349Q | 13.5 |
| POLE | V351I | 46.8 |
| POLE | V351F | 4.5 |
| POLE | V351F | 3.6 |
| POLE | V351I | 6.3 |
| POLE | V351I | 6.3 |
| POLE | V351I | 0.9 |
| POLE | V351F | 34.2 |
| POLE | V351I | 0.9 |
| POLE | V351I | 4.5 |
| POLE | V351I | 2.7 |
| POLE | Q352P | 5.4 |
| POLE | Q352P | 4.5 |
| POLE | E353D | 6.3 |
| POLE | T357I | 17.1 |
| POLE | I358N | 4.5 |
| POLE | M359I | 14.4 |
| POLE | T361P | 4.5 |
| POLE | T361A | 3.6 |
| POLE | Y362C | 5.4 |
| POLE | Y362C | 7.2 |
| POLE | G364V | 26.1 |
| POLE | G364R | 9 |
| POLE | G364W | 21.6 |
| POLE | D365N | 5.4 |
| POLE | F366C | 0.9 |
| POLE | F366L | 208.1 |
| POLE | F367L | 238.18 |
| POLE | F367L | 472.56 |
| POLE | D368N | 36 |
| POLE | F371L | 3.6 |
| POLE | E373D | 2.7 |
| POLE | A374G | 7.2 |
| POLE | R375Q | 1.8 |
| POLE | R375L | 10.8 |
| POLE | R375W | 16.2 |
| POLE | R375Q | 0 |
| POLE | R375Q | 2.7 |
| POLE | R375W | 0.9 |
| POLE | H379Y | 63.1 |
| POLE | G380S | 3.6 |
| POLE | G380C | 16.2 |
| POLE | G380C | 19.8 |
| POLE | G380S | 2.7 |
| POLE | G380S | 3.6 |

TABLE 5-continued

All unique variants identified in POLE and POLD1 tested for driver ability
Associated mutation burdens are representative for each variant

| Gene | Variant | Value |
|---|---|---|
| POLE | S382N | 1.8 |
| POLE | S382T | 4.5 |
| POLE | S382N | 4.5 |
| POLE | M383V | 1.8 |
| POLE | M383L | 6.3 |
| POLE | Q385H | 6.3 |
| POLE | Q385L | 31.5 |
| POLE | E386K | 9.9 |
| POLE | E386K | 11.7 |
| POLE | E386K | 1.8 |
| POLE | G388D | 5.4 |
| POLE | Q390* | 92.8 |
| POLE | Q390* | 11.7 |
| POLE | D392G | 59.5 |
| POLE | D392Y | 9.9 |
| POLE | S393I | 11.7 |
| POLE | S393N | 11.7 |
| POLE | Q394K | 26.1 |
| POLE | Q394R | 2.7 |
| POLE | G395R | 2.7 |
| POLE | G395V | 10.8 |
| POLE | E396Q | 0.9 |
| POLE | E396D | 35.1 |
| POLE | E396K | 55.9 |
| POLE | Y397* | 7.2 |
| POLE | K398R | 25.2 |
| POLE | A399V | 107.2 |
| POLE | A399V | 21.6 |
| POLE | A399G | 8.1 |
| POLE | P400L | 116.2 |
| POLE | Q401H | 3.6 |
| POLE | Q401* | 17.1 |
| POLE | C402F | 123.4 |
| POLE | D406E | 69.4 |
| POLE | C407Y | 2.7 |
| POLE | L408F | 108.1 |
| POLE | L408F | 131.5 |
| POLE | R409S | 37.8 |
| POLE | V411L | 699 |
| POLE | V411L | 77.5 |
| POLE | V411L | 45 |
| POLE | V411L | 39.6 |
| POLE | V411L | 500 |
| POLE | V411L | 104.5 |
| POLE | V411L | 136 |
| POLE | V411L | 371.2 |
| POLE | V411L | 578.4 |
| POLE | V411L | 345.9 |
| POLE | V411L | 315.3 |
| POLE | V411L | 100 |
| POLE | V411L | 238.7 |
| POLE | V411L | 120.7 |
| POLE | V411L | 301.8 |
| POLE | V411L | 636.9 |
| POLE | V411L | 703.6 |
| POLE | V411L | 650.5 |
| POLE | V411L | 245.9 |
| POLE | V411L | 116.2 |
| POLE | V411L | 279.3 |
| POLE | V411L | 309.9 |
| POLE | V411L | 360.4 |
| POLE | V411L | 187.4 |
| POLE | V411L | 105.4 |
| POLE | V411L | 240.5 |
| POLE | V411L | 324.3 |
| POLE | K412N | 9.9 |
| POLE | K412N | 7.2 |
| POLE | R413K | 95.5 |
| POLE | D414G | 155 |
| POLE | S415I | 19.8 |
| POLE | S415N | 668.5 |
| POLE | S415G | 1.8 |
| POLE | P418S | 71.2 |
| POLE | P418L | 9 |
| POLE | V419G | 309.9 |
| POLE | G420S | 12.6 |
| POLE | G420D | 6.3 |

TABLE 5-continued

All unique variants identified in POLE and POLD1 tested for driver ability
Associated mutation burdens are representative for each variant

| | | |
|---|---|---|
| POLE | G420D | 122.5 |
| POLE | G420C | 14.4 |
| POLE | H422Y | 5.4 |
| POLE | H422R | 10.8 |
| POLE | H422Y | 4.5 |
| POLE | H422Y | 17.1 |
| POLE | H422Y | 1.8 |
| POLE | L424I | 336 |
| POLE | L424I | 336 |
| POLE | L424P | 590 |
| POLE | L424I | 47.7 |
| POLE | L424V | 3.6 |
| POLE | L424I | 160.4 |
| POLE | L424F | 0.9 |
| POLE | L424I | 154.1 |
| POLE | L424F | 6.3 |
| POLE | L424V | 91.9 |
| POLE | L424V | 4.5 |
| POLE | L424V | 19.8 |
| POLE | L424V | 3.6 |
| POLE | L424H | 9.9 |
| POLE | L424V | 5.4 |
| POLE | L424V | 6.3 |
| POLE | K425R | 5.4 |
| POLE | K425R | 135.1 |
| POLE | K425R | 1.8 |
| POLE | K425R | 6.3 |
| POLE | A426V | 333.3 |
| POLE | A426V | 5.4 |
| POLE | A427S | 12.6 |
| POLE | A427V | 56.8 |
| POLE | A427V | 0 |
| POLE | A427V | 4.5 |
| POLE | K431N | 14.4 |
| POLE | P436S | 302 |
| POLE | P436H | 541.36 |
| POLE | P436S | 318.06 |
| POLE | P436H | 532 |
| POLE | P436H | 532 |
| POLE | P436H | 409.18 |
| POLE | P436H | 359 |
| POLE | P436S | 433 |
| POLE | P436S | 195 |
| POLE | P436S | 333.3 |
| POLE | P436T | 5.4 |
| POLE | P436L | 67.6 |
| POLE | P436R | 493.7 |
| POLE | P436L | 36 |
| POLE | P436L | 69.4 |
| POLE | V437M | 6.3 |
| POLE | V437M | 2.7 |
| POLE | V437M | 12.6 |
| POLE | E438K | 46.8 |
| POLE | L439P | 9 |
| POLE | D440N | 2.7 |
| POLE | P441L | 2.7 |
| POLE | P441L | 29.7 |
| POLE | P441L | 7.2 |
| POLE | M444K | 91.9 |
| POLE | M444K | 116.2 |
| POLE | M444K | 32.4 |
| POLE | R446Q | 4.5 |
| POLE | R446Q | 0 |
| POLE | R446Q | 7.2 |
| POLE | R446Q | 1.8 |
| POLE | R446Q | 1.8 |
| POLE | R446Q | 13.5 |
| POLE | R446Q | 5.4 |
| POLE | R446Q | 3.6 |
| POLE | R446Q | 8.1 |
| POLE | R446Q | 2.7 |
| POLE | R446Q | 0.9 |
| POLE | R446Q | 9 |
| POLE | R446W | 8.1 |
| POLE | R446Q | 0.9 |
| POLE | R446Q | 7.2 |
| POLE | R446Q | 15.3 |

TABLE 5-continued

All unique variants identified in POLE and POLD1 tested for driver ability
Associated mutation burdens are representative for each variant

| Gene | Variant | Value |
|---|---|---|
| POLE | R446W | 1.8 |
| POLE | R446Q | 4.5 |
| POLE | R446Q | 0 |
| POLE | R446Q | 4.5 |
| POLE | R446Q | 1.8 |
| POLE | R446Q | 5.4 |
| POLE | R446Q | 1.8 |
| POLE | R446Q | 1.8 |
| POLE | R446Q | 3.6 |
| POLE | R446Q | 2.7 |
| POLE | R446Q | 1.8 |
| POLE | R446Q | 4.5 |
| POLE | R446Q | 0 |
| POLE | R446Q | 27.9 |
| POLE | R446Q | 92.8 |
| POLE | R446Q | 5.4 |
| POLE | R446Q | 1.8 |
| POLE | R446Q | 4.5 |
| POLE | R446Q | 0.9 |
| POLE | R446Q | 32.4 |
| POLE | R446Q | 2.7 |
| POLE | R446Q | 2.7 |
| POLE | R446Q | 13.5 |
| POLE | R446Q | 2.7 |
| POLE | R446Q | 21.6 |
| POLE | R446Q | 6.3 |
| POLE | R446Q | 3.6 |
| POLE | R446Q | 3.6 |
| POLE | R446Q | 3.6 |
| POLE | R446Q | 23.4 |
| POLE | R446Q | 0.9 |
| POLE | R446Q | 4.5 |
| POLE | R446Q | 4.5 |
| POLE | R446Q | 21.6 |
| POLE | R446Q | 4.5 |
| POLE | R446Q | 8.1 |
| POLE | R446Q | 1.8 |
| POLE | R446Q | 5.4 |
| POLE | R446Q | 2.7 |
| POLE | R446Q | 1.8 |
| POLE | R446Q | 9.9 |
| POLE | R446Q | 2.7 |
| POLE | R446Q | 6.3 |
| POLE | M447V | 10.8 |
| POLE | M447I | 9 |
| POLE | A448V | 213.5 |
| POLE | T449M | 9.9 |
| POLE | T449M | 3.6 |
| POLE | T449M | 3.6 |
| POLE | E450K | 665.8 |
| POLE | P452T | 9.9 |
| POLE | Q453R | 22.5 |
| POLE | Q453E | 11.7 |
| POLE | Q453E | 2.7 |
| POLE | Q453E | 5.4 |
| POLE | Q453E | 20.7 |
| POLE | Q453E | 7.2 |
| POLE | Q453* | 0.9 |
| POLE | Q453R | 8.1 |
| POLE | Q453E | 3.6 |
| POLE | A456P | 33.3 |
| POLE | A456P | 226.1 |
| POLE | A456S | 6.3 |
| POLE | A456P | 200 |
| POLE | A456P | 233.3 |
| POLE | A456P | 69.4 |
| POLE | A456P | 314.4 |
| POLE | A456P | 373.9 |
| POLE | Y458H | 85.02 |
| POLE | Y458H | 342 |
| POLE | Y458C | 13.5 |
| POLE | Y458C | 753.2 |
| POLE | S459F | 295 |
| POLE | S459F | 102.7 |
| POLE | S459F | 311.7 |
| POLE | S459F | 36.9 |
| POLE | S459F | 146.8 |

TABLE 5-continued

All unique variants identified in POLE and POLD1 tested for driver ability
Associated mutation burdens are representative for each variant

| | | |
|---|---|---|
| POLE | S459F | 117.1 |
| POLE | S459C | 12.6 |
| POLE | V460M | 15.3 |
| POLE | V460M | 4.5 |
| POLE | S461P | 208 |
| POLE | S461P | 496.24 |
| POLE | S461L | 69.4 |
| POLE | S461T | 447.8 |
| POLE | D462Y | 278.4 |
| POLE | D462H | 6.3 |
| POLE | A463D | 532 |
| POLE | A463D | 359 |
| POLE | A463V | 231.5 |
| POLE | A463V | 55.9 |
| POLE | A463T | 809 |
| POLE | A465T | 238.18 |
| POLE | A465T | 472.56 |
| POLE | A465V | 214.4 |
| POLE | A465S | 21.6 |
| POLE | A465S | 9.9 |
| POLE | A465T | 28.8 |
| POLE | A465T | 0.9 |
| POLE | T466A | 2.7 |
| POLE | T466I | 155.9 |
| POLE | L469V | 2.7 |
| POLE | M471V | 3.6 |
| POLE | M471I | 22.5 |
| POLE | M471V | 4.5 |
| POLE | V474F | 35.1 |
| POLE | V474I | 7.2 |
| POLE | V474F | 9.9 |
| POLE | P476S | 59.5 |
| POLE | A480V | 7.2 |
| POLE | A480V | 55 |
| POLE | T483I | 41.4 |
| POLE | T483I | 51.4 |
| POLE | I485V | 54.1 |
| POLE | I485M | 1.8 |
| POLE | P486L | 56.8 |
| POLE | P489L | 155.9 |
| POLE | P489T | 100 |
| POLE | P489L | 226.1 |
| POLE | P489H | 8.1 |
| POLE | D490E | 5.4 |
| POLE | D490Y | 26.1 |
| POLE | D490N | 3.6 |
| POLE | D490G | 14.4 |
| POLE | D490N | 3.6 |
| POLE | D490N | 2.7 |
| POLE | D490Y | 36.9 |
| POLE | D490N | 6.3 |
| POLE | E491K | 2.7 |
| POLE | E491K | 1.8 |
| POLE | E491K | 5.4 |
| POLE | E491K | 73 |
| POLE | E491K | 1.8 |
| POLE | E491K | 409 |
| POLE | E491K | 2.7 |
| POLE | E491K | 13.5 |
| POLE | V492M | 138.7 |
| POLE | R494W | 14.4 |
| POLE | K495N | 7.2 |
| POLE | G496D | 76.6 |
| POLE | G498D | 98.2 |
| POLE | L500Q | 7.2 |
| POLE | E502A | 1.8 |
| POLE | L505P | 342.3 |
| POLE | M506I | 2.7 |
| POLE | M506V | 1.8 |
| POLE | M506V | 1.8 |
| POLE | M506V | 1.8 |
| POLE | V507A | 4.5 |
| POLE | V507A | 1.8 |
| POLE | A509V | 21.6 |
| POLE | A509T | 8.1 |
| POLE | A509G | 42.3 |
| POLE | H511Q | 0.9 |

TABLE 5-continued

All unique variants identified in POLE and POLD1 tested for driver ability
Associated mutation burdens are representative for each variant

| | | |
|---|---|---|
| POLE | N513D | 4.5 |
| POLE | N513D | 2.7 |
| POLE | I514V | 2.7 |
| POLE | I514F | 4.5 |
| POLE | P517L | 2.7 |
| POLE | P517L | 0.9 |
| POLE | P517L | 14.4 |
| POLE | P517L | 1.8 |
| POLE | P517L | 147.7 |
| POLE | P517S | 56.8 |
| POLE | N518D | 13.5 |
| POLE | K519Q | 4.5 |
| POLE | Q520R | 8.1 |
| POLE | Q520R | 6.3 |
| POLE | E521* | 9 |
| POLE | Q522E | 3.6 |
| POLE | E523K | 7.2 |
| POLE | E523V | 9 |
| POLE | F524L | 1.8 |
| POLE | N525S | 0.9 |
| POLE | N525H | 2.7 |
| POLE | N525S | 9 |
| POLE | N525H | 3.6 |
| POLE | N525H | 4.5 |
| POLE | N525H | 2.7 |
| POLE | N525S | 7.2 |
| POLE | K526R | 0.9 |
| POLE | D529G | 5.4 |
| POLE | G531R | 36.9 |
| POLE | G531R | 9 |
| POLE | G531R | 0.9 |
| POLE | G531* | 29.7 |
| POLE | V533M | 6.3 |
| POLE | V533M | 6.3 |
| POLE | V533M | 15.3 |
| POLE | V533M | 3.6 |
| POLE | V533M | 35.1 |
| POLE | V533M | 4.5 |
| POLE | V533M | 20.7 |
| POLE | S536F | 217.1 |
| POLE | E537K | 13.5 |
| POLE | E537Q | 22.5 |
| POLE | Y539C | 14.4 |
| POLE | V540F | 15.3 |
| POLE | V540F | 9.9 |
| POLE | V540F | 29.7 |
| POLE | H543Y | 34.2 |
| POLE | H543P | 23.4 |
| POLE | H543Y | 53.2 |
| POLE | V544L | 41.4 |
| POLE | V544M | 9 |
| POLE | E545D | 4.5 |
| POLE | E545Q | 64.9 |
| POLE | L547F | 48.6 |
| POLE | E548K | 22.5 |
| POLE | E548K | 1.8 |
| POLE | E548K | 1.8 |
| POLE | S549A | 9 |
| POLE | G550E | 0 |
| POLE | G550E | 70.3 |
| POLE | G550W | 37.8 |
| POLE | V551I | 35.1 |
| POLE | V551A | 3.6 |
| POLE | R553C | 22.5 |
| POLE | R553C | 62.2 |
| POLE | R553C | 27.9 |
| POLE | R553L | 4.5 |
| POLE | R553C | 3.6 |
| POLE | R553L | 12.6 |
| POLE | S554G | 4.5 |
| POLE | D555V | 13.5 |
| POLE | P557S | 9 |
| POLE | P557S | 2.7 |
| POLE | P557S | 81.1 |
| POLE | P557R | 2.7 |
| POLE | P557T | 42.3 |
| POLE | C558S | 4.5 |

TABLE 5-continued

All unique variants identified in POLE and POLD1 tested for driver ability
Associated mutation burdens are representative for each variant

| | | |
|---|---|---|
| POLE | C558Y | 4.5 |
| POLE | R559Q | 17.1 |
| POLE | R559W | 3.6 |
| POLE | R559Q | 142.3 |
| POLE | R559Q | 1.8 |
| POLE | R559Q | 43.2 |
| POLE | R559Q | 14.4 |
| POLE | R559W | 5.4 |
| POLE | M562I | 18.9 |
| POLE | A566T | 19.8 |
| POLE | F567L | 4.5 |
| POLE | D568Y | 46.8 |
| POLE | D568H | 45 |
| POLE | F569L | 8.1 |
| POLE | F569L | 0.9 |
| POLE | F569C | 6.3 |
| POLE | F569S | 3.6 |
| POLE | Q572R | 23.4 |
| POLE | R573L | 23.4 |
| POLE | R573L | 64 |
| POLE | R573Q | 5.4 |
| POLE | R573L | 14.4 |
| POLE | V574D | 14.4 |
| POLE | E575Q | 5.4 |
| POLE | E575Q | 22.5 |
| POLE | K576E | 18.9 |
| POLE | K576E | 29.7 |
| POLE | K576Q | 18 |
| POLE | H580R | 31.5 |
| POLE | A581T | 8.1 |
| POLE | A581T | 2.7 |
| POLE | A581T | 6.3 |
| POLE | A581V | 9.9 |
| POLE | L582F | 3.6 |
| POLE | E583Q | 45 |
| POLE | E585K | 5.4 |
| POLE | E585* | 27 |
| POLE | E586K | 9 |
| POLE | K587R | 4.5 |
| POLE | P589S | 28.8 |
| POLE | P589T | 5.4 |
| POLE | P589S | 13.5 |
| POLE | E591G | 7.2 |
| POLE | E591K | 9.9 |
| POLE | Q592R | 27 |
| POLE | V593A | 238.18 |
| POLE | V593A | 472.56 |
| POLE | T594A | 18 |
| POLE | T594I | 4.5 |
| POLE | T594A | 9.9 |
| POLE | N595S | 3.6 |
| POLE | E597K | 4.5 |
| POLE | E597G | 1.8 |
| POLE | E598Q | 69.4 |
| POLE | V599A | 3.6 |
| POLE | V599M | 116.2 |
| POLE | V599M | 0.9 |
| POLE | C600Y | 4.5 |
| POLE | C600S | 6.3 |
| POLE | D601V | 3.6 |
| POLE | D601V | 4.5 |
| POLE | E602K | 45.9 |
| POLE | E602A | 5.4 |
| POLE | E602Q | 5.4 |
| POLE | E602D | 8.1 |
| POLE | E602K | 11.7 |
| POLE | E602G | 80.2 |
| POLE | I603T | 3.6 |
| POLE | S609F | 7.2 |
| POLE | S609P | 51.4 |
| POLE | V613I | 4.5 |
| POLE | V613I | 46.8 |
| POLE | V613I | 27 |
| POLE | V613I | 11.7 |
| POLE | P614L | 174.8 |
| POLE | R616H | 3.6 |
| POLE | R616C | 3.6 |

TABLE 5-continued

All unique variants identified in POLE and POLD1 tested for driver ability
Associated mutation burdens are representative for each variant

| | | |
|---|---|---|
| POLE | R616H | 24.3 |
| POLE | R616H | 5.4 |
| POLE | I617N | 196 |
| POLE | E618K | 12.6 |
| POLE | E618K | 47.7 |
| POLE | C619Y | 4.5 |
| POLE | C619Y | 27.9 |
| POLE | P620S | 809 |
| POLE | L621P | 1.8 |
| POLE | L621F | 209.9 |
| POLE | I622V | 10.8 |
| POLE | I622M | 9 |
| POLE | I622V | 6.3 |
| POLE | D626Y | 9.9 |
| POLE | D626G | 238.7 |
| POLE | V627M | 15.3 |
| POLE | G628E | 5.4 |
| POLE | A629T | 0 |
| POLE | A629S | 67.6 |
| POLE | A629V | 18.9 |
| POLE | P632R | 2.7 |
| POLE | N633H | 3.6 |
| POLE | N633H | 13.5 |
| POLE | I634V | 409.18 |
| POLE | I634V | 5.4 |
| POLE | I634V | 2.7 |
| POLE | I634V | 2.7 |
| POLE | T637I | 4.5 |
| POLE | R639C | 2.7 |
| POLE | R639H | 45 |
| POLE | L640Q | 3.6 |
| POLE | Q641H | 21.6 |
| POLE | Q641H | 12.6 |
| POLE | S643F | 99.1 |
| POLE | M645I | 9 |
| POLE | D647G | 24.3 |
| POLE | D647V | 1.8 |
| POLE | D647N | 0.9 |
| POLE | E648K | 0.9 |
| POLE | E648K | 19.8 |
| POLE | E648K | 8.1 |
| POLE | A649V | 561.3 |
| POLE | A653S | 5.4 |
| POLE | A653S | 6.3 |
| POLE | A653S | 46.8 |
| POLE | A653S | 34.2 |
| POLE | A653S | 4.5 |
| POLE | A653S | 27.9 |
| POLE | N657S | 3.6 |
| POLE | K658T | 11.7 |
| POLE | P659R | 9 |
| POLE | P659S | 10.8 |
| POLE | R665W | 12.6 |
| POLE | R665Q | 0 |
| POLE | R665Q | 5.4 |
| POLE | R665W | 21.6 |
| POLE | R665W | 1.8 |
| POLE | M667L | 0 |
| POLE | A668T | 2.7 |
| POLE | W669* | 32.4 |
| POLE | W669L | 122.5 |
| POLE | Q670* | 101.8 |
| POLE | W671* | 11.7 |
| POLE | R672S | 4.5 |
| POLE | G673S | 1.8 |
| POLE | E674A | 109 |
| POLE | E674A | 0.9 |
| POLE | E674K | 5.4 |
| POLE | M676L | 17.1 |
| POLE | M676I | 27.9 |
| POLE | R680C | 0 |
| POLE | R680H | 7.2 |
| POLE | R680H | 0.9 |
| POLE | R680H | 7.2 |
| POLE | R680C | 1.8 |
| POLE | R680C | 1.8 |
| POLE | R680H | 1.8 |

TABLE 5-continued

All unique variants identified in POLE and POLD1 tested for driver ability
Associated mutation burdens are representative for each variant

| | | |
|---|---|---:|
| POLE | R680L | 7.2 |
| POLE | S681R | 1.8 |
| POLE | E682K | 7.2 |
| POLE | Y683C | 159.5 |
| POLE | R685P | 30.6 |
| POLE | R685L | 18.9 |
| POLE | R685P | 15.3 |
| POLE | Q689H | 5.4 |
| POLE | Q689L | 52.3 |
| POLE | Q689H | 38.7 |
| POLE | L690V | 3.6 |
| POLE | E693Q | 20.7 |
| POLE | E693* | 22.5 |
| POLE | E693* | 9.9 |
| POLE | K694E | 10.8 |
| POLE | F695V | 6.3 |
| POLE | F695V | 7.2 |
| POLE | F695S | 50.5 |
| POLE | F695V | 5.4 |
| POLE | F695L | 3.6 |
| POLE | F695V | 1.8 |
| POLE | P696R | 11.7 |
| POLE | P697T | 9.9 |
| POLE | P697H | 10.8 |
| POLE | P697T | 1.8 |
| POLE | P700A | 16.2 |
| POLE | P700L | 3.6 |
| POLE | P700Q | 4.5 |
| POLE | P700S | 48.6 |
| POLE | P700S | 5.4 |
| POLE | P700S | 96.4 |
| POLE | P700L | 124.3 |
| POLE | P700L | 5.4 |
| POLE | P700L | 2.7 |
| POLE | P700S | 4.5 |
| POLE | E701Q | 34.2 |
| POLE | G702W | 134.2 |
| POLE | G702W | 18.9 |
| POLE | G702R | 14.4 |
| POLE | P703L | 23.4 |
| POLE | A704S | 218 |
| POLE | A704P | 3.6 |
| POLE | R705W | 9.9 |
| POLE | R705Q | 12.6 |
| POLE | R705G | 28.8 |
| POLE | H708Y | 665.8 |
| POLE | H708R | 13.5 |
| POLE | E709K | 4.5 |
| POLE | E709K | 115.3 |
| POLE | R712C | 45.9 |
| POLE | R712C | 48.6 |
| POLE | R712C | 44.1 |
| POLE | R712C | 89.2 |
| POLE | R712G | 3.6 |
| POLE | E713* | 31.5 |
| POLE | E713K | 0.9 |
| POLE | E714K | 4.5 |
| POLE | E714K | 2.7 |
| POLE | Q715R | 8.1 |
| POLE | A716V | 532 |
| POLE | E719K | 62.2 |
| POLE | E719K | 0 |
| POLE | E719K | 67.6 |
| POLE | L723V | 44.1 |
| POLE | A724T | 12.6 |
| POLE | D725Y | 1.8 |
| POLE | D725H | 29.7 |
| POLE | Y726F | 15.3 |
| POLE | Y726S | 27.9 |
| POLE | R728W | 0 |
| POLE | R728W | 3.6 |
| POLE | R728W | 45.9 |
| POLE | R728P | 20.7 |
| POLE | R728W | 2.7 |
| POLE | R728W | 28.8 |
| POLE | R728Q | 27.9 |
| POLE | K729I | 100.9 |

TABLE 5-continued

All unique variants identified in POLE and POLD1 tested for driver ability
Associated mutation burdens are representative for each variant

| | | |
|---|---|---|
| POLE | Y731F | 16.2 |
| POLE | K732R | 9.9 |
| POLE | K733N | 69.4 |
| POLE | H735Y | 78.4 |
| POLE | K738N | 41.4 |
| POLE | K738N | 1.8 |
| POLE | V739M | 116.2 |
| POLE | E740K | 20.7 |
| POLE | E740* | 90.1 |
| POLE | E741G | 10.8 |
| POLE | E741K | 84.7 |
| POLE | E741G | 3.6 |
| POLE | E741* | 2.7 |
| POLE | E741G | 1.8 |
| POLE | R742C | 318.06 |
| POLE | R742C | 96.4 |
| POLE | L743V | 19.8 |
| POLE | T744A | 55 |
| POLE | T744A | 72.1 |
| POLE | T745A | 20.7 |
| POLE | I746V | 6.3 |
| POLE | I746T | 35.1 |
| POLE | C747F | 37.8 |
| POLE | Q748L | 5.4 |
| POLE | R749Q | 4.5 |
| POLE | R749W | 56.8 |
| POLE | R749Q | 2.7 |
| POLE | R749Q | 3.6 |
| POLE | S752F | 6.3 |
| POLE | F753L | 92.8 |
| POLE | F753L | 23.4 |
| POLE | Y754C | 6.3 |
| POLE | Y754C | 0.9 |
| POLE | V755M | 114.4 |
| POLE | V755M | 71.2 |
| POLE | V758M | 532 |
| POLE | V758G | 1.8 |
| POLE | V758M | 114.4 |
| POLE | R759C | 81.1 |
| POLE | R759H | 0 |
| POLE | R759C | 2.7 |
| POLE | R759C | 5.4 |
| POLE | R759H | 3.6 |
| POLE | A760V | 98.2 |
| POLE | R762W | 2.7 |
| POLE | R762W | 3.6 |
| POLE | R762W | 3.6 |
| POLE | R764M | 46.8 |
| POLE | R765H | 1.8 |
| POLE | R765C | 13.5 |
| POLE | R765C | 36.9 |
| POLE | R765C | 314.4 |
| POLE | E767K | 7.2 |
| POLE | F768V | 109 |
| POLE | G770R | 10.8 |
| POLE | V774G | 6.3 |
| POLE | W775* | 5.4 |
| POLE | W775* | 93.7 |
| POLE | K776R | 4.5 |
| POLE | K776R | 5.4 |
| POLE | K776R | 4.5 |
| POLE | V777E | 195 |
| POLE | K777N | 3.6 |
| POLE | K778T | 1.8 |
| POLE | K778T | 5.4 |
| POLE | L779F | 99.1 |
| POLE | S780L | 91.9 |
| POLE | S780L | 9 |
| POLE | S780L | 4.5 |
| POLE | S780L | 1.8 |
| POLE | S780L | 2.7 |
| POLE | S780L | 447.8 |
| POLE | A781S | 9 |
| POLE | A781V | 52.3 |
| POLE | A781S | 26.1 |
| POLE | A781T | 145.9 |
| POLE | A782V | 15.3 |

TABLE 5-continued

All unique variants identified in POLE and POLD1 tested for driver ability
Associated mutation burdens are representative for each variant

| | | |
|---|---|---:|
| POLE | V783M | 2.7 |
| POLE | V783M | 6.3 |
| POLE | V783M | 11.7 |
| POLE | V783M | 12.6 |
| POLE | V783L | 5.4 |
| POLE | E784D | 30.6 |
| POLE | E784D | 22.5 |
| POLE | E784* | 12.6 |
| POLE | V785L | 19.8 |
| POLE | A788V | 12.6 |
| POLE | A788V | 70.3 |
| POLE | A788V | 12.6 |
| POLE | A788T | 45 |
| POLE | A789S | 15.3 |
| POLE | A789T | 578.4 |
| POLE | A789S | 18 |
| POLE | E790* | 15.3 |
| POLE | E790K | 0.9 |
| POLE | E790Q | 6.3 |
| POLE | E790D | 55.9 |
| POLE | E790Q | 11.7 |
| POLE | K792R | 13.5 |
| POLE | R793H | 6.3 |
| POLE | C794Y | 49.5 |
| POLE | K795R | 6.3 |
| POLE | K795R | 2.7 |
| POLE | K795R | 12.6 |
| POLE | M797V | 5.4 |
| POLE | E798K | 20.7 |
| POLE | E798D | 29.7 |
| POLE | V799M | 215.3 |
| POLE | Y801C | 8.1 |
| POLE | S803* | 108.1 |
| POLE | S803L | 3.6 |
| POLE | S803L | 245.9 |
| POLE | S803L | 3.6 |
| POLE | A807S | 12.6 |
| POLE | H808Y | 1.8 |
| POLE | C810G | 854.1 |
| POLE | C810G | 154.1 |
| POLE | I811T | 3.6 |
| POLE | S814F | 101.8 |
| POLE | S814F | 9.9 |
| POLE | S814A | 4.5 |
| POLE | F815L | 91 |
| POLE | F815S | 0.9 |
| POLE | Y816C | 0 |
| POLE | Y818C | 0.9 |
| POLE | Y818C | 55.9 |
| POLE | Y818H | 2.7 |
| POLE | Y818C | 4.5 |
| POLE | M820T | 2.7 |
| POLE | M820T | 6.3 |
| POLE | M820T | 6.3 |
| POLE | R821C | 2.7 |
| POLE | R821C | 56.8 |
| POLE | R821C | 636.9 |
| POLE | R821L | 77.5 |
| POLE | R821C | 21.6 |
| POLE | R821C | 650.5 |
| POLE | R821H | 59.5 |
| POLE | R821H | 0.9 |
| POLE | A824V | 10.8 |
| POLE | R825H | 4.5 |
| POLE | W826C | 0 |
| POLE | Y827C | 44.1 |
| POLE | S828F | 56.8 |
| POLE | S828F | 5.4 |
| POLE | M829I | 2.7 |
| POLE | M829I | 1.8 |
| POLE | E830K | 6.3 |
| POLE | A832T | 590 |
| POLE | I834T | 45.9 |
| POLE | A840T | 33.3 |
| POLE | A840G | 69.4 |
| POLE | N841D | 31.5 |
| POLE | N841D | 2.7 |

TABLE 5-continued

All unique variants identified in POLE and POLD1 tested for driver ability
Associated mutation burdens are representative for each variant

| | | |
|---|---|---|
| POLE | N841D | 51.4 |
| POLE | I843V | 4.5 |
| POLE | I843V | 27 |
| POLE | T844I | 368.5 |
| POLE | T844I | 16.2 |
| POLE | Q845H | 14.4 |
| POLE | A846E | 148.6 |
| POLE | R847W | 3.6 |
| POLE | E848D | 25.2 |
| POLE | E848D | 6.3 |
| POLE | I850T | 5.4 |
| POLE | I850M | 7.2 |
| POLE | I850M | 3.6 |
| POLE | I850M | 1.8 |
| POLE | E851* | 8.1 |
| POLE | Q852R | 120.7 |
| POLE | G854V | 14.4 |
| POLE | R855W | 8.1 |
| POLE | E858K | 106.3 |
| POLE | E858* | 251.4 |
| POLE | T861I | 49.5 |
| POLE | D862G | 1.8 |
| POLE | V867L | 6.3 |
| POLE | L868V | 10.8 |
| POLE | N870S | 0 |
| POLE | S871C | 48.6 |
| POLE | S871T | 3.6 |
| POLE | S871N | 121.6 |
| POLE | S871C | 35.1 |
| POLE | P873Q | 23.4 |
| POLE | P873L | 5.4 |
| POLE | E874K | 31.5 |
| POLE | K879N | 2.7 |
| POLE | K879Q | 9 |
| POLE | T880M | 4.5 |
| POLE | T880M | 1.8 |
| POLE | T880M | 4.5 |
| POLE | T880L | 0 |
| POLE | T880L | 9 |
| POLE | T880K | 19.8 |
| POLE | T880A | 1.8 |
| POLE | T880M | 66.7 |
| POLE | T880M | 89.2 |
| POLE | T881I | 224.3 |
| POLE | N882H | 4.5 |
| POLE | K884R | 1.8 |
| POLE | P886H | 45.9 |
| POLE | P886L | 32.4 |
| POLE | V888A | 10.8 |
| POLE | S891F | 236 |
| POLE | P893S | 4.5 |
| POLE | P893L | 1.8 |
| POLE | A895V | 47.7 |
| POLE | A895V | 3.6 |
| POLE | A895V | 0 |
| POLE | A895V | 0.9 |
| POLE | A895S | 9 |
| POLE | M896V | 9.9 |
| POLE | N898S | 19.8 |
| POLE | I899V | 18.9 |
| POLE | K902N | 15.3 |
| POLE | K902N | 88.3 |
| POLE | E903K | 9 |
| POLE | E903D | 6.3 |
| POLE | G904V | 6.3 |
| POLE | G904A | 8.1 |
| POLE | T906I | 104.5 |
| POLE | Q909R | 3.6 |
| POLE | Q911P | 10.8 |
| POLE | E912Q | 9 |
| POLE | E912Q | 9.9 |
| POLE | E912* | 17.1 |
| POLE | E912Q | 17.1 |
| POLE | E912K | 3.6 |
| POLE | E912K | 13.5 |
| POLE | A914P | 15.3 |
| POLE | E915K | 82 |

TABLE 5-continued

All unique variants identified in POLE and POLD1 tested for driver ability
Associated mutation burdens are representative for each variant

| Gene | Variant | Value |
|---|---|---|
| POLE | E915Q | 27.9 |
| POLE | L919P | 3.6 |
| POLE | L919F | 0 |
| POLE | V922I | 46.8 |
| POLE | R924G | 4.5 |
| POLE | R924H | 29.7 |
| POLE | E926Q | 4.5 |
| POLE | S928N | 0 |
| POLE | I929V | 2.7 |
| POLE | F930C | 4.5 |
| POLE | E932K | 8.1 |
| POLE | V933I | 138.7 |
| POLE | D934H | 60.4 |
| POLE | D934H | 47.7 |
| POLE | D934V | 3.6 |
| POLE | G935M | 27 |
| POLE | P936S | 202.7 |
| POLE | L938F | 0 |
| POLE | L938F | 173.9 |
| POLE | L938V | 12.6 |
| POLE | L942F | 182.9 |
| POLE | L942F | 500 |
| POLE | P943S | 9 |
| POLE | P943S | 150.5 |
| POLE | P943L | 5.4 |
| POLE | S945F | 320.7 |
| POLE | S945F | 24.3 |
| POLE | E948* | 160.4 |
| POLE | E948Q | 69.4 |
| POLE | E948Q | 9.9 |
| POLE | E948K | 53.2 |
| POLE | R955M | 8.1 |
| POLE | N960S | 6.3 |
| POLE | N960S | 6.3 |
| POLE | N960S | 18.9 |
| POLE | N960S | 3.6 |
| POLE | N960S | 1.8 |
| POLE | N960S | 6.3 |
| POLE | D962N | 75.7 |
| POLE | D962G | 9 |
| POLE | D962N | 30.6 |
| POLE | G963C | 30.6 |
| POLE | G963D | 5.4 |
| POLE | G963S | 29.7 |
| POLE | G963C | 60.4 |
| POLE | G963D | 2.7 |
| POLE | G963D | 5.4 |
| POLE | S964F | 21.6 |
| POLE | A966P | 28.8 |
| POLE | A966S | 19.8 |
| POLE | G970S | 4.5 |
| POLE | G970S | 7.2 |
| POLE | E972G | 3.6 |
| POLE | E972Q | 30.6 |
| POLE | R975L | 7.2 |
| POLE | R975C | 31.5 |
| POLE | R976H | 8.1 |
| POLE | R976H | 42.3 |
| POLE | R976H | 31.5 |
| POLE | R976C | 8.1 |
| POLE | R976C | 2.7 |
| POLE | G977R | 5.4 |
| POLE | E978G | 608.02 |
| POLE | E978* | 15.3 |
| POLE | E978G | 26.1 |
| POLE | E978K | 80.2 |
| POLE | K983N | 7.2 |
| POLE | K983N | 69.4 |
| POLE | K983N | 251.4 |
| POLE | Q986* | 25.2 |
| POLE | S987F | 1.8 |
| POLE | V989L | 22.5 |
| POLE | V989L | 3.6 |
| POLE | F990C | 301.8 |
| POLE | E991Q | 20.7 |
| POLE | G996D | 18 |
| POLE | G996S | 64 |

TABLE 5-continued

All unique variants identified in POLE and POLD1 tested for driver ability
Associated mutation burdens are representative for each variant

| | | |
|---|---|---|
| POLE | G996D | 145.9 |
| POLE | G996S | 178.4 |
| POLE | T998M | 8.1 |
| POLE | T998M | 46.8 |
| POLE | T998M | 10.8 |
| POLE | T998M | 3.6 |
| POLE | T998M | 1.8 |
| POLE | E1001Q | 28.8 |
| POLE | V1002M | 3.6 |
| POLE | V1002A | 91.9 |
| POLE | S1005F | 7.2 |
| POLE | D1011Y | 34.2 |
| POLE | W1013* | 57.7 |
| POLE | D1015N | 159.5 |
| POLE | Y1018H | 5.4 |
| POLE | Y1018C | 62.2 |
| POLE | S1019I | 0.9 |
| POLE | S1019C | 15.3 |
| POLE | S1019I | 6.3 |
| POLE | K1020R | 9.9 |
| POLE | A1021E | 4.5 |
| POLE | A1021S | 3.6 |
| POLE | A1021G | 2.7 |
| POLE | M1024V | 0.9 |
| POLE | M1024I | 0.9 |
| POLE | M1024I | 9 |
| POLE | D1026H | 18.9 |
| POLE | D1026H | 11.7 |
| POLE | D1026N | 35.1 |
| POLE | S1027A | 2.7 |
| POLE | S1027C | 20.7 |
| POLE | F1030Y | 4.5 |
| POLE | F1030L | 1.8 |
| POLE | E1031D | 26.1 |
| POLE | E1031K | 3.6 |
| POLE | I1033F | 7.2 |
| POLE | R1037H | 608.02 |
| POLE | R1037C | 6.3 |
| POLE | R1037H | 3.6 |
| POLE | R1037C | 6.3 |
| POLE | S1038A | 136 |
| POLE | M1039T | 15.3 |
| POLE | R1041Q | 8.1 |
| POLE | R1041W | 5.4 |
| POLE | R1041Q | 65.8 |
| POLE | K1042R | 10.8 |
| POLE | E1048K | 1.8 |
| POLE | E1048K | 665.8 |
| POLE | Q1049H | 6.3 |
| POLE | S1051P | 3.6 |
| POLE | T1052A | 0.9 |
| POLE | T1052M | 2.7 |
| POLE | T1052M | 9 |
| POLE | I1054V | 2.7 |
| POLE | A1057V | 336 |
| POLE | A1057V | 336 |
| POLE | A1057V | 0.9 |
| POLE | R1059C | 2.7 |
| POLE | R1059L | 18 |
| POLE | R1059C | 24.3 |
| POLE | R1059C | 309.9 |
| POLE | R1059C | 318.9 |
| POLE | R1059C | 46.8 |
| POLE | A1061V | 118 |
| POLE | E1062K | 51.4 |
| POLE | F1063L | 60.4 |
| POLE | G1065E | 46.8 |
| POLE | D1066E | 1.8 |
| POLE | D1066N | 8.1 |
| POLE | D1066N | 0.9 |
| POLE | D1066N | 0 |
| POLE | D1071H | 32.4 |
| POLE | A1072T | 0.9 |
| POLE | A1072G | 3.6 |
| POLE | S1075C | 0.9 |
| POLE | S1075C | 8.1 |
| POLE | R1077H | 218 |

TABLE 5-continued

All unique variants identified in POLE and POLD1 tested for driver ability
Associated mutation burdens are representative for each variant

| | | |
|---|---|---|
| POLE | R1077H | 3.6 |
| POLE | R1077H | 17.1 |
| POLE | R1077H | 3.6 |
| POLE | R1077H | 17.1 |
| POLE | R1077L | 28.8 |
| POLE | R1077H | 12.6 |
| POLE | R1077H | 32.4 |
| POLE | Y1078F | 12.6 |
| POLE | K1083Q | 12.6 |
| POLE | K1083Q | 1.8 |
| POLE | P1084L | 182 |
| POLE | E1085K | 0.9 |
| POLE | E1085D | 9.9 |
| POLE | E1085K | 3.6 |
| POLE | E1085K | 14.4 |
| POLE | E1085* | 18 |
| POLE | E1085K | 3.6 |
| POLE | E1085K | 1.8 |
| POLE | G1086C | 33.3 |
| POLE | T1090M | 60.4 |
| POLE | T1090R | 3.6 |
| POLE | E1091K | 8.1 |
| POLE | E1091K | 16.2 |
| POLE | E1091K | 34.2 |
| POLE | R1092S | 1.8 |
| POLE | R1092K | 78.4 |
| POLE | A1093V | 109.9 |
| POLE | P1095S | 164 |
| POLE | L1096V | 1.8 |
| POLE | P1103H | 84.7 |
| POLE | T1104M | 6.3 |
| POLE | T1104M | 1.8 |
| POLE | T1104M | 2.7 |
| POLE | T1104M | 25.2 |
| POLE | T1104M | 55.9 |
| POLE | V1105L | 27.9 |
| POLE | V1105M | 76.6 |
| POLE | K1107N | 57.7 |
| POLE | F1109Y | 119.8 |
| POLE | F1109C | 6.3 |
| POLE | L1110I | 3.6 |
| POLE | L1110I | 35.1 |
| POLE | R1111Q | 5.4 |
| POLE | R1111Q | 8.1 |
| POLE | R1111P | 18.9 |
| POLE | R1111Q | 15.3 |
| POLE | R1111W | 81.1 |
| POLE | R1111W | 15.3 |
| POLE | W1113* | 668.5 |
| POLE | W1113* | 22.5 |
| POLE | L1114F | 7.2 |
| POLE | K1115N | 60.4 |
| POLE | K1115E | 11.7 |
| POLE | K1115N | 3.6 |
| POLE | S1116R | 699 |
| POLE | S1118A | 0 |
| POLE | S1118A | 3.6 |
| POLE | S1118F | 51.4 |
| POLE | D1121G | 3.6 |
| POLE | D1123H | 10.8 |
| POLE | I1124F | 8.1 |
| POLE | R1125* | 146.8 |
| POLE | R1125* | 3.6 |
| POLE | A1126V | 2.7 |
| POLE | A1126V | 3.6 |
| POLE | A1126V | 6.3 |
| POLE | I1127T | 10.8 |
| POLE | L1128M | 5.4 |
| POLE | D1129G | 4.5 |
| POLE | W1130C | 9 |
| POLE | W1130* | 92.8 |
| POLE | D1131N | 0.9 |
| POLE | D1131E | 3.6 |
| POLE | D1131G | 41.4 |
| POLE | Y1133C | 5.4 |
| POLE | Y1133H | 8.1 |
| POLE | I1134F | 21.6 |

TABLE 5-continued

All unique variants identified in POLE and POLD1 tested for driver ability
Associated mutation burdens are representative for each variant

| | | |
|---|---|---:|
| POLE | E1135D | 55 |
| POLE | E1135K | 28.8 |
| POLE | R1136W | 3.6 |
| POLE | R1136W | 4.5 |
| POLE | R1136W | 69.4 |
| POLE | R1136Q | 15.3 |
| POLE | G1138* | 45 |
| POLE | I1141M | 8.1 |
| POLE | K1143N | 6.3 |
| POLE | K1143N | 46.8 |
| POLE | T1146I | 334.2 |
| POLE | I1147V | 21.6 |
| POLE | P1148S | 10.8 |
| POLE | A1149V | 52.3 |
| POLE | A1149V | 36 |
| POLE | A1149V | 35.1 |
| POLE | A1149V | 4.5 |
| POLE | A1150T | 77.5 |
| POLE | A1150T | 0.9 |
| POLE | Q1152* | 76.6 |
| POLE | Q1153* | 2.7 |
| POLE | Q1153* | 4.5 |
| POLE | K1155N | 18.9 |
| POLE | K1155N | 5.4 |
| POLE | P1157S | 433 |
| POLE | P1157S | 4.5 |
| POLE | P1157S | 2.7 |
| POLE | P1159S | 6.3 |
| POLE | R1160H | 7.2 |
| POLE | R1160H | 0.9 |
| POLE | R1160H | 1.8 |
| POLE | P1164L | 86.5 |
| POLE | P1164L | 5.4 |
| POLE | D1165N | 3.6 |
| POLE | D1165N | 85.6 |
| POLE | D1165N | 118.9 |
| POLE | K1170* | 5.4 |
| POLE | L1172V | 9 |
| POLE | E1173G | 11.7 |
| POLE | D1176V | 7.2 |
| POLE | K1179R | 28.8 |
| POLE | K1179R | 4.5 |
| POLE | Q1180H | 9.9 |
| POLE | S1184G | 6.3 |
| POLE | E1190K | 12.6 |
| POLE | E1190G | 23.4 |
| POLE | E1190Q | 10.8 |
| POLE | G1191C | 9 |
| POLE | R1192S | 5.4 |
| POLE | R1192G | 37.8 |
| POLE | R1193I | 12.6 |
| POLE | R1193K | 9.9 |
| POLE | R1193K | 5.4 |
| POLE | R1193* | 33.3 |
| POLE | R1193G | 16.2 |
| POLE | R1193K | 7.2 |
| POLE | Q1194R | 1.8 |
| POLE | V1195I | 561.3 |
| POLE | V1195I | 2.7 |
| POLE | V1195F | 22.5 |
| POLE | V1195D | 11.7 |
| POLE | T1196M | 1.8 |
| POLE | T1196M | 75.7 |
| POLE | T1196M | 43.2 |
| POLE | T1196M | 7.2 |
| POLE | A1198V | 73 |
| POLE | A1198D | 5.4 |
| POLE | E1199K | 7.2 |
| POLE | E1199K | 6.3 |
| POLE | E1199D | 70.3 |
| POLE | E1199G | 31.5 |
| POLE | E1199K | 9.9 |
| POLE | E1199K | 7.2 |
| POLE | E1199K | 17.1 |
| POLE | A1200T | 809 |
| POLE | D1203N | 69.4 |
| POLE | D1203Y | 6.3 |

TABLE 5-continued

All unique variants identified in POLE and POLD1 tested for driver ability
Associated mutation burdens are representative for each variant

| | | |
|---|---|---|
| POLE | S1204R | 64 |
| POLE | S1204R | 2.7 |
| POLE | P1205L | 3.6 |
| POLE | P1205S | 665.8 |
| POLE | P1205L | 12.6 |
| POLE | P1205L | 12.6 |
| POLE | R1206M | 5.4 |
| POLE | R1206M | 17.1 |
| POLE | P1207L | 8.1 |
| POLE | P1207L | 4.5 |
| POLE | P1207L | 11.7 |
| POLE | P1207R | 2.7 |
| POLE | S1208R | 4.5 |
| POLE | D1211N | 72.1 |
| POLE | M1212R | 2.7 |
| POLE | D1214Y | 18 |
| POLE | G1216S | 0 |
| POLE | G1216C | 52.3 |
| POLE | G1216C | 7.2 |
| POLE | G1216D | 3.6 |
| POLE | G1216S | 18.9 |
| POLE | V1218I | 2.7 |
| POLE | V1218L | 5.4 |
| POLE | K1219Q | 23.4 |
| POLE | H1222Y | 6.3 |
| POLE | H1222Y | 91.9 |
| POLE | A1224T | 278.4 |
| POLE | A1225V | 9.9 |
| POLE | P1226L | 590 |
| POLE | P1226A | 9.9 |
| POLE | P1226L | 12.6 |
| POLE | V1227F | 5.4 |
| POLE | T1228A | 10.8 |
| POLE | T1228S | 12.6 |
| POLE | K1232T | 2.7 |
| POLE | R1233* | 214.4 |
| POLE | R1233* | 2.7 |
| POLE | R1233* | 0 |
| POLE | L1235F | 88.3 |
| POLE | L1235I | 5.4 |
| POLE | W1236L | 88.3 |
| POLE | E1237D | 6.3 |
| POLE | S1238I | 208 |
| POLE | S1238T | 14.4 |
| POLE | S1238T | 0.9 |
| POLE | Q1239H | 6.3 |
| POLE | E1240Q | 6.3 |
| POLE | E1240Q | 66.7 |
| POLE | E1240* | 54.1 |
| POLE | E1241Q | 7.2 |
| POLE | S1242F | 4.5 |
| POLE | S1242C | 8.1 |
| POLE | S1242C | 2.7 |
| POLE | S1242T | 118 |
| POLE | S1242T | 4.5 |
| POLE | S1242C | 27 |
| POLE | S1242F | 2.7 |
| POLE | S1242F | 3.6 |
| POLE | S1242F | 5.4 |
| POLE | D1244Y | 36 |
| POLE | T1246M | 70.3 |
| POLE | T1246R | 2.7 |
| POLE | T1246M | 5.4 |
| POLE | P1247S | 25.2 |
| POLE | T1248P | 5.4 |
| POLE | V1249M | 21.6 |
| POLE | E1253Q | 1.8 |
| POLE | I1254V | 2.7 |
| POLE | G1256W | 20.7 |
| POLE | Q1257L | 8.1 |
| POLE | Q1257P | 20.7 |
| POLE | A1260S | 145.9 |
| POLE | A1260S | 29.7 |
| POLE | G1262* | 65.8 |
| POLE | G1262L | 21.6 |
| POLE | G1262E | 19.8 |
| POLE | Q1265* | 36.9 |

TABLE 5-continued

All unique variants identified in POLE and POLD1 tested for driver ability
Associated mutation burdens are representative for each variant

| | | |
|---|---|---:|
| POLE | E1266A | 32.4 |
| POLE | W1268* | 110.8 |
| POLE | V1270G | 160.4 |
| POLE | V1270I | 1.8 |
| POLE | V1270F | 32.4 |
| POLE | V1270F | 6.3 |
| POLE | R1273W | 235.1 |
| POLE | R1273L | 27.9 |
| POLE | R1273W | 74.8 |
| POLE | R1273W | 5.4 |
| POLE | F1274L | 51.4 |
| POLE | K1276N | 66.7 |
| POLE | W1279L | 110.8 |
| POLE | Q1280L | 14.4 |
| POLE | Q1282L | 22.5 |
| POLE | R1284W | 2.7 |
| POLE | R1284G | 1.8 |
| POLE | R1284W | 4.5 |
| POLE | R1286C | 2.7 |
| POLE | R1286C | 650.5 |
| POLE | R1286C | 64 |
| POLE | A1288V | 3.6 |
| POLE | A1288V | 3.6 |
| POLE | A1288P | 39.6 |
| POLE | R1289C | 41.4 |
| POLE | R1289H | 3.6 |
| POLE | R1289L | 20.7 |
| POLE | R1289C | 40.5 |
| POLE | R1289L | 29.7 |
| POLE | R1289S | 4.5 |
| POLE | R1289H | 4.5 |
| POLE | R1289C | 3.6 |
| POLE | K1291N | 3.6 |
| POLE | Q1293* | 73 |
| POLE | L1295M | 3.6 |
| POLE | L1295M | 3.6 |
| POLE | E1296Q | 29.7 |
| POLE | S1297X | 218 |
| POLE | S1297L | 10.8 |
| POLE | S1297L | 4.5 |
| POLE | S1297L | 22.5 |
| POLE | S1297L | 59.5 |
| POLE | S1297L | 5.4 |
| POLE | S1297L | 7.2 |
| POLE | E1299K | 10.8 |
| POLE | E1299Q | 12.6 |
| POLE | V1301A | 8.1 |
| POLE | L1302I | 208 |
| POLE | L1302P | 14.4 |
| POLE | R1303M | 38.7 |
| POLE | G1305E | 1.8 |
| POLE | G1305E | 4.5 |
| POLE | G1305E | 4.5 |
| POLE | G1305W | 10.8 |
| POLE | G1305V | 28.8 |
| POLE | A1306D | 152.3 |
| POLE | A1306T | 561.3 |
| POLE | A1306T | 1.8 |
| POLE | A1306T | 64.9 |
| POLE | I1307V | 1.8 |
| POLE | I1307F | 28.8 |
| POLE | I1307V | 16.2 |
| POLE | R1308Q | 145.9 |
| POLE | R1308L | 4.5 |
| POLE | D1309G | 6.3 |
| POLE | D1309N | 8.1 |
| POLE | D1309N | 251.4 |
| POLE | D1309N | 1.8 |
| POLE | T1313M | 8.1 |
| POLE | G1314W | 32.4 |
| POLE | L1315M | 25.2 |
| POLE | G1316E | 114.4 |
| POLE | G1316W | 5.4 |
| POLE | G1316E | 12.6 |
| POLE | S1317C | 9.9 |
| POLE | F1318S | 636.9 |
| POLE | F1318L | 25.2 |

TABLE 5-continued

All unique variants identified in POLE and POLD1 tested for driver ability
Associated mutation burdens are representative for each variant

| Gene | Variant | Value |
|---|---|---|
| POLE | L1319F | 4.5 |
| POLE | L1319V | 64 |
| POLE | L1319S | 9.9 |
| POLE | R1320Q | 8.1 |
| POLE | R1320Q | 2.7 |
| POLE | R1320Q | 1.8 |
| POLE | R1320Q | 20.7 |
| POLE | R1320* | 111.7 |
| POLE | R1320* | 18 |
| POLE | R1320* | 318.9 |
| POLE | R1321K | 18 |
| POLE | T1322N | 4.5 |
| POLE | R1324C | 4.5 |
| POLE | R1324C | 1.8 |
| POLE | I1326V | 5.4 |
| POLE | I1326V | 18.9 |
| POLE | P1330L | 152.3 |
| POLE | P1330L | 11.7 |
| POLE | P1330S | 113.5 |
| POLE | P1330L | 24.3 |
| POLE | P1330L | 134.2 |
| POLE | P1330L | 44.1 |
| POLE | P1330L | 450.5 |
| POLE | W1331C | 5.4 |
| POLE | W1331* | 193.7 |
| POLE | W1331L | 10.8 |
| POLE | Q1332R | 1.8 |
| POLE | I1333T | 96.4 |
| POLE | Q1335* | 228.8 |
| POLE | Q1335H | 4.5 |
| POLE | I1336M | 8.1 |
| POLE | E1338K | 1.8 |
| POLE | E1338K | 18 |
| POLE | E1338K | 47.7 |
| POLE | E1338K | 12.6 |
| POLE | Q1341H | 44.1 |
| POLE | A1342S | 20.7 |
| POLE | A1342T | 10.8 |
| POLE | G1343S | 21.6 |
| POLE | L1344P | 0.9 |
| POLE | F1345L | 24.3 |
| POLE | R1346K | 313.5 |
| POLE | W1348* | 3.6 |
| POLE | W1348C | 26.1 |
| POLE | A1349V | 608.02 |
| POLE | A1349V | 6.3 |
| POLE | A1349V | 116.2 |
| POLE | A1349V | 1.8 |
| POLE | V1351L | 2.7 |
| POLE | V1351I | 0.9 |
| POLE | V1351I | 5.4 |
| POLE | V1351I | 79.3 |
| POLE | V1351I | 13.5 |
| POLE | V1351I | 9.9 |
| POLE | S1353R | 4.5 |
| POLE | D1354E | 8.1 |
| POLE | H1356D | 0.9 |
| POLE | H1356D | 8.1 |
| POLE | H1356D | 0 |
| POLE | I1358T | 40.5 |
| POLE | R1359S | 27 |
| POLE | L1360Q | 2.7 |
| POLE | S1361G | 196 |
| POLE | S1361N | 27 |
| POLE | S1361I | 333.3 |
| POLE | P1363L | 9 |
| POLE | R1364C | 3.6 |
| POLE | R1364H | 1.8 |
| POLE | R1364H | 1.8 |
| POLE | R1364C | 7.2 |
| POLE | R1364H | 2.7 |
| POLE | R1364C | 56.8 |
| POLE | R1364C | 1.8 |
| POLE | R1364C | 60.4 |
| POLE | R1364C | 8.1 |
| POLE | R1364H | 1.8 |
| POLE | R1364L | 4.5 |

TABLE 5-continued

All unique variants identified in POLE and POLD1 tested for driver ability
Associated mutation burdens are representative for each variant

| Gene | Variant | Value |
|---|---|---|
| POLE | F1366L | 134.2 |
| POLE | F1366L | 20.7 |
| POLE | Y1367H | 9 |
| POLE | Y1367H | 5.4 |
| POLE | Y1367D | 5.4 |
| POLE | V1368M | 0.9 |
| POLE | N1369S | 3.6 |
| POLE | N1369S | 10.8 |
| POLE | N1369D | 131.5 |
| POLE | Q1370R | 0.9 |
| POLE | Q1370* | 71.2 |
| POLE | R1371Q | 0 |
| POLE | R1371* | 5.4 |
| POLE | R1371* | 371.2 |
| POLE | R1371L | 0 |
| POLE | R1371L | 43.2 |
| POLE | R1371* | 1.8 |
| POLE | R1371Q | 1.8 |
| POLE | R1371Q | 20.7 |
| POLE | V1372I | 4.5 |
| POLE | A1373V | 91.9 |
| POLE | A1373V | 4.5 |
| POLE | A1375S | 0.9 |
| POLE | A1375V | 3.6 |
| POLE | A1375T | 75.7 |
| POLE | E1376G | 118.9 |
| POLE | E1376D | 12.6 |
| POLE | E1377K | 320.7 |
| POLE | G1378D | 3.6 |
| POLE | A1379T | 3.6 |
| POLE | S1380L | 96.4 |
| POLE | S1380L | 55.9 |
| POLE | S1380L | 235.1 |
| POLE | S1380L | 3.6 |
| POLE | S1380L | 634.2 |
| POLE | Y1381F | 18 |
| POLE | R1382C | 98.2 |
| POLE | R1382C | 39.6 |
| POLE | R1382C | 6.3 |
| POLE | R1382S | 1.8 |
| POLE | R1382L | 2.7 |
| POLE | R1382H | 2.7 |
| POLE | R1382H | 8.1 |
| POLE | R1382H | 34.2 |
| POLE | R1382C | 100 |
| POLE | R1382C | 2.7 |
| POLE | R1382C | 636.9 |
| POLE | R1382H | 2.7 |
| POLE | K1383* | 16.2 |
| POLE | K1383N | 36.9 |
| POLE | K1383N | 8.1 |
| POLE | R1386W | 112.6 |
| POLE | R1386Q | 0.9 |
| POLE | R1386Q | 75.7 |
| POLE | R1386W | 145.9 |
| POLE | R1386W | 7.2 |
| POLE | R1386G | 17.1 |
| POLE | R1386W | 45.9 |
| POLE | R1386Q | 5.4 |
| POLE | V1387A | 8.1 |
| POLE | V1387A | 0.9 |
| POLE | P1389S | 18.9 |
| POLE | P1389S | 91 |
| POLE | R1390C | 58.6 |
| POLE | R1390L | 15.3 |
| POLE | R1390L | 8.1 |
| POLE | R1390C | 3.6 |
| POLE | R1390C | 224.3 |
| POLE | R1390C | 18 |
| POLE | R1390C | 4.5 |
| POLE | R1390C | 9 |
| POLE | R1390C | 13.5 |
| POLE | R1390L | 9.9 |
| POLE | S1391C | 31.5 |
| POLE | S1391C | 5.4 |
| POLE | S1391F | 98.2 |
| POLE | S1391C | 6.3 |

TABLE 5-continued

All unique variants identified in POLE and POLD1 tested for driver ability
Associated mutation burdens are representative for each variant

| Gene | Variant | Value |
|---|---|---|
| POLE | M1393V | 40.5 |
| POLE | M1393I | 25.2 |
| POLE | Y1395H | 3.6 |
| POLE | L1397R | 0 |
| POLE | Y1398C | 7.2 |
| POLE | E1399K | 12.6 |
| POLE | E1399Q | 5.4 |
| POLE | Y1400C | 0.9 |
| POLE | V1402M | 0.9 |
| POLE | P1403S | 231.5 |
| POLE | P1403S | 22.5 |
| POLE | E1404D | 14.4 |
| POLE | E1404K | 20.7 |
| POLE | M1406V | 5.4 |
| POLE | M1406V | 1.8 |
| POLE | Q1408* | 9.9 |
| POLE | H1410P | 0 |
| POLE | I1411V | 7.2 |
| POLE | I1411L | 4.5 |
| POLE | N1412Y | 95.5 |
| POLE | E1417Q | 16.2 |
| POLE | E1417K | 8.1 |
| POLE | A1420S | 6.3 |
| POLE | P1421L | 1.8 |
| POLE | P1421T | 6.3 |
| POLE | E1424K | 5.4 |
| POLE | E1424K | 2.7 |
| POLE | E1424K | 6.3 |
| POLE | E1424K | 1.8 |
| POLE | E1424K | 8.1 |
| POLE | G1425C | 4.5 |
| POLE | G1425F | 34.2 |
| POLE | V1426L | 21.6 |
| POLE | E1428K | 22.5 |
| POLE | E1428Q | 3.6 |
| POLE | E1428Q | 8.1 |
| POLE | T1429S | 3.6 |
| POLE | T1429S | 4.5 |
| POLE | T1429S | 4.5 |
| POLE | T1429S | 4.5 |
| POLE | T1429S | 26.1 |
| POLE | Q1430P | 0 |
| POLE | P1432L | 8.1 |
| POLE | P1432L | 209 |
| POLE | P1432S | 130.6 |
| POLE | P1432L | 4.5 |
| POLE | P1432S | 60.4 |
| POLE | P1432T | 447.8 |
| POLE | P1432L | 4.5 |
| POLE | P1432S | 56.8 |
| POLE | P1432S | 64.9 |
| POLE | P1432S | 143.2 |
| POLE | P1432L | 318.9 |
| POLE | P1432L | 14.4 |
| POLE | F1435L | 386.5 |
| POLE | R1436W | 0 |
| POLE | R1436L | 9 |
| POLE | R1436W | 0.9 |
| POLE | R1436W | 5.4 |
| POLE | A1437T | 1.8 |
| POLE | A1437T | 7.2 |
| POLE | H1440R | 64 |
| POLE | G1442S | 1.8 |
| POLE | V1444E | 17.1 |
| POLE | V1444A | 7.2 |
| POLE | V1444M | 164.9 |
| POLE | V1444L | 12.6 |
| POLE | V1447I | 0 |
| POLE | V1447F | 82.9 |
| POLE | Q1450H | 2.7 |
| POLE | R1453S | 18.9 |
| POLE | R1453K | 561.3 |
| POLE | H1454N | 112.6 |
| POLE | G1457D | 25.2 |
| POLE | W1458* | 4.5 |
| POLE | W1458* | 53.2 |
| POLE | E1461Q | 29.7 |

TABLE 5-continued

All unique variants identified in POLE and POLD1 tested for driver ability
Associated mutation burdens are representative for each variant

| | | |
|---|---|---:|
| POLE | E1461* | 26.1 |
| POLE | A1464V | 479.3 |
| POLE | E1466Q | 4.5 |
| POLE | E1466K | 1.8 |
| POLE | E1466Q | 15.3 |
| POLE | H1467L | 12.6 |
| POLE | H1467N | 2.7 |
| POLE | H1467Y | 18.9 |
| POLE | L1468V | 5.4 |
| POLE | E1469Q | 251.4 |
| POLE | R1471H | 1.8 |
| POLE | R1471C | 6.3 |
| POLE | R1471C | 114.4 |
| POLE | R1471H | 94.6 |
| POLE | R1471C | 43.2 |
| POLE | R1471C | 9 |
| POLE | R1471C | 38.7 |
| POLE | R1471H | 21.6 |
| POLE | R1471C | 72.1 |
| POLE | R1471L | 27 |
| POLE | R1471C | 0.9 |
| POLE | S1472Y | 336 |
| POLE | S1472Y | 336 |
| POLE | S1472F | 2.7 |
| POLE | S1472T | 3.6 |
| POLE | S1472F | 25.2 |
| POLE | S1472F | 33.3 |
| POLE | F1476C | 2.7 |
| POLE | F1476C | 4.5 |
| POLE | E1480K | 7.2 |
| POLE | G1482R | 7.2 |
| POLE | S1483G | 145.9 |
| POLE | I1484V | 0.9 |
| POLE | I1484V | 2.7 |
| POLE | R1485C | 2.7 |
| POLE | R1485H | 6.3 |
| POLE | R1485H | 3.6 |
| POLE | R1485C | 12.6 |
| POLE | R1485C | 38.7 |
| POLE | R1485H | 20.7 |
| POLE | R1485C | 20.7 |
| POLE | R1485C | 9 |
| POLE | I1487S | 9 |
| POLE | H1491N | 39.6 |
| POLE | H1492R | 36.9 |
| POLE | H1492Q | 9 |
| POLE | H1492Y | 2.7 |
| POLE | H1492L | 38.7 |
| POLE | H1492Q | 7.2 |
| POLE | Q1494E | 25.2 |
| POLE | Q1494E | 40.5 |
| POLE | Q1494E | 4.5 |
| POLE | A1495V | 0.9 |
| POLE | H1496Q | 18.9 |
| POLE | K1497E | 2.7 |
| POLE | K1497R | 3.6 |
| POLE | K1497R | 2.7 |
| POLE | K1497R | 0.9 |
| POLE | G1501R | 91 |
| POLE | G1501W | 7.2 |
| POLE | I1502V | 56.8 |
| POLE | I1502N | 26.1 |
| POLE | F1503C | 445.9 |
| POLE | F1503L | 355.9 |
| POLE | I1504F | 0.9 |
| POLE | I1504V | 355.9 |
| POLE | P1505S | 295 |
| POLE | P1505S | 2.7 |
| POLE | P1505S | 1.8 |
| POLE | P1505A | 52.3 |
| POLE | P1505L | 31.5 |
| POLE | P1505S | 31.5 |
| POLE | P1505S | 100.9 |
| POLE | P1505A | 1.8 |
| POLE | Q1507R | 3.6 |
| POLE | R1508C | 2.7 |
| POLE | R1508C | 5.4 |

TABLE 5-continued

All unique variants identified in POLE and POLD1 tested for driver ability
Associated mutation burdens are representative for each variant

| | | |
|---|---|---:|
| POLE | R1509G | 5.4 |
| POLE | R1509S | 31.5 |
| POLE | A1510V | 433 |
| POLE | S1511F | 113.5 |
| POLE | V1514L | 11.7 |
| POLE | L1515P | 7.2 |
| POLE | D1516G | 4.5 |
| POLE | D1516G | 1.8 |
| POLE | R1519C | 2.7 |
| POLE | R1519C | 33.3 |
| POLE | R1519C | 27 |
| POLE | R1519C | 100.9 |
| POLE | R1519C | 854.1 |
| POLE | R1519C | 2.7 |
| POLE | R1519C | 4.5 |
| POLE | R1519C | 3.6 |
| POLE | R1519C | 155 |
| POLE | S1520N | 6.3 |
| POLE | Q1522H | 9.9 |
| POLE | Q1522H | 3.6 |
| POLE | Q1522R | 3.6 |
| POLE | Q1522R | 2.7 |
| POLE | Q1522H | 24.3 |
| POLE | M1523V | 13.5 |
| POLE | M1523I | 26.1 |
| POLE | M1523T | 3.6 |
| POLE | G1527D | 15.3 |
| POLE | A1528T | 0.9 |
| POLE | A1528T | 7.2 |
| POLE | A1528T | 4.5 |
| POLE | A1528T | 17.1 |
| POLE | S1531* | 31.5 |
| POLE | A1532T | 5.4 |
| POLE | A1532T | 0.9 |
| POLE | E1533K | 18 |
| POLE | E1533K | 4.5 |
| POLE | H1534Y | 0.9 |
| POLE | H1534L | 13.5 |
| POLE | H1534L | 24.3 |
| POLE | L1536R | 5.4 |
| POLE | L1536F | 206.3 |
| POLE | L1537F | 69.4 |
| POLE | E1539K | 809 |
| POLE | E1539Q | 9 |
| POLE | G1542S | 40.5 |
| POLE | G1542D | 8.1 |
| POLE | P1543F | 86.5 |
| POLE | E1544G | 180.2 |
| POLE | E1544K | 13.5 |
| POLE | E1544K | 12.6 |
| POLE | L1545I | 7.2 |
| POLE | L1545F | 3.6 |
| POLE | P1547S | 228.8 |
| POLE | P1547S | 80.2 |
| POLE | P1547L | 1.8 |
| POLE | P1548L | 0.9 |
| POLE | P1549R | 0.9 |
| POLE | P1549S | 35.1 |
| POLE | P1549R | 4.5 |
| POLE | P1549R | 0.9 |
| POLE | R1556P | 117.1 |
| POLE | R1556W | 2.7 |
| POLE | R1556W | 74.8 |
| POLE | R1556W | 337.8 |
| POLE | R1556W | 238.7 |
| POLE | A1557T | 31.5 |
| POLE | T1559I | 155.9 |
| POLE | R1566G | 3.6 |
| POLE | A1567V | 433 |
| POLE | A1567S | 9.9 |
| POLE | A1567T | 10.8 |
| POLE | I1568F | 4.5 |
| POLE | R1570Q | 0 |
| POLE | R1570Q | 51.4 |
| POLE | L1573F | 29.7 |
| POLE | A1574T | 7.2 |
| POLE | A1574T | 6.3 |

TABLE 5-continued

All unique variants identified in POLE and POLD1 tested for driver ability
Associated mutation burdens are representative for each variant

| Gene | Variant | Value |
|---|---|---|
| POLE | A1574T | 30.6 |
| POLE | Y1575C | 36.9 |
| POLE | Y1575C | 13.5 |
| POLE | K1576N | 4.5 |
| POLE | K1576R | 3.6 |
| POLE | E1577K | 0.9 |
| POLE | E1577D | 0 |
| POLE | E1577G | 11.7 |
| POLE | R1579G | 3.6 |
| POLE | R1579C | 226.1 |
| POLE | R1579C | 8.1 |
| POLE | R1580Q | 45.9 |
| POLE | R1580Q | 9 |
| POLE | G1581W | 23.4 |
| POLE | G1581V | 16.2 |
| POLE | G1581W | 18.9 |
| POLE | P1582S | 9.9 |
| POLE | L1584R | 57.7 |
| POLE | L1584V | 9.9 |
| POLE | I1585N | 7.2 |
| POLE | A1586V | 9 |
| POLE | A1586T | 87.4 |
| POLE | V1587F | 1.8 |
| POLE | V1587F | 3.6 |
| POLE | A1597T | 5.4 |
| POLE | S1598N | 5.4 |
| POLE | S1598I | 9.9 |
| POLE | I1600T | 4.5 |
| POLE | P1601R | 25.2 |
| POLE | P1601S | 91.9 |
| POLE | V1602L | 1.8 |
| POLE | E1604* | 8.1 |
| POLE | E1604D | 5.4 |
| POLE | E1604K | 5.4 |
| POLE | P1607S | 78.4 |
| POLE | I1611V | 25.2 |
| POLE | V1613M | 37.8 |
| POLE | D1615N | 3.6 |
| POLE | K1616E | 7.2 |
| POLE | I1617P | 1.8 |
| POLE | N1618D | 5.4 |
| POLE | G1620R | 14.4 |
| POLE | V1621F | 73 |
| POLE | V1621I | 402.7 |
| POLE | V1621F | 9 |
| POLE | W1624* | 4.5 |
| POLE | W1624* | 6.3 |
| POLE | W1624* | 3.6 |
| POLE | W1624* | 26.1 |
| POLE | R1626H | 23.4 |
| POLE | R1626C | 34.2 |
| POLE | R1626L | 6.3 |
| POLE | R1626C | 126.1 |
| POLE | R1630Q | 1.8 |
| POLE | R1630W | 0.9 |
| POLE | R1630Q | 3.6 |
| POLE | R1630W | 70.3 |
| POLE | R1630Q | 11.7 |
| POLE | R1630W | 0.9 |
| POLE | R1631C | 3.6 |
| POLE | R1631C | 0 |
| POLE | R1631L | 1.8 |
| POLE | R1631H | 62.2 |
| POLE | R1631H | 3.6 |
| POLE | R1631C | 56.8 |
| POLE | R1631C | 40.5 |
| POLE | M1632I | 24.3 |
| POLE | M1632I | 32.4 |
| POLE | I1633V | 18 |
| POLE | I1633M | 31.5 |
| POLE | R1634H | 3.6 |
| POLE | R1634H | 17.1 |
| POLE | R1634H | 3.6 |
| POLE | R1634H | 29.7 |
| POLE | R1634C | 0 |
| POLE | R1634C | 12.6 |
| POLE | R1634H | 2.7 |

TABLE 5-continued

All unique variants identified in POLE and POLD1 tested for driver ability
Associated mutation burdens are representative for each variant

| | | |
|---|---|---|
| POLE | R1634H | 12.6 |
| POLE | H1635Q | 8.1 |
| POLE | H1635R | 11.7 |
| POLE | Y1636S | 1.8 |
| POLE | L1637F | 84.7 |
| POLE | L1637F | 5.4 |
| POLE | L1639P | 1.8 |
| POLE | D1640G | 8.1 |
| POLE | C1642F | 13.5 |
| POLE | L1643V | 2.7 |
| POLE | S1644L | 7.2 |
| POLE | S1644L | 3.6 |
| POLE | S1644L | 6.3 |
| POLE | F1647S | 450.5 |
| POLE | E1648* | 18 |
| POLE | M1649I | 3.6 |
| POLE | M1649I | 17.1 |
| POLE | M1649I | 36 |
| POLE | R1651M | 17.1 |
| POLE | R1651M | 22.5 |
| POLE | Y1652C | 48.6 |
| POLE | H1654L | 164 |
| POLE | H1654Y | 5.4 |
| POLE | I1655V | 11.7 |
| POLE | P1656L | 18.9 |
| POLE | E1662K | 21.6 |
| POLE | D1663H | 5.4 |
| POLE | S1665T | 0 |
| POLE | S1665F | 7.2 |
| POLE | T1666A | 9 |
| POLE | F1667S | 309.9 |
| POLE | S1669P | 8.1 |
| POLE | L1671F | 6.3 |
| POLE | L1671F | 99.1 |
| POLE | L1671P | 22.5 |
| POLE | A1674S | 27 |
| POLE | A1674T | 12.6 |
| POLE | R1675C | 25.2 |
| POLE | R1675C | 20.7 |
| POLE | R1675H | 1.8 |
| POLE | R1675H | 2.7 |
| POLE | R1675C | 10.8 |
| POLE | R1675H | 5.4 |
| POLE | R1675C | 753.2 |
| POLE | R1675C | 10.8 |
| POLE | R1675C | 69.4 |
| POLE | Q1678* | 1.8 |
| POLE | R1679H | 26.1 |
| POLE | R1679H | 56.8 |
| POLE | R1679C | 72.1 |
| POLE | W1685C | 12.6 |
| POLE | L1686V | 2.7 |
| POLE | S1687F | 76.6 |
| POLE | P1688S | 94.6 |
| POLE | P1688S | 20.7 |
| POLE | A1690T | 7.2 |
| POLE | A1690T | 12.6 |
| POLE | R1691C | 0 |
| POLE | R1691H | 49.5 |
| POLE | R1691H | 27.9 |
| POLE | R1691C | 0.9 |
| POLE | R1691H | 3.6 |
| POLE | R1691C | 1.8 |
| POLE | R1691L | 18.9 |
| POLE | L1694P | 1.8 |
| POLE | G1695V | 5.4 |
| POLE | G1695D | 5.4 |
| POLE | G1695D | 0.9 |
| POLE | A1699S | 9 |
| POLE | D1700G | 15.3 |
| POLE | D1700V | 7.2 |
| POLE | D1701A | 0.9 |
| POLE | D1701N | 15.3 |
| POLE | N1702S | 22.5 |
| POLE | L1704V | 3.6 |
| POLE | L1704V | 10.8 |
| POLE | E1707Q | 9.9 |

TABLE 5-continued

All unique variants identified in POLE and POLD1 tested for driver ability
Associated mutation burdens are representative for each variant

| | | |
|---|---|---|
| POLE | E1707D | 4.5 |
| POLE | E1707A | 3.6 |
| POLE | F1708V | 10.8 |
| POLE | D1709N | 0.9 |
| POLE | D1709N | 7.2 |
| POLE | D1709N | 46.8 |
| POLE | D1710A | 2.7 |
| POLE | Q1711R | 114.4 |
| POLE | Q1711H | 0.9 |
| POLE | G1720D | 82.9 |
| POLE | S1723F | 167.6 |
| POLE | S1723F | 2.7 |
| POLE | S1723F | 108.1 |
| POLE | V1725A | 21.6 |
| POLE | V1725L | 47.7 |
| POLE | V1725L | 46.8 |
| POLE | V1725L | 36 |
| POLE | C1726Y | 11.7 |
| POLE | V1727L | 6.3 |
| POLE | V1727E | 7.2 |
| POLE | E1728Q | 17.1 |
| POLE | D1730H | 6.3 |
| POLE | D1730Y | 10.8 |
| POLE | L1731F | 3.6 |
| POLE | Q1732* | 4.5 |
| POLE | N1733K | 3.6 |
| POLE | A1735V | 76.6 |
| POLE | A1735V | 521.6 |
| POLE | V1736I | 336 |
| POLE | V1736I | 336 |
| POLE | V1736I | 7.2 |
| POLE | V1736I | 1.8 |
| POLE | V1736I | 5.4 |
| POLE | N1737H | 64.9 |
| POLE | Q1741* | 19.8 |
| POLE | Q1741* | 20.7 |
| POLE | H1743D | 11.7 |
| POLE | H1743Y | 27.9 |
| POLE | N1746S | 8.1 |
| POLE | N1746S | 4.5 |
| POLE | N1746S | 4.5 |
| POLE | N1746S | 0 |
| POLE | N1746H | 1.8 |
| POLE | M1748L | 52.3 |
| POLE | E1749* | 14.4 |
| POLE | E1749K | 17.1 |
| POLE | E1749Q | 11.7 |
| POLE | G1750E | 2.7 |
| POLE | G1750E | 3.6 |
| POLE | G1750W | 75.7 |
| POLE | G1750E | 9 |
| POLE | G1750R | 147.7 |
| POLE | A1751S | 5.4 |
| POLE | D1752H | 6.3 |
| POLE | D1752N | 9.9 |
| POLE | M1754R | 0 |
| POLE | M1754L | 23.4 |
| POLE | M1754L | 10.8 |
| POLE | G1755W | 71.2 |
| POLE | G1755W | 7.2 |
| POLE | I1756N | 6.3 |
| POLE | S1757I | 5.4 |
| POLE | D1759N | 14.4 |
| POLE | D1759N | 28.8 |
| POLE | Q1762* | 313.5 |
| POLE | A1764V | 129.7 |
| POLE | S1765F | 33.3 |
| POLE | S1765F | 101.8 |
| POLE | E1767K | 43.2 |
| POLE | D1768G | 19.8 |
| POLE | M1769V | 13.5 |
| POLE | M1769V | 9.9 |
| POLE | T1771M | 275.7 |
| POLE | T1771M | 105.4 |
| POLE | T1771M | 3.6 |
| POLE | T1771M | 18 |
| POLE | T1771M | 36 |

TABLE 5-continued

All unique variants identified in POLE and POLD1 tested for driver ability
Associated mutation burdens are representative for each variant

| POLE | G1773C | 27.9 |
| --- | --- | --- |
| POLE | G1773V | 4.5 |
| POLE | G1773S | 76.6 |
| POLE | Q1774* | 10.8 |
| POLE | Q1774R | 4.5 |
| POLE | A1775T | 561.3 |
| POLE | A1776V | 94.6 |
| POLE | T1777M | 318.06 |
| POLE | P1779L | 4.5 |
| POLE | P1779L | 0.9 |
| POLE | P1779S | 65.8 |
| POLE | A1780G | 2.7 |
| POLE | A1780G | 3.6 |
| POLE | S1781N | 12.6 |
| POLE | Y1782C | 9 |
| POLE | D1783N | 1.8 |
| POLE | T1785A | 0.9 |
| POLE | A1786L | 4.5 |
| POLE | C1788Y | 0.9 |
| POLE | N1790S | 170.3 |
| POLE | M1798V | 4.5 |
| POLE | V1799I | 6.3 |
| POLE | V1799I | 18.9 |
| POLE | V1799F | 360.4 |
| POLE | V1800M | 1.8 |
| POLE | V1800M | 4.5 |
| POLE | V1800M | 6.3 |
| POLE | G1801R | 5.4 |
| POLE | G1801S | 8.1 |
| POLE | G1801S | 54.1 |
| POLE | V1803G | 15.3 |
| POLE | K1804E | 180.2 |
| POLE | E1805D | 11.7 |
| POLE | T1807I | 18.9 |
| POLE | Q1808R | 3.6 |
| POLE | Q1808H | 2.7 |
| POLE | H1810Y | 145.9 |
| POLE | N1811S | 0 |
| POLE | I1812T | 5.4 |
| POLE | Y1813F | 2.7 |
| POLE | Y1813C | 6.3 |
| POLE | D1815H | 44.1 |
| POLE | D1815H | 50.5 |
| POLE | N1816S | 76.6 |
| POLE | V1818M | 0 |
| POLE | M1819I | 17.1 |
| POLE | M1819I | 19.8 |
| POLE | Y1822F | 23.4 |
| POLE | R1823C | 3.6 |
| POLE | R1823H | 3.6 |
| POLE | R1823H | 6.3 |
| POLE | R1823C | 4.5 |
| POLE | R1823C | 11.7 |
| POLE | R1823C | 3.6 |
| POLE | R1823G | 10.8 |
| POLE | W1824C | 1.8 |
| POLE | R1826W | 226.1 |
| POLE | R1826W | 33.3 |
| POLE | R1826W | 305.4 |
| POLE | R1826W | 2.7 |
| POLE | R1826W | 153.2 |
| POLE | R1826Q | 5.4 |
| POLE | R1826Q | 14.4 |
| POLE | R1826Q | 7.2 |
| POLE | R1826W | 4.5 |
| POLE | L1831P | 18 |
| POLE | A1836V | 26.1 |
| POLE | A1836V | 0 |
| POLE | L1837M | 80.2 |
| POLE | R1839H | 1.8 |
| POLE | R1839C | 3.6 |
| POLE | R1839C | 5.4 |
| POLE | R1839L | 4.5 |
| POLE | R1839H | 0.9 |
| POLE | R1839C | 121.6 |
| POLE | R1839C | 59.5 |
| POLE | T1840P | 1.8 |

TABLE 5-continued

All unique variants identified in POLE and POLD1 tested for driver ability
Associated mutation burdens are representative for each variant

| | | |
|---|---|---|
| POLE | L1841F | 0.9 |
| POLE | M1844I | 4.5 |
| POLE | M1844I | 39.6 |
| POLE | M1845R | 5.4 |
| POLE | K1846Q | 9 |
| POLE | K1846T | 7.2 |
| POLE | L1848F | 2.7 |
| POLE | L1850P | 10.8 |
| POLE | L1852F | 699 |
| POLE | I1853T | 0.9 |
| POLE | A1854T | 20.7 |
| POLE | A1854T | 2.7 |
| POLE | A1854T | 4.5 |
| POLE | A1854T | 0.9 |
| POLE | E1855* | 16.2 |
| POLE | F1856L | 233.3 |
| POLE | F1856L | 9.9 |
| POLE | K1857E | 2.7 |
| POLE | R1858H | 126.1 |
| POLE | R1858C | 9 |
| POLE | R1858C | 25.2 |
| POLE | R1858H | 279.3 |
| POLE | R1858H | 60.4 |
| POLE | G1860R | 12.6 |
| POLE | G1860R | 8.1 |
| POLE | G1860R | 3.6 |
| POLE | G1860R | 11.7 |
| POLE | S1862L | 6.3 |
| POLE | I1864T | 0.9 |
| POLE | Y1865C | 27.9 |
| POLE | N1869D | 17.1 |
| POLE | N1869Y | 18 |
| POLE | R1870H | 6.3 |
| POLE | R1870C | 6.3 |
| POLE | R1870H | 11.7 |
| POLE | R1870H | 34.2 |
| POLE | R1870C | 27 |
| POLE | R1870C | 3.6 |
| POLE | R1870H | 18 |
| POLE | I1871V | 29.7 |
| POLE | T1875S | 35.1 |
| POLE | R1878H | 18.9 |
| POLE | R1878H | 0.9 |
| POLE | R1878H | 0 |
| POLE | R1878H | 1.8 |
| POLE | R1878H | 42.3 |
| POLE | R1878C | 1.8 |
| POLE | R1878C | 100.9 |
| POLE | R1878H | 5.4 |
| POLE | R1878H | 0.9 |
| POLE | R1878H | 28.8 |
| POLE | R1878C | 154.1 |
| POLE | R1878H | 4.5 |
| POLE | R1878H | 20.7 |
| POLE | R1878C | 9.9 |
| POLE | R1878C | 62.2 |
| POLE | R1878H | 7.2 |
| POLE | R1879C | 590 |
| POLE | R1879C | 386.5 |
| POLE | R1879C | 1.8 |
| POLE | R1879C | 18.9 |
| POLE | V1880L | 28.8 |
| POLE | A1883T | 335.1 |
| POLE | I1884V | 76.6 |
| POLE | A1885T | 171.2 |
| POLE | A1885T | 3.6 |
| POLE | A1885T | 3.6 |
| POLE | A1885T | 30.6 |
| POLE | A1885T | 3.6 |
| POLE | Y1889C | 34.2 |
| POLE | I1890V | 18 |
| POLE | I1890V | 10.8 |
| POLE | T1891I | 170.3 |
| POLE | S1892I | 11.7 |
| POLE | S1893N | 12.6 |
| POLE | I1894T | 703.6 |
| POLE | K1897Q | 0.9 |

TABLE 5-continued

All unique variants identified in POLE and POLD1 tested for driver ability
Associated mutation burdens are representative for each variant

| | | |
|---|---|---|
| POLE | T1904I | 6.3 |
| POLE | I1905V | 2.7 |
| POLE | S1906Y | 203.6 |
| POLE | S1906Y | 373.9 |
| POLE | S1906Y | 240.5 |
| POLE | F1907L | 3.6 |
| POLE | S1908F | 315.3 |
| POLE | S1908C | 7.2 |
| POLE | R1909Q | 2.7 |
| POLE | R1909Q | 0.9 |
| POLE | R1909Q | 0 |
| POLE | C1910* | 91.9 |
| POLE | W1911L | 5.4 |
| POLE | L1914F | 521.6 |
| POLE | L1914I | 172.1 |
| POLE | L1914V | 12.6 |
| POLE | M1917K | 13.5 |
| POLE | M1917V | 44.1 |
| POLE | S1920P | 1.8 |
| POLE | N1921S | 5.4 |
| POLE | N1921K | 170.3 |
| POLE | N1921I | 5.4 |
| POLE | N1921S | 0.9 |
| POLE | Y1922C | 5.4 |
| POLE | Y1922N | 92.8 |
| POLE | G1923D | 47.7 |
| POLE | G1923D | 5.4 |
| POLE | G1924R | 55 |
| POLE | G1924R | 1.8 |
| POLE | G1924R | 3.6 |
| POLE | G1924R | 6.3 |
| POLE | G1924R | 4.5 |
| POLE | G1924E | 16.2 |
| POLE | G1924E | 13.5 |
| POLE | S1930* | 226.1 |
| POLE | S1930L | 445.9 |
| POLE | S1930L | 634.2 |
| POLE | S1931F | 1.8 |
| POLE | R1932C | 7.2 |
| POLE | R1932C | 6.3 |
| POLE | R1932C | 14.4 |
| POLE | R1932C | 77.5 |
| POLE | R1932C | 4.5 |
| POLE | R1932C | 4.5 |
| POLE | C1935R | 1.8 |
| POLE | G1936R | 23.4 |
| POLE | G1936V | 22.5 |
| POLE | S1940F | 34.2 |
| POLE | S1940A | 8.1 |
| POLE | S1940F | 81.1 |
| POLE | Q1941E | 0 |
| POLE | K1942R | 4.5 |
| POLE | G1945R | 126.1 |
| POLE | G1945A | 28.8 |
| POLE | E1947Q | 9 |
| POLE | E1947K | 7.2 |
| POLE | D1948G | 4.5 |
| POLE | D1948V | 0.9 |
| POLE | E1949K | 9.9 |
| POLE | E1949K | 13.5 |
| POLE | E1953K | 44.1 |
| POLE | D1954G | 0.9 |
| POLE | D1954G | 3.6 |
| POLE | D1955Y | 14.4 |
| POLE | D1955N | 7.2 |
| POLE | E1956K | 1.8 |
| POLE | E1956K | 5.4 |
| POLE | E1956K | 17.1 |
| POLE | E1956Q | 10.8 |
| POLE | E1956K | 0 |
| POLE | E1956D | 80.2 |
| POLE | E1956K | 5.4 |
| POLE | E1957Q | 7.2 |
| POLE | E1957K | 4.5 |
| POLE | E1957* | 15.3 |
| POLE | E1958G | 8.1 |
| POLE | E1958G | 6.3 |

TABLE 5-continued

All unique variants identified in POLE and POLD1 tested for driver ability
Associated mutation burdens are representative for each variant

| Gene | Variant | Value |
|---|---|---|
| POLE | R1959K | 585.6 |
| POLE | R1959G | 3.6 |
| POLE | R1959I | 6.3 |
| POLE | R1959T | 6.3 |
| POLE | G1961R | 23.4 |
| POLE | G1961L | 20.7 |
| POLE | E1962* | 5.4 |
| POLE | E1962K | 7.2 |
| POLE | E1965* | 13.5 |
| POLE | A1967V | 8.1 |
| POLE | A1967V | 3.6 |
| POLE | A1967V | 7.2 |
| POLE | A1967V | 1.8 |
| POLE | A1967V | 16.2 |
| POLE | A1967V | 447.8 |
| POLE | A1967V | 0 |
| POLE | A1967V | 0.9 |
| POLE | E1968K | 110.8 |
| POLE | E1969K | 65.8 |
| POLE | E1969* | 14.4 |
| POLE | E1969* | 30.6 |
| POLE | S1970F | 3.6 |
| POLE | S1970F | 10.8 |
| POLE | N1971S | 2.7 |
| POLE | V1972M | 7.2 |
| POLE | V1972M | 1.8 |
| POLE | V1972M | 7.2 |
| POLE | E1973D | 8.1 |
| POLE | E1977* | 182 |
| POLE | L1983W | 4.5 |
| POLE | A1989P | 0.9 |
| POLE | A1989G | 9.9 |
| POLE | S1991F | 296.4 |
| POLE | Q1993* | 12.6 |
| POLE | F1996V | 7.2 |
| POLE | F1996L | 1.8 |
| POLE | F1996L | 1.8 |
| POLE | F1996L | 9 |
| POLE | L1997F | 12.6 |
| POLE | L1997F | 24.3 |
| POLE | L1997R | 240.5 |
| POLE | M1998I | 16.2 |
| POLE | A2002V | 1.8 |
| POLE | Y2003C | 1.8 |
| POLE | V2005M | 1.8 |
| POLE | V2005M | 3.6 |
| POLE | V2005A | 854.1 |
| POLE | V2005E | 80.2 |
| POLE | A2006V | 311.7 |
| POLE | A2006V | 8.1 |
| POLE | A2006V | 26.1 |
| POLE | A2006S | 1.8 |
| POLE | V2007M | 14.4 |
| POLE | C2010Y | 0.9 |
| POLE | M2011I | 3.6 |
| POLE | M2011K | 4.5 |
| POLE | M2011L | 35.1 |
| POLE | D2013N | 41.4 |
| POLE | G2014R | 51.4 |
| POLE | R2017L | 3.6 |
| POLE | P2020A | 4.5 |
| POLE | G2021V | 28.8 |
| POLE | G2021W | 64.9 |
| POLE | S2022N | 25.2 |
| POLE | S2022N | 2.7 |
| POLE | S2022I | 0.9 |
| POLE | S2022N | 49.5 |
| POLE | S2022N | 0.9 |
| POLE | T2023A | 1.8 |
| POLE | T2023N | 4.5 |
| POLE | T2023N | 1.8 |
| POLE | P2024L | 138.7 |
| POLE | P2024L | 92.8 |
| POLE | P2024L | 67.6 |
| POLE | R2026M | 119.8 |
| POLE | R2027M | 47.7 |
| POLE | R2027S | 50.5 |

TABLE 5-continued

All unique variants identified in POLE and POLD1 tested for driver ability
Associated mutation burdens are representative for each variant

| | | |
|---|---|---:|
| POLE | R2028M | 105.4 |
| POLE | R2028T | 7.2 |
| POLE | R2028M | 29.7 |
| POLE | G2029V | 18.9 |
| POLE | G2029V | 10.8 |
| POLE | A2030S | 119.8 |
| POLE | A2030T | 2.7 |
| POLE | S2031N | 90.1 |
| POLE | S2031G | 2.7 |
| POLE | Q2032* | 40.5 |
| POLE | Q2032R | 12.6 |
| POLE | L2033F | 19.8 |
| POLE | L2033V | 2.7 |
| POLE | S2034F | 107.2 |
| POLE | E2036V | 7.2 |
| POLE | E2036V | 2.7 |
| POLE | E2036V | 5.4 |
| POLE | E2036V | 6.3 |
| POLE | E2036V | 34.2 |
| POLE | G2039W | 31.5 |
| POLE | A2040V | 500 |
| POLE | A2040E | 4.5 |
| POLE | A2040V | 26.1 |
| POLE | A2040V | 11.7 |
| POLE | A2040V | 36 |
| POLE | A2040V | 66.7 |
| POLE | L2044F | 4.5 |
| POLE | L2044F | 63.1 |
| POLE | P2045L | 174.8 |
| POLE | P2045L | 119.8 |
| POLE | P2045L | 229.7 |
| POLE | P2045L | 17.1 |
| POLE | P2045L | 152.3 |
| POLE | G2046V | 12.6 |
| POLE | G2046* | 13.5 |
| POLE | G2046* | 27.9 |
| POLE | T2049I | 114.4 |
| POLE | F2050L | 4.5 |
| POLE | F2050L | 27 |
| POLE | S2051F | 7.2 |
| POLE | Q2052R | 64 |
| POLE | Y2054D | 479.3 |
| POLE | A2056S | 12.6 |
| POLE | A2056T | 3.6 |
| POLE | N2057D | 56.8 |
| POLE | E2058G | 3.6 |
| POLE | E2058G | 2.7 |
| POLE | L2059F | 96.4 |
| POLE | L2059R | 17.1 |
| POLE | T2060I | 4.5 |
| POLE | T2060I | 1.8 |
| POLE | S2062I | 15.3 |
| POLE | S2062R | 42.3 |
| POLE | F2063L | 20.7 |
| POLE | F2063L | 636.9 |
| POLE | I2066V | 8.1 |
| POLE | T2067I | 1.8 |
| POLE | T2067A | 62.2 |
| POLE | Q2068* | 20.7 |
| POLE | K2069N | 3.6 |
| POLE | Q2071* | 18 |
| POLE | K2072N | 33.3 |
| POLE | K2072N | 2.7 |
| POLE | V2074A | 54.1 |
| POLE | S2077F | 261.3 |
| POLE | S2077F | 9.9 |
| POLE | R2078W | 278.4 |
| POLE | R2078W | 117.1 |
| POLE | E2082K | 5.4 |
| POLE | E2082K | 64.9 |
| POLE | E2082K | 19.8 |
| POLE | S2084L | 5.4 |
| POLE | S2084L | 13.5 |
| POLE | S2084L | 31.5 |
| POLE | E2085* | 48.6 |
| POLE | E2085K | 809 |
| POLE | M2086T | 4.5 |

TABLE 5-continued

All unique variants identified in POLE and POLD1 tested for driver ability
Associated mutation burdens are representative for each variant

| | | |
|---|---|---|
| POLE | M2086L | 46.8 |
| POLE | M2086T | 7.2 |
| POLE | M2086I | 20.7 |
| POLE | M2086I | 5.4 |
| POLE | P2088L | 74.8 |
| POLE | P2091S | 4.5 |
| POLE | P2091S | 3.6 |
| POLE | G2092C | 9.9 |
| POLE | G2092S | 8.1 |
| POLE | G2092S | 49.5 |
| POLE | G2092S | 3.6 |
| POLE | G2092S | 5.4 |
| POLE | S2093F | 9.9 |
| POLE | S2093F | 0.9 |
| POLE | S2093F | 3.6 |
| POLE | H2094Y | 17.1 |
| POLE | L2096V | 2.7 |
| POLE | L2096V | 10.8 |
| POLE | L2096V | 3.6 |
| POLE | L2097R | 1.8 |
| POLE | N2098D | 45 |
| POLE | A2101D | 5.4 |
| POLE | F2104L | 118 |
| POLE | K2106E | 156.8 |
| POLE | K2106R | 0.9 |
| POLE | K2106R | 3.6 |
| POLE | K2106R | 6.3 |
| POLE | V2108L | 9 |
| POLE | V2108A | 4.5 |
| POLE | V2108A | 12.6 |
| POLE | C2109W | 14.4 |
| POLE | C2109R | 1.8 |
| POLE | V2111M | 17.1 |
| POLE | L2112V | 0.9 |
| POLE | L2112V | 18 |
| POLE | L2112V | 1.8 |
| POLE | L2112P | 1.8 |
| POLE | S2113C | 18 |
| POLE | D2115E | 112.6 |
| POLE | I2118M | 69.4 |
| POLE | T2119P | 64 |
| POLE | V2122M | 22.5 |
| POLE | R2127P | 3.6 |
| POLE | R2127* | 2.7 |
| POLE | D2128N | 45.9 |
| POLE | R2131H | 15.3 |
| POLE | R2131C | 0.9 |
| POLE | R2131H | 7.2 |
| POLE | R2131C | 11.7 |
| POLE | R2131L | 29.7 |
| POLE | R2131H | 58.6 |
| POLE | R2131H | 1.8 |
| POLE | V2133L | 49.5 |
| POLE | V2135D | 15.3 |
| POLE | G2136S | 18 |
| POLE | E2137Q | 8.1 |
| POLE | E2137K | 0.9 |
| POLE | E2137D | 19.8 |
| POLE | E2137K | 6.3 |
| POLE | E2137K | 155 |
| POLE | F2138V | 7.2 |
| POLE | S2139F | 130.6 |
| POLE | S2139F | 156.8 |
| POLE | E2140Q | 5.4 |
| POLE | E2141Q | 57.7 |
| POLE | A2142S | 4.5 |
| POLE | F2144L | 5.4 |
| POLE | R2145Q | 9 |
| POLE | R2145* | 54.1 |
| POLE | R2145Q | 27.9 |
| POLE | R2145* | 1.8 |
| POLE | R2145Q | 27.9 |
| POLE | R2145* | 15.3 |
| POLE | P2147S | 2.7 |
| POLE | P2147S | 8.1 |
| POLE | S2150F | 3.6 |
| POLE | S2150F | 81.1 |

TABLE 5-continued

All unique variants identified in POLE and POLD1 tested for driver ability
Associated mutation burdens are representative for each variant

| | | |
|---|---|---:|
| POLE | S2150F | 38.7 |
| POLE | Y2151C | 23.4 |
| POLE | Y2151N | 9.9 |
| POLE | Y2151C | 10.8 |
| POLE | Y2151C | 4.5 |
| POLE | P2154T | 699 |
| POLE | E2155K | 13.5 |
| POLE | E2155K | 27 |
| POLE | V2156I | 6.3 |
| POLE | V2156I | 5.4 |
| POLE | I2157N | 93.7 |
| POLE | I2157V | 4.5 |
| POLE | R2159H | 18.9 |
| POLE | R2159L | 11.7 |
| POLE | R2159H | 50.5 |
| POLE | S2160C | 7.2 |
| POLE | S2160I | 7.2 |
| POLE | C2161S | 2.7 |
| POLE | F2163I | 2.7 |
| POLE | C2164F | 25.2 |
| POLE | R2165C | 4.5 |
| POLE | R2165C | 0.9 |
| POLE | R2165C | 2.7 |
| POLE | R2165C | 35.1 |
| POLE | R2165C | 1.8 |
| POLE | R2165C | 6.3 |
| POLE | D2166N | 9 |
| POLE | D2166Y | 5.4 |
| POLE | D2166Y | 14.4 |
| POLE | C2170R | 3.6 |
| POLE | C2170R | 28.8 |
| POLE | C2170R | 27.9 |
| POLE | D2172H | 9.9 |
| POLE | S2173C | 91 |
| POLE | S2174F | 83.8 |
| POLE | S2174F | 12.6 |
| POLE | S2174F | 12.6 |
| POLE | S2174F | 142.3 |
| POLE | F2175V | 122.5 |
| POLE | E2177Q | 9 |
| POLE | E2177Q | 9 |
| POLE | G2179A | 0 |
| POLE | A2180V | 51.4 |
| POLE | A2180V | 46.8 |
| POLE | A2180V | 230.6 |
| POLE | A2180V | 3.6 |
| POLE | A2180V | 450.5 |
| POLE | A2180V | 44.1 |
| POLE | A2180V | 176.6 |
| POLE | A2180V | 10.8 |
| POLE | A2180V | 65.8 |
| POLE | A2180V | 13.5 |
| POLE | A2180V | 6.3 |
| POLE | A2180V | 2.7 |
| POLE | V2181E | 4.5 |
| POLE | V2181F | 6.3 |
| POLE | P2183F | 93.7 |
| POLE | Q2184R | 29.7 |
| POLE | W2185R | 4.5 |
| POLE | W2185* | 122.5 |
| POLE | L2186F | 68.5 |
| POLE | Q2191H | 21.6 |
| POLE | A2192V | 2.7 |
| POLE | A2192V | 7.2 |
| POLE | A2192V | 71.2 |
| POLE | A2192V | 1.8 |
| POLE | A2192V | 2.7 |
| POLE | Y2194* | 3.6 |
| POLE | D2195N | 1.8 |
| POLE | D2195H | 30.6 |
| POLE | D2195N | 10.8 |
| POLE | D2195N | 22.5 |
| POLE | D2195N | 5.4 |
| POLE | D2195N | 34.2 |
| POLE | S2197Y | 2.7 |
| POLE | S2197F | 18.9 |
| POLE | S2197F | 3.6 |

TABLE 5-continued

All unique variants identified in POLE and POLD1 tested for driver ability
Associated mutation burdens are representative for each variant

| Gene | Variant | Value |
|---|---|---|
| POLE | E2200D | 22.5 |
| POLE | E2200* | 20.7 |
| POLE | E2200K | 15.3 |
| POLE | M2201L | 9.9 |
| POLE | M2201V | 6.3 |
| POLE | T2202M | 2.7 |
| POLE | T2202M | 0.9 |
| POLE | T2202M | 9 |
| POLE | T2202M | 2.7 |
| POLE | T2202M | 7.2 |
| POLE | L2207V | 4.5 |
| POLE | M2212V | 45 |
| POLE | T2215S | 9.9 |
| POLE | T2215I | 48.6 |
| POLE | Q2217* | 131.5 |
| POLE | Q2217* | 25.2 |
| POLE | D2218N | 36.9 |
| POLE | V2220I | 7.2 |
| POLE | C2221S | 17.1 |
| POLE | C2221R | 14.4 |
| POLE | K2223R | 2.7 |
| POLE | K2223R | 3.6 |
| POLE | K2223R | 20.7 |
| POLE | K2223R | 1.8 |
| POLE | K2223R | 1.8 |
| POLE | K2223R | 3.6 |
| POLE | K2223R | 1.8 |
| POLE | K2223R | 3.6 |
| POLE | K2223R | 6.3 |
| POLE | K2223R | 1.8 |
| POLE | R2225H | 1.8 |
| POLE | R2225G | 45 |
| POLE | R2225C | 5.4 |
| POLE | R2225C | 12.6 |
| POLE | G2226W | 40.5 |
| POLE | G2226W | 16.2 |
| POLE | G2226R | 53.2 |
| POLE | G2226A | 9.9 |
| POLE | G2226R | 0 |
| POLE | G2226R | 14.4 |
| POLE | G2226R | 1.8 |
| POLE | G2226R | 9 |
| POLE | E2229D | 4.5 |
| POLE | E2229K | 100.9 |
| POLE | S2231G | 33.3 |
| POLE | S2231N | 126.1 |
| POLE | P2233L | 182 |
| POLE | P2233S | 20.7 |
| POLE | Y2235* | 455.9 |
| POLE | C2238Y | 2.7 |
| POLE | C2238W | 46.8 |
| POLE | A2239T | 0.9 |
| POLE | A2239T | 9 |
| POLE | A2239T | 46.8 |
| POLE | G2240R | 25.2 |
| POLE | D2241H | 2.7 |
| POLE | F2242L | 5.4 |
| POLE | A2243T | 7.2 |
| POLE | A2243T | 3.6 |
| POLE | T2245S | 3.6 |
| POLE | T2245S | 4.5 |
| POLE | I2246M | 2.7 |
| POLE | I2246T | 1.8 |
| POLE | I2246V | 1.8 |
| POLE | Q2249L | 18 |
| POLE | Q2249* | 71.2 |
| POLE | F2251L | 6.3 |
| POLE | F2251L | 6.3 |
| POLE | F2251L | 15.3 |
| POLE | F2251L | 3.6 |
| POLE | F2251L | 20.7 |
| POLE | M2252V | 3.6 |
| POLE | M2252L | 12.6 |
| POLE | M2252V | 1.8 |
| POLE | E2253Q | 5.4 |
| POLE | E2253Q | 5.4 |
| POLE | E2253Q | 21.6 |

TABLE 5-continued

All unique variants identified in POLE and POLD1 tested for driver ability
Associated mutation burdens are representative for each variant

| Gene | Variant | Value |
|---|---|---|
| POLE | Q2254H | 28.8 |
| POLE | Q2254R | 1.8 |
| POLE | I2255V | 1.8 |
| POLE | G2256A | 3.6 |
| POLE | G2256A | 2.7 |
| POLE | G2256A | 5.4 |
| POLE | R2259W | 72.1 |
| POLE | R2259Q | 2.7 |
| POLE | R2259Q | 42.3 |
| POLE | R2259W | 44.1 |
| POLE | Q2263* | 10.8 |
| POLE | Q2263* | 8.1 |
| POLE | Q2263* | 3.6 |
| POLE | G2266F | 15.3 |
| POLE | G2266S | 18 |
| POLE | M2267I | 0 |
| POLE | M2267I | 31.5 |
| POLE | S2268L | 333.3 |
| POLE | S2268* | 2.7 |
| POLE | S2268L | 7.2 |
| POLE | S2268L | 5.4 |
| POLE | E2272* | 5.4 |
| POLE | E2272K | 31.5 |
| POLE | E2275K | 561.3 |
| POLE | E2275D | 36 |
| POLE | W2276L | 36 |
| POLE | W2276C | 10.8 |
| POLE | W2276C | 1.8 |
| POLE | L2278P | 8.1 |
| POLE | Q2279H | 1.8 |
| POLE | K2280N | 24.3 |
| POLE | N2281K | 2.7 |
| POLE | P2282T | 9 |
| POLE | Q2283* | 1.8 |
| POLE | G2285C | 2.7 |
| POLE | G2285S | 1.8 |
| POLE | *2287Y | 5.4 |
| POLE | Q2217fs*8 | 59.5 |
| POLE | Y1398fs*1 | 22.5 |
| POLE | E36fs*18 | 7.2 |
| POLE | L1766_E1767insEDMM | 12.6 |
| POLE | L2112fs*23 | 8.1 |
| POLE | A706fs*86 | 6.3 |
| POLE | F699fs*11 | 36 |
| POLE | splice site 3459 + 1G > T | 29.7 |
| POLE | K778fs*12 | 7.2 |
| POLE | splice site 726_801 + 128del204 | 9.9 |
| POLE | splice site 1021 − 1G > T | 34.2 |
| POLE | L1983fs*16 | 9 |
| POLE | splice site 4290 + 1G > A | 2.7 |
| POLE | S752del | 40.5 |
| POLE | E1947_D1948insDEQENED | 0.9 |
| POLE | splice site 6137 − 20_6165 > GAGTGA | 3.6 |
| POLE | K495fs*11 | 7.2 |
| POLE | F699fs*11 | 22.5 |
| POLE | Y1398fs*53 | 4.5 |
| POLE | splice site 5552 + 1G > T | 7.2 |
| POLE | E1707fs*4 | 4.5 |
| POLE | I230fs*6 | 0.9 |
| POLE | splice site 910 − 1G > A | 179.3 |
| POLE | S80fs*10 | 13.5 |
| POLE | A1946fs*4 | 24.3 |
| POLE | splice site 5378 + 1G > T | 3.6 |
| POLE | Y1398fs*1 | 9 |
| POLE | A840fs*10 | 18 |
| POLE | K1550fs*12 | 9.9 |
| POLE | N2260fs*28+ | 2.7 |
| POLE | splice site 2561 + 1G > A | 27.9 |
| POLE | Q125_G126 > HC | 17.1 |
| POLE | I1144del | 8.1 |
| POLE | H1680fs*81 | 18 |
| POLE | G302fs*42 | 4.5 |
| POLE | E396fs*16 | 56.8 |
| POLE | splice site 3795 + 1G > A | 3.6 |
| POLE | splice site 802 − 2A > T | 12.6 |
| POLE | V2234fs*54+ | 17.1 |
| POLE | Q453fs*19 | 76.6 |

TABLE 5-continued

All unique variants identified in POLE and POLD1 tested for driver ability
Associated mutation burdens are representative for each variant

| | | |
|---|---|---|
| POLE | E1202fs*10 | 5.4 |
| POLE | Q1152fs*3 | 31.5 |
| POLE | splice site 2026 + 1_2026 + 45del45 | 5.4 |
| POLE | splice site 5174 − 2A > C | 11.7 |
| POLE | splice site 5174 − 2A > T | 21.6 |
| POLE | G542fs*21 | 56.8 |
| POLE | E740fs*52 | 13.5 |
| POLE | T1891del | 2.7 |
| POLE | V1725fs*36 | 14.4 |
| POLE | splice site 4445 − 1G > A | 16.2 |
| POLE | N751fs*41 | 42.3 |
| POLE | L698fs*94 | 8.1 |
| POLE | F699fs*11 | 1.8 |
| POLE | F675fs*117 | 31.5 |
| POLE | splice site 3266_3275 + 16del26 | 9.9 |
| POLE | splice site 6658 − 2A > G | 8.1 |
| POLE | Q1494fs*50 | 6.3 |
| POLE | splice site 62 + 1G > T | 17.1 |
| POLE | V1446fs*3 | 30.6 |
| POLE | V1446fs*3 | 42.3 |
| POLE | splice site 5379 − 7_5382delCTTTCAGGATC | 6.3 |
| POLE | splice site 4291 − 1G > T | 17.1 |
| POLE | splice site 4499_4551 + 93del146 | 7.2 |
| POLE | K175del | 39.6 |
| POLE | V1447fs*7 | 33.3 |
| POLE | splice site 3795 + 1G > A | 114.4 |
| POLE | V1089fs*35 | 6.3 |
| POLE | A2030fs*29 | 7.2 |
| POLE | V574fs*1 | 8.1 |
| POLE | splice site 6137 − 1G > C | 12.6 |
| POLE | A939fs*10 | 3.6 |
| POLE | splice site 3460 − 2A > G | 14.4 |
| POLE | V2025fs*1 | 8.1 |
| POLE | L999fs*13 | 17.1 |
| POLE | K1550fs*12 | 58.6 |
| POLE | V82_D83 > VSTA*AVVLSA*AVVLLRQ | 9.9 |
| POLE | D490fs*12 | 2.7 |
| POLE | K1276del | 40.5 |
| POLE | V2220fs*69+ | 27 |
| POLE | splice site 6331 − 41_6337del48 | 4.5 |
| POLE | V2025fs*1 | 9 |
| POLE | K1181del | 2.7 |
| POLE | C501fs*1 | 6.3 |
| POLE | splice site 2026 + 1_2026 + 45del45 | 2.7 |
| POLE | M900_V901del | 1.8 |
| POLE | D1211fs*1 | 4.5 |
| POLE | V1518fs*27 | 15.3 |
| POLE | splice site 3276 − 1G > C | 0.9 |
| POLE | P135fs*68 | 72.1 |
| POLE | L698fs*94 | 5.4 |
| POLE | splice site 6331 − 2A > G | 57.7 |
| POLE | D2218fs*3 | 2.7 |
| POLE | P269fs*26 | 7.2 |
| POLE | splice site 4006 − 1G > C | 14.4 |
| POLE | G904fs*37 | 15.3 |
| POLE | R762fs*29 | 4.5 |
| POLE | L698fs*94 | 109 |
| POLE | D490fs*12 | 2.7 |
| POLE | K2228del | 0 |
| POLE | splice site 801_801 + 1delTG | 31.5 |
| POLE | A2030fs*18 | 56.8 |
| POLE | E137fs*12 | 2.7 |
| POLE | F699fs*11 | 27 |
| POLE | splice site 3060 + 1G > A | 9 |
| POLE | P1223_A1224insA | 0.9 |
| POLE | S1139fs*15 | 7.2 |
| POLE | L698fs*94 | 64.9 |
| POLE | splice site 3266_3275 + 16del26 | 4.5 |
| POLE | E2036_A2037del | 26.1 |
| POLE | K1181del | 3.6 |
| POLE | E740fs*51 | 5.4 |
| POLE | splice site 424 − 1G > A | 3.6 |
| POLE | S871fs*38 | 2.7 |
| POLE | A2040fs*19 | 18.9 |
| POLE | splice site 1795 − 1G > T | 96.4 |
| POLE | K175del | 24.3 |
| POLE | R1364fs*5 | 69.4 |

TABLE 5-continued

All unique variants identified in POLE and POLD1 tested for driver ability
Associated mutation burdens are representative for each variant

| Gene | Variant | Value |
|---|---|---|
| POLE | K1550fs*12 | 9.9 |
| POLE | S30fs*24 | 7.2 |
| POLE | splice site 2468 + 1G > T | 14.4 |
| POLE | L1831fs*3 | 1.8 |
| POLE | E396fs*28 | 27 |
| POLE | splice site 1795 − 2A > T | 28.8 |
| POLE | V1446fs*3 | 222.5 |
| POLE | P1223__A1224insA | 5.4 |
| POLE | splice site 331 − 1G > A | 2.7 |
| POLE | C600fs*1 | 8.1 |
| POLE | L1171fs*6 | 153.2 |
| POLE | splice site 1923 + 1G > T | 27.9 |
| POLE | L698fs*94 | 59.5 |
| POLE | V1518fs*44 | 18 |
| POLE | splice site 3582 + 1G > T | 19.8 |
| POLE | F699fs*11 | 52.3 |
| POLE | E521fs*7 | 6.3 |
| POLE | K1050fs*25 | 9.9 |
| POLE | K1174fs*45 | 9.9 |
| POLE | splice site 4290 + 1G > T | 18.9 |
| POLE | P1223__A1224insA | 2.7 |
| POLE | G1927fs*70 | 76.6 |
| POLE | splice site 1021 − 21__1030 > ACTGTCTGCTCTTTCTCTTCTTCAAGCTAT | 33.3 |
| POLE | N1790fs*1 | 3.6 |
| POLE | R222fs*14 | 5.4 |
| POLE | S2173fs*115+ | 7.2 |
| POLE | N1369fs*6 | 6.3 |
| POLE | splice site 1473 + 2T > C | 45 |
| POLE | E396fs*16 | 22.5 |
| POLE | L1848fs*56 | 2.7 |
| POLE | V2025fs*34 | 41.4 |
| POLE | R1308fs*53 | 95.5 |
| POLE | G1542fs*20 | 14.4 |
| POLE | L46fs*6 | 18 |
| POLE | splice site 3266__3275 + 16del26 | 7.2 |
| POLE | C1788fs*8 | 6.3 |
| POLE | splice site 2026 + 1__2026 + 45del45 | 3.6 |
| POLE | D339fs*2 | 35.1 |
| POLE | G1262fs*99 | 18.9 |
| POLE | L698fs*94 | 39.6 |
| POLE | D316fs*28 | 2.7 |
| POLE | K1550fs*12 | 368.5 |
| POLE | splice site 6651__6657 + 6 > TGC | 2.7 |
| POLE | L1850fs*54 | 2.7 |
| POLE | K1170fs*49 | 42.3 |
| POLE | N1843del | 4.5 |
| POLE | T26fs*18 | 1.8 |
| POLE | V1446fs*3 | 46.8 |
| POLE | G24fs*30 | 132.4 |
| POLE | E1237fs*124 | 79.3 |
| POLE | K1550fs*12 | 36 |
| POLE | splice site 3266__3275 + 16del26 | 1.8 |
| POLE | splice site 4006 − 1G > C | 25.2 |
| POLE | S5fs*49 | 7.2 |
| POLE | L1986fs*13 | 45 |
| POLE | F699fs*11 | 15.3 |
| POLE | splice site 1686 + 1G > T | 19.8 |
| POLE | splice site 4149 + 1G > A | 4.5 |
| POLE | F699fs*11 | 123.4 |
| POLE | K175del | 2.7 |
| POLE | K2228del | 2.7 |
| POLE | L493fs*13 | 4.5 |
| POLE | I1414fs*38 | 17.1 |
| POLE | L1295__V1301del | 35.1 |
| POLE | E2229del | 8.1 |
| POLE | splice site 4953 − 2A > G | 10.8 |
| POLE | L698fs*94 | 38.7 |
| POLE | splice site 3460 − 1G > A | 264 |
| POLE | F2175fs*26 | 1.8 |
| POLE | V1446fs*3 | 2.7 |
| POLE | splice site 4552 − 2__4552 − 1AG > TT | 36 |
| POLE | I2157fs*45 | 5.4 |
| POLE | splice site 3266__3275 + 16del26 | 12.6 |
| POLE | K1276del | 55.9 |
| POLE | K1550fs*12 | 32.4 |
| POLE | splice site 1106 + 1G > T | 9 |
| POLE | L698fs*94 | 79.3 |

TABLE 5-continued

All unique variants identified in POLE and POLD1 tested for driver ability
Associated mutation burdens are representative for each variant

| Gene | Variant | Mutation burden |
|---|---|---|
| POLE | F931fs*10 | 18 |
| POLE | splice site 6005 − 1G > A | 87.4 |
| POLE | D1954_D1955insDEEERDG | 6.3 |
| POLE | splice site 3266_3275 + 16del26 | 103.6 |
| POLE | splice site 3271 + 99_3275del104 | 5.4 |
| POLE | splice site 3253_3275 + 2del25 | 2.7 |
| POLE | V783fs*9 | 2.7 |
| POLE | S2173fs*115+ | 18 |
| POLE | V1725fs*36 | 4.5 |
| POLE | splice site 4729 − 2A > T | 106.3 |
| POLE | N1396fs*55 | 5.4 |
| POLE | I344fs*26 | 1.8 |
| POLE | splice site 2026 + 1_2026 + 45del45 | 2.7 |
| POLE | splice site 4006 − 1G > T | 6.3 |
| POLE | splice site 5173 + 1G > T | 16.2 |
| POLE | E903fs*38 | 26.1 |
| POLE | P1223_A1224insA | 5.4 |
| POLE | splice site 6137 − 1_6137GG > AA | 23.4 |
| POLE | splice site 3379 − 2A > G | 9 |
| POLE | splice site 286 − 1G > A | 6.3 |
| POLE | splice site 6531 + 1G > A | 18 |
| POLE | C1788fs*8 | 1.8 |
| POLE | P1223_A1224insA | 67.6 |
| POLE | W243fs*20 | 30.6 |
| POLE | S2197fs*91+ | 159.5 |
| POLE | splice site 2561 + 1G > T | 16.2 |
| POLE | Q2071fs*52 | 1.8 |
| POLE | splice site 1687 − 1G > C | 19.8 |
| POLE | splice site 2864 + 1G > A | 9.9 |
| POLE | L120fs*82 | 4.5 |
| POLE | splice site 5378 + 1G > T | 7.2 |
| POLE | D319fs*3 | 21.6 |
| POLE | R10fs*16 | 0.9 |
| POLE | splice site 3266_3275 + 16del27 | 2.7 |
| POLE | splice site 6747 + 1G > T | 9.9 |
| POLE | splice site 3266_3275 + 16del26 | 8.1 |
| POLE | I1326fs*58 | 2.7 |
| POLE | splice site 4291 − 1G > T | 1.8 |
| POLE | splice site 2173 + 2T > A | 13.5 |
| POLE | V1863_I1864insI | 9 |
| POLE | Q2254fs*28+ | 10.8 |
| POLE | F699fs*11 | 1.8 |
| POLE | splice site 5553 − 1G > A | 34.2 |
| POLE | F1708fs*53 | 80.2 |
| POLE | splice site 6658 − 2A > G | 3.6 |
| POLE | F699fs*11 | 68.5 |
| POLE | V1887fs*36 | 12.6 |
| POLE | splice site 6658 − 2A > G | 21.6 |
| POLE | K1550fs*11 | 54.1 |
| POLE | I128fs*21 | 23.4 |

| POLD1 Gene | AA change | Mutation burden |
|---|---|---|
| POLD1 | M1L | 4.5 |
| POLD1 | M1T | 17.1 |
| POLD1 | D2H | 4.5 |
| POLD1 | G3S | 9 |
| POLD1 | R6W | 48.6 |
| POLD1 | R6W | 6.3 |
| POLD1 | R6W | 7.2 |
| POLD1 | P7S | 23.4 |
| POLD1 | P7S | 64 |
| POLD1 | P9L | 69.4 |
| POLD1 | P9S | 64 |
| POLD1 | P9S | 104.5 |
| POLD1 | G10E | 73.9 |
| POLD1 | P11H | 230.6 |
| POLD1 | G12R | 0 |
| POLD1 | G12R | 2.7 |
| POLD1 | G12W | 41.4 |
| POLD1 | G12V | 87.4 |
| POLD1 | V13L | 6.3 |
| POLD1 | V13L | 2.7 |
| POLD1 | V13L | 25.2 |
| POLD1 | V13M | 1.8 |
| POLD1 | V13M | 6.3 |

TABLE 5-continued

All unique variants identified in POLE and POLD1 tested for driver ability
Associated mutation burdens are representative for each variant

| | | |
|---|---|---|
| POLD1 | P14S | 15.3 |
| POLD1 | K16E | 4.5 |
| POLD1 | K16E | 4.5 |
| POLD1 | R17L | 7.2 |
| POLD1 | A18T | 76.6 |
| POLD1 | A18S | 15.3 |
| POLD1 | R19L | 49.5 |
| POLD1 | R19L | 9.9 |
| POLD1 | G20R | 38.7 |
| POLD1 | G21S | 96.4 |
| POLD1 | G21S | 8.1 |
| POLD1 | G21C | 2.7 |
| POLD1 | G21V | 18.9 |
| POLD1 | G21N | 47.7 |
| POLD1 | G21V | 9.9 |
| POLD1 | G21C | 12.6 |
| POLD1 | L22F | 0.9 |
| POLD1 | L22P | 2.7 |
| POLD1 | D24N | 9 |
| POLD1 | D27N | 26.1 |
| POLD1 | D27G | 4.5 |
| POLD1 | A28T | 31.5 |
| POLD1 | P29H | 91.9 |
| POLD1 | R30L | 31.5 |
| POLD1 | R30L | 10.8 |
| POLD1 | P31Q | 165.8 |
| POLD1 | F34L | 0.9 |
| POLD1 | F34I | 67.6 |
| POLD1 | F34L | 208.1 |
| POLD1 | E35K | 2.7 |
| POLD1 | E35K | 0.9 |
| POLD1 | E35K | 4.5 |
| POLD1 | D37N | 4.5 |
| POLD1 | D37N | 1.8 |
| POLD1 | D37N | 2.7 |
| POLD1 | D37N | 29.7 |
| POLD1 | D37N | 9 |
| POLD1 | A39T | 44.1 |
| POLD1 | A39T | 114.4 |
| POLD1 | M41L | 2.7 |
| POLD1 | E42* | 25.2 |
| POLD1 | M44V | 5.4 |
| POLD1 | M44V | 42.3 |
| POLD1 | M44I | 20.7 |
| POLD1 | E47K | 4.5 |
| POLD1 | H48Y | 668.5 |
| POLD1 | R49S | 8.1 |
| POLD1 | E52K | 30.6 |
| POLD1 | Q53L | 10.8 |
| POLD1 | E54V | 24.3 |
| POLD1 | E57K | 75.7 |
| POLD1 | E57K | 48.6 |
| POLD1 | L58V | 72.1 |
| POLD1 | Q59H | 28.8 |
| POLD1 | Q59H | 4.5 |
| POLD1 | S60P | 15.3 |
| POLD1 | S60L | 4.5 |
| POLD1 | S60P | 48.6 |
| POLD1 | E63* | 19.8 |
| POLD1 | E63K | 1.8 |
| POLD1 | E63K | 3.6 |
| POLD1 | E63K | 0.9 |
| POLD1 | E63K | 3.6 |
| POLD1 | V65L | 2.7 |
| POLD1 | D67N | 4.5 |
| POLD1 | D67N | 13.5 |
| POLD1 | G68W | 33.3 |
| POLD1 | G68A | 23.4 |
| POLD1 | G68V | 16.2 |
| POLD1 | G68W | 18 |
| POLD1 | G68R | 27.9 |
| POLD1 | G68R | 5.4 |
| POLD1 | G68R | 0.9 |
| POLD1 | P71S | 122.5 |
| POLD1 | S73L | 19.8 |
| POLD1 | P77F | 31.5 |
| POLD1 | P77L | 121.6 |

TABLE 5-continued

All unique variants identified in POLE and POLD1 tested for driver ability
Associated mutation burdens are representative for each variant

| | | |
|---|---|---|
| POLD1 | R78C | 26.1 |
| POLD1 | R78C | 5.4 |
| POLD1 | R78C | 3.6 |
| POLD1 | R78H | 10.8 |
| POLD1 | R78C | 15.3 |
| POLD1 | R78C | 2.7 |
| POLD1 | R81Q | 107.2 |
| POLD1 | R81W | 3.6 |
| POLD1 | R81Q | 15.3 |
| POLD1 | R81Q | 55 |
| POLD1 | R81P | 6.3 |
| POLD1 | T83I | 9 |
| POLD1 | A86P | 2.7 |
| POLD1 | A86V | 2.7 |
| POLD1 | A86G | 6.3 |
| POLD1 | A86V | 24.3 |
| POLD1 | A86V | 2.7 |
| POLD1 | A86S | 0.9 |
| POLD1 | A86V | 753.2 |
| POLD1 | L87P | 0.9 |
| POLD1 | P89S | 27.9 |
| POLD1 | Q90R | 2.7 |
| POLD1 | Q90L | 4.5 |
| POLD1 | E92* | 6.3 |
| POLD1 | E92Q | 13.5 |
| POLD1 | E92K | 368.5 |
| POLD1 | L94F | 83.8 |
| POLD1 | I95F | 12.6 |
| POLD1 | I95V | 153.2 |
| POLD1 | Q97* | 4.5 |
| POLD1 | E100* | 28.8 |
| POLD1 | D102Y | 45 |
| POLD1 | H103Q | 94.6 |
| POLD1 | Y104C | 6.3 |
| POLD1 | V105A | 6.3 |
| POLD1 | V105M | 1.8 |
| POLD1 | G106C | 30.6 |
| POLD1 | A108V | 55.9 |
| POLD1 | A108S | 84.7 |
| POLD1 | A108V | 0 |
| POLD1 | A108V | 24.3 |
| POLD1 | A108V | 493.7 |
| POLD1 | Q109* | 8.1 |
| POLD1 | Q109E | 2.7 |
| POLD1 | P110R | 7.2 |
| POLD1 | P110H | 59.5 |
| POLD1 | V111L | 10.8 |
| POLD1 | V111A | 0.9 |
| POLD1 | P112H | 541.36 |
| POLD1 | P112H | 63.1 |
| POLD1 | G113V | 52.3 |
| POLD1 | G114V | 48.6 |
| POLD1 | G114W | 6.3 |
| POLD1 | R119C | 10.8 |
| POLD1 | R119C | 12.6 |
| POLD1 | R119C | 9.9 |
| POLD1 | R119C | 122.5 |
| POLD1 | R119C | 3.6 |
| POLD1 | R119C | 1.8 |
| POLD1 | R119C | 2.7 |
| POLD1 | R119C | 37.8 |
| POLD1 | R119C | 3.6 |
| POLD1 | R119C | 2.7 |
| POLD1 | G120R | 1.8 |
| POLD1 | G120S | 4.5 |
| POLD1 | G120S | 4.5 |
| POLD1 | G120N | 48.6 |
| POLD1 | G120R | 12.6 |
| POLD1 | G120V | 20.7 |
| POLD1 | S121F | 74.8 |
| POLD1 | S121F | 22.5 |
| POLD1 | S121F | 98.2 |
| POLD1 | S121F | 4.5 |
| POLD1 | S121F | 27 |
| POLD1 | S121F | 36 |
| POLD1 | V122M | 5.4 |
| POLD1 | V122M | 4.5 |

TABLE 5-continued

All unique variants identified in POLE and POLD1 tested for driver ability
Associated mutation burdens are representative for each variant

| | | |
|---|---|---|
| POLD1 | P123H | 118 |
| POLD1 | P123L | 521.6 |
| POLD1 | P123H | 31.5 |
| POLD1 | R126C | 55.9 |
| POLD1 | R126C | 5.4 |
| POLD1 | R126L | 28.8 |
| POLD1 | R126C | 101.8 |
| POLD1 | R126H | 5.4 |
| POLD1 | R126H | 73 |
| POLD1 | R126C | 6.3 |
| POLD1 | R126C | 64 |
| POLD1 | R126H | 19.8 |
| POLD1 | R126H | 76.6 |
| POLD1 | A127T | 2.7 |
| POLD1 | A127V | 32.4 |
| POLD1 | F128S | 587 |
| POLD1 | G129R | 55.9 |
| POLD1 | G129R | 6.3 |
| POLD1 | V130I | 3.6 |
| POLD1 | V130I | 455.9 |
| POLD1 | D132N | 3.6 |
| POLD1 | D132N | 305.4 |
| POLD1 | D132Y | 20.7 |
| POLD1 | D132Y | 15.3 |
| POLD1 | S136F | 0.9 |
| POLD1 | S136A | 455.9 |
| POLD1 | S136F | 215.3 |
| POLD1 | V137F | 8.1 |
| POLD1 | C138Y | 170.3 |
| POLD1 | C138Y | 72.1 |
| POLD1 | C139* | 6.3 |
| POLD1 | G143C | 19.8 |
| POLD1 | G143V | 8.1 |
| POLD1 | G143S | 4.5 |
| POLD1 | G143S | 94.6 |
| POLD1 | G143S | 65.8 |
| POLD1 | G143S | 0.9 |
| POLD1 | G143C | 37.8 |
| POLD1 | G143S | 2.7 |
| POLD1 | P146L | 24.3 |
| POLD1 | P146S | 2.7 |
| POLD1 | P151L | 214.4 |
| POLD1 | P151L | 458.6 |
| POLD1 | A152S | 27 |
| POLD1 | P153S | 27 |
| POLD1 | P153L | 1.8 |
| POLD1 | P153L | 7.2 |
| POLD1 | P154S | 37.8 |
| POLD1 | P154S | 155 |
| POLD1 | P154S | 47.7 |
| POLD1 | P154R | 8.1 |
| POLD1 | G155A | 5.4 |
| POLD1 | P158T | 11.7 |
| POLD1 | P158S | 0.9 |
| POLD1 | E159K | 39.6 |
| POLD1 | E159K | 18 |
| POLD1 | E159K | 95.5 |
| POLD1 | E159K | 1.8 |
| POLD1 | E159K | 14.4 |
| POLD1 | E159K | 8.1 |
| POLD1 | E159K | 3.6 |
| POLD1 | H160Y | 7.2 |
| POLD1 | H160Y | 5.4 |
| POLD1 | H160Q | 7.2 |
| POLD1 | D163Y | 7.2 |
| POLD1 | R166W | 3.6 |
| POLD1 | R166W | 20.7 |
| POLD1 | R166W | 4.5 |
| POLD1 | R166Q | 0 |
| POLD1 | R166W | 0.9 |
| POLD1 | R166W | 4.5 |
| POLD1 | R166Q | 7.2 |
| POLD1 | R166W | 18 |
| POLD1 | R166Q | 6.3 |
| POLD1 | R166W | 3.6 |
| POLD1 | L170F | 455.9 |
| POLD1 | L170S | 59.5 |

TABLE 5-continued

All unique variants identified in POLE and POLD1 tested for driver ability
Associated mutation burdens are representative for each variant

| | | |
|---|---|---|
| POLD1 | I172M | 21.6 |
| POLD1 | R174L | 9.9 |
| POLD1 | R174W | 72.1 |
| POLD1 | R174W | 1.8 |
| POLD1 | R174W | 10.8 |
| POLD1 | R174L | 6.3 |
| POLD1 | D175F | 11.7 |
| POLD1 | S176R | 9 |
| POLD1 | R177H | 25.2 |
| POLD1 | R177H | 11.7 |
| POLD1 | R177C | 301.8 |
| POLD1 | G178W | 5.4 |
| POLD1 | G178W | 25.2 |
| POLD1 | G178V | 18.9 |
| POLD1 | G178R | 20.7 |
| POLD1 | G178R | 1.8 |
| POLD1 | G178R | 2.7 |
| POLD1 | G178V | 119.8 |
| POLD1 | G178R | 2.7 |
| POLD1 | G178R | 2.7 |
| POLD1 | G178R | 2.7 |
| POLD1 | L182M | 0 |
| POLD1 | G184R | 4.5 |
| POLD1 | G184E | 178.4 |
| POLD1 | G184R | 75.7 |
| POLD1 | G184V | 51.4 |
| POLD1 | G184W | 50.5 |
| POLD1 | A186V | 133.3 |
| POLD1 | A186V | 1.8 |
| POLD1 | V187M | 0 |
| POLD1 | V187L | 9.9 |
| POLD1 | V187G | 7.2 |
| POLD1 | L188R | 3.6 |
| POLD1 | L188R | 2.7 |
| POLD1 | L188R | 3.6 |
| POLD1 | L188R | 4.5 |
| POLD1 | L188R | 1.8 |
| POLD1 | A189S | 28.8 |
| POLD1 | A189S | 4.5 |
| POLD1 | A189D | 51.4 |
| POLD1 | A189S | 6.3 |
| POLD1 | V190L | 19.8 |
| POLD1 | R195L | 15.3 |
| POLD1 | E196K | 65.8 |
| POLD1 | M198L | 36.9 |
| POLD1 | M198V | 9.9 |
| POLD1 | Y201H | 0.9 |
| POLD1 | Y201H | 21.6 |
| POLD1 | H202N | 44.1 |
| POLD1 | H202Q | 0.9 |
| POLD1 | H202Q | 12.6 |
| POLD1 | G203V | 12.6 |
| POLD1 | G203R | 0.9 |
| POLD1 | G203W | 9 |
| POLD1 | G203V | 34.2 |
| POLD1 | G203R | 105.4 |
| POLD1 | G203R | 4.5 |
| POLD1 | G203R | 18.9 |
| POLD1 | G203R | 1.8 |
| POLD1 | H204Q | 79.3 |
| POLD1 | G205S | 112.6 |
| POLD1 | G205S | 7.2 |
| POLD1 | G205C | 8.1 |
| POLD1 | G205S | 6.3 |
| POLD1 | P206S | 98.2 |
| POLD1 | S207F | 100.9 |
| POLD1 | S207F | 16.2 |
| POLD1 | S207F | 104.5 |
| POLD1 | P208L | 74.8 |
| POLD1 | P208L | 38.7 |
| POLD1 | P208L | 27.9 |
| POLD1 | P208S | 445.9 |
| POLD1 | P208L | 30.6 |
| POLD1 | P208R | 89.2 |
| POLD1 | P208L | 0 |
| POLD1 | P208S | 9.9 |
| POLD1 | P208S | 53.2 |

TABLE 5-continued

All unique variants identified in POLE and POLD1 tested for driver ability
Associated mutation burdens are representative for each variant

| | | |
|---|---|---|
| POLD1 | L210M | 94.6 |
| POLD1 | L210V | 3.6 |
| POLD1 | R211C | 14.4 |
| POLD1 | R211H | 4.5 |
| POLD1 | R211C | 578.4 |
| POLD1 | R211P | 2.7 |
| POLD1 | R211H | 4.5 |
| POLD1 | R211H | 2.7 |
| POLD1 | R211H | 10.8 |
| POLD1 | R211H | 0.9 |
| POLD1 | R211H | 5.4 |
| POLD1 | R211H | 7.2 |
| POLD1 | R211H | 35.1 |
| POLD1 | R211H | 5.4 |
| POLD1 | R211C | 9 |
| POLD1 | R211H | 9 |
| POLD1 | R211H | 12.6 |
| POLD1 | R211H | 2.7 |
| POLD1 | R211L | 4.5 |
| POLD1 | R211P | 2.7 |
| POLD1 | V214M | 2.7 |
| POLD1 | V214M | 8.1 |
| POLD1 | V214M | 11.7 |
| POLD1 | A215V | 238.18 |
| POLD1 | A215V | 0.9 |
| POLD1 | A215V | 10.8 |
| POLD1 | A215V | 9 |
| POLD1 | A215V | 155 |
| POLD1 | A215V | 7.2 |
| POLD1 | L216M | 27 |
| POLD1 | R218L | 22.5 |
| POLD1 | R218L | 18.9 |
| POLD1 | V220L | 22.5 |
| POLD1 | A221S | 18.9 |
| POLD1 | A221T | 108.1 |
| POLD1 | A221S | 14.4 |
| POLD1 | A221S | 0.9 |
| POLD1 | P222L | 12.6 |
| POLD1 | P222S | 445.9 |
| POLD1 | P222L | 6.3 |
| POLD1 | P222L | 52.3 |
| POLD1 | A223T | 318.9 |
| POLD1 | R224H | 37.8 |
| POLD1 | R224C | 1.8 |
| POLD1 | R224C | 12.6 |
| POLD1 | R224H | 3.6 |
| POLD1 | R224C | 13.5 |
| POLD1 | R224H | 114.4 |
| POLD1 | R224H | 11.7 |
| POLD1 | R224C | 4.5 |
| POLD1 | R224C | 10.8 |
| POLD1 | R224H | 4.5 |
| POLD1 | R224C | 58.6 |
| POLD1 | R224C | 5.4 |
| POLD1 | R224C | 1.8 |
| POLD1 | R224H | 2.7 |
| POLD1 | R225H | 9 |
| POLD1 | R225H | 45 |
| POLD1 | R225H | 10.8 |
| POLD1 | R225H | 0.9 |
| POLD1 | R225P | 71.2 |
| POLD1 | R225H | 2.7 |
| POLD1 | R225C | 18 |
| POLD1 | R225H | 2.7 |
| POLD1 | R225H | 8.1 |
| POLD1 | R225C | 12.6 |
| POLD1 | R225H | 3.6 |
| POLD1 | R225C | 2.7 |
| POLD1 | L227M | 665.8 |
| POLD1 | E228K | 36 |
| POLD1 | E228Q | 27.9 |
| POLD1 | Q229R | 0 |
| POLD1 | Q229R | 8.1 |
| POLD1 | Q229H | 8.1 |
| POLD1 | G230D | 14.4 |
| POLD1 | R232H | 587 |
| POLD1 | R232H | 64.9 |

TABLE 5-continued

All unique variants identified in POLE and POLD1 tested for driver ability
Associated mutation burdens are representative for each variant

| Gene | Variant | Value |
|---|---|---|
| POLD1 | R232C | 3.6 |
| POLD1 | R232C | 650.5 |
| POLD1 | R232C | 224.3 |
| POLD1 | R232C | 108.1 |
| POLD1 | V233L | 13.5 |
| POLD1 | G235S | 6.3 |
| POLD1 | T238M | 5.4 |
| POLD1 | T238M | 3.6 |
| POLD1 | T238M | 4.5 |
| POLD1 | T238M | 2.7 |
| POLD1 | T238M | 2.7 |
| POLD1 | T238M | 5.4 |
| POLD1 | T238M | 1.8 |
| POLD1 | A242T | 43.2 |
| POLD1 | A242T | 4.5 |
| POLD1 | A242V | 3.6 |
| POLD1 | A242V | 5.4 |
| POLD1 | A242T | 56.8 |
| POLD1 | A242T | 1.8 |
| POLD1 | A242V | 159.5 |
| POLD1 | P243S | 112.6 |
| POLD1 | Y244F | 36 |
| POLD1 | E245K | 76.6 |
| POLD1 | E245K | 122.5 |
| POLD1 | E245K | 85.6 |
| POLD1 | A246V | 51.4 |
| POLD1 | A246T | 0.9 |
| POLD1 | V248I | 12.6 |
| POLD1 | D249Y | 4.5 |
| POLD1 | D249N | 68.5 |
| POLD1 | E251D | 44.1 |
| POLD1 | E251Q | 36 |
| POLD1 | R253Q | 5.4 |
| POLD1 | R253L | 6.3 |
| POLD1 | F254L | 20.7 |
| POLD1 | F254L | 4.5 |
| POLD1 | M255I | 8.1 |
| POLD1 | D259N | 65.8 |
| POLD1 | D259Y | 9.9 |
| POLD1 | V261I | 64.9 |
| POLD1 | V261I | 3.6 |
| POLD1 | V261I | 6.3 |
| POLD1 | V261F | 1.8 |
| POLD1 | V261I | 8.1 |
| POLD1 | C263Y | 230.6 |
| POLD1 | C263Y | 668.5 |
| POLD1 | C263Y | 5.4 |
| POLD1 | N264D | 18.9 |
| POLD1 | W265R | 36.9 |
| POLD1 | E267Q | 15.3 |
| POLD1 | P269S | 103.6 |
| POLD1 | P269S | 334.2 |
| POLD1 | G271R | 5.4 |
| POLD1 | G271R | 1.8 |
| POLD1 | A274T | 60.4 |
| POLD1 | A274T | 2.7 |
| POLD1 | A274S | 10.8 |
| POLD1 | A274T | 76.6 |
| POLD1 | A274T | 0.9 |
| POLD1 | A274V | 119.8 |
| POLD1 | L275V | 37.8 |
| POLD1 | R276M | 51.4 |
| POLD1 | R276S | 5.4 |
| POLD1 | R276M | 59.5 |
| POLD1 | K278N | 0.9 |
| POLD1 | E279D | 44.1 |
| POLD1 | A281V | 21.6 |
| POLD1 | T282M | 82.9 |
| POLD1 | T282M | 2.7 |
| POLD1 | T282M | 0.9 |
| POLD1 | T282M | 41.4 |
| POLD1 | T282M | 4.5 |
| POLD1 | T282M | 159.5 |
| POLD1 | C284Y | 7.2 |
| POLD1 | E287* | 9.9 |
| POLD1 | E287Q | 6.3 |
| POLD1 | A288T | 7.2 |

TABLE 5-continued

All unique variants identified in POLE and POLD1 tested for driver ability
Associated mutation burdens are representative for each variant

| | | |
|---|---|---|
| POLD1 | A288T | 9 |
| POLD1 | A288V | 116.2 |
| POLD1 | A288T | 0 |
| POLD1 | D289N | 68.5 |
| POLD1 | V290M | 608.02 |
| POLD1 | V290M | 2.7 |
| POLD1 | V290M | 65.8 |
| POLD1 | V290M | 0.9 |
| POLD1 | V290M | 154.1 |
| POLD1 | V290L | 19.8 |
| POLD1 | L291P | 3.6 |
| POLD1 | W292L | 20.7 |
| POLD1 | V295L | 28.8 |
| POLD1 | V296G | 12.6 |
| POLD1 | P299S | 154.1 |
| POLD1 | P299S | 159.5 |
| POLD1 | P300L | 5.4 |
| POLD1 | P300L | 226.1 |
| POLD1 | P300T | 20.7 |
| POLD1 | P300L | 5.4 |
| POLD1 | P300L | 92.8 |
| POLD1 | E301K | 18.9 |
| POLD1 | G302K | 145.9 |
| POLD1 | P303S | 74.8 |
| POLD1 | W304S | 27 |
| POLD1 | W304M | 33.3 |
| POLD1 | R306C | 10.8 |
| POLD1 | R306H | 4.5 |
| POLD1 | R306H | 156.8 |
| POLD1 | R306H | 17.1 |
| POLD1 | R306H | 45 |
| POLD1 | R306H | 19.8 |
| POLD1 | R306C | 3.6 |
| POLD1 | R306C | 31.5 |
| POLD1 | R306C | 69.4 |
| POLD1 | A308V | 4.5 |
| POLD1 | R311H | 2.7 |
| POLD1 | R311C | 314.4 |
| POLD1 | V312M | 141.4 |
| POLD1 | V312M | 0.9 |
| POLD1 | V312M | 7.2 |
| POLD1 | V312M | 15.3 |
| POLD1 | V312M | 753.2 |
| POLD1 | V312M | 0 |
| POLD1 | S314C | 20.7 |
| POLD1 | D316N | 2.7 |
| POLD1 | D316N | 2.7 |
| POLD1 | E318K | 182 |
| POLD1 | E318K | 13.5 |
| POLD1 | E318A | 19.8 |
| POLD1 | E318V | 64.9 |
| POLD1 | C319Y | 587 |
| POLD1 | C319Y | 90.1 |
| POLD1 | A320S | 12.6 |
| POLD1 | A320P | 5.4 |
| POLD1 | A320T | 15.3 |
| POLD1 | A320T | 64 |
| POLD1 | A320S | 36 |
| POLD1 | A320T | 18 |
| POLD1 | G321C | 36.9 |
| POLD1 | G321D | 65.8 |
| POLD1 | R322H | 9 |
| POLD1 | R322H | 29.7 |
| POLD1 | R322C | 1.8 |
| POLD1 | R322H | 2.7 |
| POLD1 | R322C | 38.7 |
| POLD1 | R322H | 56.8 |
| POLD1 | R322H | 4.5 |
| POLD1 | G324C | 53.2 |
| POLD1 | G324D | 15.3 |
| POLD1 | I325M | 22.5 |
| POLD1 | I325V | 1.8 |
| POLD1 | I325M | 4.5 |
| POLD1 | P327S | 170.3 |
| POLD1 | P327S | 9 |
| POLD1 | P327R | 10.8 |
| POLD1 | E328D | 15.3 |

TABLE 5-continued

All unique variants identified in POLE and POLD1 tested for driver ability
Associated mutation burdens are representative for each variant

| | | |
|---|---|---|
| POLD1 | E330Q | 29.7 |
| POLD1 | E330K | 3.6 |
| POLD1 | E330Q | 12.6 |
| POLD1 | R331W | 371.2 |
| POLD1 | R331Q | 66.7 |
| POLD1 | R331P | 16.2 |
| POLD1 | R331Q | 0 |
| POLD1 | R331W | 4.5 |
| POLD1 | R331Q | 62.2 |
| POLD1 | R331Q | 5.4 |
| POLD1 | R331W | 753.2 |
| POLD1 | R331W | 18.9 |
| POLD1 | R331W | 2.7 |
| POLD1 | P333L | 163.1 |
| POLD1 | P333S | 7.2 |
| POLD1 | V334A | 162.2 |
| POLD1 | Q336H | 52.3 |
| POLD1 | Q336P | 10.8 |
| POLD1 | S339L | 1.8 |
| POLD1 | S339L | 854.1 |
| POLD1 | S339L | 98.2 |
| POLD1 | S339T | 11.7 |
| POLD1 | G341D | 5.4 |
| POLD1 | R343C | 238.18 |
| POLD1 | R343C | 2.7 |
| POLD1 | R343H | 56.8 |
| POLD1 | R343H | 4.5 |
| POLD1 | R343C | 0 |
| POLD1 | R343H | 14.4 |
| POLD1 | W344* | 22.5 |
| POLD1 | E346Q | 35.1 |
| POLD1 | E346K | 155 |
| POLD1 | E346D | 64.9 |
| POLD1 | P347L | 0.9 |
| POLD1 | P347L | 64.9 |
| POLD1 | P347L | 0.9 |
| POLD1 | E348Q | 2.7 |
| POLD1 | R352H | 0 |
| POLD1 | R352H | 9 |
| POLD1 | R352C | 37.8 |
| POLD1 | R352H | 5.4 |
| POLD1 | R352C | 11.7 |
| POLD1 | R352H | 9.9 |
| POLD1 | R352H | 650.5 |
| POLD1 | R352H | 4.5 |
| POLD1 | R352C | 49.5 |
| POLD1 | R352C | 31.5 |
| POLD1 | L353V | 5.4 |
| POLD1 | T356I | 6.3 |
| POLD1 | R358L | 14.4 |
| POLD1 | R358Q | 26.1 |
| POLD1 | R358Q | 27.9 |
| POLD1 | P359H | 60.4 |
| POLD1 | A361S | 5.4 |
| POLD1 | A361V | 26.1 |
| POLD1 | A361V | 9 |
| POLD1 | A361V | 6.3 |
| POLD1 | P362S | 112.6 |
| POLD1 | P362S | 98.2 |
| POLD1 | L364P | 7.2 |
| POLD1 | L364M | 55.9 |
| POLD1 | G365R | 1.8 |
| POLD1 | G365S | 20.7 |
| POLD1 | A366P | 7.2 |
| POLD1 | Q369H | 160.4 |
| POLD1 | S370N | 1.8 |
| POLD1 | S370N | 118.9 |
| POLD1 | E372K | 104.5 |
| POLD1 | E372K | 3.6 |
| POLD1 | E372K | 1.8 |
| POLD1 | E372K | 0.9 |
| POLD1 | K373E | 5.4 |
| POLD1 | K373R | 8.1 |
| POLD1 | E375K | 122.5 |
| POLD1 | W381S | 9 |
| POLD1 | S382F | 100.9 |
| POLD1 | T383A | 4.5 |

TABLE 5-continued

All unique variants identified in POLE and POLD1 tested for driver ability
Associated mutation burdens are representative for each variant

| | | |
|---|---|---:|
| POLD1 | F384I | 2.7 |
| POLD1 | F384V | 17.1 |
| POLD1 | R386H | 4.5 |
| POLD1 | R386H | 0 |
| POLD1 | I387N | 51.4 |
| POLD1 | I387M | 36.9 |
| POLD1 | M388I | 100 |
| POLD1 | D389Y | 49.5 |
| POLD1 | P390A | 12.6 |
| POLD1 | P390A | 17.1 |
| POLD1 | P390R | 30.6 |
| POLD1 | D391Y | 17.1 |
| POLD1 | D391E | 14.4 |
| POLD1 | V392M | 6.3 |
| POLD1 | V392L | 37.8 |
| POLD1 | V392M | 68.5 |
| POLD1 | V392M | 2.7 |
| POLD1 | V392L | 9 |
| POLD1 | V392M | 5.4 |
| POLD1 | V392M | 12.6 |
| POLD1 | V392M | 2.7 |
| POLD1 | V392M | 11.7 |
| POLD1 | V392M | 0 |
| POLD1 | V392M | 0 |
| POLD1 | I393V | 19.8 |
| POLD1 | T394I | 13.5 |
| POLD1 | G395S | 4.5 |
| POLD1 | N397D | 115.3 |
| POLD1 | I398M | 5.4 |
| POLD1 | I398M | 9 |
| POLD1 | I398M | 13.5 |
| POLD1 | I398M | 7.2 |
| POLD1 | D402N | 52.3 |
| POLD1 | D402Y | 17.1 |
| POLD1 | D402H | 9.9 |
| POLD1 | D402N | 26.1 |
| POLD1 | D402N | 9.9 |
| POLD1 | D402N | 7.2 |
| POLD1 | D402N | 54.1 |
| POLD1 | D402N | 315.3 |
| POLD1 | D402N | 8.1 |
| POLD1 | L403I | 67.6 |
| POLD1 | P404L | 119.8 |
| POLD1 | L406P | 311.7 |
| POLD1 | L406F | 8.1 |
| POLD1 | S408F | 11.7 |
| POLD1 | R409Q | 4.5 |
| POLD1 | R409W | 27.9 |
| POLD1 | R409L | 8.1 |
| POLD1 | R409W | 56.8 |
| POLD1 | R409Q | 4.5 |
| POLD1 | Q411H | 2.7 |
| POLD1 | T412I | 55 |
| POLD1 | K414* | 21.6 |
| POLD1 | V415I | 320.7 |
| POLD1 | V415L | 26.1 |
| POLD1 | P419S | 103.6 |
| POLD1 | P419S | 33.3 |
| POLD1 | P419S | 62.2 |
| POLD1 | P419S | 20.7 |
| POLD1 | G422D | 7.2 |
| POLD1 | R423L | 14.4 |
| POLD1 | R423H | 35.1 |
| POLD1 | R423C | 48.6 |
| POLD1 | R423H | 13.5 |
| POLD1 | R423H | 12.6 |
| POLD1 | V424L | 8.1 |
| POLD1 | A425S | 6.3 |
| POLD1 | A425S | 2.7 |
| POLD1 | A425T | 264 |
| POLD1 | A425S | 1.8 |
| POLD1 | A425T | 46.8 |
| POLD1 | G426S | 0 |
| POLD1 | G426S | 2.7 |
| POLD1 | G426S | 12.6 |
| POLD1 | G426C | 16.2 |
| POLD1 | G426S | 59.5 |

TABLE 5-continued

All unique variants identified in POLE and POLD1 tested for driver ability
Associated mutation burdens are representative for each variant

| | | |
|---|---|---|
| POLD1 | N430S | 2.7 |
| POLD1 | N430S | 0 |
| POLD1 | I431V | 3.6 |
| POLD1 | I431V | 2.7 |
| POLD1 | I431V | 3.6 |
| POLD1 | I431V | 0.9 |
| POLD1 | R432W | 31.5 |
| POLD1 | R432W | 0.9 |
| POLD1 | R432W | 35.1 |
| POLD1 | R432W | 7.2 |
| POLD1 | R432W | 0.9 |
| POLD1 | R432W | 31.5 |
| POLD1 | R432W | 67.6 |
| POLD1 | R432W | 7.2 |
| POLD1 | R432G | 5.4 |
| POLD1 | R432W | 4.5 |
| POLD1 | R432L | 29.7 |
| POLD1 | R432W | 27 |
| POLD1 | R432W | 2.7 |
| POLD1 | S434A | 0.9 |
| POLD1 | S434C | 8.1 |
| POLD1 | S435L | 38.7 |
| POLD1 | Q437R | 35.1 |
| POLD1 | Q440* | 10.8 |
| POLD1 | Q440H | 1.8 |
| POLD1 | G442C | 9 |
| POLD1 | R443Q | 3.6 |
| POLD1 | R443W | 67.6 |
| POLD1 | R444W | 9 |
| POLD1 | R444Q | 7.2 |
| POLD1 | R444Q | 8.1 |
| POLD1 | R444W | 1.8 |
| POLD1 | R444W | 109 |
| POLD1 | K447M | 175.7 |
| POLD1 | V449A | 541.36 |
| POLD1 | V449I | 180.2 |
| POLD1 | M451I | 18.9 |
| POLD1 | V452L | 15.3 |
| POLD1 | V452L | 18.9 |
| POLD1 | V452L | 41.4 |
| POLD1 | G453D | 98.2 |
| POLD1 | R454L | 31.5 |
| POLD1 | R454C | 12.6 |
| POLD1 | R454C | 23.4 |
| POLD1 | R454C | 14.4 |
| POLD1 | R454C | 34.2 |
| POLD1 | R454C | 14.4 |
| POLD1 | V455L | 25.2 |
| POLD1 | V455L | 45.9 |
| POLD1 | Q456E | 1.8 |
| POLD1 | Q456E | 0.9 |
| POLD1 | Q456L | 4.5 |
| POLD1 | D458G | 590 |
| POLD1 | D458Y | 25.2 |
| POLD1 | L460R | 180.2 |
| POLD1 | V462G | 5.4 |
| POLD1 | V462L | 7.2 |
| POLD1 | L464Q | 21.6 |
| POLD1 | R465L | 15.3 |
| POLD1 | R465Q | 114.4 |
| POLD1 | R465W | 11.7 |
| POLD1 | R465Q | 11.7 |
| POLD1 | E466K | 39.6 |
| POLD1 | R470C | 74.8 |
| POLD1 | R470H | 4.5 |
| POLD1 | R470C | 58.6 |
| POLD1 | R470H | 39.6 |
| POLD1 | S471Y | 590 |
| POLD1 | T473M | 10.8 |
| POLD1 | T473M | 4.5 |
| POLD1 | T473M | 28.8 |
| POLD1 | T473A | 25.2 |
| POLD1 | T473M | 6.3 |
| POLD1 | N475S | 1.8 |
| POLD1 | A476V | 25.2 |
| POLD1 | A476S | 53.2 |
| POLD1 | A476V | 53.2 |

TABLE 5-continued

All unique variants identified in POLE and POLD1 tested for driver ability
Associated mutation burdens are representative for each variant

| | | |
|---|---|---|
| POLD1 | V477M | 0.9 |
| POLD1 | V477M | 19.8 |
| POLD1 | V477M | 42.3 |
| POLD1 | V477M | 1.8 |
| POLD1 | S478I | 6.3 |
| POLD1 | S478I | 12.6 |
| POLD1 | F479S | 1.8 |
| POLD1 | F479V | 5.4 |
| POLD1 | F479S | 29.7 |
| POLD1 | G483R | 9 |
| POLD1 | E484K | 170.3 |
| POLD1 | K486N | 279.3 |
| POLD1 | E487Q | 5.4 |
| POLD1 | E487Q | 32.4 |
| POLD1 | E487V | 1.8 |
| POLD1 | E487* | 12.6 |
| POLD1 | V489M | 0.9 |
| POLD1 | V489M | 7.2 |
| POLD1 | V489M | 4.5 |
| POLD1 | V489M | 115.3 |
| POLD1 | V489L | 62.2 |
| POLD1 | S492G | 9 |
| POLD1 | I493M | 7.2 |
| POLD1 | D496N | 9.9 |
| POLD1 | Q498K | 65.8 |
| POLD1 | Q498L | 22.5 |
| POLD1 | G500R | 2.7 |
| POLD1 | N501H | 0 |
| POLD1 | D502H | 15.3 |
| POLD1 | D502Y | 8.1 |
| POLD1 | D502E | 34.2 |
| POLD1 | Q503E | 0.9 |
| POLD1 | R505C | 5.4 |
| POLD1 | R505H | 12.6 |
| POLD1 | R506C | 9 |
| POLD1 | R506C | 13.5 |
| POLD1 | R506P | 10.8 |
| POLD1 | R506C | 3.6 |
| POLD1 | R506C | 8.1 |
| POLD1 | R507H | 97.3 |
| POLD1 | R507C | 1.8 |
| POLD1 | R507H | 25.2 |
| POLD1 | A509P | 12.6 |
| POLD1 | A509V | 26.1 |
| POLD1 | V510L | 10.8 |
| POLD1 | V510M | 94.6 |
| POLD1 | C512R | 2.7 |
| POLD1 | D515N | 26.1 |
| POLD1 | L518M | 23.4 |
| POLD1 | L518M | 19.8 |
| POLD1 | L518M | 16.2 |
| POLD1 | P519L | 8.1 |
| POLD1 | L520P | 32.4 |
| POLD1 | R521W | 302 |
| POLD1 | R521W | 17.1 |
| POLD1 | R525W | 8.1 |
| POLD1 | R525Q | 10.8 |
| POLD1 | R525Q | 10.8 |
| POLD1 | R525W | 44.1 |
| POLD1 | R525Q | 4.5 |
| POLD1 | R525Q | 2.7 |
| POLD1 | N531S | 5.4 |
| POLD1 | A532T | 608.02 |
| POLD1 | A532V | 1.8 |
| POLD1 | A532V | 142.3 |
| POLD1 | V533M | 14.4 |
| POLD1 | V533M | 9 |
| POLD1 | E534D | 19.8 |
| POLD1 | E534D | 3.6 |
| POLD1 | A536G | 99.1 |
| POLD1 | A536V | 455.9 |
| POLD1 | A536V | 4.5 |
| POLD1 | G540C | 3.6 |
| POLD1 | V541M | 590 |
| POLD1 | V541L | 8.1 |
| POLD1 | V541M | 1.8 |
| POLD1 | V541M | 0 |

TABLE 5-continued

All unique variants identified in POLE and POLD1 tested for driver ability
Associated mutation burdens are representative for each variant

| | | |
|---|---|---|
| POLD1 | L546V | 20.7 |
| POLD1 | L546M | 49.5 |
| POLD1 | L547P | 11.7 |
| POLD1 | L547F | 386.5 |
| POLD1 | S548C | 23.4 |
| POLD1 | S548I | 4.5 |
| POLD1 | R549S | 40.5 |
| POLD1 | R549C | 5.4 |
| POLD1 | R549H | 5.4 |
| POLD1 | R549H | 2.7 |
| POLD1 | R549H | 0 |
| POLD1 | R549C | 171.2 |
| POLD1 | V556I | 1.8 |
| POLD1 | V556I | 6.3 |
| POLD1 | V556I | 9.9 |
| POLD1 | V556I | 2.7 |
| POLD1 | V556I | 5.4 |
| POLD1 | V556I | 18.9 |
| POLD1 | V556I | 9 |
| POLD1 | V556I | 17.1 |
| POLD1 | V556I | 2.7 |
| POLD1 | V556A | 45.9 |
| POLD1 | S557F | 3.6 |
| POLD1 | S557F | 64 |
| POLD1 | Q558R | 109 |
| POLD1 | Q558* | 3.6 |
| POLD1 | R561Q | 56.8 |
| POLD1 | R561L | 2.7 |
| POLD1 | R561Q | 12.6 |
| POLD1 | R561Q | 2.7 |
| POLD1 | Q562H | 57.7 |
| POLD1 | A563V | 21.6 |
| POLD1 | H565P | 7.2 |
| POLD1 | H565P | 7.2 |
| POLD1 | H565L | 73 |
| POLD1 | L569P | 12.6 |
| POLD1 | L569R | 2.7 |
| POLD1 | P571L | 112.6 |
| POLD1 | P571L | 130.6 |
| POLD1 | V572M | 1.8 |
| POLD1 | V572M | 0.9 |
| POLD1 | V572M | 50.5 |
| POLD1 | V573L | 4.5 |
| POLD1 | S575L | 10.8 |
| POLD1 | S575L | 5.4 |
| POLD1 | G578S | 32.4 |
| POLD1 | G578D | 51.4 |
| POLD1 | G578C | 10.8 |
| POLD1 | E579Q | 7.2 |
| POLD1 | E579K | 3.6 |
| POLD1 | E579K | 4.5 |
| POLD1 | E579K | 7.2 |
| POLD1 | D580G | 81.98 |
| POLD1 | D580H | 52.3 |
| POLD1 | T582M | 7.2 |
| POLD1 | T582M | 0 |
| POLD1 | T582M | 0.9 |
| POLD1 | T582M | 9.9 |
| POLD1 | G583R | 22.5 |
| POLD1 | G583V | 119.8 |
| POLD1 | G583V | 8.1 |
| POLD1 | G583R | 18 |
| POLD1 | V586F | 1.8 |
| POLD1 | E588K | 4.5 |
| POLD1 | G592R | 33.3 |
| POLD1 | G592R | 9 |
| POLD1 | Y593H | 324.3 |
| POLD1 | V596I | 42.3 |
| POLD1 | P597S | 100.9 |
| POLD1 | P597S | 13.5 |
| POLD1 | T600S | 9.9 |
| POLD1 | F603L | 23.4 |
| POLD1 | S604Y | 4.5 |
| POLD1 | S604Y | 0 |
| POLD1 | L606M | 196 |
| POLD1 | L606M | 295 |
| POLD1 | L606M | 228.8 |

TABLE 5-continued

All unique variants identified in POLE and POLD1 tested for driver ability
Associated mutation burdens are representative for each variant

| | | |
|---|---|---|
| POLD1 | L606M | 51.4 |
| POLD1 | L606M | 311.7 |
| POLD1 | L606V | 3.6 |
| POLD1 | Y607C | 68.5 |
| POLD1 | P608L | 2.7 |
| POLD1 | M612T | 1.8 |
| POLD1 | A613G | 7.2 |
| POLD1 | A613V | 315.3 |
| POLD1 | A613G | 23.4 |
| POLD1 | L616M | 2.7 |
| POLD1 | C617G | 5.4 |
| POLD1 | T620M | 57.7 |
| POLD1 | T620M | 650.5 |
| POLD1 | T620M | 44.1 |
| POLD1 | L622F | 69.4 |
| POLD1 | R623Q | 236.9 |
| POLD1 | R623L | 39.6 |
| POLD1 | R623W | 311.7 |
| POLD1 | R623W | 12.6 |
| POLD1 | R623W | 155 |
| POLD1 | R623W | 4.5 |
| POLD1 | R623W | 3.6 |
| POLD1 | R623W | 3.6 |
| POLD1 | R623Q | 8.1 |
| POLD1 | R623Q | 80.2 |
| POLD1 | R623W | 373.9 |
| POLD1 | R623W | 215.3 |
| POLD1 | R623W | 23.4 |
| POLD1 | R623W | 5.4 |
| POLD1 | G625R | 107.2 |
| POLD1 | T626I | 3.6 |
| POLD1 | A627T | 76.6 |
| POLD1 | A627T | 235.1 |
| POLD1 | A627T | 51.4 |
| POLD1 | K629I | 9.9 |
| POLD1 | K629I | 0.9 |
| POLD1 | G631D | 8.1 |
| POLD1 | G631R | 90.1 |
| POLD1 | L632M | 141 |
| POLD1 | L632M | 228 |
| POLD1 | L632M | 296 |
| POLD1 | L632M | 121 |
| POLD1 | E634K | 9 |
| POLD1 | E634A | 66.7 |
| POLD1 | E634K | 9.9 |
| POLD1 | D635N | 578.4 |
| POLD1 | F637L | 170.3 |
| POLD1 | I638V | 3.6 |
| POLD1 | R639K | 45.9 |
| POLD1 | T640A | 1.8 |
| POLD1 | T640I | 122.5 |
| POLD1 | T640N | 5.4 |
| POLD1 | T640N | 0 |
| POLD1 | T640N | 3.6 |
| POLD1 | P641L | 25.2 |
| POLD1 | T642I | 112.6 |
| POLD1 | G643W | 83.8 |
| POLD1 | G643W | 79.3 |
| POLD1 | G643L | 7.2 |
| POLD1 | D644G | 6.3 |
| POLD1 | D644N | 2.7 |
| POLD1 | D644N | 23.4 |
| POLD1 | D644N | 9.9 |
| POLD1 | D644E | 4.5 |
| POLD1 | D644N | 26.1 |
| POLD1 | D644A | 36 |
| POLD1 | E645D | 33.3 |
| POLD1 | E645K | 231.5 |
| POLD1 | E645K | 3.6 |
| POLD1 | E645K | 9 |
| POLD1 | F646C | 4.5 |
| POLD1 | F646Y | 14.4 |
| POLD1 | F646Y | 9.9 |
| POLD1 | L648I | 228 |
| POLD1 | K648N | 6.3 |
| POLD1 | T649P | 3.6 |
| POLD1 | T649P | 8.1 |

TABLE 5-continued

All unique variants identified in POLE and POLD1 tested for driver ability
Associated mutation burdens are representative for each variant

| | | |
|---|---|---:|
| POLD1 | T649I | 229.7 |
| POLD1 | T649P | 8.1 |
| POLD1 | S650L | 45 |
| POLD1 | V651L | 49.5 |
| POLD1 | R652W | 27.9 |
| POLD1 | R652W | 47.7 |
| POLD1 | R652Q | 36.9 |
| POLD1 | R652Q | 13.5 |
| POLD1 | R652Q | 5.4 |
| POLD1 | R652W | 13.5 |
| POLD1 | R652W | 447.8 |
| POLD1 | R652Q | 3.6 |
| POLD1 | R652L | 16.2 |
| POLD1 | R652Q | 8.1 |
| POLD1 | K653N | 65.8 |
| POLD1 | G654V | 26.1 |
| POLD1 | G654L | 12.6 |
| POLD1 | G654V | 12.6 |
| POLD1 | L656M | 56.8 |
| POLD1 | P657L | 1.8 |
| POLD1 | N662D | 8.1 |
| POLD1 | S665N | 4.5 |
| POLD1 | S665N | 23.4 |
| POLD1 | S665C | 22.5 |
| POLD1 | R667L | 14.4 |
| POLD1 | K671M | 19.8 |
| POLD1 | A675V | 5.4 |
| POLD1 | A675S | 17.1 |
| POLD1 | E677Q | 49.5 |
| POLD1 | D679G | 56.8 |
| POLD1 | P680L | 3.6 |
| POLD1 | P680L | 9 |
| POLD1 | P680L | 3.6 |
| POLD1 | P680A | 29.7 |
| POLD1 | P680L | 6.3 |
| POLD1 | L681V | 0 |
| POLD1 | R682W | 311.7 |
| POLD1 | R682W | 46.8 |
| POLD1 | R682L | 34.2 |
| POLD1 | R682Q | 6.3 |
| POLD1 | R682L | 18.9 |
| POLD1 | R683H | 4.5 |
| POLD1 | R683C | 64 |
| POLD1 | R683H | 64 |
| POLD1 | V685F | 9 |
| POLD1 | D687H | 18.9 |
| POLD1 | D687Y | 19.8 |
| POLD1 | D687Y | 131.5 |
| POLD1 | G688* | 27.9 |
| POLD1 | G688E | 3.6 |
| POLD1 | R689W | 259.5 |
| POLD1 | R689W | 585.6 |
| POLD1 | R689W | 578.4 |
| POLD1 | R689L | 12.6 |
| POLD1 | R689W | 447.8 |
| POLD1 | R689W | 12.6 |
| POLD1 | R689P | 6.3 |
| POLD1 | Q690* | 12.6 |
| POLD1 | A692V | 4.5 |
| POLD1 | A692S | 4.5 |
| POLD1 | L693M | 35.1 |
| POLD1 | V695M | 4.5 |
| POLD1 | A697T | 699 |
| POLD1 | N698I | 57.7 |
| POLD1 | S699F | 138.7 |
| POLD1 | S699F | 118.9 |
| POLD1 | S699F | 53.2 |
| POLD1 | S699F | 159.5 |
| POLD1 | S699F | 29.7 |
| POLD1 | S699F | 156.8 |
| POLD1 | S699T | 445.9 |
| POLD1 | S699F | 98.2 |
| POLD1 | V700I | 0.9 |
| POLD1 | V700I | 0 |
| POLD1 | V700I | 3.6 |
| POLD1 | V700I | 80.2 |
| POLD1 | V700I | 7.2 |

TABLE 5-continued

All unique variants identified in POLE and POLD1 tested for driver ability
Associated mutation burdens are representative for each variant

| | | |
|---|---|---:|
| POLD1 | T704A | 9.9 |
| POLD1 | G705C | 176.6 |
| POLD1 | G705S | 20.7 |
| POLD1 | A706T | 13.5 |
| POLD1 | A706T | 52.3 |
| POLD1 | A706S | 15.3 |
| POLD1 | G709C | 3.6 |
| POLD1 | P712S | 98.2 |
| POLD1 | C713G | 230.6 |
| POLD1 | C713F | 110.8 |
| POLD1 | C713W | 48.6 |
| POLD1 | C713F | 49.5 |
| POLD1 | E715K | 15.3 |
| POLD1 | E715K | 0.9 |
| POLD1 | E715D | 72.1 |
| POLD1 | I716V | 10.8 |
| POLD1 | S717A | 230.6 |
| POLD1 | S717* | 73.9 |
| POLD1 | L719Q | 228 |
| POLD1 | V720I | 17.1 |
| POLD1 | G724R | 9.9 |
| POLD1 | R725C | 2.7 |
| POLD1 | R725C | 64.9 |
| POLD1 | R725C | 145.9 |
| POLD1 | R725H | 12.6 |
| POLD1 | R725H | 2.7 |
| POLD1 | R725C | 27 |
| POLD1 | Q726* | 86.5 |
| POLD1 | I728M | 107.2 |
| POLD1 | E729Q | 2.7 |
| POLD1 | K730Q | 82.9 |
| POLD1 | K730Q | 10.8 |
| POLD1 | T731I | 608.02 |
| POLD1 | Q733E | 2.7 |
| POLD1 | V735M | 114.4 |
| POLD1 | E736G | 2.7 |
| POLD1 | S737C | 5.4 |
| POLD1 | S737Y | 301.8 |
| POLD1 | S737C | 1.8 |
| POLD1 | T740A | 2.7 |
| POLD1 | T740A | 7.2 |
| POLD1 | V741M | 3.6 |
| POLD1 | E742D | 4.5 |
| POLD1 | E742G | 0.9 |
| POLD1 | E742D | 7.2 |
| POLD1 | E742Q | 5.4 |
| POLD1 | G744V | 20.7 |
| POLD1 | G744D | 2.7 |
| POLD1 | S746G | 57.7 |
| POLD1 | T747I | 38.7 |
| POLD1 | S748G | 29.7 |
| POLD1 | A749P | 11.7 |
| POLD1 | A749T | 13.5 |
| POLD1 | V751M | 7.2 |
| POLD1 | Y753H | 5.4 |
| POLD1 | G754S | 75.7 |
| POLD1 | V759G | 18 |
| POLD1 | R762P | 11.7 |
| POLD1 | R762* | 70.3 |
| POLD1 | R762* | 2.7 |
| POLD1 | R762* | 0.9 |
| POLD1 | R762* | 8.1 |
| POLD1 | G764D | 2.7 |
| POLD1 | V765M | 4.5 |
| POLD1 | V765M | 8.1 |
| POLD1 | V765M | 1.8 |
| POLD1 | V765M | 18.9 |
| POLD1 | S767L | 1.8 |
| POLD1 | A769G | 13.5 |
| POLD1 | E770D | 8.1 |
| POLD1 | E770K | 19.8 |
| POLD1 | E770K | 11.7 |
| POLD1 | A771V | 0.9 |
| POLD1 | L774V | 6.3 |
| POLD1 | L774V | 1.8 |
| POLD1 | G775R | 52.3 |
| POLD1 | R776Q | 25.2 |

TABLE 5-continued

All unique variants identified in POLE and POLD1 tested for driver ability
Associated mutation burdens are representative for each variant

| | | |
|---|---|---|
| POLD1 | R776W | 5.4 |
| POLD1 | R776W | 1.8 |
| POLD1 | R776Q | 107.2 |
| POLD1 | R776Q | 5.4 |
| POLD1 | R776L | 17.1 |
| POLD1 | R776W | 7.2 |
| POLD1 | R776W | 5.4 |
| POLD1 | R776W | 27.9 |
| POLD1 | R776W | 17.1 |
| POLD1 | E777K | 4.5 |
| POLD1 | E777K | 3.6 |
| POLD1 | A778V | 3.6 |
| POLD1 | A778V | 28.8 |
| POLD1 | A778V | 159.5 |
| POLD1 | A778V | 0 |
| POLD1 | A779T | 50.5 |
| POLD1 | A779V | 141.4 |
| POLD1 | A779V | 46.8 |
| POLD1 | A779T | 13.5 |
| POLD1 | D780N | 25.2 |
| POLD1 | D780N | 63.1 |
| POLD1 | D780H | 13.5 |
| POLD1 | D780E | 6.3 |
| POLD1 | W781* | 156.8 |
| POLD1 | W781C | 34.2 |
| POLD1 | W781L | 3.6 |
| POLD1 | S783L | 13.5 |
| POLD1 | S783T | 5.4 |
| POLD1 | H785Y | 45.9 |
| POLD1 | H785N | 133.3 |
| POLD1 | P787L | 5.4 |
| POLD1 | P787L | 0.9 |
| POLD1 | P787L | 7.2 |
| POLD1 | P787L | 67.6 |
| POLD1 | P787L | 17.1 |
| POLD1 | P787L | 37.8 |
| POLD1 | S788L | 4.5 |
| POLD1 | S788L | 15.3 |
| POLD1 | S788L | 0.9 |
| POLD1 | P789L | 6.3 |
| POLD1 | R791L | 20.7 |
| POLD1 | R791W | 141.4 |
| POLD1 | R791W | 152.3 |
| POLD1 | R791W | 94.6 |
| POLD1 | E795Q | 9.9 |
| POLD1 | E795Q | 4.5 |
| POLD1 | E795D | 30.6 |
| POLD1 | E795D | 28.8 |
| POLD1 | E795K | 27 |
| POLD1 | E795K | 19.8 |
| POLD1 | E795Q | 11.7 |
| POLD1 | Y798C | 15.3 |
| POLD1 | F799L | 2.7 |
| POLD1 | P800S | 78.4 |
| POLD1 | I804M | 14.4 |
| POLD1 | I804M | 7.2 |
| POLD1 | S805I | 25.2 |
| POLD1 | K806* | 12.6 |
| POLD1 | R808H | 123.4 |
| POLD1 | Y809* | 9.9 |
| POLD1 | Y809* | 6.3 |
| POLD1 | A810E | 1.8 |
| POLD1 | A810S | 13.5 |
| POLD1 | G811A | 54.1 |
| POLD1 | G811N | 97.3 |
| POLD1 | L812V | 8.1 |
| POLD1 | F814L | 2.7 |
| POLD1 | S815F | 8.1 |
| POLD1 | S815F | 100 |
| POLD1 | S815F | 21.6 |
| POLD1 | S816C | 8.1 |
| POLD1 | R817Q | 0 |
| POLD1 | R817L | 35.1 |
| POLD1 | P818L | 9 |
| POLD1 | D819N | 37.8 |
| POLD1 | D819N | 1.8 |
| POLD1 | D819N | 9.9 |

TABLE 5-continued

All unique variants identified in POLE and POLD1 tested for driver ability
Associated mutation burdens are representative for each variant

| | | |
|---|---|---|
| POLD1 | A820S | 39.6 |
| POLD1 | A820T | 1.8 |
| POLD1 | A820T | 9.9 |
| POLD1 | A820T | 1.8 |
| POLD1 | A820T | 9 |
| POLD1 | H821Q | 2.7 |
| POLD1 | R823G | 229.7 |
| POLD1 | R823L | 18.9 |
| POLD1 | M824I | 76.6 |
| POLD1 | C826Y | 126.1 |
| POLD1 | L829P | 76.6 |
| POLD1 | E830* | 9.9 |
| POLD1 | E830* | 6.3 |
| POLD1 | A831S | 16.2 |
| POLD1 | V832L | 9 |
| POLD1 | V832L | 8.1 |
| POLD1 | R833L | 33.3 |
| POLD1 | R833C | 9.9 |
| POLD1 | R833L | 9.9 |
| POLD1 | R833L | 21.6 |
| POLD1 | R834M | 4.5 |
| POLD1 | R834S | 12.6 |
| POLD1 | D835N | 8.1 |
| POLD1 | D835E | 13.5 |
| POLD1 | C837R | 56.8 |
| POLD1 | P838S | 75.7 |
| POLD1 | P838S | 182 |
| POLD1 | P838L | 86.5 |
| POLD1 | P838S | 41.4 |
| POLD1 | L839F | 98.2 |
| POLD1 | L839V | 4.5 |
| POLD1 | V840M | 54.1 |
| POLD1 | N842K | 41.4 |
| POLD1 | V844I | 10.8 |
| POLD1 | A846V | 12.6 |
| POLD1 | S847L | 8.1 |
| POLD1 | R849C | 4.5 |
| POLD1 | R849C | 0.9 |
| POLD1 | R849C | 0.9 |
| POLD1 | R849C | 0.9 |
| POLD1 | R849C | 0.9 |
| POLD1 | R849C | 9.9 |
| POLD1 | R849C | 20.7 |
| POLD1 | R850C | 2.7 |
| POLD1 | L852P | 20.7 |
| POLD1 | L852F | 0.9 |
| POLD1 | D854H | 4.5 |
| POLD1 | D854Y | 45 |
| POLD1 | D854Y | 1.8 |
| POLD1 | R855* | 7.2 |
| POLD1 | R855L | 7.2 |
| POLD1 | R855L | 0.9 |
| POLD1 | R855Q | 6.3 |
| POLD1 | R855G | 76.6 |
| POLD1 | R855G | 2.7 |
| POLD1 | R855L | 5.4 |
| POLD1 | R855L | 0.9 |
| POLD1 | D856H | 9.9 |
| POLD1 | E858K | 23.4 |
| POLD1 | E858D | 9 |
| POLD1 | A860V | 4.5 |
| POLD1 | A860V | 854.1 |
| POLD1 | A860T | 33.3 |
| POLD1 | A860V | 105.4 |
| POLD1 | A860V | 0.9 |
| POLD1 | A860V | 38.7 |
| POLD1 | A862P | 118.9 |
| POLD1 | H863Y | 15.3 |
| POLD1 | A864P | 9.9 |
| POLD1 | A864P | 4.5 |
| POLD1 | A864T | 16.2 |
| POLD1 | A864T | 0.9 |
| POLD1 | A864S | 17.1 |
| POLD1 | A864S | 14.4 |
| POLD1 | D866E | 4.5 |
| POLD1 | I868V | 164.9 |
| POLD1 | S869L | 4.5 |

TABLE 5-continued

All unique variants identified in POLE and POLD1 tested for driver ability
Associated mutation burdens are representative for each variant

| | | |
|---|---|---|
| POLD1 | S869L | 42.3 |
| POLD1 | R875C | 541.36 |
| POLD1 | R875C | 5.4 |
| POLD1 | R875C | 0.9 |
| POLD1 | R875H | 63.1 |
| POLD1 | R875C | 12.6 |
| POLD1 | R875S | 72.1 |
| POLD1 | R875H | 45.9 |
| POLD1 | R875C | 3.6 |
| POLD1 | D877Y | 275.7 |
| POLD1 | D877N | 37.8 |
| POLD1 | D877N | 455.9 |
| POLD1 | D877G | 13.5 |
| POLD1 | V882L | 56.8 |
| POLD1 | V882I | 11.7 |
| POLD1 | I883T | 53.2 |
| POLD1 | T884I | 226.1 |
| POLD1 | E886K | 1.8 |
| POLD1 | E886K | 150.5 |
| POLD1 | E886K | 5.4 |
| POLD1 | R889H | 3.6 |
| POLD1 | R889H | 0.9 |
| POLD1 | R889H | 3.6 |
| POLD1 | R889H | 6.3 |
| POLD1 | R889C | 14.4 |
| POLD1 | A890V | 2.7 |
| POLD1 | A890V | 6.3 |
| POLD1 | A890V | 18 |
| POLD1 | A890T | 73 |
| POLD1 | A890V | 14.4 |
| POLD1 | A890T | 753.2 |
| POLD1 | A890V | 0.9 |
| POLD1 | A890V | 0 |
| POLD1 | D893N | 82.9 |
| POLD1 | D893N | 6.3 |
| POLD1 | A895S | 4.5 |
| POLD1 | G896S | 23.4 |
| POLD1 | G896S | 18.9 |
| POLD1 | G896S | 9 |
| POLD1 | G896D | 74.8 |
| POLD1 | G896D | 237.8 |
| POLD1 | G896S | 7.2 |
| POLD1 | A899T | 6.3 |
| POLD1 | A899S | 13.5 |
| POLD1 | A899V | 124.3 |
| POLD1 | V901M | 14.4 |
| POLD1 | V901M | 13.5 |
| POLD1 | E902Q | 5.4 |
| POLD1 | A904S | 16.2 |
| POLD1 | E905K | 0.9 |
| POLD1 | E905K | 8.1 |
| POLD1 | M907I | 23.4 |
| POLD1 | M907I | 21.6 |
| POLD1 | R908K | 7.2 |
| POLD1 | R908K | 64.9 |
| POLD1 | R908K | 43.2 |
| POLD1 | R910Q | 3.6 |
| POLD1 | R910W | 156.8 |
| POLD1 | R910Q | 18.9 |
| POLD1 | R910Q | 29.7 |
| POLD1 | R910Q | 10.8 |
| POLD1 | P912S | 521.6 |
| POLD1 | G913R | 2.7 |
| POLD1 | G913R | 4.5 |
| POLD1 | G913R | 1.8 |
| POLD1 | A915V | 91.9 |
| POLD1 | D920Y | 14.4 |
| POLD1 | D920N | 0 |
| POLD1 | D920N | 4.5 |
| POLD1 | D920N | 5.4 |
| POLD1 | D920N | 9.9 |
| POLD1 | D920N | 3.6 |
| POLD1 | D920Y | 6.3 |
| POLD1 | R921H | 6.3 |
| POLD1 | R921H | 45 |
| POLD1 | R921C | 9.9 |
| POLD1 | V922I | 17.1 |

TABLE 5-continued

All unique variants identified in POLE and POLD1 tested for driver ability
Associated mutation burdens are representative for each variant

| | | |
|---|---|---|
| POLD1 | P923L | 174.8 |
| POLD1 | P923S | 64.9 |
| POLD1 | P923R | 15.3 |
| POLD1 | P923S | 135.1 |
| POLD1 | V925M | 43.2 |
| POLD1 | V925M | 2.7 |
| POLD1 | V925M | 0.9 |
| POLD1 | V925G | 20.7 |
| POLD1 | I926L | 1.8 |
| POLD1 | I927L | 9 |
| POLD1 | I927L | 5.4 |
| POLD1 | S928T | 6.3 |
| POLD1 | S928T | 6.3 |
| POLD1 | A930V | 386.5 |
| POLD1 | G932R | 2.7 |
| POLD1 | G932V | 93.7 |
| POLD1 | G932D | 130.6 |
| POLD1 | G932R | 9 |
| POLD1 | G932A | 10.8 |
| POLD1 | V933L | 3.6 |
| POLD1 | A935T | 2.7 |
| POLD1 | A935T | 6.3 |
| POLD1 | A935T | 23.4 |
| POLD1 | A935V | 5.4 |
| POLD1 | A935T | 5.4 |
| POLD1 | A935T | 4.5 |
| POLD1 | A935T | 20.7 |
| POLD1 | A935T | 0.9 |
| POLD1 | M937L | 0.9 |
| POLD1 | S939A | 36 |
| POLD1 | S939P | 128.8 |
| POLD1 | E940K | 67.6 |
| POLD1 | E940V | 5.4 |
| POLD1 | D941H | 22.5 |
| POLD1 | D941Y | 15.3 |
| POLD1 | D941N | 4.5 |
| POLD1 | D941G | 6.3 |
| POLD1 | P942S | 2.7 |
| POLD1 | P942R | 4.5 |
| POLD1 | P942L | 57.7 |
| POLD1 | F944L | 56.8 |
| POLD1 | V945L | 18 |
| POLD1 | V945M | 2.7 |
| POLD1 | V945M | 85.6 |
| POLD1 | V945M | 60.4 |
| POLD1 | I952T | 3.6 |
| POLD1 | I952T | 18 |
| POLD1 | T954M | 3.6 |
| POLD1 | T954M | 6.3 |
| POLD1 | T954M | 0.9 |
| POLD1 | T954M | 155 |
| POLD1 | T954M | 26.1 |
| POLD1 | T954M | 4.5 |
| POLD1 | Y956H | 29.7 |
| POLD1 | Q961R | 5.4 |
| POLD1 | A963S | 2.7 |
| POLD1 | K964N | 10.8 |
| POLD1 | K964N | 3.6 |
| POLD1 | P965F | 101.8 |
| POLD1 | P965L | 112.6 |
| POLD1 | L966F | 14.4 |
| POLD1 | L966V | 10.8 |
| POLD1 | L967V | 0.9 |
| POLD1 | L967P | 49.5 |
| POLD1 | L967P | 1.8 |
| POLD1 | R968C | 3.6 |
| POLD1 | R968H | 29.7 |
| POLD1 | R968C | 21.6 |
| POLD1 | R968H | 68.5 |
| POLD1 | R968H | 37.8 |
| POLD1 | I969M | 6.3 |
| POLD1 | E971K | 237.8 |
| POLD1 | E971K | 5.4 |
| POLD1 | P972S | 5.4 |
| POLD1 | G975C | 60.4 |
| POLD1 | E976K | 0 |
| POLD1 | E976* | 9.9 |

TABLE 5-continued

All unique variants identified in POLE and POLD1 tested for driver ability
Associated mutation burdens are representative for each variant

| | | |
|---|---|---|
| POLD1 | E976K | 0.9 |
| POLD1 | E976D | 20.7 |
| POLD1 | G977C | 70.3 |
| POLD1 | R978H | 8.1 |
| POLD1 | R978C | 94.6 |
| POLD1 | R978H | 3.6 |
| POLD1 | A979V | 32.4 |
| POLD1 | E980V | 23.4 |
| POLD1 | E980* | 163.1 |
| POLD1 | E980K | 0.9 |
| POLD1 | E980K | 0.9 |
| POLD1 | E980K | 9.9 |
| POLD1 | A981V | 2.7 |
| POLD1 | A981S | 20.7 |
| POLD1 | R985L | 25.2 |
| POLD1 | R985Q | 0.9 |
| POLD1 | R985W | 0 |
| POLD1 | R985Q | 3.6 |
| POLD1 | G986R | 11.7 |
| POLD1 | G986R | 33.3 |
| POLD1 | D987N | 52.3 |
| POLD1 | D987E | 9 |
| POLD1 | D987N | 7.2 |
| POLD1 | H988Y | 116.2 |
| POLD1 | T989M | 4.5 |
| POLD1 | T989M | 3.6 |
| POLD1 | T989M | 56.8 |
| POLD1 | T989M | 6.3 |
| POLD1 | R990C | 6.3 |
| POLD1 | R990H | 6.3 |
| POLD1 | C991W | 6.3 |
| POLD1 | C991W | 2.7 |
| POLD1 | C991Y | 10.8 |
| POLD1 | T993M | 5.4 |
| POLD1 | T993M | 51.4 |
| POLD1 | T993M | 87.4 |
| POLD1 | L995I | 493.7 |
| POLD1 | L995F | 9 |
| POLD1 | T996M | 41.4 |
| POLD1 | G997S | 0.9 |
| POLD1 | G997S | 5.4 |
| POLD1 | G997S | 19.8 |
| POLD1 | G997S | 8.1 |
| POLD1 | V999M | 18.9 |
| POLD1 | G1000S | 230.6 |
| POLD1 | G1000D | 89.2 |
| POLD1 | G1001S | 2.7 |
| POLD1 | G1001S | 23.4 |
| POLD1 | G1001F | 10.8 |
| POLD1 | A1004V | 65.8 |
| POLD1 | A1004T | 170.3 |
| POLD1 | A1004P | 5.4 |
| POLD1 | A1004V | 14.4 |
| POLD1 | A1006I | 159.5 |
| POLD1 | R1008C | 5.4 |
| POLD1 | R1008C | 2.7 |
| POLD1 | R1008H | 21.6 |
| POLD1 | R1008C | 68.5 |
| POLD1 | R1009C | 493.7 |
| POLD1 | R1009L | 11.7 |
| POLD1 | R1009C | 7.2 |
| POLD1 | R1009H | 4.5 |
| POLD1 | R1009C | 4.5 |
| POLD1 | R1009H | 25.2 |
| POLD1 | R1009H | 3.6 |
| POLD1 | R1009L | 16.2 |
| POLD1 | R1009C | 0.9 |
| POLD1 | R1009C | 4.5 |
| POLD1 | N1010T | 31.5 |
| POLD1 | C1011Y | 3.6 |
| POLD1 | C1012G | 100.9 |
| POLD1 | C1012Y | 24.3 |
| POLD1 | I1013T | 4.5 |
| POLD1 | I1013T | 14.4 |
| POLD1 | I1013T | 1.8 |
| POLD1 | R1016C | 31.5 |
| POLD1 | R1016H | 39.6 |

TABLE 5-continued

All unique variants identified in POLE and POLD1 tested for driver ability
Associated mutation burdens are representative for each variant

| | | |
|---|---|---|
| POLD1 | R1016H | 29.7 |
| POLD1 | R1016C | 6.3 |
| POLD1 | R1016H | 315.3 |
| POLD1 | R1016H | 69.4 |
| POLD1 | R1016H | 636.9 |
| POLD1 | R1016H | 49.5 |
| POLD1 | R1016P | 13.5 |
| POLD1 | T1017S | 3.6 |
| POLD1 | S1020N | 4.5 |
| POLD1 | S1020N | 4.5 |
| POLD1 | H1021P | 1.8 |
| POLD1 | Q1022* | 10.8 |
| POLD1 | G1023R | 3.6 |
| POLD1 | G1023R | 1.8 |
| POLD1 | V1025L | 18.9 |
| POLD1 | V1025L | 0 |
| POLD1 | C1026S | 5.4 |
| POLD1 | E1027K | 91 |
| POLD1 | E1027K | 2.7 |
| POLD1 | E1027Q | 3.6 |
| POLD1 | E1027K | 8.1 |
| POLD1 | F1028L | 233.3 |
| POLD1 | C1029Y | 38.7 |
| POLD1 | C1029S | 16.2 |
| POLD1 | Q1030* | 24.3 |
| POLD1 | P1031L | 313.5 |
| POLD1 | R1032Q | 0.9 |
| POLD1 | R1032Q | 0 |
| POLD1 | E1033* | 11.7 |
| POLD1 | E1035Q | 48.6 |
| POLD1 | E1035Q | 9 |
| POLD1 | E1035Q | 2.7 |
| POLD1 | E1035Q | 9 |
| POLD1 | Y1037C | 34.2 |
| POLD1 | Q1038E | 30.6 |
| POLD1 | Q1038E | 18.9 |
| POLD1 | E1040A | 472.56 |
| POLD1 | E1040Q | 14.4 |
| POLD1 | E1040K | 77.5 |
| POLD1 | V1041A | 16.2 |
| POLD1 | V1041L | 5.4 |
| POLD1 | L1044V | 48.6 |
| POLD1 | A1046V | 450.5 |
| POLD1 | A1046G | 4.5 |
| POLD1 | A1046V | 30.6 |
| POLD1 | E1048K | 38.7 |
| POLD1 | E1049K | 132.4 |
| POLD1 | E1049K | 1.8 |
| POLD1 | E1049K | 52.3 |
| POLD1 | R1050C | 541.36 |
| POLD1 | R1050C | 500 |
| POLD1 | R1050S | 29.7 |
| POLD1 | R1050H | 5.4 |
| POLD1 | S1052* | 32.4 |
| POLD1 | S1052P | 5.4 |
| POLD1 | S1052W | 178.4 |
| POLD1 | S1052L | 3.6 |
| POLD1 | S1052L | 2.7 |
| POLD1 | S1052L | 20.7 |
| POLD1 | S1052L | 9 |
| POLD1 | R1053C | 541.36 |
| POLD1 | R1053H | 3.6 |
| POLD1 | R1053H | 2.7 |
| POLD1 | R1053L | 8.1 |
| POLD1 | W1055* | 10.8 |
| POLD1 | W1055V | 23.4 |
| POLD1 | T1056S | 35.1 |
| POLD1 | T1056K | 1.8 |
| POLD1 | Q1057R | 6.3 |
| POLD1 | C1058Y | 13.5 |
| POLD1 | Q1059* | 1.8 |
| POLD1 | R1060C | 4.5 |
| POLD1 | R1060H | 33.3 |
| POLD1 | R1060H | 19.8 |
| POLD1 | R1060H | 32.4 |
| POLD1 | G1063C | 15.3 |
| POLD1 | G1063C | 69.4 |

TABLE 5-continued

All unique variants identified in POLE and POLD1 tested for driver ability
Associated mutation burdens are representative for each variant

| | | |
|---|---|---|
| POLD1 | H1066R | 40.5 |
| POLD1 | H1066D | 73.9 |
| POLD1 | H1066Y | 31.5 |
| POLD1 | H1066R | 4.5 |
| POLD1 | E1067D | 9.9 |
| POLD1 | E1067V | 36 |
| POLD1 | D1068N | 14.4 |
| POLD1 | I1070M | 22.5 |
| POLD1 | S1073T | 3.6 |
| POLD1 | R1074Q | 19.8 |
| POLD1 | R1074W | 18.9 |
| POLD1 | R1074W | 213.5 |
| POLD1 | R1074Q | 9.9 |
| POLD1 | R1074W | 21.6 |
| POLD1 | D1075H | 76.6 |
| POLD1 | P1077S | 34.2 |
| POLD1 | P1077A | 5.4 |
| POLD1 | P1077A | 11.7 |
| POLD1 | P1077L | 4.5 |
| POLD1 | F1079L | 0.9 |
| POLD1 | F1079L | 38.7 |
| POLD1 | F1079L | 29.7 |
| POLD1 | F1079L | 9.9 |
| POLD1 | Y1080H | 11.7 |
| POLD1 | M1081K | 0 |
| POLD1 | M1081I | 1.8 |
| POLD1 | R1082H | 2.7 |
| POLD1 | R1082C | 11.7 |
| POLD1 | R1082H | 43.2 |
| POLD1 | K1083N | 16.2 |
| POLD1 | V1085L | 0.9 |
| POLD1 | R1086W | 238.18 |
| POLD1 | R1086W | 472.56 |
| POLD1 | R1086W | 7.2 |
| POLD1 | R1086W | 13.5 |
| POLD1 | R1086W | 12.6 |
| POLD1 | R1086W | 5.4 |
| POLD1 | R1086W | 4.5 |
| POLD1 | R1086P | 7.2 |
| POLD1 | E1090K | 2.7 |
| POLD1 | E1090K | 3.6 |
| POLD1 | D1091N | 0.9 |
| POLD1 | D1091N | 18.9 |
| POLD1 | D1091N | 7.2 |
| POLD1 | E1093K | 381.1 |
| POLD1 | E1093K | 2.7 |
| POLD1 | E1093K | 402.7 |
| POLD1 | E1093K | 3.6 |
| POLD1 | Q1094H | 13.5 |
| POLD1 | R1097G | 119.8 |
| POLD1 | R1097Q | 5.4 |
| POLD1 | R1097Q | 5.4 |
| POLD1 | R1097W | 5.4 |
| POLD1 | R1097W | 2.7 |
| POLD1 | R1097W | 70.3 |
| POLD1 | R1097Q | 0 |
| POLD1 | R1098C | 4.5 |
| POLD1 | R1098C | 18.9 |
| POLD1 | R1098C | 70.3 |
| POLD1 | R1098L | 3.6 |
| POLD1 | R1098C | 6.3 |
| POLD1 | F1099L | 7.2 |
| POLD1 | F1099L | 5.4 |
| POLD1 | G1100V | 7.2 |
| POLD1 | P1101S | 3.6 |
| POLD1 | P1101S | 79.3 |
| POLD1 | P1101L | 20.7 |
| POLD1 | P1101L | 71.2 |
| POLD1 | P1102L | 0.9 |
| POLD1 | G1103* | 4.5 |
| POLD1 | G1103A | 12.6 |
| POLD1 | P1104T | 4.5 |
| POLD1 | P1104L | 164.9 |
| POLD1 | E1105* | 5.4 |
| POLD1 | A1106D | 1.8 |
| POLD1 | W1107C | 95.5 |
| POLD1 | D987fs*58 | 78.4 |

TABLE 5-continued

All unique variants identified in POLE and POLD1 tested for driver ability
Associated mutation burdens are representative for each variant

| | | |
|---|---|---|
| POLD1 | D819fs*69 | 45.9 |
| POLD1 | R180fs*72 | 40.5 |
| POLD1 | M727del | 32.4 |
| POLD1 | M457fs*179 | 1.8 |
| POLD1 | D987fs*58 | 45 |
| POLD1 | G724fs*15 | 13.5 |
| POLD1 | splice site 590 − 2A > G | 0 |
| POLD1 | Y147fs*22 | 9 |
| POLD1 | L543fs*92 | 28.8 |
| POLD1 | D987fs*58 | 91 |
| POLD1 | splice site 316 + 1delG | 8.1 |
| POLD1 | R823fs*68 | 6.3 |
| POLD1 | P1102fs*7+ | 36.9 |
| POLD1 | E346fs*47 | 54.1 |
| POLD1 | P116fs*53 | 51.4 |
| POLD1 | D987fs*58 | 214.4 |
| POLD1 | L188fs*89 | 44.1 |
| POLD1 | I172fs*80 | 2.7 |
| POLD1 | D987fs*41 | 16.2 |
| POLD1 | E795fs*1 | 3.6 |
| POLD1 | T642fs*6 | 107.2 |
| POLD1 | P116fs*53 | 47.7 |
| POLD1 | A28_P29 > DAP | 3.6 |
| POLD1 | F34fs*9 | 24.3 |
| POLD1 | splice site 2954 − 2insT | 26.1 |
| POLD1 | P116fs*53 | 30.6 |
| POLD1 | D987fs*58 | 75.7 |
| POLD1 | D987fs*58 | 15.3 |
| POLD1 | R358fs*27 | 7.2 |
| POLD1 | E159fs*10 | 13.5 |
| POLD1 | C338del | 38.7 |
| POLD1 | splice site 2251 − 1G > A | 7.2 |
| POLD1 | D987fs*58 | 37.8 |
| POLD1 | splice site 1495 − 1G > A | 3.6 |
| POLD1 | V111fs*58 | 42.3 |
| POLD1 | R823_M824insPDAHDR | 12.6 |
| POLD1 | C1029fs*1 | 2.7 |
| POLD1 | W265fs*1 | 12.6 |
| POLD1 | splice site 1893 − 2A > G | 278.4 |
| POLD1 | P116fs*53 | 29.7 |
| POLD1 | F209fs*67 | 63.1 |
| POLD1 | D987fs*58 | 39.6 |
| POLD1 | R180fs*3 | 56.8 |
| POLD1 | P404fs*74 | 3.6 |
| POLD1 | splice site 1384 − 2A > G | 43.2 |
| POLD1 | P116fs*53 | 56.8 |
| POLD1 | V61fs*42 | 5.4 |
| POLD1 | L839fs*20 | 28.8 |
| POLD1 | P116fs*53 | 85.6 |
| POLD1 | D987fs*58 | 42.3 |
| POLD1 | D987fs*58 | 31.5 |
| POLD1 | splice site 1686 + 2T > C | 60.4 |
| POLD1 | D987fs*41 | 39.6 |
| POLD1 | P116fs*53 | 37.8 |
| POLD1 | K486del | 0 |
| POLD1 | splice site 1243 − 1G > T | 21.6 |
| POLD1 | D987fs*58 | 68.5 |
| POLD1 | D987fs*58 | 57.7 |
| POLD1 | D515fs*16 | 9 |
| POLD1 | splice site 1137 + 1G > A | 5.4 |
| POLD1 | splice site 203 − 1G > A | 5.4 |
| POLD1 | Y801fs*1 | 9.9 |
| POLD1 | R1032fs*13 | 58.6 |
| POLD1 | P1102fs*7+ | 7.2 |
| POLD1 | D987fs*58 | 40.5 |
| POLD1 | P1102fs*7+ | 1.8 |
| POLD1 | E279del | 6.3 |
| POLD1 | R180fs*72 | 17.1 |
| POLD1 | D987fs*58 | 57.7 |
| POLD1 | S719fs*19 | 7.2 |
| POLD1 | splice site 1137 + 2T > C | 5.4 |
| POLD1 | D987fs*58 | 36 |
| POLD1 | P942fs*100 | 6.3 |
| POLD1 | E279del | 0 |
| POLD1 | E196_S197del | 99.1 |
| POLD1 | E279del | 9 |
| POLD1 | R817fs*67 | 5.4 |

TABLE 5-continued

All unique variants identified in POLE and POLD1 tested for driver ability
Associated mutation burdens are representative for each variant

| Gene | Variant | Burden |
|---|---|---|
| POLD1 | P116fs*53 | 66.7 |
| POLD1 | R253fs*23 | 5.4 |
| POLD1 | T642fs*6 | 7.2 |
| POLD1 | D987fs*58 | 5.4 |
| POLD1 | splice site 1494 + 2T > A | 7.2 |
| POLD1 | D987fs*58 | 70.3 |
| POLD1 | K931_Y936del | 5.4 |
| POLD1 | D987fs*58 | 65.8 |
| POLD1 | splice site 1495 − 1G > A | 14.4 |
| POLD1 | P116fs*53 | 109 |
| POLD1 | D987fs*58 | 57.7 |
| POLD1 | P116fs*53 | 36 |
| POLD1 | D987fs*58 | 45.9 |
| POLD1 | D987fs*58 | 48.6 |
| POLD1 | D987fs*58 | 122.5 |
| POLD1 | P116fs*53 | 44.1 |
| POLD1 | V111fs*58 | 63.1 |
| POLD1 | E279del | 8.1 |
| POLD1 | E346fs*47 | 59.5 |
| POLD1 | T183fs*93 | 4.5 |
| POLD1 | splice site 2953 + 1G > A | 27.9 |
| POLD1 | splice site 3116_3120 + 11delAGGAGGTGAGAGGGCC | 13.5 |
| POLD1 | P1102fs*7+ | 49.5 |
| POLD1 | P116fs*17 | 53.2 |
| POLD1 | D987fs*41 | 26.1 |
| POLD1 | P116fs*53 | 40.5 |
| POLD1 | T642fs*97 | 73 |
| POLD1 | D987fs*58 | 27 |
| POLD1 | splice site 2155 − 1G > T | 23.4 |
| POLD1 | D987fs*58 | 43.2 |
| POLD1 | K897fs*54 | 0.9 |
| POLD1 | P154fs*15 | 96.4 |
| POLD1 | Q628fs*5 | 96.4 |
| POLD1 | P1102fs*7+ | 14.4 |
| POLD1 | D987fs*58 | 69.4 |
| POLD1 | splice site 1893 − 2A > T | 28.8 |
| POLD1 | splice site 1892 + 1G > A | 38.7 |
| POLD1 | R180fs*3 | 11.7 |
| POLD1 | splice site 317 − 9_333del26 | 5.4 |
| POLD1 | K732fs*156 | 1.8 |
| POLD1 | I212fs*35 | 2.7 |
| POLD1 | D987fs*58 | 75.7 |
| POLD1 | E42_E45del | 9.9 |
| POLD1 | splice site 1495 − 1G > A | 13.5 |
| POLD1 | D987fs*58 | 153.2 |
| POLD1 | A979fs*66 | 84.7 |
| POLD1 | R180fs*72 | 43.2 |
| POLD1 | D987fs*58 | 70.3 |
| POLD1 | S816del | 9 |
| POLD1 | P116fs*53 | 67.6 |
| POLD1 | E279del | 9.9 |
| POLD1 | R180fs*3 | 55 |
| POLD1 | D987fs*58 | 70.3 |
| POLD1 | splice site 2953 + 1G > T | 4.5 |
| POLD1 | R180fs*3 | 279.3 |
| POLD1 | splice site 2389 − 1G > A | 5.4 |
| POLD1 | D987fs*58 | 17.1 |
| POLD1 | S605del | 14.4 |
| POLD1 | splice site 971 − 1G > T | 73 |
| POLD1 | D987fs*41 | 42.3 |
| POLD1 | D987fs*58 | 64 |
| POLD1 | P116fs*53 | 80.2 |
| POLD1 | W1055fs*50 | 68.5 |
| POLD1 | D987fs*58 | 36.9 |
| POLD1 | D987fs*58 | 32.4 |
| POLD1 | D987fs*58 | 35.1 |
| POLD1 | D987fs*58 | 50.5 |
| POLD1 | splice site 2953 + 1G > A | 21.6 |
| POLD1 | D987fs*58 | 14.4 |
| POLD1 | splice site 758 + 1G > T | 26.1 |
| POLD1 | D987fs*58 | 42.3 |
| POLD1 | V111fs*58 | 9.9 |
| POLD1 | S816del | 31.5 |
| POLD1 | E742fs*8 | 2.7 |
| POLD1 | F814_S815 > S | 4.5 |
| POLD1 | R180fs*3 | 67.6 |
| POLD1 | P1102fs*7+ | 12.6 |

TABLE 5-continued

All unique variants identified in POLE and POLD1 tested for driver ability
Associated mutation burdens are representative for each variant

| | | |
|---|---|---|
| POLD1 | D76fs*25 | 17.1 |
| POLD1 | D987fs*58 | 118.9 |
| POLD1 | D987fs*58 | 40.5 |
| POLD1 | D987fs*58 | 8.1 |
| POLD1 | R180fs*3 | 45 |
| POLD1 | A18_G20del | 2.7 |
| POLD1 | splice site 759 − 1G > T | 36.9 |
| POLD1 | R180fs*72 | 109 |
| POLD1 | S816del | 11.7 |
| POLD1 | L966fs*75 | 6.3 |
| POLD1 | R667fs*28 | 4.5 |
| POLD1 | D987fs*58 | 49.5 |
| POLD1 | P116fs*53 | 55.9 |
| POLD1 | K648fs*46 | 17.1 |
| POLD1 | splice site 1495 − 1G > T | 20.7 |
| POLD1 | P115fs*19 | 36 |
| POLD1 | D987fs*41 | 61.3 |
| POLD1 | D987fs*58 | 36 |
| POLD1 | L681fs*13 | 22.5 |
| POLD1 | V933fs*21 | 70.3 |
| POLD1 | E346fs*47 | 87.4 |
| POLD1 | L839fs*49 | 48.6 |
| POLD1 | splice site 2564 + 1G > A | 4.5 |
| POLD1 | splice site 316 + 1G > T | 50.5 |
| POLD1 | S605del | 8.1 |
| POLD1 | E346fs*47 | 42.3 |
| POLD1 | S605del | 80.2 |
| POLD1 | S816del | 6.3 |
| POLD1 | P116fs*53 | 78.4 |
| POLD1 | Q707fs*21 | 3.6 |
| POLD1 | D987fs*58 | 164.9 |
| POLD1 | P116fs*53 | 16.2 |
| POLD1 | D987fs*58 | 70.3 |
| POLD1 | D987fs*58 | 159.5 |
| POLD1 | splice site 2821 − 1G > A | 7.2 |
| POLD1 | S847_R850 > C | 2.7 |
| POLD1 | splice site 841 − 2A > G | 16.2 |
| POLD1 | R823fs*65 | 16.2 |
| POLD1 | splice site 2821 − 1G > T | 25.2 |
| POLD1 | S816del | 23.4 |
| POLD1 | P116fs*53 | 76.6 |
| POLD1 | splice site 1495 − 1G > A | 7.2 |
| POLD1 | T91fs*78 | 2.7 |
| POLD1 | D987fs*58 | 68.5 |
| POLD1 | S240_P243del | 19.8 |
| POLD1 | D987fs*58 | 40.5 |
| POLD1 | D987fs*58 | 75.7 |
| POLD1 | D987fs*58 | 12.6 |
| POLD1 | D987fs*58 | 52.3 |
| POLD1 | splice site 2821 − 1G > C | 27 |
| POLD1 | D987fs*58 | 65.8 |
| POLD1 | splice site 2251 − 1G > A | 7.2 |
| POLD1 | E47fs*44 | 5.4 |
| POLD1 | L1089fs*20+ | 62.2 |
| POLD1 | splice site 2250 + 1G > A | 3.6 |
| POLD1 | splice site 3218 + 2T > G | 10.8 |
| POLD1 | S816del | 7.2 |
| POLD1 | E57del | 3.6 |
| POLD1 | S783fs*106 | 5.4 |
| POLD1 | R180fs*3 | 19.8 |
| POLD1 | A28_P29 > VAP | 18.9 |
| POLD1 | D987fs*58 | 69.4 |
| POLD1 | P116fs*53 | 45 |

TABLE 6

POLE and POLD Mutations

| Specimen ID | Tumour Type | Gene | Driver Mutation | Mutation Burden | Stage | Status |
|---|---|---|---|---|---|---|
| | | Drivers POLE | | | | |
| 1 | Colorectal Carcinoma | POLE | Y458H | 342 | Adult | New |
| 2 | Brain PNET | POLE | Y458H | 85.02 | Pediatric | New |
| 3 | Colon adenocarcinoma (CRC) | POLE | Y458C | 753.2 | Adult | New |
| 4 | Colon adenocarcinoma (CRC) | POLE | Y458C | 13.5 | Adult | New |
| 5 | Colon adenocarcinoma (CRC) | POLE | V411L | 703.6 | Adult | Known |
| 6 | Brain glioblastoma | POLE | V411L | 699 | Pediatric | Known |
| 7 | Ovary carcinosarcoma | POLE | V411L | 650.5 | Adult | Known |
| 8 | Uterus endometrial adenocarcinoma (NOS) | POLE | V411L | 636.9 | Adult | Known |
| 9 | Brain glioblastoma (GBM) | POLE | V411L | 578.4 | Adult | Known |
| 10 | Kidney urothelial carcinoma | POLE | V411L | 500 | Adult | Known |
| 11 | Prostate neuroendocrine carcinoma | POLE | V411L | 371.2 | Adult | Known |
| 12 | Colon adenocarcinoma (CRC) | POLE | V411L | 360.4 | Adult | Known |
| 13 | Uterus endometrial adenocarcinoma endometrioid | POLE | V411L | 345.9 | Adult | Known |
| 14 | Uterus endometrial adenocarcinoma (NOS) | POLE | V411L | 324.3 | Adult | Known |
| 15 | Brain glioma (NOS) | POLE | V411L | 315.3 | Adult | Known |
| 16 | Ovary epithelial carcinoma (NOS) | POLE | V411L | 309.9 | Adult | Known |
| 17 | Prostate acinar adenocarcinoma | POLE | V411L | 301.8 | Adult | Known |
| 18 | Prostate neuroendocrine carcinoma | POLE | V411L | 279.3 | Adult | Known |
| 19 | Prostate acinar adenocarcinoma | POLE | V411L | 245.9 | Adult | Known |
| 20 | Rectum adenocarcinoma (CRC) | POLE | V411L | 240.5 | Adult | Known |
| 21 | Uterus endometrial adenocarcinoma (NOS) | POLE | V411L | 238.7 | Adult | Known |
| 22 | Uterus endometrial adenocarcinoma (NOS) | POLE | V411L | 187.4 | Adult | Known |
| 23 | Colon adenocarcinoma (CRC) | POLE | V411L | 136 | Adult | Known |
| 24 | Colon adenocarcinoma (CRC) | POLE | V411L | 120.7 | Adult | Known |
| 25 | Colon adenocarcinoma (CRC) | POLE | V411L | 116.2 | Adult | Known |
| 26 | Ovary clear cell carcinoma | POLE | V411L | 105.4 | Adult | Known |
| 27 | Colon adenocarcinoma (CRC) | POLE | V411L | 104.5 | Adult | Known |
| 28 | Rectum adenocarcinoma (CRC) | POLE | V411L | 100 | Adult | Known |
| 29 | Uterus carcinosarcoma | POLE | V411L | 77.5 | Adult | Known |
| 30 | Brain glioblastoma (GBM) | POLE | V411L | 45 | Adult | Known |
| 31 | Colon adenocarcinoma (CRC) | POLE | V411L | 39.6 | Adult | Known |
| 32 | Brain glioblastoma (GBM) | POLE | S461I | 447.8 | Adult | Known |
| 33 | Brain glioblastoma | POLE | S461P | 496.24 | Pediatric | Known |
| 34 | Brain glioblastoma | POLE | S461P | 208 | Pediatric | Known |
| 35 | Unknown primary carcinoma (NOS) | POLE | S459F | 311.7 | Adult | Known |
| 36 | Brain glioblastoma | POLE | S459F | 295 | Pediatric | Known |
| 37 | Rectum adenocarcinoma (CRC) | POLE | S459F | 146.8 | Adult | Known |
| 38 | Brain glioblastoma (GBM) | POLE | S459F | 117.1 | Adult | Known |
| 39 | Uterus endometrial adenocarcinoma (NOS) | POLE | S459F | 102.7 | Adult | Known |
| 40 | Duodenum adenocarcinoma | POLE | S459F | 36.9 | Adult | Known |
| 41 | Brain glioblastoma (GBM) | POLE | S297F | 386.5 | Adult | Known |
| 42 | Brain glioblastoma | POLE | S297F | 218 | Pediatric | Known |
| 43 | Skin melanoma | POLE | S297F | 115.3 | Adult | Known |
| 44 | Uterus endometrial adenocarcinoma (NOS) | POLE | S297F | 39.6 | Adult | Known |
| 45 | Colorectal Carcinoma | POLE | P436S | 433 | Adult | New |
| 46 | Brain glioblastoma (GBM) | POLE | P436S | 333.3 | Adult | New |
| 47 | Brain glioblastoma | POLE | P436S | 318.06 | Pediatric | New |
| 48 | Brain glioblastoma | POLE | P436S | 302 | Pediatric | New |
| 49 | Osteochondroma | POLE | P436S | 195 | Pediatric | New |
| 50 | Colon adenocarcinoma (CRC) | POLE | P436R | 493.7 | Adult | New |
| 51 | Brain glioblastoma | POLE | P436H | 541.36 | Pediatric | New |
| 52 | Brain glioblastoma | POLE | P436H | 532 | Pediatric | New |
| 53 | Brain glioblastoma | POLE | P436H | 409.18 | Pediatric | New |
| 54 | Brain glioblastoma | POLE | P436H | 359 | Pediatric | New |
| 55 | Skin basal cell carcinoma | POLE | P286S | 58.6 | Adult | New |
| 56 | Unknown primary melanoma | POLE | P286S | 42.3 | Adult | New |
| 57 | Uterus endometrial adenocarcinoma (NOS) | POLE | P286R | 493.7 | Adult | Known |
| 58 | Colon adenocarcinoma (CRC) | POLE | P286R | 479.3 | Adult | Known |
| 59 | Brain glioblastoma (GBM) | POLE | P286R | 450.5 | Adult | Known |
| 60 | Colon adenocarcinoma (CRC) | POLE | P286R | 394.6 | Adult | Known |
| 61 | Colon adenocarcinoma (CRC) | POLE | P286R | 342.3 | Adult | Known |
| 62 | Colon adenocarcinoma (CRC) | POLE | P286R | 305.4 | Adult | Known |

TABLE 6-continued

POLE and POLD Mutations

| Specimen ID | Tumour Type | Gene | Driver Mutation | Mutation Burden | Stage | Status |
|---|---|---|---|---|---|---|
| 63 | Colon adenocarcinoma (CRC) | POLE | P286R | 259.5 | Adult | Known |
| 64 | Colon adenocarcinoma (CRC) | POLE | P286R | 245 | Adult | Known |
| 65 | Brain glioblastoma (GBM) | POLE | P286R | 227.9 | Adult | Known |
| 66 | Colon adenocarcinoma (CRC) | POLE | P286R | 226.1 | Adult | Known |
| 67 | Rectum adenocarcinoma (CRC) | POLE | P286R | 223.4 | Adult | Known |
| 68 | Colon adenocarcinoma (CRC) | POLE | P286R | 216.2 | Adult | Known |
| 69 | Uterus endometrial adenocarcinoma (NOS) | POLE | P286R | 208.1 | Adult | Known |
| 70 | Uterus endometrial adenocarcinoma (NOS) | POLE | P286R | 203.6 | Adult | Known |
| 71 | Colon adenocarcinoma (CRC) | POLE | P286R | 172.1 | Adult | Known |
| 72 | Uterus carcinosarcoma | POLE | P286R | 168.5 | Adult | Known |
| 73 | Ovary neuroendocrine carcinoma | POLE | P286R | 163.1 | Adult | Known |
| 74 | Rectum adenocarcinoma (CRC) | POLE | P286R | 162.2 | Adult | Known |
| 75 | Colon adenocarcinoma (CRC) | POLE | P286R | 155 | Adult | Known |
| 76 | Uterus endometrial adenocarcinoma (NOS) | POLE | P286R | 153.2 | Adult | Known |
| 77 | Uterus endometrial adenocarcinoma (NOS) | POLE | P286R | 145.9 | Adult | Known |
| 78 | Colon adenocarcinoma (CRC) | POLE | P286R | 133.3 | Adult | Known |
| 79 | Uterus endometrial adenocarcinoma (NOS) | POLE | P286R | 123.4 | Adult | Known |
| 80 | Pancreas ductal adenocarcinoma | POLE | P286R | 100.9 | Adult | Known |
| 81 | Uterus endometrial adenocarcinoma (NOS) | POLE | P286R | 84.7 | Adult | Known |
| 82 | rectum neuroendocrine carcinoma | POLE | P286R | 80.2 | Adult | Known |
| 83 | Colon adenocarcinoma (CRC) | POLE | P286R | 62.2 | Adult | Known |
| 84 | Brain glioblastoma (GBM) | POLE | P286H | 212 | Adult | New |
| 85 | Brain glioblastoma (GBM) | POLE | M444K | 116.2 | Adult | Known |
| 86 | Colon adenocarcinoma (CRC) | POLE | M444K | 91.9 | Adult | Known |
| 87 | Uterus neuroendocrine carcinoma | POLE | M444K | 32.4 | Adult | Known |
| 88 | Colorectal carcinoma | POLE | L424P | 590 | Pediatric | New |
| 89 | Brain glioblastoma | POLE | L424I | 336 | Pediatric | Known |
| 90 | Brain glioblastoma (GBM) | POLE | L424I | 160.4 | Adult | Known |
| 91 | Lung adenocarcinoma | POLE | L424I | 154.1 | Adult | Known |
| 92 | Liver cholangiocarcinoma | POLE | L424I | 47.7 | Adult | Known |
| 93 | Brain glioblastoma | POLE | F367L | 472.56 | Pediatric | New |
| 94 | Brain glioblastoma | POLE | F367L | 238.18 | Pediatric | New |
| 95 | Unknown primary squamous cell carcinoma (SCC) | POLE | E978K | 80.2 | Adult | New |
| 96 | Brain glioblastoma | POLE | E978G | 608.02 | Pediatric | New |
| 97 | Uterus carcinosarcoma | POLE | E978G | 26.1 | Adult | New |
| 98 | Appendix adenocarcinoma | POLE | D368N | 36 | Adult | New |
| 99 | Lung adenocarcinoma | POLE | D275V | 43.2 | Adult | Known |
| 100 | Brain glioblastoma (GBM) | POLE | D275V | 17.1 | Adult | Known |
| 101 | Pancreas ductal adenocarcinoma | POLE | D275G | 318.9 | Adult | Known |
| 102 | Brain glioblastoma (GBM) | POLE | D275A | 226.1 | Adult | Known |
| 103 | Rectum adenocarcinoma (CRC) | POLE | C810G | 854.1 | Adult | New |
| 104 | Brain glioblastoma (GBM) | POLE | C810G | 154.1 | Adult | New |
| 105 | Lung squamous cell carcinoma (SCC) | POLE | A463V | 231.5 | Adult | New |
| 106 | Uterus endometrial adenocarcinoma (NOS) | POLE | A463V | 55.9 | Adult | New |
| 107 | Brain oligodendroglioma | POLE | A463T | 809 | Adult | New |
| 108 | Brain glioblastoma | POLE | A463D | 532 | Pediatric | New |
| 109 | Brain glioblastoma | POLE | A463D | 359 | Pediatric | New |
| 110 | Colon adenocarcinoma (CRC) | POLE | A456P | 373.9 | Adult | Known |
| 111 | Colon adenocarcinoma (CRC) | POLE | A456P | 314.4 | Adult | Known |
| 112 | Colon adenocarcinoma (CRC) | POLE | A456P | 233.3 | Adult | Known |
| 113 | Uterus endometrial adenocarcinoma (NOS) | POLE | A456P | 226.1 | Adult | Known |
| 114 | Colon adenocarcinoma (CRC) | POLE | A456P | 200 | Adult | Known |
| 115 | Ovary endometrioid adenocarcinoma | POLE | A456P | 69.4 | Adult | Known |
| 116 | Cervix squamous cell carcinoma (SCC) | POLE | A456P | 33.3 | Adult | Known |
| 117 | Brain glioblastoma (GBM) | POLE | A288V | 578.4 | Adult | New |
| 118 | Brain glioblastoma (GBM) | POLE | A288V | 386.5 | Adult | New |
| 119 | Stomach neuroendocrine carcinoma | POLE | A288V | 155.9 | Adult | New |
| | Drivers POLD1 | | | | | |
| 1 | Colon adenocarcinoma (CRC) | POLD1 | R689W | 259.5 | Adult | Known |
| 2 | Brain oligodendroglioma | POLD1 | R689W | 585.6 | Adult | Known |
| 3 | Brain glioblastoma (GBM) | POLD1 | R689W | 578.4 | Adult | Known |

TABLE 6-continued

POLE and POLD Mutations

| Specimen ID | Tumour Type | Gene | Driver Mutation | Mutation Burden | Stage | Status |
|---|---|---|---|---|---|---|
| 4 | Brain glioblastoma (GBM) | POLD1 | R689W | 447.8 | Adult | Known |
| 5 | Colon adenocarcinoma (CRC) | POLD1 | R689W | 12.6 | Adult | Known |
| 6 | Vulva squamous cell carcinoma (SCC) | POLD1 | R1016H | 39.6 | Adult | New |
| 7 | Colon adenocarcinoma (CRC) | POLD1 | R1016H | 29.7 | Adult | New |
| 8 | Brain glioma (NOS) | POLD1 | R1016H | 315.3 | Adult | New |
| 9 | Unknown primary adenocarcinoma | POLD1 | R1016H | 69.4 | Adult | New |
| 10 | Uterus endometrial adenocarcinoma (NOS) | POLD1 | R1016H | 636.9 | Adult | New |
| 11 | Colon adenocarcinoma (CRC) | POLD1 | R1016H | 49.5 | Adult | New |
| 12 | Brain medullobastoma | POLD1 | L632M | 141 | Pediatric | New |
| 13 | Brain glioblastoma | POLD1 | L632M | 228 | Pediatric | New |
| 14 | Brain glioblastoma | POLD1 | L632M | 296 | Pediatric | New |
| 15 | Brain Glioblastoma | POLD1 | L632M | 121 | Pediatric | New |
| 16 | Brain PNET | POLD1 | L606M | 196 | Pediatric | Known |
| 17 | Brain PNET | POLD1 | L606M | 295 | Pediatric | Known |
| 18 | Brain glioblastoma (GBM) | POLD1 | L606M | 228.8 | Adult | Known |
| 19 | Brain glioblastoma (GBM) | POLD1 | L606M | 51.4 | Adult | Known |
| 20 | Uterus carcinosarcoma | POLD1 | L606M | 311.7 | Adult | Known |
| 21 | Brain PNET | POLD1 | E318K | 182 | Pediatric | New |
| 22 | Lung non-small cell lung carcinoma (NOS) | POLD1 | E318K | 13.5 | Adult | New |
| 23 | Colon adenocarcinoma (CRC) | POLD1 | E245K | 76.6 | Adult | New |
| 24 | Liver cholangiocarcinoma | POLD1 | E245K | 122.5 | Adult | New |
| 25 | Colon adenocarcinoma (CRC) | POLD1 | E245K | 85.6 | Adult | New |

TABLE 7

Tumour samples with germline replication repair deficiency analysed by exome sequencing

| Sample | Tissue | Germline | Somatic POLE | Somatic POLD1 | TMB |
|---|---|---|---|---|---|
| 1 | Brain | bMMRD | X | | UHM |
| 2 | Brain | bMMRD | | X | UHM |
| 3 | Brain | bMMRD | X | | UHM |
| 4 | Brain | bMMRD | | X | UHM |
| 5 | Brain | bMMRD | X | | UHM |
| 6 | Colon | bMMRD | | | HM |
| 7 | Colon | bMMRD | | | HM |
| 8 | Colon | bMMRD | | | HM |
| 9 | Colon | bMMRD | | | HM |
| 10 | Colon | bMMRD | | | HM |
| 11 | Brain | bMMRD | | | UHM |
| 12 | Leukemia | bMMRD | | | HM |
| 13 | Brain | bMMRD | X | | UHM |
| 14 | Brain | bMMRD | X | | UHM |
| 15 | Brain | bMMRD | X | | UHM |
| 16 | Brain | bMMRD | X | | HM |
| 17 | Brain | bMMRD | X | | UHM |
| 18 | Brain | bMMRD | X | | UHM |
| 19 | Brain | bMMRD | X | | UHM |
| 20 | Brain | bMMRD | X | | UHM |
| 21 | Small Intestine | bMMRD | | | HM |
| 22 | Brain | POLE | | | UHM |
| 23 | Brain | bMMRD | X | | UHM |
| 24 | Brain | Lynch | | | HM |
| 25 | Breast | bMMRD | | | HM |
| 26 | Colon | bMMRD | | X | UHM |
| 27 | Colon | bMMRD | X | | UHM |
| 28 | Brain | bMMRD | X | | UHM |
| 29 | Brain | bMMRD | X | | UHM |
| 30 | Brain | bMMRD | | X | UHM |
| 31 | Leukemia | bMMRD | | | HM |
| 32 | Brain | bMMRD | X | | UHM |
| 33 | Brain | bMMRD | X | | UHM |
| 34 | Brain | bMMRD | X | | UHM |
| 35 | Brain | bMMRD | X | | UHM |
| 36 | Brain | bMMRD | X | | UHM |
| 37 | Brain | bMMRD | X | | UHM |
| 38 | Brain | bMMRD | | X | UHM |
| 39 | Brain | bMMRD | X | | UHM |
| 40 | Leukemia | bMMRD | | | HM |
| 41 | Brain | bMMRD | X | | UHM |
| 42 | Brain | bMMRD | | X | UHM |
| 43 | Brain | bMMRD | X | | UHM |
| 44 | Brain | bMMRD | | X | UHM |
| 45 | Colon | POLE | | | UHM |
| 46 | Brain | Lynch | | | UHM |
| 47 | Colon | bMMRD | X | | UHM |
| 48 | Colon | bMMRD | X | | UHM |
| 49 | Adrenal Gland | bMMRD | | | HM |
| 50 | Bone | bMMRD | X | | UHM |
| 51 | Brain | bMMRD | X | | UHM |
| 52 | Brain | bMMRD | X | | UHM |
| 53 | Brain | bMMRD | X | | UHM |
| 54 | Brain | bMMRD | X | | UHM |
| 55 | Brain | bMMRD | X | | UHM |
| 56 | Brain | bMMRD | X | | HM |

What is claimed is:

1. A method of profiling a tumour, the method comprising:
sequencing nucleic acid from a sample obtained from the tumour to obtain nucleic acid sequences;
identifying mutations in the nucleic acid sequences relative to a reference sequence obtained from a healthy tissue, wherein each of said mutations is defined with respect to the pyrimidine of a base pair;
determining for the tumour, using the mutations, relative proportions of each of 96 mutation types, wherein the 96 mutation types are defined as each of six possible pyrimidine base changes C>A, C>G, C>T, T>A, T>C, or T>G in the context of each of four possible nucleotides (A, C, G, or T) at the position immediately 5' to the mutation and each of four possible nucleotides (A, C, G, or T) at the position immediately 3' to the mutation, comparing the relative proportions of at least 48 of the 96 mutation types for the tumour to corresponding mean proportions for the mutation types for clusters 1 to 3 depicted in Table 1A:

TABLE 1A

| Mut | 5' | 3' | Mean Proportion for Clusters | | |
|---|---|---|---|---|---|
| | | | 1 | 2 | 3 |
| C > A | A | A | 6.7E-05 | 0.001303 | 0.00119 |
| C > A | A | C | 0.002389 | 0.003823 | 0.003755 |
| C > A | A | G | 0 | 0.00119 | 0.000792 |
| C > A | A | T | 0.009421 | 0.002499 | 0.006822 |
| C > A | C | A | 0.003067 | 0.00708 | 0.003819 |
| C > A | C | C | 0.004592 | 0.011953 | 0.002766 |
| C > A | C | G | 0.00161 | 0.007254 | 0.002327 |
| C > A | C | T | 0.037945 | 0.029925 | 0.014682 |
| C > A | G | A | 0.001125 | 0.002937 | 0.002638 |
| C > A | G | C | 0.005352 | 0.004551 | 0.002743 |
| C > A | G | G | 0.001282 | 0.002862 | 0.00103 |
| C > A | G | T | 0.032471 | 0.008021 | 0.008659 |
| C > A | T | A | 0.002468 | 0.002416 | 0.030984 |
| C > A | T | C | 0.006074 | 0.004215 | 0.008444 |
| C > A | T | G | 0.000658 | 0.001553 | 0.003072 |
| C > A | T | T | 0.041834 | 0.006319 | 0.190779 |
| C > G | A | A | 0.000569 | 0.001268 | 0.000741 |
| C > G | A | C | 0.000114 | 0.002475 | 0.000842 |
| C > G | A | G | 0.000251 | 0.001332 | 0.000468 |
| C > G | A | T | 0 | 0.001943 | 0.000872 |
| C > G | C | A | 0.00032 | 0.00168 | 0.00023 |
| C > G | C | C | 0.000559 | 0.002767 | 0.001219 |
| C > G | C | G | 0.000379 | 0.003067 | 0.000998 |
| C > G | C | T | 0.000202 | 0.001803 | 0.001843 |
| C > G | G | A | 0.000238 | 0.001606 | 0.000929 |
| C > G | G | C | 0.000404 | 0.003352 | 0.001803 |
| C > G | G | G | 5.71E-05 | 0.001414 | 0.00021 |
| C > G | G | T | 7.05E-05 | 0.001991 | 0.001271 |
| C > G | T | A | 0 | 0.001682 | 0.000244 |
| C > G | T | C | 0.000343 | 0.002414 | 0.000753 |
| C > G | T | G | 0 | 0.001217 | 0.000503 |
| C > G | T | T | 0.001043 | 0.004031 | 0.000942 |
| C > T | A | A | 0.009098 | 0.015807 | 0.002356 |
| C > T | A | C | 0.021673 | 0.014512 | 0.007633 |
| C > T | A | G | 0.080822 | 0.098997 | 0.029695 |
| C > T | A | T | 0.01273 | 0.008974 | 0.006131 |
| C > T | C | A | 0.005011 | 0.009953 | 0.002726 |
| C > T | C | C | 0.013316 | 0.012312 | 0.003786 |
| C > T | C | G | 0.075944 | 0.103416 | 0.024621 |
| C > T | C | T | 0.013479 | 0.012866 | 0.006972 |
| C > T | G | A | 0.024254 | 0.028917 | 0.005288 |
| C > T | G | C | 0.059279 | 0.046541 | 0.024879 |
| C > T | G | G | 0.222447 | 0.148718 | 0.070994 |
| C > T | G | T | 0.038951 | 0.030229 | 0.021253 |
| C > T | T | A | 0.007213 | 0.010064 | 0.004939 |
| C > T | T | C | 0.028449 | 0.011086 | 0.016469 |
| C > T | T | G | 0.078732 | 0.052801 | 0.219143 |
| C > T | T | T | 0.027756 | 0.008177 | 0.02943 |
| T > A | A | A | 0.000295 | 0.001176 | 0.000209 |
| T > A | A | C | 0.001226 | 0.003815 | 0.000852 |
| T > A | A | G | 0.0004 | 0.001401 | 0.000458 |
| T > A | A | T | 0.001352 | 0.002917 | 0.001796 |
| T > A | C | A | 0 | 0.000781 | 0.000352 |
| T > A | C | C | 0.000369 | 0.002485 | 0.001001 |
| T > A | C | G | 0.0005 | 0.004052 | 0.001149 |
| T > A | C | T | 0.000809 | 0.001423 | 0.000821 |
| T > A | G | A | 0 | 0.0012 | 0.000226 |
| T > A | G | C | 0.002031 | 0.002942 | 0.000182 |

TABLE 1A-continued

| Mut | 5' | 3' | Mean Proportion for Clusters | | |
|---|---|---|---|---|---|
| | | | 1 | 2 | 3 |
| T > A | G | G | 0.00019 | 0.003729 | 0.000445 |
| T > A | G | T | 0.000321 | 0.00107 | 0.000202 |
| T > A | T | A | 0 | 0.000781 | 0.000138 |
| T > A | T | C | 0.001246 | 0.00113 | 0.000725 |
| T > A | T | G | 0.000229 | 0.000808 | 0.00015 |
| T > A | T | T | 0.000267 | 0.000915 | 0.00279 |
| T > C | A | A | 0.006228 | 0.010066 | 0.004417 |
| T > C | A | C | 0.005627 | 0.00713 | 0.004952 |
| T > C | A | G | 0.004509 | 0.021637 | 0.005165 |
| T > C | A | T | 0.00324 | 0.007429 | 0.004211 |
| T > C | C | A | 0.001378 | 0.007187 | 0.000923 |
| T > C | C | C | 0.004677 | 0.009799 | 0.003691 |
| T > C | C | G | 0.003798 | 0.025847 | 0.003957 |
| T > C | C | T | 0.002998 | 0.009297 | 0.003321 |
| T > C | G | A | 0.014476 | 0.017372 | 0.01155 |
| T > C | G | C | 0.012038 | 0.011524 | 0.015514 |
| T > C | G | G | 0.012999 | 0.020376 | 0.008717 |
| T > C | G | T | 0.008026 | 0.011538 | 0.012768 |
| T > C | T | A | 0.002157 | 0.00638 | 0.002805 |
| T > C | T | C | 0.003458 | 0.007139 | 0.00666 |
| T > C | T | G | 0.002926 | 0.009561 | 0.005562 |
| T > C | T | T | 0.002948 | 0.005824 | 0.005819 |
| T > G | A | A | 6.7E-05 | 0.000486 | 0.001478 |
| T > G | A | C | 0.001077 | 0.001094 | 0.003775 |
| T > G | A | G | 0.000499 | 0.001114 | 0.001846 |
| T > G | A | T | 0.003055 | 0.00097 | 0.011338 |
| T > G | C | A | 0.000196 | 0.00167 | 0.002233 |
| T > G | C | C | 0.000731 | 0.004141 | 0.001955 |
| T > G | C | G | 0.000628 | 0.00923 | 0.003836 |
| T > G | C | T | 0.003131 | 0.005064 | 0.015868 |
| T > G | G | A | 0.000365 | 0.000912 | 0.001333 |
| T > G | G | C | 0.001875 | 0.001146 | 0.002466 |
| T > G | G | G | 0.001543 | 0.002292 | 0.00168 |
| T > G | G | T | 0.003994 | 0.003071 | 0.004097 |
| T > G | T | A | 0 | 0.000364 | 0.004756 |
| T > G | T | C | 0.001569 | 0.001778 | 0.006492 |
| T > G | T | G | 0.000386 | 0.001434 | 0.001971 |
| T > G | T | T | 0.006112 | 0.001191 | 0.048665 | assigning the tumour to one of the clusters 1 to 3 based on the comparing, wherein:
cluster 1 is indicative of an ultra-hypermutant tumour with microsatellite stability, a germline MMR gene mutation, or a POLE gene mutation secondary an MMR mutation;
cluster 2 is indicative of a hypermutant tumour with microsatellite instability, or an early MMR gene mutation; and
cluster 3 is indicative of an ultra-hypermutant tumour with microsatellite stability, an early POLE gene mutation, or an MMR gene mutation secondary to a POLE gene mutation; and
after assigning the tumor to one of the clusters 1 to 3, administering to the patient an immunotherapy or an immune checkpoint inhibitor.

2. The method of claim 1, wherein the comparing is carried out using the relative proportions of the 96 mutation types determined for the tumour.

3. The method of claim 1, wherein the step of assigning is carried out by matching the relative proportions determined for the tumour to one of the clusters by highest cosine similarity.

4. The method of claim 3, wherein the matching requires a minimum cosine similarity of 0.75.

5. The method of claim 1, wherein the at least one tumour characteristic is further determined based on the presence of one or more driver mutations as defined in Table 6:

TABLE 6

| Specimen ID | Tumour Type | Gene | Driver Mutation | Mutation Burden | Stage | Status |
|---|---|---|---|---|---|---|
| | | Drivers POLE | | | | |
| 1 | Colorectal Carcinoma | POLE | Y458H | 342 | Adult | New |
| 2 | Brain PNET | POLE | Y458H | 85.02 | Pediatric | New |
| 3 | Colon adenocarcinoma (CRC) | POLE | Y458C | 753.2 | Adult | New |
| 4 | Colon adenocarcinoma (CRC) | POLE | Y458C | 13.5 | Adult | New |
| 5 | Colon adenocarcinoma (CRC) | POLE | V411L | 703.6 | Adult | Known |
| 6 | Brain glioblastoma | POLE | V411L | 699 | Pediatric | Known |
| 7 | Ovary carcinosarcoma | POLE | V411L | 650.5 | Adult | Known |
| 8 | Uterus endometrial adenocarcinoma (NOS) | POLE | V411L | 636.9 | Adult | Known |
| 9 | Brain glioblastoma (GBM) | POLE | V411L | 578.4 | Adult | Known |
| 10 | Kidney urothelial carcinoma | POLE | V411L | 500 | Adult | Known |
| 11 | Prostate neuroendocrine carcinoma | POLE | V411L | 371.2 | Adult | Known |
| 12 | Colon adenocarcinoma (CRC) | POLE | V411L | 360.4 | Adult | Known |
| 13 | Uterus endometrial adenocarcinoma endometrioid | POLE | V411L | 345.9 | Adult | Known |
| 14 | Uterus endometrial adenocarcinoma (NOS) | POLE | V411L | 324.3 | Adult | Known |
| 15 | Brain glioma (NOS) | POLE | V411L | 315.3 | Adult | Known |
| 16 | Ovary epithelial carcinoma (NOS) | POLE | V411L | 309.9 | Adult | Known |
| 17 | Prostate acinar adenocarcinoma | POLE | V411L | 301.8 | Adult | Known |
| 18 | Prostate neuroendocrine carcinoma | POLE | V411L | 279.3 | Adult | Known |
| 19 | Prostate acinar adenocarcinoma | POLE | V411L | 245.9 | Adult | Known |
| 20 | Rectum adenocarcinoma (CRC) | POLE | V411L | 240.5 | Adult | Known |
| 21 | Uterus endometrial adenocarcinoma (NOS) | POLE | V411L | 238.7 | Adult | Known |
| 22 | Uterus endometrial adenocarcinoma (NOS) | POLE | V411L | 187.4 | Adult | Known |
| 23 | Colon adenocarcinoma (CRC) | POLE | V411L | 136 | Adult | Known |
| 24 | Colon adenocarcinoma (CRC) | POLE | V411L | 120.7 | Adult | Known |
| 25 | Colon adenocarcinoma (CRC) | POLE | V411L | 116.2 | Adult | Known |
| 26 | Ovary clear cell carcinoma | POLE | V411L | 105.4 | Adult | Known |
| 27 | Colon adenocarcinoma (CRC) | POLE | V411L | 104.5 | Adult | Known |
| 28 | Rectum adenocarcinoma (CRC) | POLE | V411L | 100 | Adult | Known |
| 29 | Uterus carcinosarcoma | POLE | V411L | 77.5 | Adult | Known |
| 30 | Brain glioblastoma (GBM) | POLE | V411L | 45 | Adult | Known |
| 31 | Colon adenocarcinoma (CRC) | POLE | V411L | 39.6 | Adult | Known |
| 32 | Brain glioblastoma (GBM) | POLE | S461T | 447.8 | Adult | Known |
| 33 | Brain glioblastoma | POLE | S461P | 496.24 | Pediatric | Known |
| 34 | Brain glioblastoma | POLE | S461P | 208 | Pediatric | Known |
| 35 | Unknown primary carcinoma (NOS) | POLE | S459F | 311.7 | Adult | Known |
| 36 | Brain glioblastoma | POLE | S459F | 295 | Pediatric | Known |
| 37 | Rectum adenocarcinoma (CRC) | POLE | S459F | 146.8 | Adult | Known |
| 38 | Brain glioblastoma (GBM) | POLE | S459F | 117.1 | Adult | Known |
| 39 | Uterus endometrial adenocarcinoma (NOS) | POLE | S459F | 102.7 | Adult | Known |
| 40 | Duodenum adenocarcinoma | POLE | S459F | 36.9 | Adult | Known |
| 41 | Brain glioblastoma (GBM) | POLE | S297F | 386.5 | Adult | Known |
| 42 | Brain glioblastoma | POLE | S297F | 218 | Pediatric | Known |
| 43 | Skin melanoma | POLE | S297F | 115.3 | Adult | Known |
| 44 | Uterus endometrial adenocarcinoma (NOS) | POLE | S297F | 39.6 | Adult | Known |
| 45 | Colorectal Carcinoma | POLE | P436S | 433 | Adult | New |
| 46 | Brain glioblastoma (GBM) | POLE | P436S | 333.3 | Adult | New |
| 47 | Brain glioblastoma | POLE | P436S | 318.06 | Pediatric | New |
| 48 | Brain glioblastoma | POLE | P436S | 302 | Pediatric | New |
| 49 | Osteochondroma | POLE | P436S | 195 | Pediatric | New |
| 50 | Colon adenocarcinoma (CRC) | POLE | P436R | 493.7 | Adult | New |
| 51 | Brain glioblastoma | POLE | P436H | 541.36 | Pediatric | New |
| 52 | Brain glioblastoma | POLE | P436H | 532 | Pediatric | New |
| 53 | Brain glioblastoma | POLE | P436H | 409.18 | Pediatric | New |
| 54 | Brain glioblastoma | POLE | P436H | 359 | Pediatric | New |
| 55 | Skin basal cell carcinoma | POLE | P286S | 58.6 | Adult | New |
| 56 | Unknown primary melanoma | POLE | P286S | 42.3 | Adult | New |
| 57 | Uterus endometrial adenocarcinoma (NOS) | POLE | P286R | 493.7 | Adult | Known |
| 58 | Colon adenocarcinoma (CRC) | POLE | P286R | 479.3 | Adult | Known |

TABLE 6-continued

| Specimen ID | Tumour Type | Gene | Driver Mutation | Mutation Burden | Stage | Status |
|---|---|---|---|---|---|---|
| 59 | Brain glioblastoma (GBM) | POLE | P286R | 450.5 | Adult | Known |
| 60 | Colon adenocarcinoma (CRC) | POLE | P286R | 394.6 | Adult | Known |
| 61 | Colon adenocarcinoma (CRC) | POLE | P286R | 342.3 | Adult | Known |
| 62 | Colon adenocarcinoma (CRC) | POLE | P286R | 305.4 | Adult | Known |
| 63 | Colon adenocarcinoma (CRC) | POLE | P286R | 259.5 | Adult | Known |
| 64 | Colon adenocarcinoma (CRC) | POLE | P286R | 245 | Adult | Known |
| 65 | Brain glioblastoma (GBM) | POLE | P286R | 227.9 | Adult | Known |
| 66 | Colon adenocarcinoma (CRC) | POLE | P286R | 226.1 | Adult | Known |
| 67 | Rectum adenocarcinoma (CRC) | POLE | P286R | 223.4 | Adult | Known |
| 68 | Colon adenocarcinoma (CRC) | POLE | P286R | 216.2 | Adult | Known |
| 69 | Uterus endometrial adenocarcinoma (NOS) | POLE | P286R | 208.1 | Adult | Known |
| 70 | Uterus endometrial adenocarcinoma (NOS) | POLE | P286R | 203.6 | Adult | Known |
| 71 | Colon adenocarcinoma (CRC) | POLE | P286R | 172.1 | Adult | Known |
| 72 | Uterus carcinosarcoma | POLE | P286R | 168.5 | Adult | Known |
| 73 | Ovary neuroendocrine carcinoma | POLE | P286R | 163.1 | Adult | Known |
| 74 | Rectum adenocarcinoma (CRC) | POLE | P286R | 162.2 | Adult | Known |
| 75 | Colon adenocarcinoma (CRC) | POLE | P286R | 155 | Adult | Known |
| 76 | Uterus endometrial adenocarcinoma (NOS) | POLE | P286R | 153.2 | Adult | Known |
| 77 | Uterus endometrial adenocarcinoma (NOS) | POLE | P286R | 145.9 | Adult | Known |
| 78 | Colon adenocarcinoma (CRC) | POLE | P286R | 133.3 | Adult | Known |
| 79 | Uterus endometrial adenocarcinoma (NOS) | POLE | P286R | 123.4 | Adult | Known |
| 80 | Pancreas ductal adenocarcinoma | POLE | P286R | 100.9 | Adult | Known |
| 81 | Uterus endometrial adenocarcinoma (NOS) | POLE | P286R | 84.7 | Adult | Known |
| 82 | rectum neuroendocrine carcinoma | POLE | P286R | 80.2 | Adult | Known |
| 83 | Colon adenocarcinoma (CRC) | POLE | P286R | 62.2 | Adult | Known |
| 84 | Brain glioblastoma (GBM) | POLE | P286H | 212 | Adult | New |
| 85 | Brain glioblastoma (GBM) | POLE | M444K | 116.2 | Adult | Known |
| 86 | Colon adenocarcinoma (CRC) | POLE | M444K | 91.9 | Adult | Known |
| 87 | Uterus neuroendocrine carcinoma | POLE | M444K | 32.4 | Adult | Known |
| 88 | Colorectal carcinoma | POLE | L424P | 590 | Pediatric | New |
| 89 | Brain glioblastoma | POLE | L424I | 336 | Pediatric | Known |
| 90 | Brain glioblastoma (GBM) | POLE | L424I | 160.4 | Adult | Known |
| 91 | Lung adenocarcinoma | POLE | L424I | 154.1 | Adult | Known |
| 92 | Liver cholangiocarcinoma | POLE | L424I | 47.7 | Adult | Known |
| 93 | Brain glioblastoma | POLE | F367L | 472.56 | Pediatric | New |
| 94 | Brain glioblastoma | POLE | F367L | 238.18 | Pediatric | New |
| 95 | Unknown primary squamous cell carcinoma (SCC) | POLE | E978K | 80.2 | Adult | New |
| 96 | Brain glioblastoma | POLE | E978G | 608.02 | Pediatric | New |
| 97 | Uterus carcinosarcoma | POLE | E978G | 26.1 | Adult | New |
| 98 | Appendix adenocarcinoma | POLE | D368N | 36 | Adult | New |
| 99 | Lung adenocarcinoma | POLE | D275V | 43.2 | Adult | Known |
| 100 | Brain glioblastoma (GBM) | POLE | D275V | 17.1 | Adult | Known |
| 101 | Pancreas ducta adenocarcinoma | POLE | D275G | 318.9 | Adult | Known |
| 102 | Brain glioblastoma (GBM) | POLE | D275A | 226.1 | Adult | Known |
| 103 | Rectum adenocarcinoma (CRC) | POLE | C810G | 854.1 | Adult | New |
| 104 | Brain glioblastoma (GBM) | POLE | C810G | 154.1 | Adult | New |
| 105 | Lung squamous cell carcinoma (SCC) | POLE | A463V | 231.5 | Adult | New |
| 106 | Uterus endometrial adenocarcinoma (NOS) | POLE | A463V | 55.9 | Adult | New |
| 107 | Brain oligodendroglioma | POLE | A463T | 809 | Adult | New |
| 108 | Brain glioblastoma | POLE | A463D | 532 | Pediatric | New |
| 109 | Brain glioblastoma | POLE | A463D | 359 | Pediatric | New |
| 110 | Colon adenocarcinoma (CRC) | POLE | A456P | 373.9 | Adult | Known |
| 111 | Colon adenocarcinoma (CRC) | POLE | A456P | 314.4 | Adult | Known |
| 112 | Colon adenocarcinoma (CRC) | POLE | A456P | 233.3 | Adult | Known |
| 113 | Uterus endometrial adenocarcinoma (NOS) | POLE | A456P | 226.1 | Adult | Known |
| 114 | Colon adenocarcinoma (CRC) | POLE | A456P | 200 | Adult | Known |
| 115 | Ovary endometrioid adenocarcinoma | POLE | A456P | 69.4 | Adult | Known |

TABLE 6-continued

| Specimen ID | Tumour Type | Gene | Driver Mutation | Mutation Burden | Stage | Status |
|---|---|---|---|---|---|---|
| 116 | Cervix squamous cel carcinoma (SCC) | POLE | A456P | 33.3 | Adult | Known |
| 117 | Brain glioblastoma (GBM) | POLE | A288V | 578.4 | Adult | New |
| 118 | Brain glioblastoma (GBM) | POLE | A288V | 386.5 | Adult | New |
| 119 | Stomach neuroendocrine carcinoma | POLE | A288V | 155.9 | Adult | New |
| Drivers POLD1 | | | | | | |
| 1 | Colon adenocarcinoma (CRC) | POLD1 | R689W | 259.5 | Adult | Known |
| 2 | Brain oligodendroglioma | POLD1 | R689W | 585.6 | Adult | Known |
| 3 | Brain glioblastoma (GBM) | POLD1 | R689W | 578.4 | Adult | Known |
| 4 | Brain glioblastoma (GBM) | POLD1 | R689W | 447.8 | Adult | Known |
| 5 | Colon adenocarcinoma (CRC) | POLD1 | R689W | 12.6 | Adult | Known |
| 6 | Vulva squamous cell carcinoma (SCC) | POLD1 | R1016H | 39.6 | Adult | New |
| 7 | Colon adenocarcinoma (CRC) | POLD1 | R1016H | 29.7 | Adult | New |
| 8 | Brain glioma (NOS) | POLD1 | R1016H | 315.3 | Adult | New |
| 9 | Unknown primary adenocarcinoma | POLD1 | R1016H | 69.4 | Adult | New |
| 10 | Uterus endometrial adenocarcinoma (NOS) | POLD1 | R1016H | 636.9 | Adult | New |
| 11 | Colon adenocarcinoma (CRC) | POLD1 | R1016H | 49.5 | Adult | New |
| 12 | Brain medullobastoma | POLD1 | L632M | 141 | Pediatric | New |
| 13 | Brain glioblastoma | POLD1 | L632M | 228 | Pediatric | New |
| 14 | Brain glioblastoma | POLD1 | L632M | 296 | Pediatric | New |
| 15 | Brain Glioblastoma | POLD1 | L632M | 121 | Pediatric | New |
| 16 | Brain PNET | POLD1 | L606M | 196 | Pediatric | Known |
| 17 | Brain PNET | POLD1 | L606M | 295 | Pediatric | Known |
| 18 | Brain glioblastoma (GBM) | POLD1 | L606M | 228.8 | Adult | Known |
| 19 | Brain glioblastoma (GBM) | POLD1 | L606M | 51.4 | Adult | Known |
| 20 | Uterus carcinosarcoma | POLD1 | L606M | 311.7 | Adult | Known |
| 21 | Brain PNET | POLD1 | E318K | 182 | Pediatric | New |
| 22 | Lung non-small cell lung carcinoma (NOS) | POLD1 | E318K | 13.5 | Adult | New |
| 23 | Colon adenocarcinoma (CRC) | POLD1 | E245K | 76.6 | Adult | New |
| 24 | Liver cholangiocarcinoma | POLD1 | E245K | 122.5 | Adult | New |
| 25 | Colon adenocarcinoma (CRC) | POLD1 | E245K | 85.6 | Adult | New. |

6. The method of claim 1, wherein the tumour is a hypermutant tumour.

7. The method of claim 6, wherein the hypermutant tumour has mutation frequency of at least 5 mutations per megabase (Mb), and the tumour is a pediatric tumour.

8. The method of claim 6, wherein the hypermutant tumour has a mutation frequency of at least 9.9 mutations per megabase (Mb), and the tumour is from an adult.

9. The method of claim 6, wherein the hypermutant tumour is an ultra-hypermutant tumour having a mutation frequency of at least 100 mutations per megabase (Mb).

10. The method of claim 2, wherein the step of assigning is carried out by matching the relative proportions determined for the tumour to one of the clusters by highest cosine similarity.

11. The method of claim 10, wherein the matching requires a minimum cosine similarity of 0.75.

* * * * *